(12) United States Patent
Taniguchi et al.

(10) Patent No.: US 12,297,187 B2
(45) Date of Patent: May 13, 2025

(54) COMPOUND HAVING CYCLIC STRUCTURE

(71) Applicant: Daiichi Sankyo Company, Limited, Tokyo (JP)

(72) Inventors: Toru Taniguchi, Bunkyo-ku (JP); Osamu Iwamoto, Yokohama (JP); Keiji Saito, Atsugi (JP); Katsuyoshi Nakajima, Shinagawa-ku (JP); Yasuyuki Ogawa, Yokosuka (JP); Nobuya Kurikawa, Shinagawa-ku (JP); Seiko Nagata, Shinagawa-ku (JP); Kaori Ito, Koto-ku (JP); Eriko Kioi, Yokohama (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 18/057,511

(22) Filed: Nov. 21, 2022

(65) Prior Publication Data
US 2023/0331700 A1    Oct. 19, 2023

Related U.S. Application Data

(63) Continuation of application No. 16/646,130, filed as application No. PCT/JP2018/033909 on Sep. 13, 2018, now Pat. No. 11,512,067.

(30) Foreign Application Priority Data

Sep. 14, 2017   (JP) .................................. 2017-176891

(51) Int. Cl.
| | | |
|---|---|---|
| *C07D 401/14* | (2006.01) | |
| *C07D 403/14* | (2006.01) | |
| *C07D 405/14* | (2006.01) | |
| *C07D 413/14* | (2006.01) | |
| *C07D 471/04* | (2006.01) | |
| *C07D 498/10* | (2006.01) | |

(52) U.S. Cl.
CPC ......... *C07D 401/14* (2013.01); *C07D 403/14* (2013.01); *C07D 405/14* (2013.01); *C07D 413/14* (2013.01); *C07D 471/04* (2013.01); *C07D 498/10* (2013.01); *C07B 2200/13* (2013.01)

(58) Field of Classification Search
CPC .. C07D 401/14; C07D 403/14; C07D 405/14; C07D 413/14; C07D 471/04; C07D 498/10; C07B 2200/13
See application file for complete search history.

(56) References Cited

U.S. PATENT DOCUMENTS

| | | |
|---|---|---|
| 2006/0122397 A1 | 6/2006 | Arora et al. |
| 2007/0259916 A1 | 11/2007 | Isaac et al. |
| 2007/0259923 A1 | 11/2007 | Isaac et al. |
| 2011/0105460 A1 | 5/2011 | Yoshimura et al. |
| 2015/0210727 A1 | 7/2015 | Hedstrom et al. |

FOREIGN PATENT DOCUMENTS

| | | |
|---|---|---|
| WO | 03/080053 A1 | 10/2003 |
| WO | 2004/058730 A2 | 7/2004 |
| WO | 2004/058741 A1 | 7/2004 |

(Continued)

OTHER PUBLICATIONS

Gu, X., et al., "Discovery of 4-heteroarylbicyclo[2.2.2]octyltriazoles as Potent and Selective Inhibitors of 11B-HSD1: Novel Therapeutic Agents for the Treatment of Metabolic Syndrome," Bioorganic & Medicinal Chemistry Letters 15(23):5266-5269, 2005.

Monji, A., "The Neuroinflammation Hypothesis of Psychiatric Disorders," Psychiatria et Neurologia Japonica 114(2):124-133, 2012.

(Continued)

*Primary Examiner* — Timothy R Rozof
(74) *Attorney, Agent, or Firm* — FINNEGAN, HENDERSON, FARABOW, GARRETT & DUNNER, LLP

(57) ABSTRACT

An object of the present invention is to provide a compound having an anti-inflammatory activity or a pharmacologically acceptable salt thereof.

The solution of the present invention is a compound of general formula (1) or a pharmacologically acceptable salt thereof.

[Formula 1]

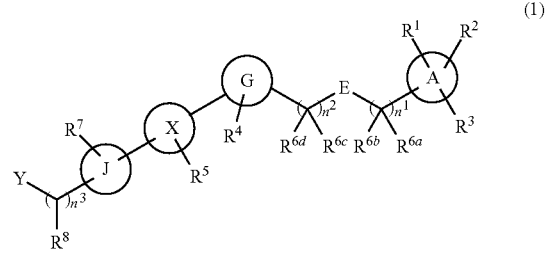

wherein the symbols in the formula are defined below: A: e.g., Benzene, E: e.g., —$CH_2$—, G: e.g., a 5-membered aromatic heterocyclic ring, X: e.g., cyclohexane, J: e.g., a 5-membered aromatic heterocyclic ring, Y: e.g., a phenyl group, $R^1$, $R^2$, $R^3$: e.g., a halogen atom, $R^4$: e.g., a C1-C6 alkyl group, $R^5$: e.g., a hydrogen atom, $R^{6a}$, $R^{6b}$, $R^{6c}$, $R^{6d}$: e.g., a hydrogen atom, $R^7$: e.g., a hydrogen atom, $R^8$: e.g., a hydrogen atom, $n^1$, $n^2$, $n^3$: e.g., 1.

10 Claims, 4 Drawing Sheets

(56) References Cited

FOREIGN PATENT DOCUMENTS

| WO | 2005/080386 A1 | 9/2005 |
| WO | 2006/113140 A3 | 10/2006 |
| WO | 2007/047625 A3 | 4/2007 |
| WO | 2007/087150 A2 | 8/2007 |
| WO | 2007/130820 A2 | 11/2007 |
| WO | 2007/130821 A2 | 11/2007 |
| WO | 2009/054786 A1 | 4/2009 |
| WO | 2009/054791 A1 | 4/2009 |
| WO | 2009/054793 A1 | 4/2009 |
| WO | 2019/054427 A1 | 3/2019 |

OTHER PUBLICATIONS

Paprocka, R. et al., "Synthesis and anti-inflammatory activity of new 1,2,4-triazole derivatives", Bioorganic & Medicinal Chemistry Letters, <http://dx.doi.org/http://dx.doi.org/10.1016/j.bmcl.2015.04.07925>, (13): 2664 -2667, Jul. 2015.

Suzumura, A., "Microglia in Neurodegenerative Disorders and Neuroinflammation," Clinical Neurology 54(12):1119-1121, 2014.

Brazilian Preliminary Office Action mailed Jul. 8, 2022, issued in corresponding Application No. BR1120200051748, filed Sep. 13, 2018, 7 pages.

Colombian Office Action mailed Jul. 18, 2022, issued in corresponding Application No. NC2020/0003114, filed Sep. 13, 2018, 13 pages.

International Search Report mailed Dec. 11, 2018, issued in corresponding International Application No. PCT/JP2018/033909, filed Sep. 13, 2018, 6 pages.

Mexican Examination Report mailed Jun. 29, 2022, issued in corresponding Application No. MX/a/2020/002944, filed Sep. 13, 2018, 20 pages.

[Figure 1]
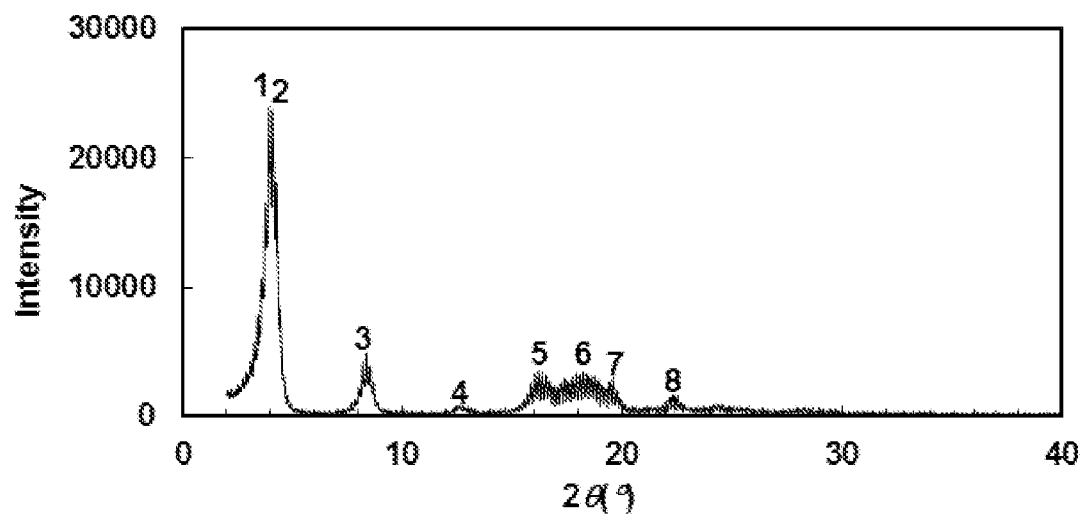
[Figure 2]
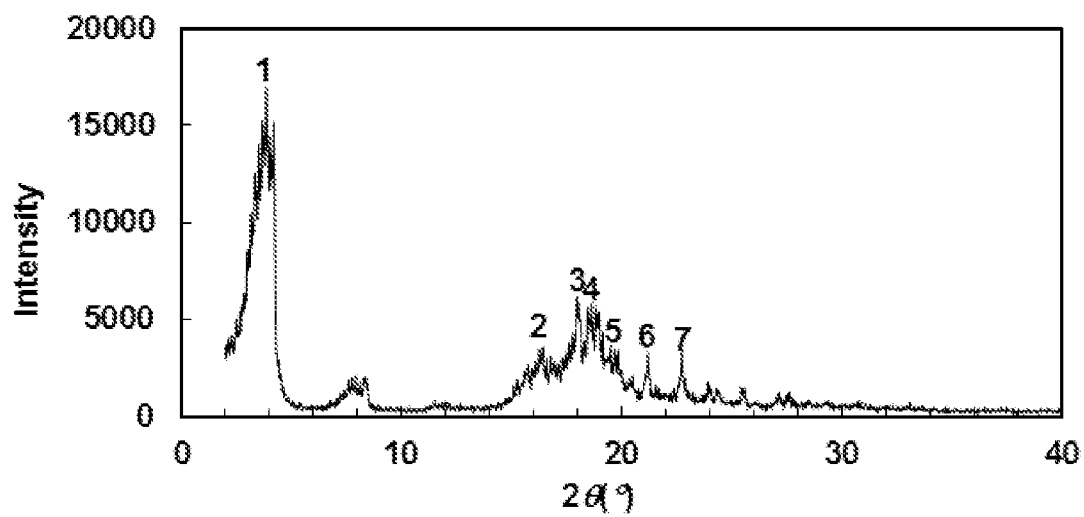

[Figure 3]
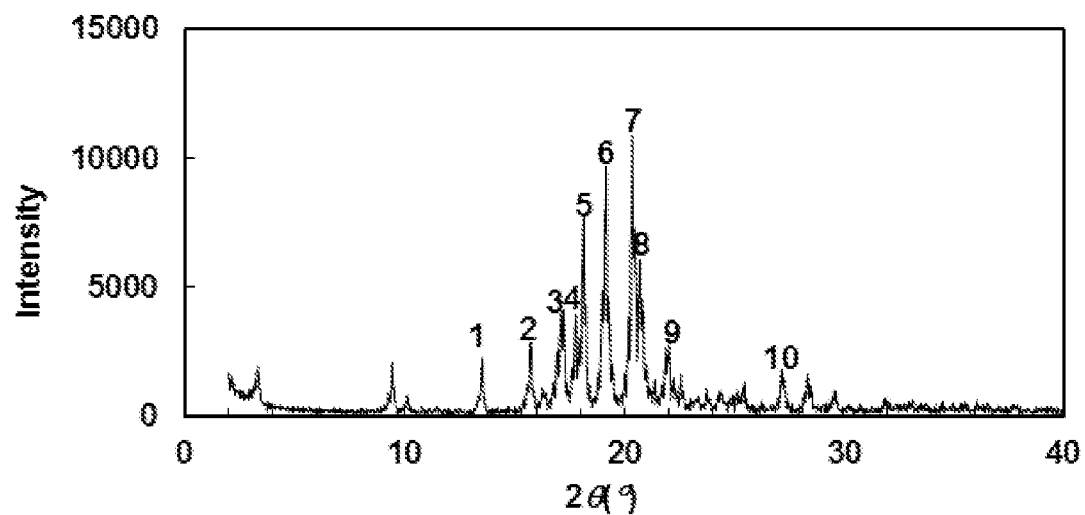
[Figure 4]
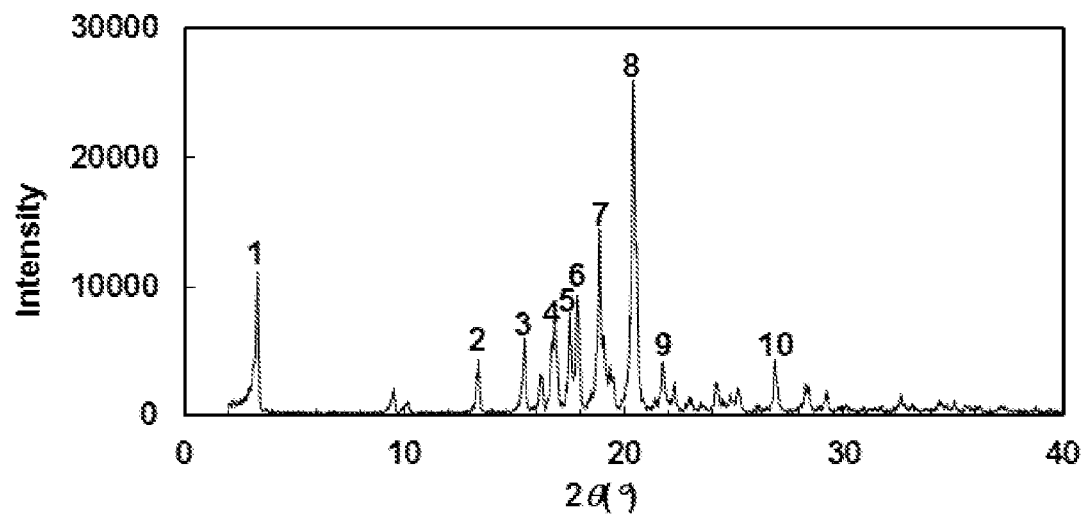

[Figure 5]
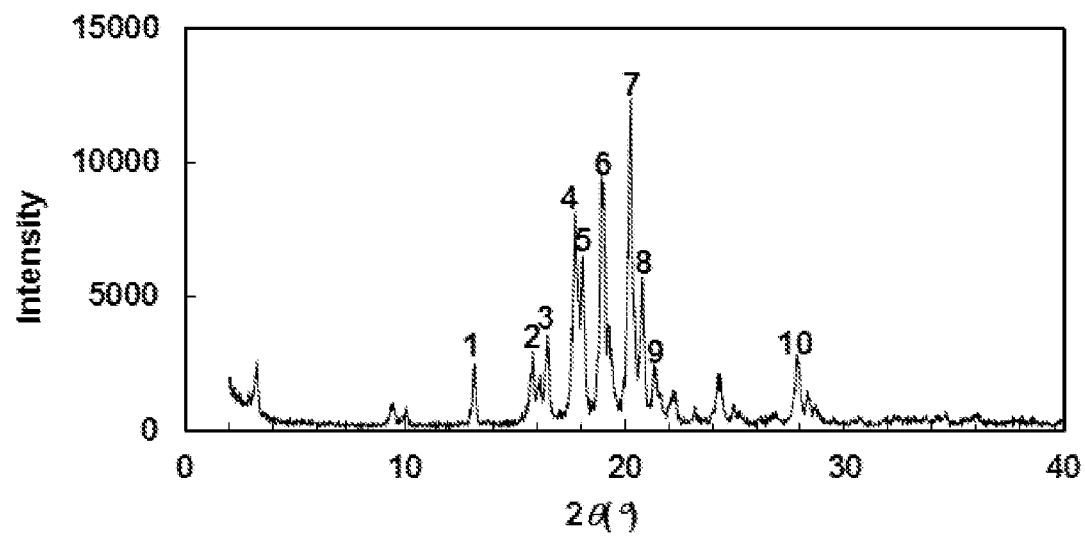
[Figure 6]
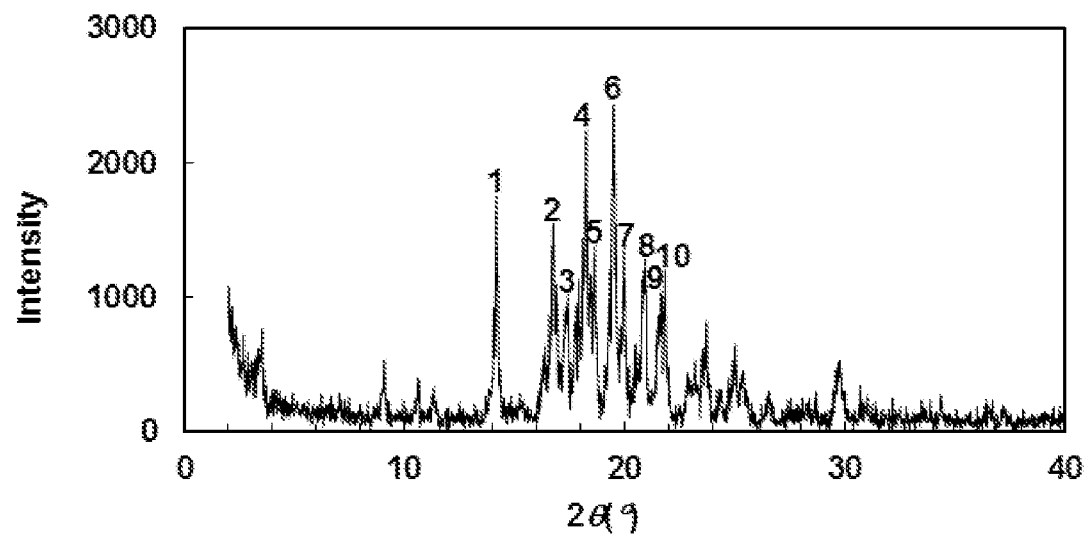

[Figure 7]
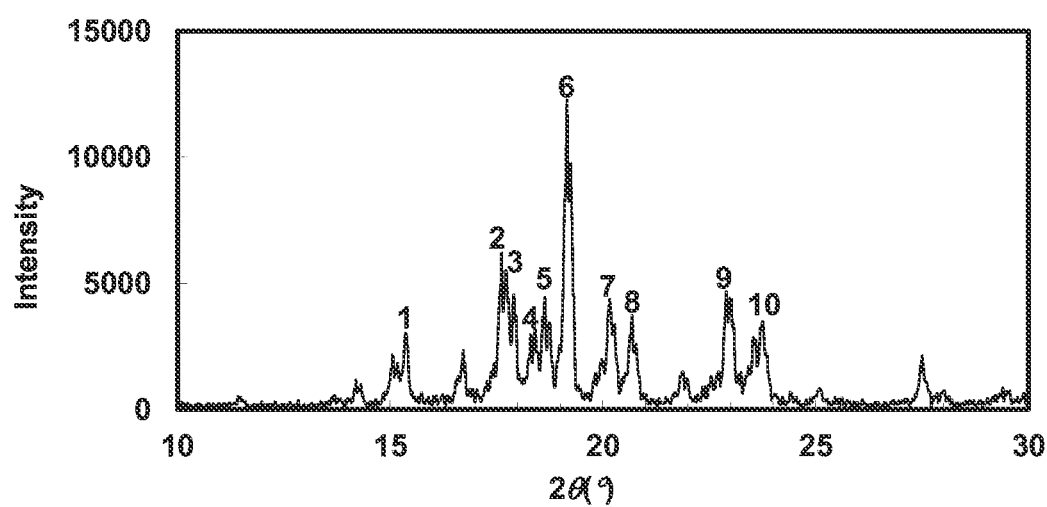

COMPOUND HAVING CYCLIC STRUCTURE

CROSS REFERENCE TO RELATED APPLICATIONS

This application is a continuation of U.S. patent application Ser. No. 16/646,130, filed on Jul. 20, 2020, which is the U.S. national phase of PCT/JP2018/033909, filed on Sep. 13, 2018, which claims priority to Japanese Application No. 2017-176891, filed on Sep. 14, 2017, each expressly incorporated herein by reference in its entirety.

TECHNICAL FIELD

The present invention relates to a compound having a specific chemical structure having a peripheral and/or central anti-inflammatory activity or a pharmacologically acceptable salt thereof, and a production method thereof, or the like. The present invention also relates to a mechanism of action, a pharmaceutical composition, a production method of the pharmaceutical composition, a method of prevention and/or treatment and the like, regarding the compound or a pharmacologically acceptable salt thereof.

BACKGROUND ART

Patent Reference 1 reports the following 5-membered aromatic heterocyclic compounds, but the anti-inflammatory activity of these compounds is not known.

[Formula 1]

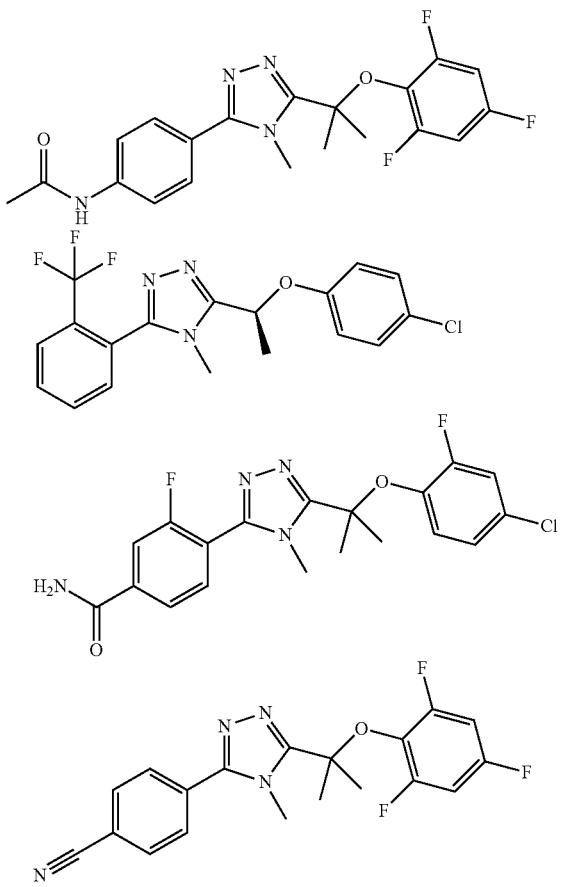

Along with advances in research, relationships between psychiatric or neurodegenerative diseases and inflammation have been reported in recent years (Non patent References 1 and 2).

It has been reported that stress increases production of inflammatory cytokines from microglia and that patients with mental diseases (such as depression and schizophrenia) have high levels of blood cytokines (TNFα or the like), suggesting the involvement of brain inflammation in psychiatric diseases. Furthermore, in neurodegenerative diseases such as Alzheimer's disease, it has been suggested that proteins, which are considered to be the cause of the disease, provoke brain inflammation through microglia activation.

CITATION LIST

Patent Reference

Patent Reference 1: WO2010/001946

Non Patent References

Non patent Reference 1: Kadota Akira, Hypothesis of neuroinflammation of mental illness, Psychiatria et Neurologia Japonica, (2012), 114(2): 124-133

Non patent Reference 2: Suzumura Akio, Neurodegenerative disease, Neuroinflammation and microglia, Clinical Neurology, (2014), 54: 1119-1121

SUMMARY OF INVENTION

Technical Problem

The present invention provides a compound and a pharmacologically acceptable salt thereof or the like, having a specific chemical structure having an anti-inflammatory activity, which are useful as an active ingredient for preventing and/or treating an inflammatory disease. The present invention also provides a novel production method and an intermediate therefor. Since the compound and a pharmacologically acceptable salt thereof of the present invention have different properties from known anti-inflammatory drugs in various aspects, they are considered to be useful as a novel medicine.

The compound and a pharmacologically acceptable salt thereof of the present invention have excellent properties in terms of anti-inflammatory activity, bioavailability, solubility, cell membrane permeability, oral absorbability, blood concentration, metabolic stability, tissue migration, in vitro activity, in vivo activity, ex vivo activity, rapid onset of drug efficacy, sustained drug efficacy, physical stability, drug interaction, safety (such as cardiotoxicity or hepatotoxicity) and the like, and have been found to be useful as a medicinal drug.

Solution to Problem

The present inventors conducted intensive studies for developing a compound which is useful as an active ingredient for preventing and/or treating an inflammatory disease, a pharmacologically acceptable salt thereof or the like. As a result, they found the compound and a pharmacologically acceptable salt thereof or the like of the present invention. More specifically, the present invention is as described below.

[1]
A compound of general formula (1) or a pharmacologically acceptable salt thereof:

[Formula 2]

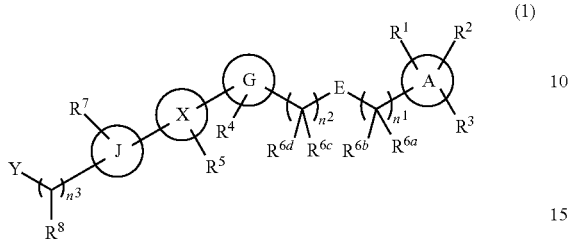

(1)

wherein the symbols in the formula are defined below:
A: a 5- to 6-membered aromatic heterocycle, a 4- to 7-membered saturated heterocycle, benzene, cyclohexane or a ring having the following structure, wherein each of the rings has at least one bond;

[Formula 3]

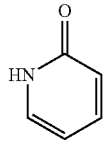

E: —CH$_2$—, —O—, or a single bond;
G: a 5-membered aromatic heterocycle, wherein the ring has at least two bonds; if the ring has a nitrogen atom(s), at least one of the nitrogen atom(s) is next to an atom that is attached to a right-hand portion, wherein the right-hand portion refers to the following portion in the compound of general formula (1):

[Formula 4]

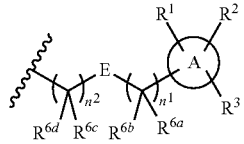

wherein the symbols indicating the respective substituents are the same as defined above;
X: any ring selected from the following rings, wherein the any ring includes a ring condensed with additional atoms to form a bicyclic ring, and wherein the any ring has at least two bonds:

[Formula 5]

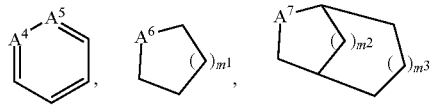

wherein
$A^4$, $A^5$: each independently, —CH= or —N=,
$A^6$, $A^7$: each independently, —CH$_2$—, —O—, or —NH—;
$m^1$, $m^2$, $m^3$: each independently, 0, 1, 2, or 3;

J: a 5-membered aromatic heterocycle wherein J is optionally condensed with X to have a bicyclic structure, or a 5-membered unsaturated heterocycle, wherein the ring has at least two bonds;
Y:
an amino group optionally substituted with 1-2 groups independently selected from Substituent group $Y^1$,
a phenyl group optionally substituted with 1-3 groups independently selected from Substituent group $Y^1$,
a C3-C8 cycloalkyl group optionally substituted with 1-3 groups independently selected from Substituent group $Y^1$, wherein the C3-C8 cycloalkyl group optionally has the following bridged structures:

[Formula 6]

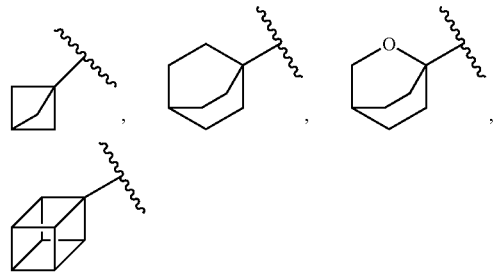

a C3-C8 cycloalkenyl group optionally substituted with 1-3 groups independently selected from Substituent group $Y^1$,
a 4- to 7-membered saturated heterocyclic group optionally substituted with 1-3 groups independently selected from Substituent group $Y^1$,
a 4- to 7-membered unsaturated heterocyclic group optionally substituted with 1-3 groups independently selected from Substituent group $Y^1$, or
a group formed by attachment to $R^7$, optionally substituted with 1-3 groups independently selected from Substituent group $Y^1$, selected from the following:

[Formula 7]

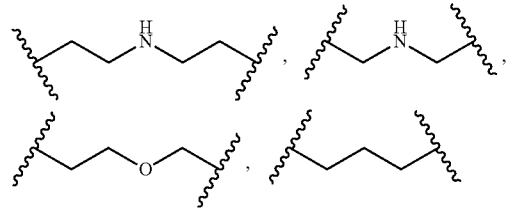

Substituent group $Y^1$:
a hydroxyl group,
an amino group optionally substituted with 1-2 groups independently selected from Substituent group $Y^2$,
a cyano group,
a halogen atom;
a C1-C6 alkyl group optionally substituted with 1-3 groups independently selected from Substituent group $Y^2$,
a C1-C6 alkoxy group optionally substituted with 1-3 groups independently selected from Substituent group $Y^2$, a 4- to 7-membered saturated heterocyclic group optionally substituted with 1-3 groups independently selected from Substituent group $Y^2$, and any group optionally substituted with 1-3 groups independently selected from Substituent group $Y^2$, selected from the following:

[Formula 8]

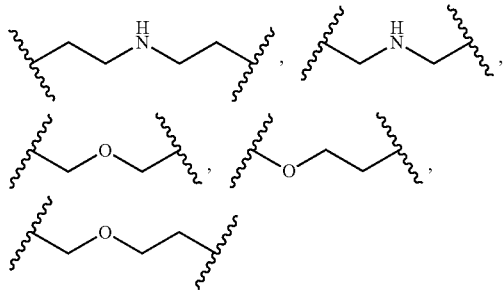

Substituent group $Y^2$:
a hydroxyl group,
a halogen atom,
a C1-C6 alkyl group optionally substituted with 1-3 groups independently selected from Substituent group $Y^3$,
a C1-C6 alkoxy group optionally substituted with 1-3 groups independently selected from Substituent group $Y^3$,
an amino group optionally substituted with 1-2 groups independently selected from Substituent group $Y^3$,
a 4- to 7-membered saturated heterocyclic group optionally substituted with 1-3 groups independently selected from Substituent group $Y^3$, and
any group optionally substituted with 1-3 groups independently selected from Substituent group $Y^3$, selected from the following:

[Formula 9]

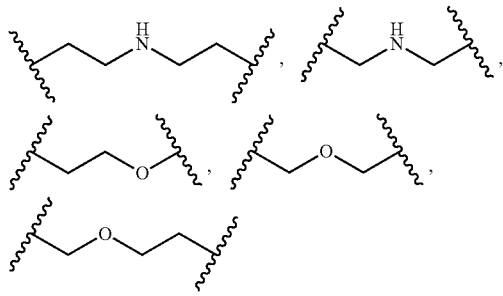

Substituent group $Y^3$:
a hydroxyl group,
a halogen atom,
a cyano group,
a C1-C6 alkyl group,
a C1-C6 alkoxy group,
a C1-C6 alkyl group optionally substituted with 1-3 groups independently selected from Substituent group $Y^4$,
a C1-C6 alkoxy group optionally substituted with 1-3 groups independently selected from Substituent group $Y^4$, and any group optionally substituted with 1-3 groups independently selected from Substituent group $Y^4$, selected from the following:

[Formula 10]

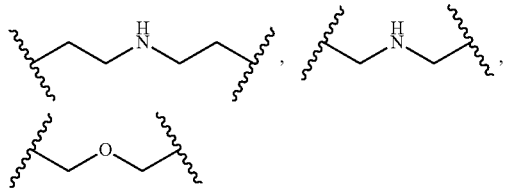

Substituent group $Y^4$:
a fluorine atom.

$R^1$, $R^2$, $R^3$: each independently, a hydrogen atom, a carboxyl group, a cyano group, a halogen atom, a C1-C6 alkyl group, a C1-C6 alkoxy group, a C3-C8 cycloalkyl group, a C3-C8 cycloalkoxy group, a hydroxy C1-C6 alkyl group, a halo C1-C6 alkyl group, a halo C1-C6 alkoxy group, a C1-C6 alkoxycarbonyl group, a C1-C6 alkyl C3-C8 cycloalkyl group, a C3-C8 cycloalkyl C1-C6 alkoxy group, a 4- to 7-membered unsaturated heterocyclic group, a C1-C6 alkyl 4- to 7-membered unsaturated heterocyclic group, a di(C1-C6 alkyl)amino 4- to 7-membered unsaturated heterocyclic group, a 4- to 7-membered unsaturated heterocyclic carbonyl group, or a C3-C8 cycloalkylcarbonyl group.

$R^4$: a hydrogen atom, a C1-C6 alkyl group, a halo C1-C6 alkyl group, or a group formed by attachment to $R^{6c}$ or $R^{6d}$, selected from the following:

[Formula 11]

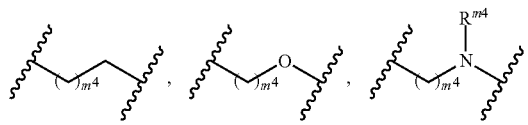

wherein $m^4$ is 0, 1, or 2, and $R^{m4}$ is a hydrogen atom or a methyl group, $R^5$: a hydrogen atom, a halogen atom, or a C1-C6 alkyl group, $R^{6a}$, $R^{6b}$, $R^{6c}$, $R^{6d}$: each independently, a hydrogen atom or a C1-C6 alkyl group, $R^7$: a single bond, a hydrogen atom, or a methyl group, $R^8$: a hydrogen atom or a methyl group, and $n^1$, $n^2$, $n^3$: each independently, 0, 1, or 2.

[2]
A compound or a pharmacologically acceptable salt thereof according to [1], wherein A is a 6-membered aromatic heterocycle or benzene, each of which has at least one bond.

[3]
A compound or a pharmacologically acceptable salt thereof according to [1], wherein A is pyridine or benzene, each of which has at least one bond.

[4]
A compound or a pharmacologically acceptable salt thereof according to any one of [1] to [3], wherein each of $R^{6a}$, $R^{6b}$, $R^{6c}$ is a hydrogen atom, $R^{6d}$ is a hydrogen atom or a methyl group, $n^1$ is 0, $n^2$ is 1, and E is —O—.

[5]
A compound or a pharmacologically acceptable salt thereof according to any one of [1] to [4], wherein G is the following:

[Formula 12]

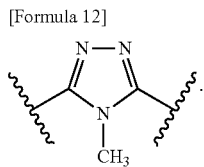

[6]
A compound or a pharmacologically acceptable salt thereof according to any one of [1] to [5], wherein X is benzene, pyridine or cyclohexane, each of which has at least two bonds, and $R^5$ is the same as defined above.

[7]
A compound or a pharmacologically acceptable salt thereof according to any one of [1] to [6], wherein J is a ring selected from the following ring group:

[Formula 13]

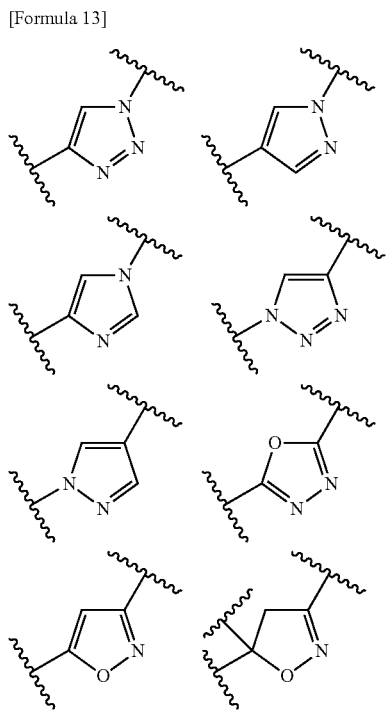

and $R^7$ is a hydrogen atom, or a single bond.

[8]
A compound or a pharmacologically acceptable salt thereof according to any one of [1] to [7], wherein $R^1$, $R^2$, and $R^3$ are, each independently, a hydrogen atom, a carboxyl group, a cyano group, a fluorine atom, a chlorine atom, a methyl group, an isopropyl group, a t-butyl group, a trifluoromethyl group, a trifluoromethoxy group, a cyclopropylmethoxy group, a 1,1-difluoro-2-methylpropyl group, a 1,1-difluoro-2,2-dimethylpropyl group, a 1-methyl-1-cyclobutyl group, a methoxycarbonyl group, an ethoxycarbonyl group, an isopropoxycarbonyl group, a 1-hydroxy-1-methylethyl group, an azetidine-1-carbonyl group, a 3-methyloxetan-3-yl group, a 4,5-dihydrooxazol-2-yl group, or a cyclopropylcarbonyl group.

[9]
A compound of general formula (1') or a pharmacologically acceptable salt thereof:

[Formula 14]

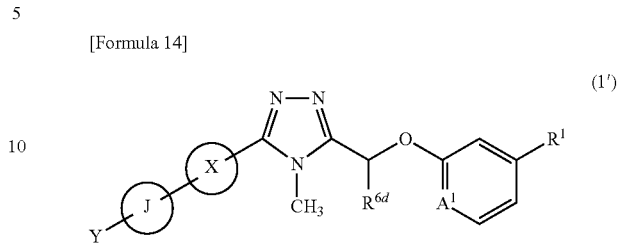

(1')

wherein the symbols in the formula are defined below:
$R^1$: a hydrogen atom, a carboxyl group, a cyano group, a fluorine atom, a chlorine atom, a methyl group, an isopropyl group, a t-butyl group, a trifluoromethyl group, a trifluoromethoxy group, a cyclopropylmethoxy group, a 1,1-difluoro-2-methylpropyl group, a 1,1-difluoro-2,2-dimethylpropyl group, a 1-methyl-1-cyclobutyl group, a methoxycarbonyl group, an ethoxycarbonyl group, an isopropoxycarbonyl group, a 1-hydroxy-1-methylethyl group, an azetidine-1-carbonyl group, a 3-methyloxetan-3-yl group, a 4,5-dihydrooxazol-2-yl group, or a cyclopropylcarbonyl group;
$R^{6d}$: a hydrogen atom or a methyl group;
$A^1$: =N—, or =CH—;
X: benzene, pyridine or cyclohexane, each of which has two bonds;
J: any ring selected from the following ring group:

[Formula 15]

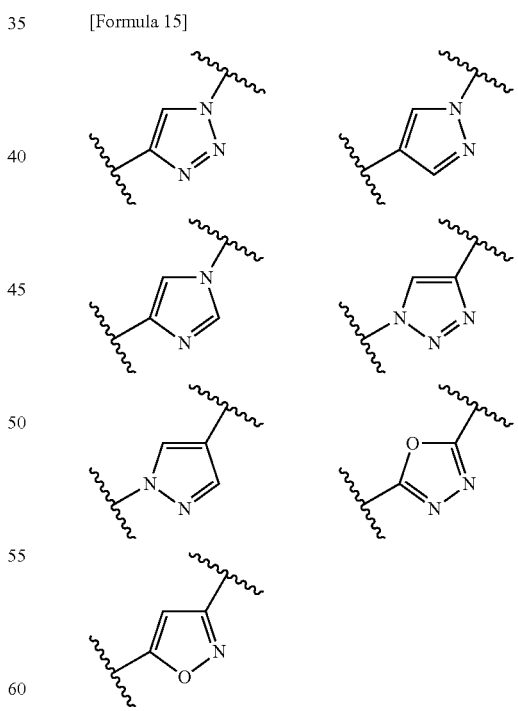

Y:
an amino group optionally substituted with 1-2 groups independently selected from Substituent group $Y^1$,
a phenyl group optionally substituted with 1-3 groups independently selected from Substituent group $Y^1$, any group optionally substituted with 1-3 groups independently selected from Substituent group $Y^1$, selected from the following:
a cyclobutyl group, a cyclopentyl group, a cyclohexyl group,

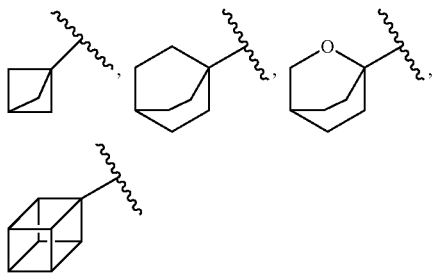
[Formula 16]

a cyclohexenyl group optionally substituted with 1-3 groups independently selected from Substituent group $Y^1$,
any group optionally substituted with 1-3 groups independently selected from Substituent group $Y^1$, selected from the following:
a piperidinyl group, an azetidinyl group, a tetrahydropyranyl group, a morpholinyl group, or
a tetrahydropyridinyl group optionally substituted with 1-3 groups independently selected from Substituent group $Y^1$;

Substituent group $Y^1$:
a hydroxyl group,
an amino group optionally substituted with 1-2 groups independently selected from Substituent group $Y^2$,
a cyano group,
a fluorine atom,
a methyl group, an ethyl group or an isopropyl group optionally substituted with 1-3 groups independently selected from Substituent group $Y^2$,
a methoxy group optionally substituted with 1-3 groups independently selected from Substituent group $Y^2$,
an azetidinyl group, a pyrrolidinyl group or a morpholinyl group optionally substituted with 1-3 groups independently selected from Substituent group $Y^2$, and
any group optionally substituted with 1-3 groups independently selected from Substituent group $Y^2$, selected from the following:

[Formula 17]
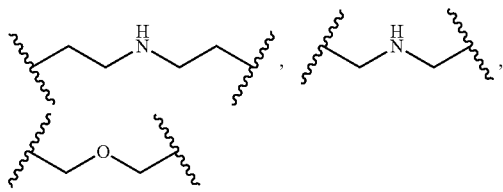

Substituent group $Y^2$:
a hydroxyl group,
a fluorine atom,
a methyl group optionally substituted with 1-3 groups independently selected from Substituent group $Y^3$, a methoxy group optionally substituted with 1-3 groups independently selected from Substituent group $Y^3$,
an amino group optionally substituted with 1-2 groups independently selected from Substituent group $Y^3$,
an azetidinyl group, a pyrrolidinyl group or a morpholinyl group optionally substituted with 1-3 groups independently selected from Substituent group $Y^3$, and
any group optionally substituted with 1-3 groups independently selected from Substituent group $Y^3$, selected from the following:

[Formula 18]
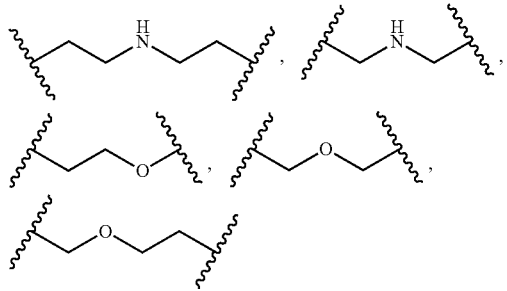

Substituent group $Y^3$:
a hydroxyl group,
a fluorine atom,
a cyano group,
a methyl group optionally substituted with 1-3 groups independently selected from Substituent group $Y^4$, and
a methoxy group optionally substituted with 1-3 groups independently selected from Substituent group $Y^4$;

Substituent group $Y^4$:
a fluorine atom.

[10]
A compound or a pharmacologically acceptable salt thereof selected from the following group:
4-Fluoro-1-methyl-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine,
4-{4-[(1R)-1-(Azetidin-1-yl)ethyl]phenyl}-1-[trans-4-(4-methyl-5-{[3-(propan-2-yl)phenoxy]methyl}-4H-1,2,4-triazol-3-yl)cyclohexyl]-1H-1,2,3-triazole,
(3R,6S)—N,N-Dimethyl-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine,
4-Fluoro-1-methyl-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine,
3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro[1,2,4]triazolo[4,3-a]pyridine,
1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol,
2-({5-[trans-4-(1-{trans-4-[3-(Fluoromethyl)azetidin-1-yl]cyclohexyl}-1H-1,2,3-triazol-4-yl)cyclohexyl]-4-methyl-4H-1,2,4-triazol-3-yl}methoxy)-4-(trifluoromethyl)pyridine,
3-(trans-4-{1-[trans-4-(Azetidin-1-yl)cyclohexyl]-1H-pyrazol-4-yl}cyclohexyl)-4-methyl-5-{[3-(trifluoromethyl)phenoxy]methyl}-4H-1,2,4-triazole, 4-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]morpholine, 6-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane, 6-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane, 2-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-6-oxa-2-azaspiro[3.4]octane, {1-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-1H-pyrazol-1-yl) cyclohexyl]azetidine-3,3-diyl}dimethanol, Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate, and 8-Methyl-3-[trans-4-(4-methyl-5-{(1R)-1-[3-(propan-2-yl) phenoxy]ethyl}-4H-1,2,4-triazol-3-yl)cyclohexyl]-1-oxa-2,8-diazaspiro[4.5]dec-2-ene.

[11]
4-Fluoro-1-methyl-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine.

[12]
(3R,6S)—N,N-Dimethyl-6-{1-[trans-4-(4-methyl-5-{(1R)-1-[3-(propan-2-yl)phenoxy]ethyl}-4H-1,2,4-triazol-3-yl) cyclohexyl]-1H-1,2,3-triazol-4-yl}tetrahydro-2H-pyran-3-amine.

[13]
2-({5-[trans-4-(1-{trans-4-[3-(Fluoromethyl)azetidin-1-yl] cyclohexyl}-1H-1,2,3-triazol-4-yl)cyclohexyl]-4-methyl-4H-1,2,4-triazol-3-yl}methoxy)-4-(trifluoromethyl)pyridine.

[14]
6-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane.

[15]
6-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane.

[16]
2-[trans-4-(4-{trans-4-[4-Methyl-5-({[4-(trifluoromethyl) pyridin-2-yl]oxy}methyl)-4H-1,2,4-triazol-3-yl]cyclohexyl}-1H-pyrazol-1-yl)cyclohexyl]-6-oxa-2-azaspiro[3.4]octane.

[17]
Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate.

[18]
A compound or a pharmacologically acceptable salt thereof according to any one of [1] to [17], for increasing IL10.

[19]
A pharmaceutical composition comprising a compound or a pharmacologically acceptable salt thereof according to any one of [1] to [18] as an active ingredient.

[20]
A pharmaceutical composition according to [19], for preventing and/or treating an inflammatory disease.

[21]
A pharmaceutical composition according to [20], wherein the inflammatory disease is a peripheral inflammatory disease.

[22]
A pharmaceutical composition according to [20], wherein the inflammatory disease is a central inflammatory disease.

[23]
A pharmaceutical composition according to [21], wherein the peripheral inflammatory disease is a disease selected from the group consisting of rheumatoid arthritis, systemic lupus erythematosus, scleroderma, bronchial asthma, asthmatic bronchitis, diffuse interstitial pneumonia, chronic obstructive pulmonary disease, ulcerative colitis, Crohn's disease, celiac disease, anal fistula, radiation enterocolitis, acute hepatitis, chronic hepatitis, fulminant hepatitis, autoimmune hepatitis, primary biliary cirrhosis, primary sclerosing cholangitis, alcoholic hepatitis, non-alcoholic steatohepatitis, cirrhosis, peripheral neuritis, ankylosing spondylitis, eczema (acute, subacute, chronic), contact dermatitis, sunlight (ultraviolet light) dermatitis, radiation dermatitis, atopic dermatitis, seborrheic dermatitis, psoriasis vulgaris, arthropathic psoriasis, psoriatic erythroderma, pustular psoriasis, lichen planus, erythema, rosacea, urticaria, alopecia areata, pemphigus, erythroderma, acne vulgaris, pressure sore, wound, burn, conjunctivitis, keratitis, scleritis, acute/chronic otitis media, perennial allergic rhinitis, hay fever, sinusitis, laryngitis, esophagitis, refractory stomatitis, glossitis, acute/chronic salivary gland inflammation, angular cheilitis, cheilitis, Behcet's disease, multiple sclerosis, Type I diabetes, Type II diabetes, atherosclerosis, pancreatitis and chronic heart failure.

[24]
A pharmaceutical composition according to [21], wherein the peripheral inflammatory disease is a disease selected from the group consisting of rheumatoid arthritis, systemic lupus erythematosus, bronchial asthma, ulcerative colitis, Crohn's disease, celiac disease, anal fistula, radiation enterocolitis, acute hepatitis, autoimmune hepatitis, primary biliary cirrhosis, primary sclerosing cholangitis, alcoholic hepatitis, nonalcoholic steatohepatitis, ankylosing spondylitis, contact dermatitis, sunlight (ultraviolet light) dermatitis, atopic dermatitis, seborrheic dermatitis, psoriasis vulgaris, arthropathic psoriasis, psoriatic erythroderma, pustular psoriasis, lichen planus, erythema, rosacea, alopecia areata, pemphigus, erythroderma, acne vulgaris, pressure sore, wound, burn, sinusitis, laryngitis, esophagitis, refractory stomatitis, glossitis, acute/chronic salivary gland inflammation, angular cheilitis, cheilitis and Behcet's disease.

[25]
A pharmaceutical composition according to [21], wherein the peripheral inflammatory disease is a disease selected from the group consisting of rheumatoid arthritis, systemic lupus erythematosus, ulcerative colitis, Crohn's disease, celiac disease, anal fistula, radiation enterocolitis, autoimmune hepatitis, alcoholic hepatitis, nonalcoholic steatohepatitis, ankylosing spondylitis, wound, refractory stomatitis, glossitis and Behcet's disease.

[26]
A pharmaceutical composition according to [22], wherein the central inflammatory disease is a disease selected from the group consisting of Alzheimer's disease, Parkinson's disease, dementia with Lewy bodies, multiple system atrophy, Pick's disease, progressive supranuclear palsy, basal ganglia degeneration, frontotemporal lobar degeneration, Huntington's disease, amyotrophic lateral sclerosis, bulbar spinal muscular atrophy, spinal muscular atrophy, spinocerebellar degeneration, multiple sclerosis, Creutzfeldt-Jakob disease, lethal familial insomnia, Gerstmann-Streisler-Shinker syndrome, Down syndrome, Niemann-Pick disease, cerebral amyloid angiopathy, HIV encephalopathy, influenza encephalopathy, hepatic encephalopathy, progressive multifocal leukoencephalopathy, anti-NMDA receptor antibody encephalitis, cerebrovascular disorder, traumatic brain injury, spinal cord injury, hypoxia encephalopathy, epilepsy, optic neuritis, congenital metabolic brain disease, Wernicke encephalopathy, autism spectrum disorder, attention deficit/hyperactivity disorder, tic disorder, schizophrenia, bipolar disorder, major depressive disorder (treatment-resistant depression, postpartum depression), persistent depressive disorder (dysthymia), menstruation pre-discomfort mood disorder, anxiety disorder, localized phobia, panic disorder, obsessive compulsive disorder, trauma and stress factor related disorder, eating disorder, circadian rhythm sleep/wake disorder, narcolepsy, substance-related disorder (alcohol dependence, drug dependence), impulse control disorder, delirium, personality disorder, and Rett syndrome.

[27]

A pharmaceutical composition according to [22], wherein the central inflammatory disease is a disease selected from the group consisting of Alzheimer's disease, Parkinson's disease, dementia with Lewy bodies, multiple system atrophy, Pick's disease, progressive supranuclear palsy, basal ganglia degeneration, frontotemporal lobar degeneration, Huntington's disease, amyotrophic lateral sclerosis, bulbar spinal muscular atrophy, spinal muscular atrophy, spinocerebellar degeneration, multiple sclerosis, Creutzfeldt-Jakob disease, schizophrenia, bipolar disorder, major depressive disorder (treatment-resistant depression, postpartum depression), persistent depressive disorder (dysthymia), menstruation pre-discomfort mood disorder, anxiety disorder, localized phobia, panic disorder, obsessive compulsive disorder, trauma and stress factor related disorder, eating disorder, circadian rhythm sleep/wake disorder, narcolepsy, substance-related disorder (alcohol dependence, drug dependence), impulse control disorder, delirium, personality disorder, and Rett syndrome.

[28]

A pharmaceutical composition according to [22], wherein the central inflammatory disease is a disease selected from the group consisting of schizophrenia, bipolar disorder, major depressive disorder (treatment-resistant depression, postpartum depression), persistent depressive disorder (dysthymia), menstruation pre-discomfort mood disorder, anxiety disorder, localized phobia, panic disorder, and obsessive compulsive disorder.

[29]

A compound or a pharmacologically acceptable salt thereof according to any one of [1] to [17], for use in the treatment of an inflammatory disease.

[30]

A method of preventing and/or treating an inflammatory disease, comprising administering an effective amount of a pharmaceutical composition according to [19].

[31]

A crystal of a compound according to [11] (Example 4), having peaks at diffraction angles (2θ(°)) of about 3.9, 4.1, 8.34, 12.6, 16.2, 18.4, 19.5 and 22.3 by powder X-ray diffraction.

[32]

A crystal of a compound according to [11] (Example 4), having an X-ray diffraction pattern shown in FIG. 1.

[33]

A crystal of a compound according to [12] (Example 8), having peaks at diffraction angles (2θ(°)) of about 3.8, 16.4, 18.0, 18.6, 19.8, 21.2 and 22.7 by powder X-ray diffraction.

[34]

A crystal of a compound according to [12] (Example 8), having an X-ray diffraction pattern shown in FIG. 2.

[35]

A crystal of a compound according to [13] (Example 20), having peaks at diffraction angles (2θ(°)) of about 13.5, 15.7, 17.2, 17.8, 18.2, 19.2, 20.4, 20.8, 22.0 and 27.2 by powder X-ray diffraction.

[36]

A crystal of a compound according to [13] (Example 20), having an X-ray diffraction pattern shown in FIG. 3.

[37]

A crystal of a compound according to [14] (Example 24), having peaks at diffraction angles (2θ(°)) of about 3.3, 13.4, 15.5, 16.8, 17.5, 17.9, 18.9, 20.4, 21.8 and 26.9 by powder X-ray diffraction.

[38]

A crystal of a compound according to [14] (Example 24), having an X-ray diffraction pattern shown in FIG. 4.

[39]

A crystal of a compound according to [15] (Example 25), having peaks at diffraction angles (2θ(°)) of about 13.2, 15.8, 16.5, 17.8, 18.1, 20.3, 20.8, 21.4 and 27.9 by powder X-ray diffraction.

[40]

A crystal of a compound according to [15] (Example 25), having an X-ray diffraction pattern shown in FIG. 5.

[41]

A crystal of a compound according to [16] (Example 27), having peaks at diffraction angles (2θ(°)) of about 14.2, 16.8, 17.4, 18.2, 18.6, 19.5, 20.0, 20.9, 21.6 and 21.8 by powder X-ray diffraction.

[42]

A crystal of a compound according to [16] (Example 27), having an X-ray diffraction pattern shown in FIG. 6.

[43]

A crystal of a compound according to [17] (Example 31), having peaks at diffraction angles (2θ(°)) of about 15.4, 17.6, 17.9, 18.4, 18.7, 19.2, 20.2, 20.7, 23.0 and 23.8 by powder X-ray diffraction.

[44]

A crystal of a compound according to [17] (Example 31), having an X-ray diffraction pattern shown in FIG. 7.

Advantageous Effects of the Invention

Since the compound and a pharmacologically acceptable salt thereof of the present invention, having a specific chemical structure having a peripheral and/or central anti-inflammatory activity, have different properties from known anti-inflammatory drugs in various aspects, the compound or a pharmacologically acceptable salt thereof is considered to be useful as a novel medicine.

The compounds and pharmacologically acceptable salts thereof of the present invention also have excellent properties in terms of anti-inflammatory activity, bioavailability, in vitro activity, in vivo activity, rapid onset of drug efficacy, sustained drug efficacy, physical stability, drug interaction, toxicity, and the like, thus they are useful as a medicinal drug.

BRIEF DESCRIPTION OF DRAWINGS

FIG. 1 shows a powder X-ray diffraction pattern of the compound of Example 4. The vertical axis represents intensity (cps) and the horizontal axis represents diffraction angle (2θ(°)).

FIG. 2 shows a powder X-ray diffraction pattern of the compound of Example 8. The vertical axis represents intensity (cps) and the horizontal axis represents diffraction angle (2θ(°)).

FIG. 3 shows a powder X-ray diffraction pattern of the compound of Example 20. The vertical axis represents intensity (cps) and the horizontal axis represents diffraction angle (2θ(°)).

FIG. 4 shows a powder X-ray diffraction pattern of the compound of Example 24. The vertical axis represents intensity (cps) and the horizontal axis represents diffraction angle (2θ(°)).

FIG. 5 shows a powder X-ray diffraction pattern of the compound of Example 25. The vertical axis represents intensity (cps) and the horizontal axis represents diffraction angle (2θ(°)).

FIG. 6 shows a powder X-ray diffraction pattern of the compound of Example 27. The vertical axis represents intensity (cps) and the horizontal axis represents diffraction angle (2θ(°)).

FIG. 7 shows a powder X-ray diffraction pattern of the compound of Example 31. The vertical axis represents intensity (cps) and the horizontal axis represents diffraction angle (2θ(°)).

DESCRIPTION OF EMBODIMENTS

Now, the present invention will be more specifically described below.

Explanation of Substituents and Terms

An embodiment of the present invention is directed to a compound of general formula (1) or a pharmacologically acceptable salt thereof.

[Formula 19]

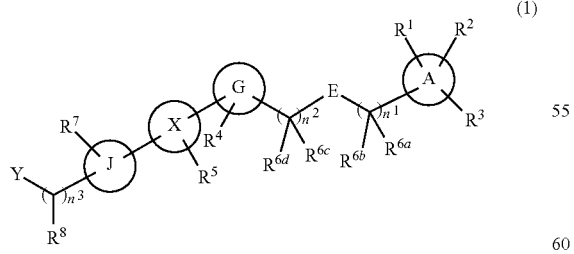

(1)

wherein the symbols indicating the respective substituents are the same as defined above.

A preferred embodiment of the present invention is directed to a compound of general formula (1') or a pharmacologically acceptable salt thereof.

[Formula 20]

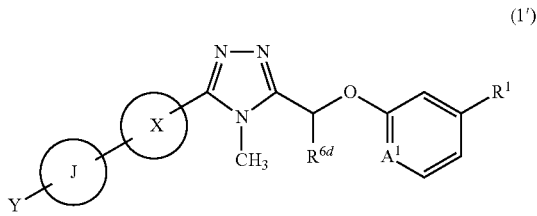

(1')

wherein the symbols indicating the respective substituents are the same as defined above.

Suitable combinations of the substituents of the compound of the general formula (1') are as follows.

$R^1$: a hydrogen atom, a carboxyl group, a cyano group, a fluorine atom, a chlorine atom, a methyl group, an isopropyl group, a t-butyl group, a trifluoromethyl group, a trifluoromethoxy group, a cyclopropylmethoxy group, a 1,1-difluoro-2-methylpropyl group, a 1,1-difluoro-2,2-dimethylpropyl group, a 1-methyl-1-cyclobutyl group, a methoxycarbonyl group, an ethoxycarbonyl group, an isopropoxycarbonyl group, a 1-hydroxy-1-methylethyl group, an azetidine-1-carbonyl group, a 3-methyloxetan-3-yl group, a 4,5-dihydrooxazol-2-yl group, or a cyclopropylcarbonyl group, $R^{6d}$: a hydrogen atom or a methyl group, $A^1$: =N—, or =CH—, X: benzene, pyridine or cyclohexane, each of which has two bonds, J: a ring selected from the following ring groups:

[Formula 21]

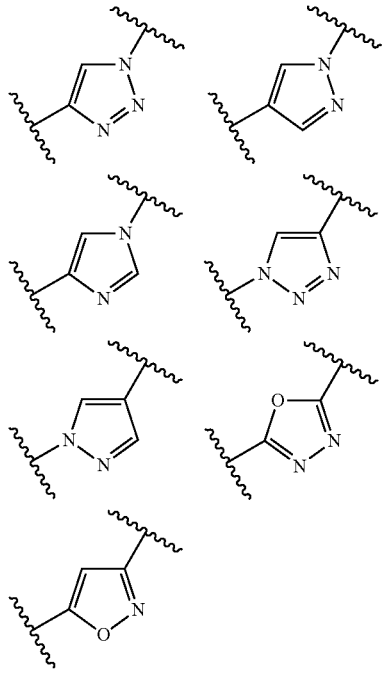

Y:

a cyclohexenyl group optionally substituted with 1-3 groups independently selected from Substituent group $Y^1$, Substituent group $Y^1$:

any group optionally substituted with 1-3 groups independently selected from Substituent group $Y^2$, selected from the following:

[Formula 22]

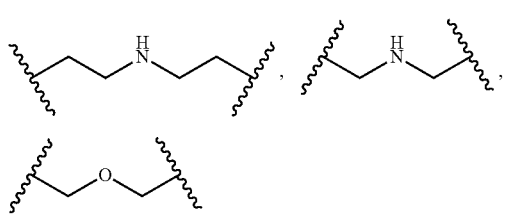

Substituent group $Y^2$:
any group selected from the following:

[Formula 23]

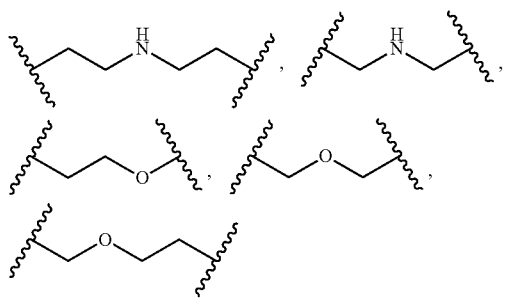

Further preferred embodiments of the present invention are directed to a compound described in the Examples or a pharmacologically acceptable salt thereof.

Now, substituents and terms used to represent the compounds of the present invention or a pharmacologically acceptable salt thereof will be described below.

The term "5- to 6-membered aromatic heterocycle" as used herein is a monocyclic 5- to 6-membered aromatic heterocycle containing 1-4 atoms selected from the group consisting of a nitrogen atom, an oxygen atom and a sulfur atom. Examples of the 5-membered aromatic heterocycle include rings as shown below:

[Formula 24]

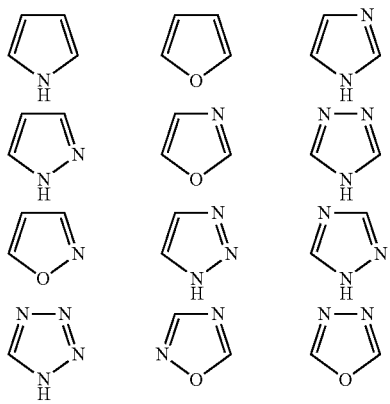

Examples of the 6-membered aromatic heterocycle include rings as shown below:

[Formula 25]

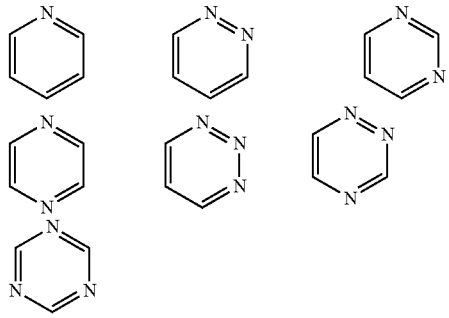

The term "5-membered aromatic heterocycle" as used herein is a monocyclic 5-membered aromatic heterocycle containing 1-4 atoms selected from the group consisting of a nitrogen atom, an oxygen atom and a sulfur atom, and examples thereof include rings as shown below.

[Formula 26]

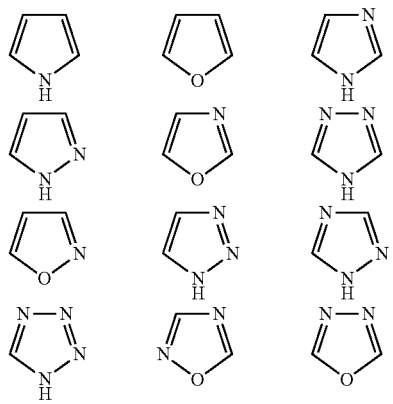

The term "4- to 7-membered saturated heterocycle" as used herein is a monocyclic 4- to 7-membered saturated heterocycle containing 1-3 atoms selected from the group consisting of a nitrogen atom, an oxygen atom, and a sulfur atom, and examples thereof include azetidine, pyrrolidine, imidazolidine, pyrazolidine, oxazolidine, thiazolidine, piperidine, piperazine, hexahydropyrimidine, morpholine, thiomorpholine, oxetane, tetrahydrofuran, tetrahydropyran, dioxane, and preferably includes rings as shown below.

[Formula 27]

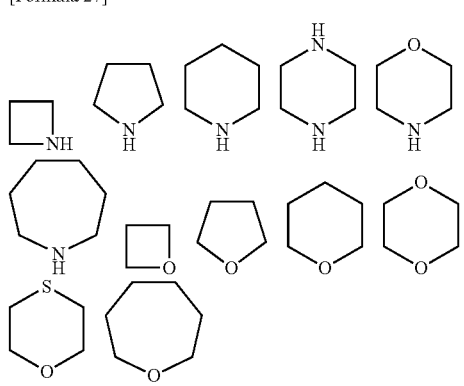

The term "4- to 7-membered unsaturated heterocycle" as used herein is a monocyclic 4- to 7-membered heterocycle containing 1-3 atoms selected from the group consisting of a nitrogen atom, an oxygen atom and a sulfur atom in which the ring is formed from a saturated heterocycle that is partially oxidized or an aromatic heterocycle that is partially reduced, and examples thereof include rings as shown below.

[Formula 28]

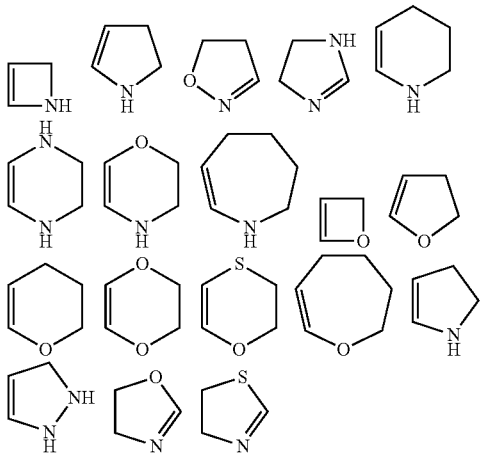

Examples of the term "5-membered unsaturated heterocycle" as used herein include pyrroline, imidazoline, pyrazoline, oxazoline, and thiazoline, and preferably include rings as shown below.

[Formula 29]

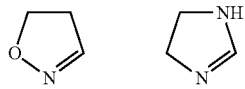

The term "C3-C8 cycloalkyl group" as used herein represents a cyclic alkyl group having 3 to 8 carbon atoms, and preferably a cyclopropyl group, a cyclobutyl group, a cyclopentyl group, a cyclohexyl group, a cycloheptyl group, or a cyclooctyl group.

The term "C3-C8 cycloalkenyl group" as used herein represents a cyclic alkenyl group having 3 to 8 carbon atoms, and preferably a cyclopropenyl group, a cyclobutenyl group, a cyclopentenyl group, or a cyclohexenyl group.

The term "C3-C8 cycloalkoxy group" as used herein is a group, in which an oxygen atom is bonded to a C3-C8 cycloalkyl group, and preferably a cyclopropyloxy group, a cyclobutyloxy group, a cyclopentyloxy group, or a cyclohexyloxy group.

The term "C1-C6 alkyl C3-C8 cycloalkyl group" as used herein is a group in which a C1-C6 alkyl group is bonded to a C3-C8 cycloalkyl group, and preferably a methylcyclobutanyl group, a methylcyclopentanyl group, a methylcyclohexyl group, an ethylcyclobutanyl group, an ethylcyclopentanyl group, and an ethylcyclohexyl group.

The term "C3-C8 cycloalkyl C1-C6 alkoxy group" as used herein is a group in which a C3-C8 cycloalkyl group is bonded to a C1-C6 alkoxy group, and preferably a cyclobutanylmethoxy group, a cyclopentanylmethoxy group, a cyclohexylmethoxy group, a cyclobutanylethoxy group, a cyclopentanylethoxy group, and a cyclohexylethoxy group.

The term "C1-C6 alkyl group" as used herein represents a linear or branched alkyl group having 1 to 6 carbon atoms, and examples thereof include a methyl group, an ethyl group, a 1-propyl group, an isopropyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group, and a 2,3-dimethyl-1-butyl group, preferably a methyl group, an ethyl group, a 1-propyl group, and an isopropyl group.

The term "di(C1-C6 alkyl) amino group" as used herein represents a group in which two identical or different C1-C6 alkyl groups are bonded to an amino group, and examples thereof include a dimethylamino group, a methylethylamino group, a methylpropylamino group [such as N-methyl-N-(1-propyl) amino group], a methylbutylamino group [such as N-(1-butyl)-N-methylamino group], a methylpentylamino group, a methylhexylamino group, a diethylamino group, an ethylpropylamino group [such as N-ethyl-N-(1-propyl) amino group], an ethylbutylamino group, a dipropylamino group, a propylbutylamino group, a dibutylamino group, a dipentylamino group, and a dihexylamino group, preferably a dimethylamino group and a diethylamino group.

The term "C1-C6 alkoxy group" as used herein represents a group in which an oxygen atom is bonded to a C1-C6 alkyl group, and examples thereof include a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group a 3-methyl-2-butoxy group, a 1-hexyloxy group, a 2-hexyloxy group, a 3-hexyloxy group, a 2-methyl-1-pentyloxy group, and a 3-methyl-1-pentyloxy group, preferably a methoxy group, an ethoxy group, a 1-propoxy group, and a 2-propoxy group.

The term "halogen atom" as used herein is a fluorine atom, a chlorine atom, a bromine atom, or an iodine atom, and preferably a fluorine atom or a chlorine atom.

The term "hydroxy C1-C6 alkyl group" as used herein is a group in which a hydroxyl group is bonded to a C1-C6 alkyl group, and preferably a hydroxymethyl group, a hydroxyethyl group, a hydroxypropyl group, a hydroxyisopropyl group, or a hydroxyisobutyl group.

The term "halo C1-C6 alkyl group" as used herein is a group in which a C1-C6 alkyl group is substituted with an appropriate number of halogen atoms, and preferably a difluoromethyl group, a trifluoromethyl group, or a difluoroethyl group.

The term "halo C1-C6 alkoxy group" as used herein is a group in which a C1-C6 alkoxy group is substituted with an appropriate number of halogen atoms, and preferably a difluoromethoxy group, a trifluoromethoxy group, or a difluoroethoxy group.

The term "C1-C6 alkylcarbonyl group" as used herein is a group in which a C1-C6 alkyl group is bonded to a carbonyl group, and preferably an acetyl group, an ethylcarbonyl group, or a propylcarbonyl group.

The term "C1-C6 alkoxycarbonyl group" as used herein is a group in which a C1-C6 alkoxy group is bonded to a carbonyl group, and preferably a methoxycarbonyl group, an ethoxycarbonyl group, or a t-butoxycarbonyl group.

The term "C1-C6 alkyl 4- to 7-membered unsaturated heterocyclic group" as used herein is a group in which a C1-C6 alkyl group is bonded to a 4- to 7-membered unsaturated heterocyclic group.

The term "di(C1-C6 alkyl) amino 4- to 7-membered unsaturated heterocyclic group" as used herein is a group in which a di(C1-C6 alkyl) amino group is bonded to a 4- to 7-membered unsaturated heterocyclic group.

The term "4- to 7-membered unsaturated heterocyclic carbonyl group" as used herein is a group in which a 4- to 7-membered unsaturated heterocyclic group is bonded to a carbonyl group.

The term "pharmacologically acceptable salt thereof" refers to a salt which can be used as a medicinal drug. In the case of a compound having an acidic group or a basic group, a basic salt or an acid salt can be produced if a base or an acid is reacted with the group. The salt thus obtained represents a pharmacologically acceptable salt.

Preferred examples of a pharmacologically acceptable "basic salt" of a compound include an alkali metal salt such as a sodium salt, a potassium salt and a lithium salt; an alkaline earth metal salt such as a magnesium salt and a calcium salt; an organic base salt such as a N-methyl morpholine salt, a triethylamine salt, a tributylamine salt, a diisopropylethylamine salt, a dicyclohexylamine salt, a N-methyl piperidine salt, a pyridine salt, a 4-pyrrolidinopyridine salt, and a picoline salt; and an amino acid salt such as a glycine salt, a lysine salt, an arginine salt, an ornithine salt, glutamate, and aspartate. Preferably, an alkali metal salt is mentioned.

Preferred examples of a pharmacologically acceptable "acidic salt" of a compound include inorganic acid salts including a hydrohalic acid salt such as a hydrofluoride, a hydrochloride, a hydrobromide and a hydroiodide, a nitrate, a perchlorate, a sulfate and a phosphate; organic acid salts including a lower alkanesulfonate such as a methanesulfonate, a trifluoromethanesulfonate and an ethanesulfonate, an aryl sulfonate such as a benzenesulfonate and p-toluene sulfonate, an acetate, a malate, a fumarate, a succinate, a citrate, an ascorbate, a tartrate, an oxalate and a maleate; and amino acid salts such as a glycine salt, a lysine salt, an arginine salt, an ornithine salt, glutamate and aspartate. Most preferably, a hydrohalic acid salt (particularly, hydrochloride) is mentioned.

The compound of the present invention or a pharmacologically acceptable salt thereof sometimes absorbs water or adsorbs moisture or forms a hydrate when it is left alone in the air or by re-crystallization. These various hydrates, solvates and polymorphic compounds are also included in the present invention.

The compound of the present invention, a pharmacologically acceptable salt thereof or a solvate thereof may have various type of isomers including geometric isomers such as a cis isomer and a trans isomer, tautomers, and optical isomers such as d-form and l-form depending on the types and combinations of substituents. However, unless otherwise specified, all isomers, stereoisomers and a mixture of these isomers and stereoisomers in any mixing ratio are included in the compound of the present invention. A mixture of these isomers can be separated by a separation means known in the art.

As the compound of the present invention, a labeled compound, more specifically, a compound having 1 or 2 or more atoms substituted with an isotope (for example, 2H, 3H, 13C, 14C, 35S), is also included.

In the present invention, a so-called prodrug is also included. The term prodrug refers to a compound having a group that can be converted into an amino group, a hydroxyl group or a carboxyl group by hydrolysis or in physiological conditions. The groups involved in forming such prodrugs are described in Prog. Med., vol. 5, 2157-2161 pages, 1985. More specifically, the prodrug can be as mentioned below.

(1) When an amino group is present in the compound, a compound having an acylated, alkylated or phosphorylated amino group (for example, a compound having an eicosanoylated, alanylated, pentylaminocarbonylated, (5-methyl-2-oxo-1,3-dioxolen-4-yl)methoxycarbonylated, tetrahydrofuranylated, pyrrolidyl methylated, pivaloyloxymethylated or tert-butylated amino group) or the like can be mentioned.

(2) When a hydroxyl group is present in the compound, a compound having an acylated, alkylated, phosphorylated or borated hydroxyl group (for example, a compound having an acetylated, palmitoylated, propanoylated, pivaloylated, succinylated, fumarylated, alanylated or dimethylaminomethylcarbonylated hydroxyl group) or the like can be mentioned.

(3) When a carboxyl group is present in the compound, a compound having an esterified or amidated carboxyl group (for example, a compound having an ethyl-esterified, phenyl-esterified, carboxymethyl-esterified, dimethylaminomethyl-esterified, pivaloyloxymethyl-esterified, ethoxycarbonyloxyethyl-esterified, amidated or methylamidated carboxyl group) or the like can be mentioned.

Herein, unless otherwise stated, the value of the powder X-ray diffraction analysis is a value obtained using Cu-Kα rays. When X-rays other than Cu-Kα rays are used, 2θ(°) varies according to the equation $2d \sin \theta = \lambda$, in which d is the distance between the two surfaces, n is an integer, and λ is the wavelength of the X-ray. However, these are just representations of the crystal of the present invention by other substantially equivalent expression methods, and are included in the scope of the present invention, which can be easily understood by those skilled in the crystal art. In addition, the relative intensity of the peaks indicated by these charts may vary depending on, for example, the degree of crystallization or the method of preparation of the sample. 2θ(°) does not substantially vary, but may vary within a range of error (generally, a range of ±0.2°) which is recognized by those skilled in the crystal art. In the characteristic peak of powder X-ray diffraction represented by an angle 2θ, The term "about" indicates ±0.2°, and in another embodiment, ±0.1°.

The value of the powder X-ray diffraction analysis should not be interpreted strictly, since, due to the nature of the data, the crystal lattice spacing and overall pattern are important for determining the identity of the crystal, and the relative intensity can vary somewhat depending on the direction of crystal growth, grain size, and measurement conditions.

(Production Method)

Now, the production method will be described. However, the present invention is not limited by the methods described below.

When the structure represented by J in the compound of the general formula (1) is the following 1,2,3-triazole:

[Formula 30]

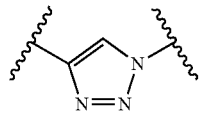

the compound (A-V) of the present invention can be produced, for example, using the following Method A.

[Method A]

Method A is a method of producing the compound (A-V) of the present invention

[Formula 31]

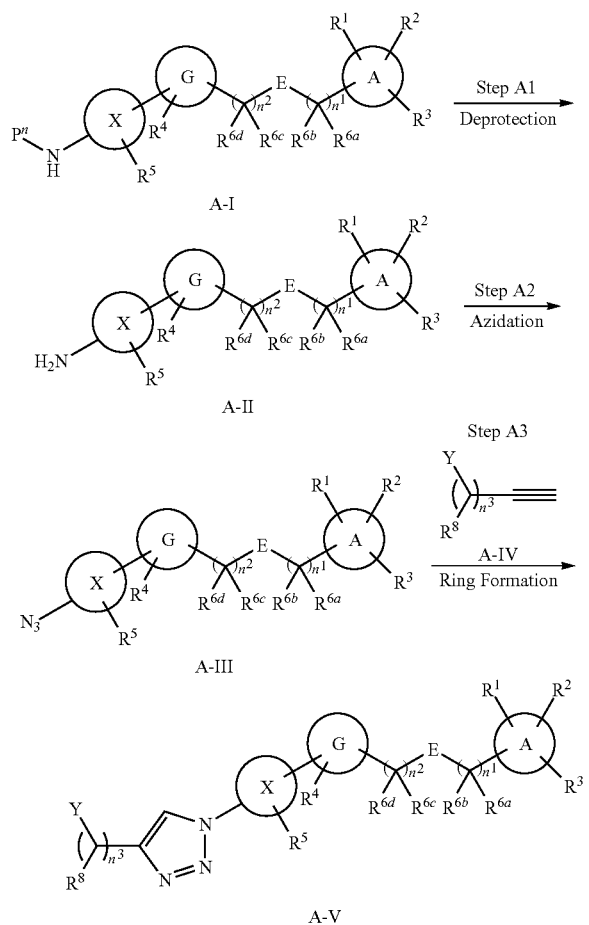

wherein the symbols used in the formula are as defined above. $P^n$ represents an amino group-protecting group.

(Step A1) Step of Deprotecting Amino Group

This is a step of obtaining a compound (A-II) by deprotecting the amino group-protecting group from a compound (A-I). For example, when the protecting group is a tert-butoxycarbonyl group, the compound (A-II) can be obtained by dissolving the compound (A-I) in a solvent and adding an acid. The reaction temperature is usually about −20 to 100° C. and the reaction time is usually about 1 to 24 hours.

Examples of the acid used include trifluoroacetic acid and hydrochloric acid.

The solvents used are not particularly limited as long as they do not inhibit the reaction, and examples thereof include dichloromethane, chloroform, methanol, ethyl acetate, and 1,4-dioxane, and a mixture of these.

(Step A2) Step of Converting Amino Group into Azide Group

This is a step of converting the amino group of the compound (A-II) into an azide group. A compound (A-III) can be obtained by dissolving the compound (A-II) in a solvent and reacting with tert-butyl nitrate to diazotize, and then converting it into an azide group by addition of trimethylsilylazide and trifluoroacetic acid.

The solvents used are not particularly limited as long as they do not inhibit the reaction, and examples thereof include water, acetonitrile, dichloromethane, tetrahydrofuran, 1,4-dioxane, methanol, ethanol, acetic acid, and hydrochloric acid, and a mixture of these. The reaction temperature is usually about 0 to 60° C. and the reaction time is usually about 0.5 to 24 hours.

This step can also be performed, for example, by stirring 2-azido-1,3-dimethylimidazolinium hexafluorophosphate and triethylamine in a dichloromethane solvent at about 0 to 60° C. for about 0.5 to 24 hours.

(Step A3) Step of Forming Triazole Ring

This is a step of producing the compound (A-V) by reacting the compound (A-III) with a corresponding alkyne (A-IV). The compound (A-V) can be obtained by dissolving the corresponding alkyne (A-IV) and the compound (A-III) in a solvent, and adding diisopropylethylamine and copper iodide at 0° C. to room temperature. The reaction temperature is usually about room temperature to 80° C. and the reaction time is usually about 1 to 24 hours.

Examples of the base used include tertiary amines such as diisopropylethylamine and triethylamine.

Examples of the metal catalyst used include copper iodide and copper sulfate.

Examples of the ligand used include tris[(1-benzyl-1H-1,2,3-triazol-4-yl)methyl]amine and tris(benzimidazole)amine.

The solvents used are not particularly limited as long as they do not inhibit the reaction, and examples thereof include water, methanol, ethanol, tert-butyl alcohol, tetrahydrofuran, 1,4-dioxane, acetonitrile, ethyl acetate, acetone, dichloromethane, N,N-dimethylformamide, toluene, and a mixture of these.

When the structure represented by G in the compound of general formula (1) of the present invention is the following 1,2,4-triazole:

[Formula 32]

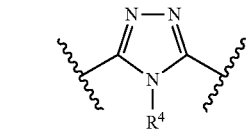

wherein the symbol used in the formula is the same as defined above, a compound equivalent to the compound (A-I) that is used in Method A can be produced, for example, using the following Method B.

[Method B]

Method B is a method of producing a compound (B-III) (equivalent to the compound (A-I) that is used in Method A).

[Formula 33]

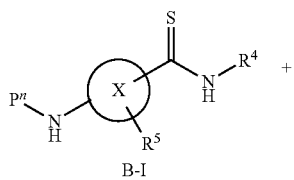

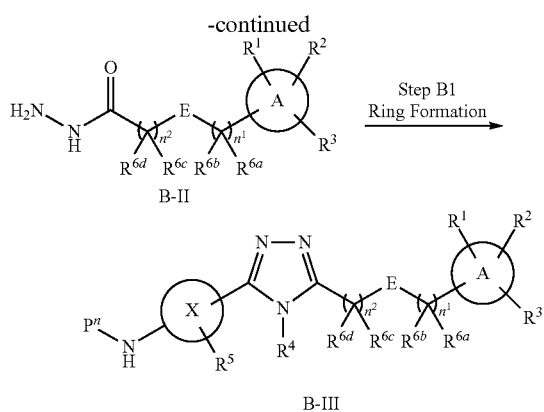

wherein the symbols used in the formula are the same as defined above. $P^n$ represents an amino group-protecting group.

(Step B1) Step of Forming Triazole Ring

This is a step of producing the compound (B-III) by reacting a compound (B-I) with an alkylating agent such as methyl iodide to convert it into the corresponding thioimidate, and reacting the thioimidate with a compound (B-II).

The solvent used in the reaction of the compound (B-I) and methyl iodide is not particularly limited as long as it does not inhibit the reaction, and examples thereof include tetrahydrofuran and 1,4-dioxane. The reaction temperature is usually about room temperature to 80° C. and the reaction time is usually about 1 to 24 hours.

Furthermore, the solvent used in the reaction of the thioimidate and the compound (B-II) is not particularly limited as long as it does not inhibit the reaction, and examples thereof include tetrahydrofuran and 1,4-dioxane. The reaction temperature is usually about room temperature to 120° C. and the reaction time is usually about 1 to 24 hours.

[Method C]

Method C is a method of producing a compound (C-III) (equivalent to the compound (B-I) that is used in Method B).

[Formula 34]

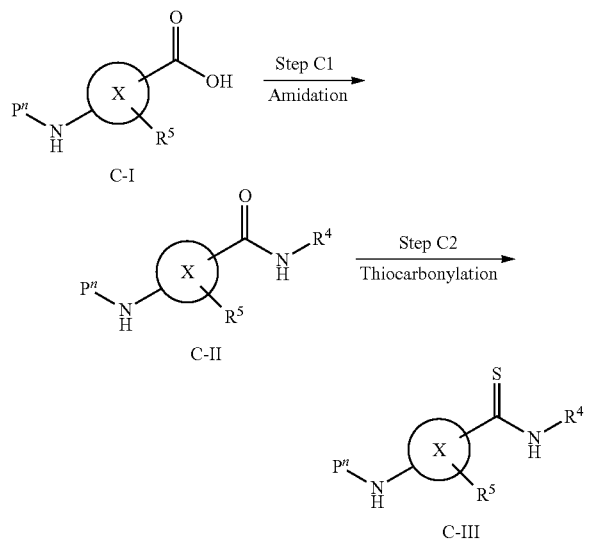

wherein the symbols used in the formula are the same as defined above.

(Step C1) Step of Forming Amide by Condensation

This is a step of (i) producing a compound (C-II) by activating a carboxylic acid (C-I), which is commercially available or can be synthesized by a known method, as an acid chloride, and reacting the acid chloride with the corresponding amine, or (ii) producing a compound (C-II) by reacting the carboxylic acid (C-I) with the corresponding amine in the presence of a condensing agent.

In the case of (i), the compound (C-II) can be obtained, for example, by adding oxalyl chloride and a small amount of dimethylformamide to a solution of the carboxylic acid (C-I) in dichloromethane at 0° C. to room temperature, allowing to stand still for a while, and then adding the corresponding amine and a base such as pyridine at 0° C. to room temperature. The reaction temperature is usually about room temperature to 80° C. and the reaction time is usually about 1 to 24 hours.

In the case of (ii), the compound (C-II) can be obtained, for example, by adding a base and a condensing agent to a solution of the carboxylic acid (C-I) and a corresponding amine in dimethylformamide or dichloromethane. The reaction temperature is usually about room temperature to 80° C. and the reaction time is usually about 1 to 24 hours.

Examples of the base used include tertiary amines such as diisopropylethylamine.

Examples of the condensing agent used include 4-(4,6-dimethoxy-1,3,5-triazin-2-yl)-4-methylmorpholinium chloride (DMT-MM), N,N,N',N'-tetramethyl-O-(benzotriazol-1-yl)uronium hexafluorophosphate (HBTU), hexafluorophosphate O-(7-azabenzotriazol-1-yl)-N,N,N',N'-tetramethyluronium (HATU), and 1-ethyl-3-(3-dimethylaminopropyl)carbodiimide hydrochloride (EDCI).

(Step C2) Step of Thiocarbonylation

This is a step of obtaining a compound (C-III) by reacting the compound (C-II) with a sulfurizing agent such as Lawesson's reagent in a solvent.

The solvents used are not particularly limited as long as they do not inhibit the reaction, and examples thereof include tetrahydrofuran, 1,4-dioxane, and a mixture of these. The reaction temperature is usually about 0 to 100° C. and the reaction time is usually about 0.5 to 24 hours.

[Method D]

Method D is a method of producing a compound (D-II) (equivalent to the compound (B-II) that is used in Method B).

[Formula 35]

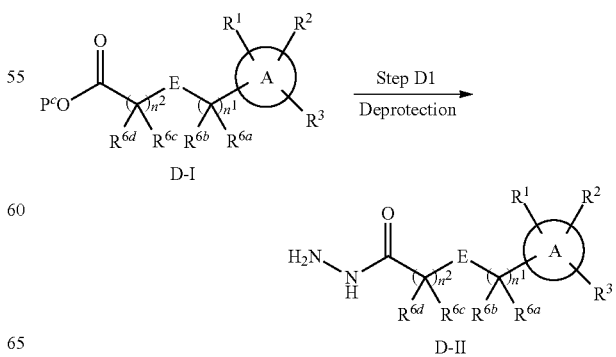

wherein the symbols used in the formula are the same as defined above. P^C represents a carboxyl group-protecting group.

(Step D1) Step of Forming Hydrazide

This is a step of producing the compound (D-II) by heating a compound (D-I) that is commercially available or can be synthesized by a known method, with hydrazine in a solvent.

The solvents used are not particularly limited as long as they do not inhibit the reaction, and examples thereof include methanol, ethanol, water, and a mixture of these. The reaction temperature is usually about room temperature to 100° C. and the reaction time is usually about 0.5 to 24 hours.

[Method E]

Method E is a method of producing a compound (E-X) (equivalent to the compound (A-V) in Method A) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 36]

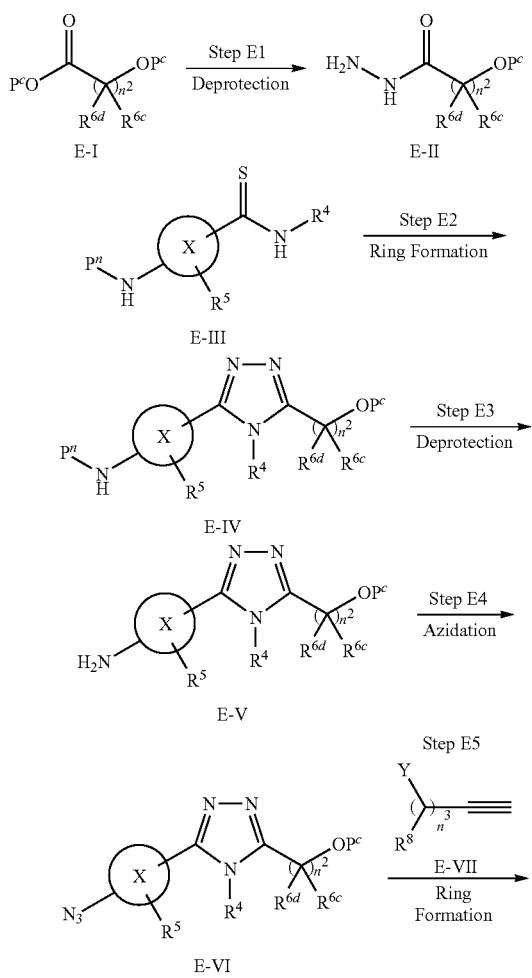

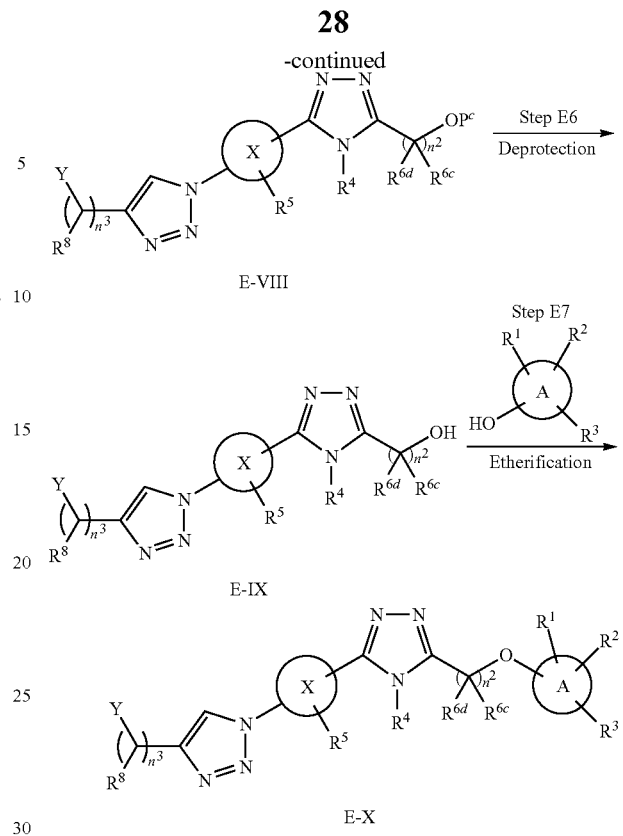

wherein the symbols used in the formula are the same as defined above. P^c represents a carboxyl group-protecting group or a hydroxyl group-protecting group. P^n represents an amino group-protecting group.

(Step E1) Step of Forming Hydrazide

This is a step of producing a compound (E-II) from a compound (E-I) that is commercially available or can be synthesized by a known method, under the same conditions as in Step D1 of Method D.

(Step E2) Step of Forming Triazole Ring

This is a step of producing a compound (E-IV) from the compound (E-II) and a compound (E-III) (equivalent to (C-III) in Method C) under the same conditions as in Step B1 of Method B.

(Step E3) Step of Deprotecting Amino Group-Protecting Group

This is a step of obtaining a compound (E-V) by deprotecting the amino group-protecting group from the compound (E-IV) under the same conditions as in Step A1 of Method A.

(Step E4) Step of Converting Amino Group into Azide Group

This is a step of obtaining a compound (E-VI) from the compound (E-V) by converting an amino group into an azide group under the same conditions as in Step A2 of Method A.

(Step E5) Step of Forming Triazole Ring

This is a step of producing a compound (E-VIII) from the compound (E-VI) by reacting the compound (E-VI) with a corresponding alkyne (E-VII) under the same conditions as in Step A3 of Method A.

(Step E6) This is a step of obtaining a compound (E-IX) by deprotecting the hydroxyl group-protecting group from the compound (E-VIII). For example, when the protecting group is a tert-butyldiphenylsilyl group, the compound (E-IX) can be obtained by dissolving the compound (E-VIII) in a solvent and adding tetra-n-butylammonium fluoride. The reaction temperature is usually about 0 to 80° C. and the reaction time is usually about 0.5 to 24 hours.

Examples of the reagent used include hydrochloric acid, sulfuric acid, hydrofluoric acid, p-toluenesulfonic acid (PPTS), acetic acid, trifluoroacetic acid, tetra-n-butylammonium fluoride, potassium fluoride, cerium fluoride, hydrogen fluoride, and hydrogen fluoride-pyridine.

The solvents are not particularly limited as long as they do not inhibit the reaction, and examples thereof include methanol, ethanol, diethyl ether, tetrahydrofuran, 1,4-dioxane, 1,2-dimethoxyethane, acetonitrile, water, and a mixture of these.

(Step E7) Step of Etherification by Mitsunobu Reaction

This is a step of obtaining a compound (E-X) from the compound (E-IX) by use of the corresponding alcohol in the presence of cyanomethyltributylphosphorane.

The solvents used are not particularly limited as long as they do not inhibit the reaction, and examples thereof include tetrahydrofuran, 1,4-dioxane, toluene and a mixture of these. The reaction temperature is usually about 0 to 120° C. and the reaction time is usually about 0.5 to 24 hours.

Furthermore, in this step, the compound (E-X) can be obtained from the compound (E-IX) by use of a corresponding alcohol in the presence of phosphine and azodicarboxylate or diazodicarboxamide. The reaction temperature is usually about 0 to 100° C. and the reaction time is usually about 0.5 to 24 hours.

[Method F]

Method F is a method of producing the compound (F-VI) of the present invention

[Formula 37]

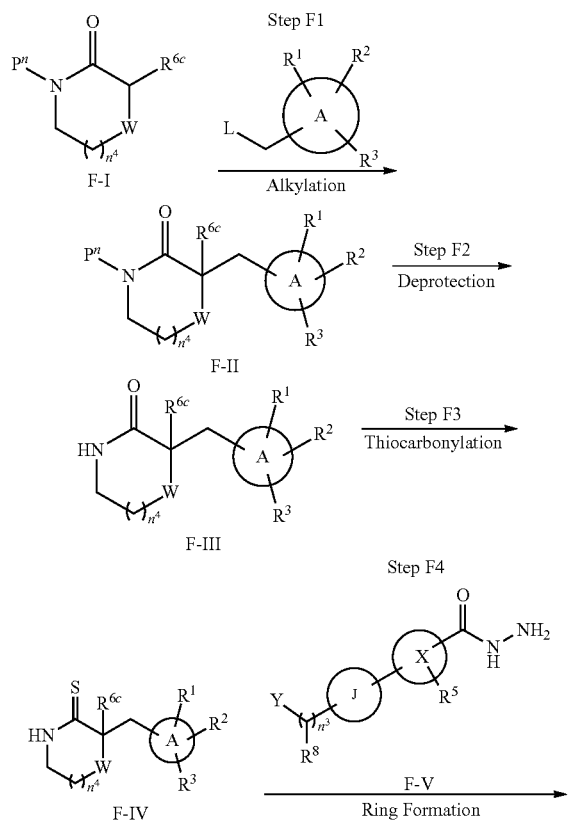

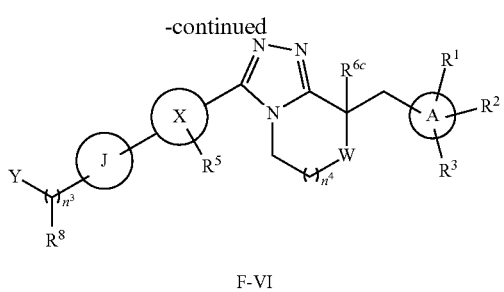

wherein the symbols used in the formula are the same as defined above. L represents a leaving group. W represents, each independently, —$CH_2$—, —O—, or —NMe-.

(Step F1) Step of Alkylation

This is a step of producing a compound (F-II) from a compound (F-I) that is commercially available or can be synthesized by a known method, using the corresponding alkyl halide in a solvent in the presence of an organolithium reagent.

Examples of the organolithium reagent include n-butyllithium, lithium diisopropylamide, lithium hexamethyldisilazide, and lithium 2,2,6,6-tetramethylpiperidine.

The solvents are not particularly limited as long as they do not inhibit the reaction, and examples thereof include diethyl ether, tetrahydrofuran, toluene, n-hexane, and a mixture of these.

The reaction temperature is usually about −78 to 100° C., and the reaction time is usually about 1 to 48 hours.

(Step F2) Step of Deprotecting Amino Group-Protecting Group

This is a step of obtaining a compound (F-III) by deprotecting the amino group-protecting group from the compound (F-II). When the protecting group is a p-methoxybenzyl group, the compound (F-III) can be obtained by dissolving the compound (F-II) in an acid and heating.

Examples of the acid used include trifluoroacetic acid and hydrochloric acid.

The solvents used are not particularly limited as long as they do not inhibit the reaction, and examples thereof include dichloromethane, chloroform, methanol, ethyl acetate, 1,4-dioxane and a mixture of these. The reaction temperature is usually about 100 to 150° C. and the reaction time is usually about 1 to 48 hours.

(Step F3) Step of Thiocarbonylation

This is a step of obtaining a compound (F-IV) by reacting the compound (F-III) with a sulfurizing agent such as Lawesson's reagent in a solvent under the same conditions as in Step C2 of Method C.

(Step F4) Step of Forming Triazole Ring

This is a step of producing the compound (F-VI) by reacting the compound (F-IV) with an alkylating agent such as methyl iodide to convert it into the corresponding thioimidate, and reacting the thioimidate with a corresponding compound (F-V) under the same conditions as in Step B1 of Method B.

[Method G]

Method G is a method of producing the compound (G-V) of the present invention.

[Formula 38]

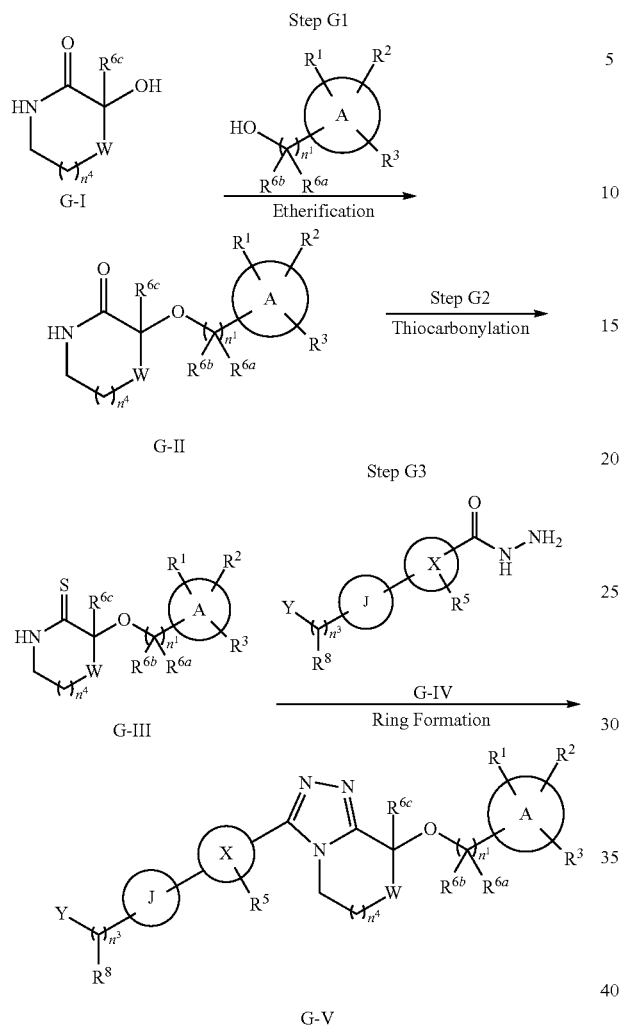

wherein the symbols used in the formula are the same as defined above. W represents, each independently, —$CH_2$—, —O—, or —NMe-.

(Step G1) Step of Etherification by Mitsunobu Reaction

This is a step of producing a compound (G-II) from a compound (G-I) that is commercially available or can be synthesized by a known method, under the same conditions as in Step E7 of Method E.

(Step G2) Step of Thiocarbonylation

This is a step of obtaining a compound (G-III) by reacting the compound (G-II) with a sulfurizing agent such as Lawesson's reagent in a solvent under the same conditions as in Step C2 of Method C.

(Step G3) Step of Forming Triazole Ring

This is a step of producing the compound (G-V) by reacting the compound (G-III) with an alkylating agent such as methyl iodide to convert it into the corresponding thioimidate, and reacting the thioimidate with a compound (G-IV) under the same conditions as in Step B1 of Method B.

When the structure represented by J in the compound of the present invention is the following 1,2,3-triazole:

[Formula 39]

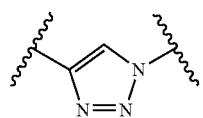

the compound (F-V) that is used in Method F or the compound (G-IV) that is used in Method G can be produced, for example, using the following Method H.

[Method H]

Method H is a method of producing a compound (H-V) (equivalent to the compound (F-V) that is used in Method F or the compound (G-IV) that is used in Method G).

[Formula 40]

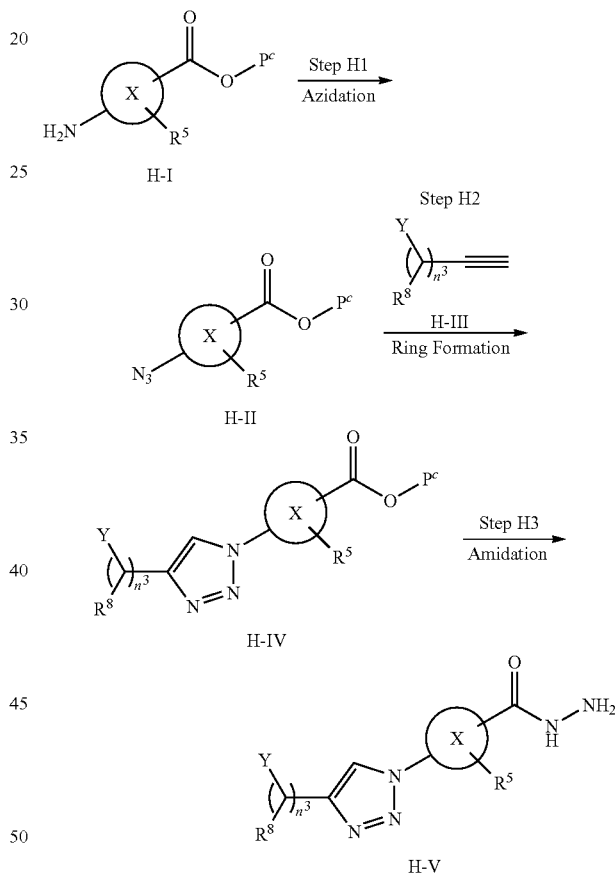

wherein the symbols used in the formula are as defined above. $P^c$ represents a carboxyl group-protecting group or a hydroxyl group-protecting group.

(Step H1) Step of Converting Amino Group into Azide Group

This is a step of obtaining a compound (H-II) from a compound (H-I) that is commercially available or can be synthesized by a known method, by converting an amino group into an azide group under the same conditions as in Step A2 of Method A.

(Step H2) Step of Forming Triazole Ring

This is a step of producing a compound (H-IV) from the compound (H-II) by reacting the compound (H-II) with a corresponding alkyne (H-III) under the same conditions as in Step A3 of Method A.

(Step H3) Step of Forming Hydrazide

This is a step of producing a compound (H-V) from a compound (H-IV) under the same conditions as in Step D1 of Method D.

When the structure represented by J in the compound of the present invention is the following pyrazole:

[Formula 41]

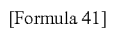

the compound (I-VI) of the present invention can be produced, for example, using the following Method I.

[Method I]

Method I is a method of producing the compound (I-VI) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 42]

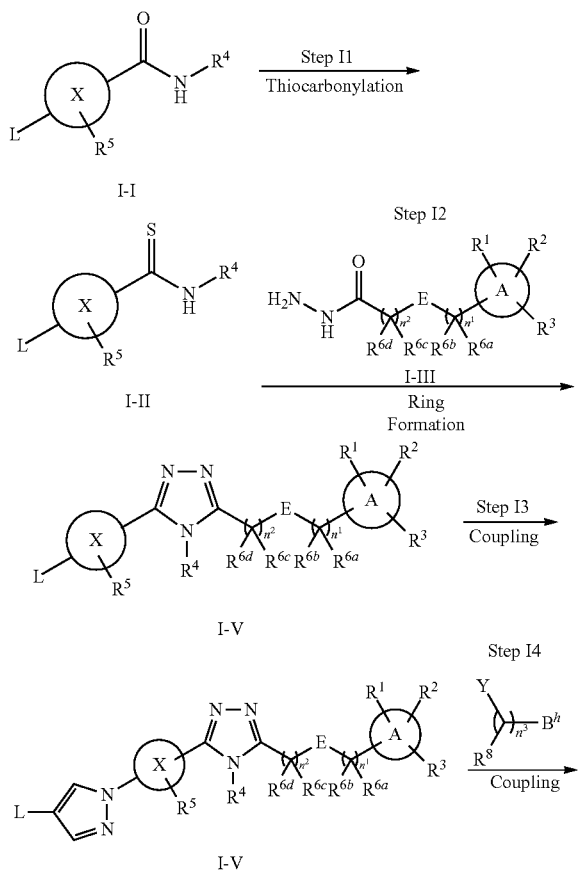

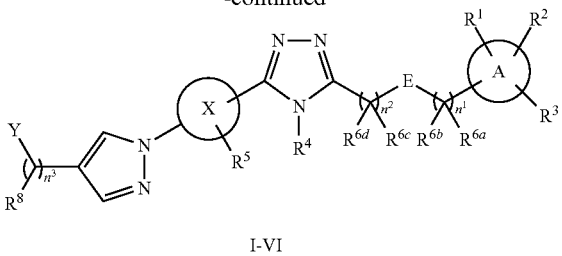

wherein the symbols used in the formula are the same as defined above. L represents a leaving group. $B^h$ represents boronic acid or boronic acid pinacol ester.

(Step I1) Step of Thiocarbonylation

This is a step of obtaining a compound (I-II) by reacting a compound (I-I) that is commercially available or can be synthesized by a known method, with a sulfurizing agent such as Lawesson's reagent in a solvent under the same conditions as in Step C2 of Method C.

(Step I2) Step of Forming Triazole Ring

This is a step of producing a compound (I-IV) by reacting the compound (I-II) with an alkylating agent such as methyl iodide to convert it into the corresponding thioimidate, and reacting the thioimidate with a compound (I-III) (equivalent to the compound (D-II) produced in Method D) under the same conditions as in Step B1 of Method B.

(Step I3) Step of Coupling Reaction Using Transition Metal Catalyst

This is a step of obtaining a compound (I-V) by reacting the compound (I-IV) with the corresponding pyrazole using a transition metal as a catalyst in the presence of a base.

Examples of the transition metal catalyst used include copper iodide, copper chloride, and copper acetate.

Examples of the base include triethylamine, diisopropylethylamine, 1,8-diazabicyclo[5.4.0]-7-undecene (DBU), 1,5-diazabicyclo[4.3.0]-5-nonene (DBN), potassium hydrogen carbonate, sodium hydrogen carbonate, potassium carbonate, sodium carbonate, cesium carbonate, potassium hydroxide, sodium hydroxide, potassium phosphate and sodium phosphate.

The solvents used are not particularly limited as long as they do not inhibit the reaction, and examples thereof include methanol, ethanol, tetrahydrofuran, 1,4-dioxane, water, N,N-dimethylformamide, dimethylsulfoxide, toluene and a mixture of these. The reaction temperature is usually about 60 to 200° C. and the reaction time is usually about 0.5 to 24 hours.

(Step I4) Step of Coupling Reaction Using Transition Metal Catalyst

This is a step of obtaining the compound (I-VI) from the compound (I-V) by use of a palladium catalyst and a corresponding boronic acid or boronic acid pinacol ester in the presence of a base.

Examples of the palladium catalyst used include tetrakis(triphenylphosphine)palladium, [1,1'-bis(diphenylphosphino)ferrocene]dichloropalladium, tris(dibenzylideneacetone)dipalladium, palladium acetate, acetylacetone palladium and bis(triphenylphosphine)palladium dichloride.

Examples of the base used include triethylamine, diisopropylethylamine, 1,8-diazabicyclo[5.4.0]-7-undecene (DBU), 1,5-diazabicyclo[4.3.0]-5-nonene (DBN), potassium hydrogen carbonate, sodium hydrogen carbonate, potassium carbonate, sodium carbonate, potassium hydroxide, sodium hydroxide, potassium phosphate and sodium phosphate.

The solvents used are not particularly limited as long as they do not inhibit the reaction, and examples thereof include methanol, ethanol, tetrahydrofuran, 1,4-dioxane, water, N,N-dimethylformamide, dimethylsulfoxide, toluene and a mixture of these. The reaction temperature is usually about 60 to 120° C. and the reaction time is usually about 0.5 to 24 hours.

[Method J]

Method J is a method of producing a compound (J-V) (equivalent to the compound (I-V) that is used in Method J).

[Formula 43]

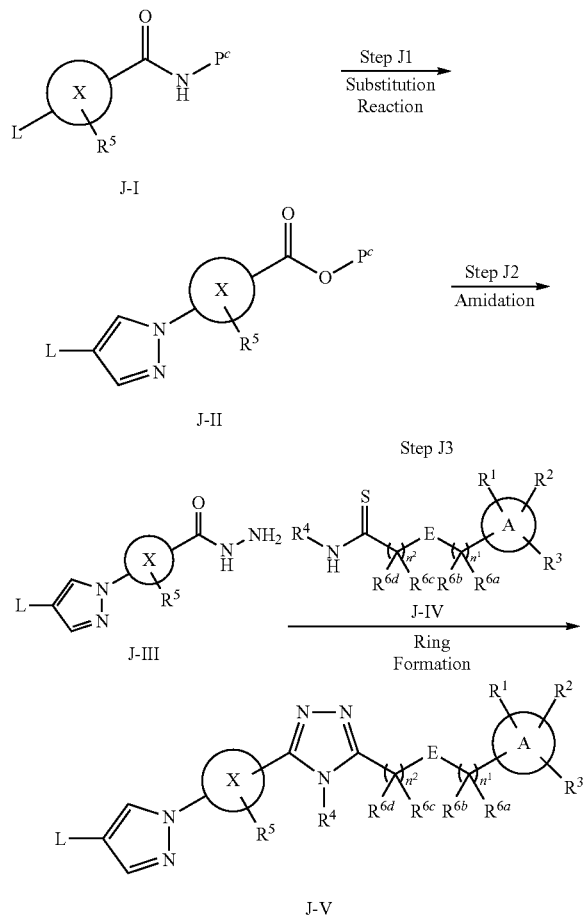

wherein the symbols used in the formula are the same as defined above. $P^C$ represents a carboxyl group-protecting group. L represents a leaving group.

(Step J1) Step of Introducing Pyrazole Ring by Substitution Reaction

This is a step of obtaining a compound (J-II) by reacting a compound (J-I) that is commercially available or can be synthesized by a known method, with the corresponding pyrazole in the presence of a base.

Examples of the base include triethylamine, diisopropylethylamine, 1,8-diazabicyclo[5.4.0]-7-undecene (DBU), 1,5-diazabicyclo[4.3.0]-5-nonene (DBN), potassium hydrogen carbonate, sodium hydrogen carbonate, potassium carbonate, sodium carbonate, cesium carbonate, potassium hydroxide, sodium hydroxide, potassium phosphate and sodium phosphate.

The solvents used are not particularly limited as long as they do not inhibit the reaction, and examples thereof include methanol, ethanol, tetrahydrofuran, 1,4-dioxane, water, N,N-dimethylformamide, dimethylsulfoxide, toluene, and a mixture of these. The reaction temperature is usually about 60 to 100° C. and the reaction time is usually about 1 to 24 hours.

(Step J2) Step of Forming Hydrazide

This is a step of producing a compound (J-III) from the compound (J-II) under the same conditions as in Step D1 of Method D.

(Step J3) Step of Forming Triazole Ring

This is a step of producing a compound (J-V) by reacting a compound (J-IV) with an alkylating agent such as methyl iodide to convert it into the corresponding thioimidate, and reacting the thioimidate with the compound (J-III) under the same conditions as in Step B1 of Method B.

[Method K]

Method K is a method of producing a compound (K-II) (equivalent to the compound (J-IV) that is used in Method J).

[Formula 44]

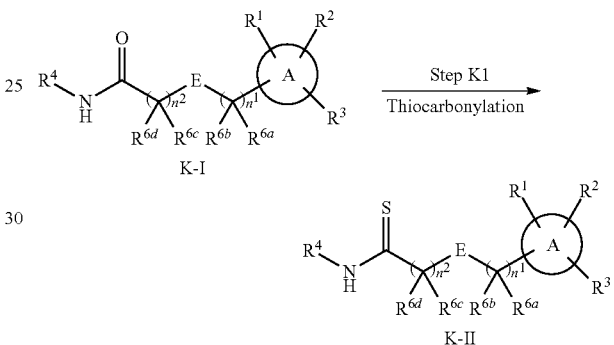

wherein the symbols used in the formula are the same as defined above.

(Step K1) Step of Thiocarbonylation

This is a step of obtaining a compound (K-II) by reacting a compound (K-I) that is commercially available or can be synthesized by a known method, with a sulfurizing agent such as Lawesson's reagent in a solvent under the same conditions as in Step C2 of Method C.

When the structure represented by J in the compound of the present invention is the following imidazole:

[Formula 45]

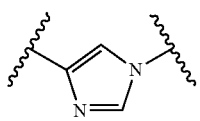

the compound (L-V) of the present invention can be produced, for example, using the following Method L.

[Method L]

Method L is a method of producing the compound (L-V) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 46]

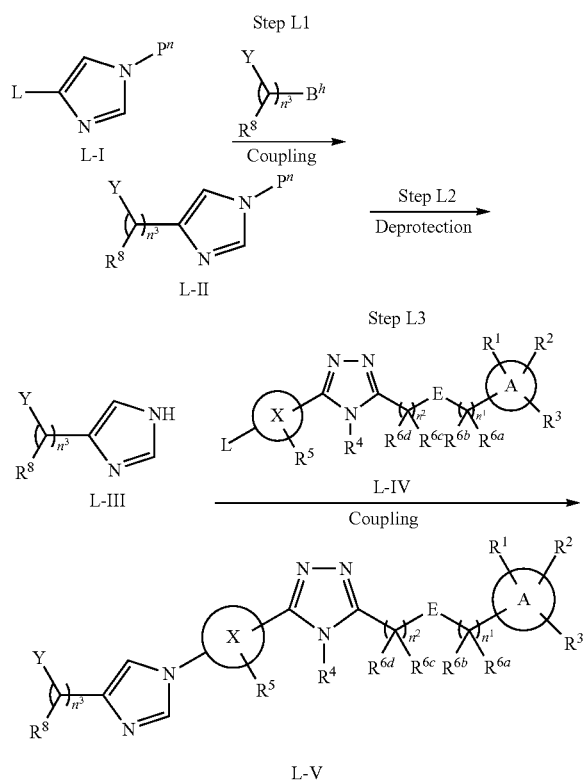

wherein the symbols used in the formula are as defined above. $P^n$ represents an amino group-protecting group. L represents a leaving group. $B^h$ represents boronic acid or boronic acid pinacol ester.

(Step L1) Step of Coupling Reaction Using Transition Metal Catalyst

This is a step of obtaining a compound (L-II) from a compound (L-1) that is commercially available or can be synthesized by a known method, by use of a palladium catalyst and a corresponding boronic acid or boronic acid pinacol ester in the presence of a base under the same conditions as in Step I4 of Method I.

(Step L2) Step of Deprotecting Amino Group-Protecting Group

This is a step of obtaining a compound (L-III) by deprotecting the amino group-protecting group from the compound (L-II). When the protecting group is a dimethylaminosulfonyl group, the compound (L-III) can be obtained by adding an acid to the compound (L-II).

Examples of the acid used include concentrated hydrochloric acid.

The solvents used are not particularly limited as long as they do not inhibit the reaction, and examples thereof include dichloromethane, chloroform, methanol, ethyl acetate, 1,4-dioxane and a mixture of these. The reaction temperature is usually about 0 to 100° C. and the reaction time is usually about 15 minutes to 12 hours.

(Step L3) Step of Coupling Reaction Using Transition Metal Catalyst

This is a step of obtaining the compound (L-V) by reacting the compound (L-III) with a compound (L-IV) (equivalent to the compound (I-IV) that is produced in Method I) using a transition metal such as copper as a catalyst in the presence of a base under the same conditions as in Step I3 of Method I.

When the structure represented by J in the compound of the present invention is the following 1,2,3-triazole:

[Formula 47]

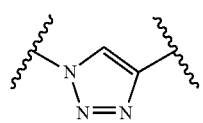

the compound (M-X) of the present invention can be produced, for example, using the following Method M.

[Method M]

Method M is a method of producing the compound (M-X) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 48]

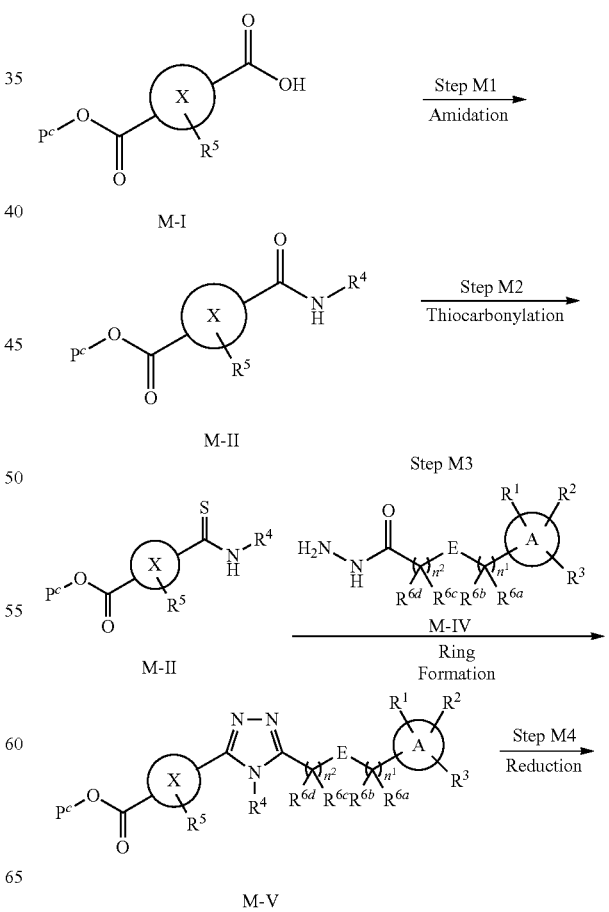

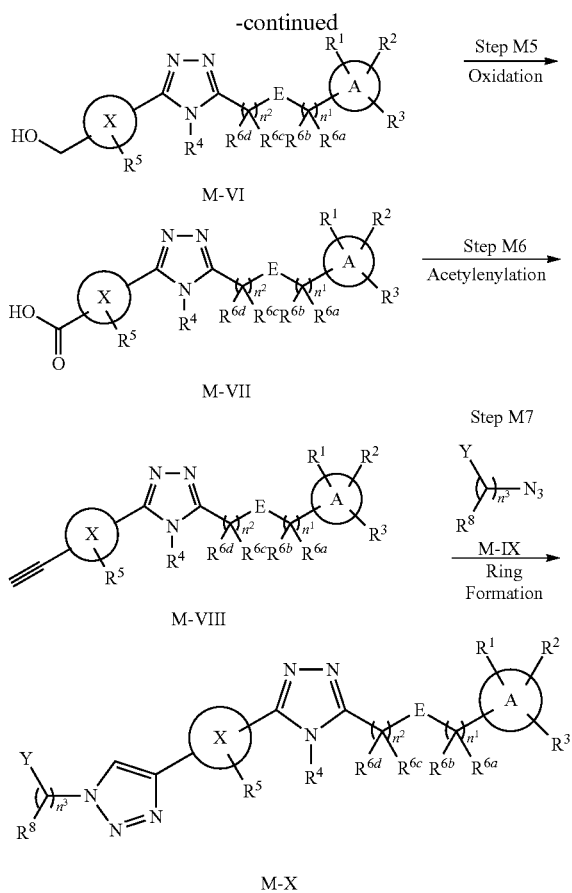

M-VI

M-VII

M-VIII

M-X wherein the symbols used in the formula are as defined above. $P^c$ represents a carboxyl group-protecting group.

(Step M1) Step of Forming Amide by Condensation

This is a step of producing a compound (M-II) from a compound (M-I) that is commercially available or can be synthesized by a known method, and the corresponding amine under the same conditions as in Step C1 of Method C.

(Step M2) Step of Thiocarbonylation

This is a step of obtaining a compound (M-III) by reacting the compound (M-II) with a sulfurizing agent such as Lawesson's reagent in a solvent under the same conditions as in Step C2 of Method C.

(Step M3) Step of Forming Triazole Ring

This is a step of producing a compound (M-V) by reacting a compound (M-III) with an alkylating agent such as methyl iodide to convert it into a corresponding thioimidate, and reacting the thioimidate with a compound (M-IV) (equivalent to the compound (D-II) that is used in Method D) under the same conditions as in Step B1 of Method B.

(Step M4) Step of Reducing Ester to Form Alcohol

This is a step of producing a compound (M-VI) by reacting the compound (M-V) with a reducing agent in a solvent.

Examples of the reducing agent used include lithium aluminium hydride (LAH) and diisobutylaluminium hydride (DIBAL).

The solvents used are not particularly limited as long as they do not inhibit the reaction, and examples thereof include toluene, diethyl ether, and tetrahydrofuran, and a mixture of these. The reaction temperature is usually about −78 to 100° C. and the reaction time is usually about 0.5 to 24 hours.

(Step M5) Step of Oxidizing Alcohol to Form Aldehyde

This is a step of producing a compound (M-VII) by reacting the compound (M-VI) with an oxidizing agent in a solvent.

Examples of the oxidizing agent used include manganese dioxide, potassium permanganate, pyridinium chlorochromate (PCC), pyridinium dichromate (PDC), a Dess-Martin reagent, 2,2,6,6-tetramethylpiperidine-1-oxyl radical (TEMPO), 2-azaadamantane-N-oxyl (AZADO), and tetrapropylammonium perruthenate (TPAP).

The solvents used are not particularly limited as long as they do not inhibit the reaction, and examples thereof include dichloromethane, toluene, diethyl ether, tetrahydrofuran, acetonitrile, acetone, N,N-dimethylformamide, and dimethyl sulfoxide, and a mixture of these. The reaction temperature is usually about −20 to 100° C. and the reaction time is usually about 0.5 to 24 hours.

(Step M6) Step of Increasing Carbon in Aldehyde to Form Alkyne

This is a step of producing a compound (M-VIII) by reacting the compound (M-VII) with an α-diazophosphonate compound in the presence of a base.

Examples of the α-diazophosphonate compound include dimethyl(1-diazo-2-oxopropyl)phosphonate (Ohira-Bestmann reagent).

Examples of the base used include potassium hydrogen carbonate, sodium hydrogen carbonate, potassium carbonate, and sodium carbonate.

The solvents used are not particularly limited as long as they do not inhibit the reaction, and examples thereof include methanol, ethanol, diethyl ether, tetrahydrofuran, and acetonitrile, and a mixture of these. The reaction temperature is usually about −20 to 100° C. and the reaction time is usually about 0.5 to 24 hours.

(Step M7) Step of Forming Triazole Ring

This is a step of producing the compound (M-X) by reacting a compound (M-VIII) with the corresponding azide (M-IX) under the same conditions as in Step A3 of Method A.

[Method N]

Method N is a method of producing a compound (N-VIII) (equivalent to the compound (M-VIII) that is used in Method M).

[Formula 49]

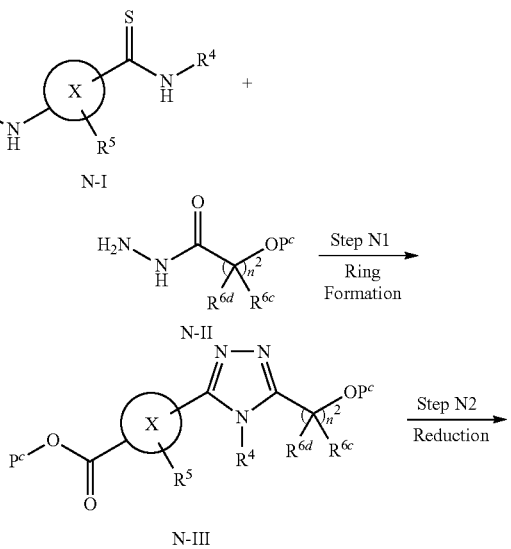

N-I

N-II

N-III

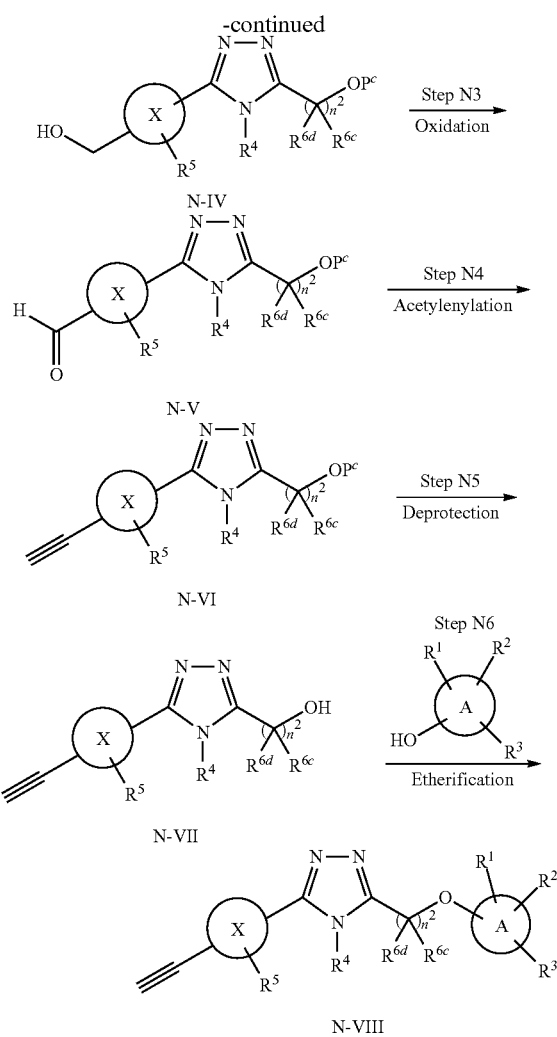

N-IV

N-V

N-VI

N-VII

N-VIII wherein the symbols used in the formula are the same as defined above. $P^c$ represents a carboxyl group-protecting group or a hydroxyl group-protecting group.

(Step N1) Step of Forming Triazole Ring

This is a step of producing a compound (N-III) by reacting a compound (N-I) (equivalent to the compound (M-III) that is used in Method M) with an alkylating agent such as methyl iodide to convert it into the corresponding thioimidate, and reacting the thioimidate with a compound (N-II) (equivalent to the compound (E-II) that is used in Method E) under the same conditions as in Step B1 of Method B.

(Step N2) Step of Reducing Ester to Form Alcohol

This is a step of producing a compound (N-IV) by reacting the compound (N-III) with a reducing agent in a solvent under the same conditions as in Step M4 of Method M.

(Step N3) Step of Oxidizing Alcohol to Form Aldehyde

This is a step of producing a compound (N-V) by reacting the compound (N-IV) with an oxidizing agent in a solvent under the same conditions as in Step M5 of Method M.

(Step N4) Step of Increasing Carbon in Aldehyde to Form Alkyne

This is a step of producing a compound (N-VI) by reacting the compound (N-V) with an α-diazophosphonate compound in the presence of a base under the same conditions as in Step M6 of Method M.

(Step N5) This is a step of obtaining a compound (N-VII) by deprotecting the hydroxyl group of the compound (N-VI) under the same conditions as in Step E6 of Method E.

(Step N6) Step of Etherification by Mitsunobu Reaction

This is a step of obtaining a compound (N-VIII) by reacting the compound (N-VII) with the corresponding alcohol in the presence of cyanomethylene tributylphosphorane under the same conditions as in Step E7 of Method E.

When the structure represented by J in the compound of the present invention is the following pyrazole:

[Formula 50]

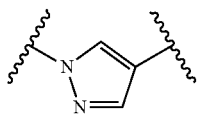

the compound (O-VIII) of the present invention can be produced, for example, using the following Method O.

[Method O]

Method O is a method of producing the compound (O-VIII) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 51]

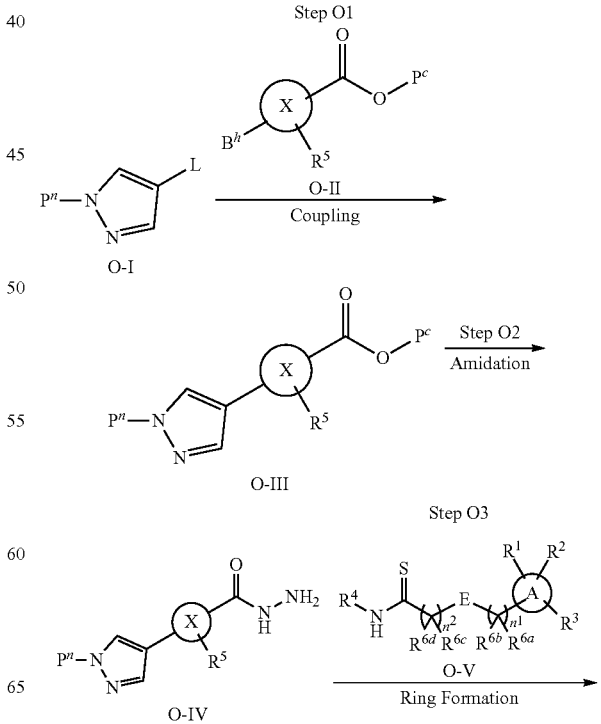

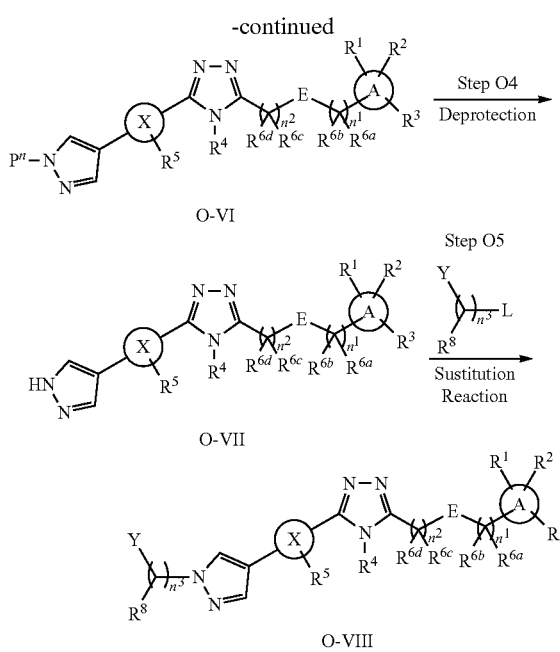

wherein the symbols used in the formula are as defined above. P$^c$ represents a carboxyl group-protecting group or a hydroxyl group-protecting group. P$^n$ represents an amino group-protecting group. L represents a leaving group. B$^h$ represents boronic acid or boronic acid pinacol ester.

(Step O1) Step of Coupling Reaction Using Transition Metal Catalyst

This is a step of obtaining a compound (O-III) from a compound (O-I) that is commercially available or can be synthesized by a known method, by use of a palladium catalyst and the compound (O-II) having the corresponding boronic acid or boronic acid pinacol ester in the presence of a base under the same conditions as in Step I4 of Method I.

(Step O2) Step of Forming Hydrazide

This is a step of producing a compound (O-IV) from a compound (O-III) under the same conditions as in Step D1 of Method D.

(Step O3) Step of Forming Triazole Ring

This is a step of producing a compound (O-VI) by reacting a compound (O-V) (equivalent to the compound (K-II) that is used in Method K) with an alkylating agent such as methyl iodide to convert it into the corresponding thioimidate, and reacting the thioimidate with the compound (O-IV) under the same conditions as in Step B1 of Method B.

(Step O4) Step of Deprotecting Amino Group-Protecting Group

This is a step of obtaining a compound (O-VII) by deprotecting an amino group-protecting group from the compound (O-VI). When the protecting group is a tetrahydropyranyl group, the compound (O-VII) can be obtained by dissolving the compound (O-VI) in a solvent and adding an acid.

Examples of the acid include hydrochloric acid, sulfuric acid, acetic acid, p-toluenesulfonic acid and pyridinium p-toluenesulfonate.

Examples of the solvent include methanol, ethanol, tetrahydrofuran, 1,4-dioxane, ethyl acetate, water, and a mixture of these. The reaction temperature is usually about 0 to 80° C. and the reaction time is usually about 0.5 to 24 hours.

(Step O5) Step of Introducing Substituent by Substitution Reaction

This is a step of obtaining the compound (O-VIII) by reacting the compound (O-VII) with a compound having the corresponding leaving group in the presence of a base under the same conditions as in Step J1 of Method J.

[Method P]

Method P is a method of producing a compound (P-VII) (equivalent to the compound (O-VIII) in Method O) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 52]

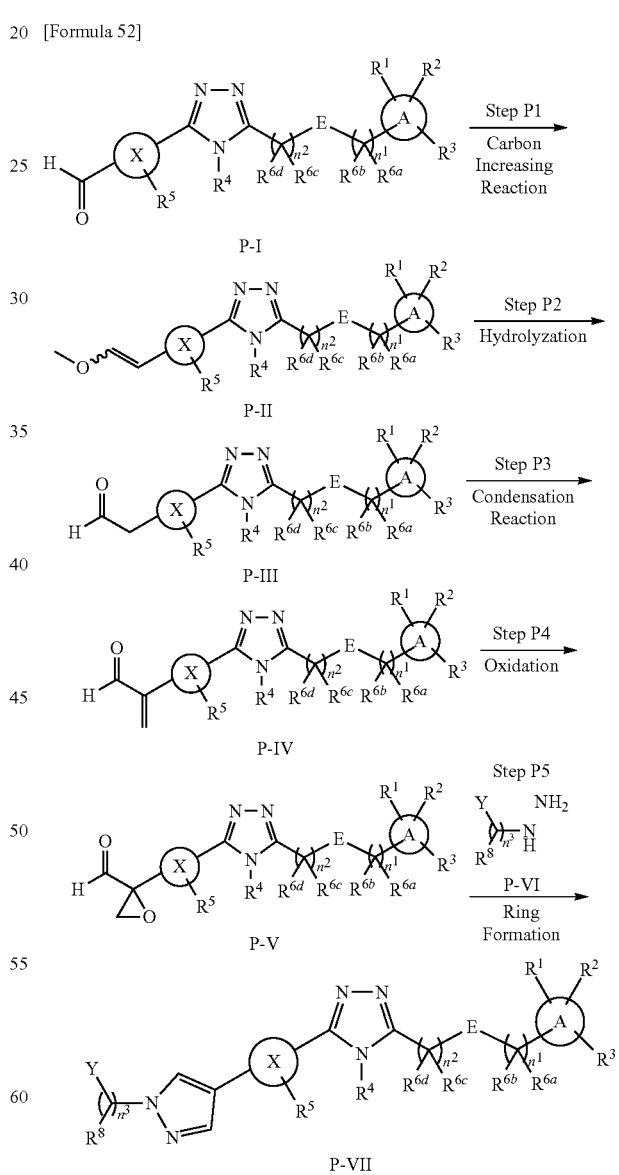

wherein the symbols used in the formula are the same as defined above. P-II represents a mixture of E and Z isomers.

(Step P1) Step of Increasing Carbon in Aldehyde to Form Enol Ether

This is a step of producing a compound (P-II) by reacting a compound (P-I) (equivalent to the compound (M-VII) that is used in Method M) with a phosphonate compound (such as (methoxymethyl)triphenylphosphonium chloride) in the presence of a base.

Examples of the base used include sodium methylate, potassium tert-butoxide, sodium hydride, potassium hydride, sodium bistrimethylsilylamide, and lithium bistrimethylsilylamide.

The solvents used are not particularly limited as long as they do not inhibit the reaction, and examples thereof include diethyl ether, tetrahydrofuran, toluene, hexane, N,N-dimethylformamide, dimethyl sulfoxide, acetic acid, and a mixture of these. The reaction temperature is usually about 0 to 80° C. and the reaction time is usually about 5 minutes to 24 hours.

(Step P2) Step of Hydrolyzing Enol Ether to Form Aldehyde

This is a step of producing a compound (P-III) by hydrolyzing a compound (P-II) with an acid in a solvent.

Examples of the acid used include hydrochloric acid, sulfuric acid, phosphoric acid, nitric acid, perchloric acid, p-toluenesulfonic acid (PPTS), methanesulfonic acid, acetic acid, and formic acid.

The solvents used are not particularly limited as long as they do not inhibit the reaction, and examples thereof include water, acetone, methyl ethyl ketone, diethyl ether, tetrahydrofuran, 1,4-dioxane, N,N-dimethylformamide, dimethyl sulfoxide, toluene, dichloromethane, and a mixture of these. The reaction temperature is usually about 0 to 100° C. and the reaction time is usually about 5 minutes to 24 hours.

(Step P3) Step of Forming Exomethylene Aldehyde

This is a step of producing a compound (P-IV) by reacting a compound (P-III) with a corresponding aldehyde (for example, formaldehyde) in the presence of a catalyst.

Examples of the catalyst used include L-proline, dimethylamine, diethylamine, diethanolamine, morpholine, piperidine, pyrrolidine, pyrazole, and indole.

The solvents used are not particularly limited as long as they do not inhibit the reaction, and examples thereof include water, ethanol, isopropyl alcohol, tetrahydrofuran, N,N-dimethylformamide, toluene, dichloromethane, acetic acid, and a mixture of these. The reaction temperature is usually about 0 to 100° C. and the reaction time is usually about 5 minutes to 72 hours.

(Step P4) Step of Oxidizing Exomethylene to Form Epoxide

This is a step of producing a compound (P-V) by reacting a compound (P-IV) with an oxidizing agent in a solvent.

Examples of the oxidizing agent used include peracetic acid, trifluoroperacetic acid, metachloroperacetic acid, hydrogen peroxide, benzoyl peroxide, tert-butyl hydroperoxide, tert-amyl hydroperoxide, and oxone.

The solvents used are not particularly limited as long as they do not inhibit the reaction, and examples thereof include dichloromethane, chloroform, diethyl ether, toluene, xylene, acetone, acetonitrile, N,N-dimethylformamide, dimethyl sulfoxide, acetic acid and a mixture of these. The reaction temperature is usually about −78 to 100° C. and the reaction time is usually about 5 minutes to 48 hours.

(Step P5) Step of Forming Pyrazole Ring

This is a step of producing a compound (P-VII) by reacting a compound (P-V) with a corresponding hydrazine (P-VI) or a salt adduct thereof in a solvent.

The solvents used are not particularly limited as long as they do not inhibit the reaction, and examples thereof include water, methanol, ethanol, isopropyl alcohol, tetrahydrofuran, N,N-dimethylformamide, toluene, dichloromethane, and a mixture of these. The reaction temperature is usually about 0 to 100° C. and the reaction time is usually about 0.5 to 72 hours.

[Method Q]

Method Q is a method of producing the compound (Q-IX) (equivalent to the compound (O-VIII) that is used in Method O) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 53]

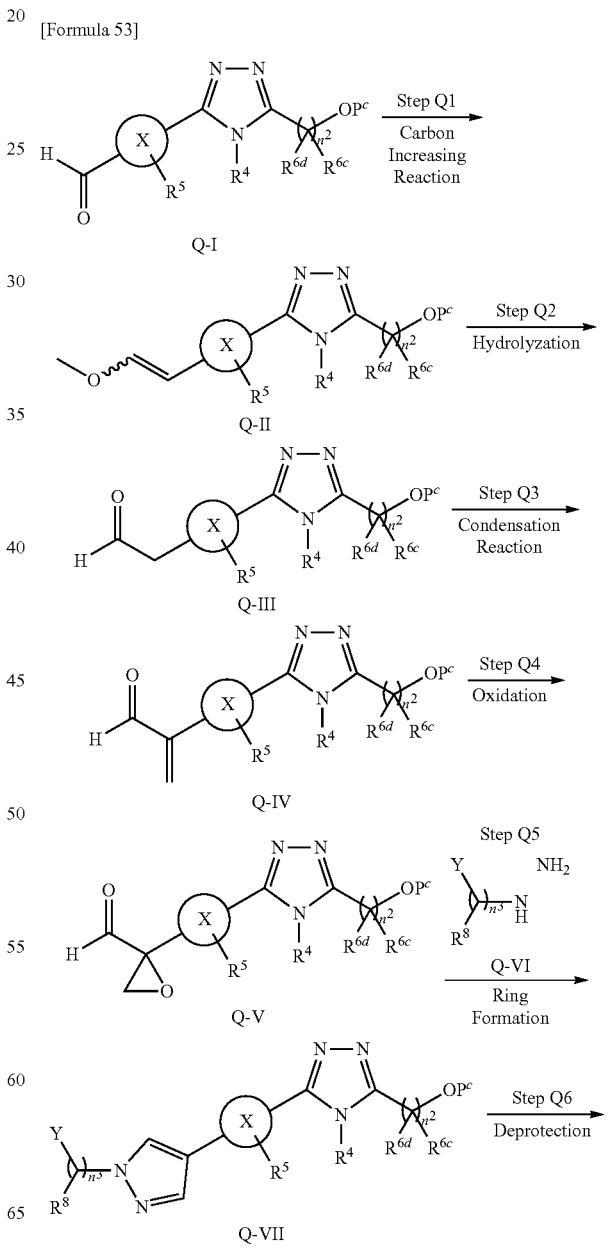

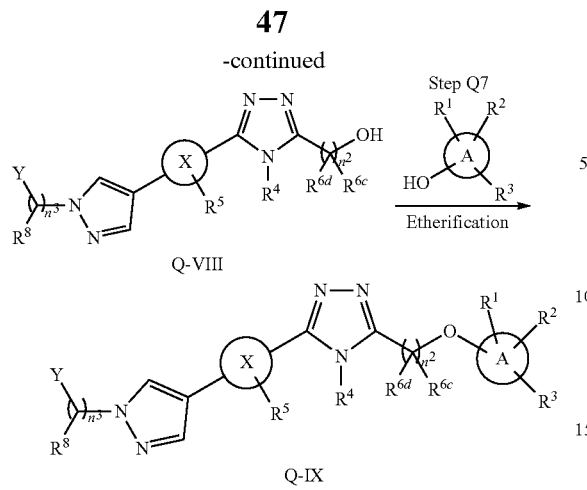

Q-VIII

Q-IX wherein the symbols used in the formula are as defined above. $P^c$ represents a hydroxyl group-protecting group. Q-II represents a mixture of E and Z isomers.

(Step Q1) Step of Increasing Carbon in Aldehyde to Form Enol Ether

This is a step of producing a compound (Q-II) by reacting a compound (Q-I) (equivalent to the compound (N-V) that is used in Method N) with a phosphonate compound (for example, (methoxymethyl)triphenylphosphonium chloride) in the presence of a base under the same conditions as in Step P1 of Method P.

(Step Q2) Step of Hydrolyzing Enol Ether to Form Aldehyde

This is a step of producing a compound (Q-III) by hydrolyzing the compound (Q-II) with an acid in a solvent under the same conditions as in Step P2 of Method P.

(Step Q3) Step of Forming Exomethylene Aldehyde

This is a step of producing a compound (Q-IV) by reacting the compound (Q-III) with a corresponding aldehyde (for example, formaldehyde) in the presence of a catalyst under the same conditions as in Step P3 of Method P.

(Step Q4) Step of Oxidizing Exomethylene to Form Epoxide

This is a step of producing a compound (Q-V) by reacting the compound (Q-IV) with an oxidizing agent in a solvent under the same conditions as in Step P4 of Method P.

(Step Q5) Step of Forming Pyrazole Ring

This is a step of producing a compound (Q-VII) by reacting the compound (Q-V) with the corresponding hydrazine (Q-VI) in a solvent under the same conditions as in Step P5 of Method P.

(Step Q6) This is a step of obtaining a compound (Q-VIII) by deprotecting the hydroxyl group of the compound (Q-VII) under the same conditions as Step E6 of Method E.

(Step Q7) Step of Etherification by Mitsunobu Reaction

This is a step of obtaining the compound (Q-IX) by reacting the compound (Q-VIII) with the corresponding alcohol in the presence of cyanomethylene tributylphosphorane under the same conditions as in Step E7 of Method E.

[Method R]

Method R is a method of producing a compound (R-V) (equivalent to the compound (P-VI) in Method P and the compound (Q-VI) in Method Q).

[Formula 54]

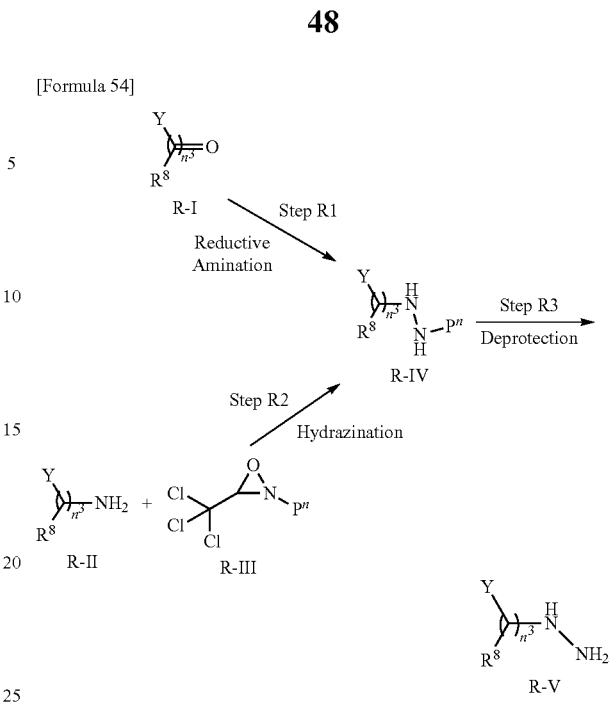

wherein the symbols used in the formula are as defined above. $P^n$ represents an amino group-protecting group.

(Step R1) Step of Forming N-Protected Hydrazine by Reductive Amination

This is a step of producing a compound (R-IV) by reacting a compound (R-I) that is commercially available or can be synthesized by a known method, with N-protected hydrazine (for example, benzyl carbazate or tert-butyl carbazate) and a reducing agent in a solvent.

Examples of the reducing agent to be used include sodium triacetoxyborohydride, sodium cyanoborohydride, sodium borohydride, lithium borohydride, pyridine borane, and 2-picolineborane.

The solvents used are not particularly limited as long as they do not inhibit the reaction, and examples thereof include methanol, ethanol, isopropyl alcohol, tetrahydrofuran, acetonitrile, dichloromethane, chloroform, 1,2-dichloroethane, N,N-dimethylformamide, water, acetic acid, and a mixture of these. The reaction temperature is usually about −20 to 100° C. and the reaction time is usually about 5 minutes to 72 hours.

In this step, the reaction may be promoted by adding an acid to the reaction system.

(Step R2) Step of Forming N-Protected Hydrazine Using Oxaziridine Reagent

This is a step of producing a compound (R-IV) by reacting a compound (R-II) that is commercially available or can be synthesized by a known method, with an oxaziridine that is commercially available or can be synthesized by a known method, in a solvent.

Examples of the base used include triethylamine, diisopropylethylamine, 1,8-diazabicyclo[5.4.0]-7-undecene (DBU), and 1,5-diazabicyclo[4.3.0]-5-nonene (DBN).

The solvents used are not particularly limited as long as they do not inhibit the reaction, and examples thereof include tetrahydrofuran, 1,4-dioxane, dichloromethane, N,N-dimethylacetamide, and a mixture of these. The reaction temperature is usually about −78 to 100° C. and the reaction time is usually about 0.5 to 24 hours.

(Step R3) Step of Deprotecting Amino Group-Protecting Group

This is a step of obtaining a compound (R-V) by deprotecting an amino group-protecting group from the compound (R-IV).

(i) For example, when the protecting group is a tert-butoxycarbonyl (Boc) group, the compound (R-V) can be obtained by dissolving the compound (R-IV) in a solvent and adding an acid. The reaction temperature is usually about −20 to 100° C. and the reaction time is usually about 1 to 24 hours.

Examples of the acid used include trifluoroacetic acid and hydrochloric acid.

The solvents used are not particularly limited as long as they do not inhibit the reaction, and examples thereof include dichloromethane, chloroform, methanol, ethyl acetate, and 1,4-dioxane, and a mixture of these.

(ii) The compound (R-V) can be obtained, for example, when the protecting group is a benzyloxycarbonyl (Cbz) group, by dissolving the compound (R-IV) in a solvent in the presence of a metal catalyst such as 10% palladium carbon.

The solvents used are not particularly limited as long as they do not inhibit the reaction, and examples thereof include tetrahydrofuran, 1,4-dioxane, methanol, ethanol, acetic acid, and a mixture of these. The reaction temperature is usually about room temperature to 60° C. and the reaction time is usually about 0.5 to 24 hours.

In this step, the reaction may be promoted by adding an acid to the reaction system.

[Method S]

Method S is a method of producing the compound (S-III) (equivalent to the compound (O-VIII) that is used in Method O) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 55]

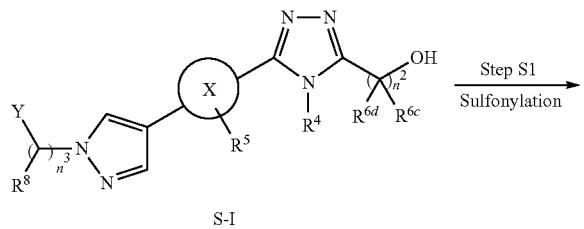

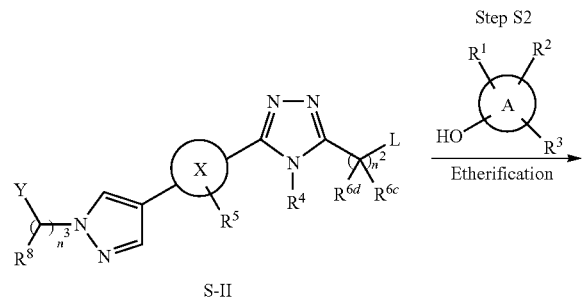

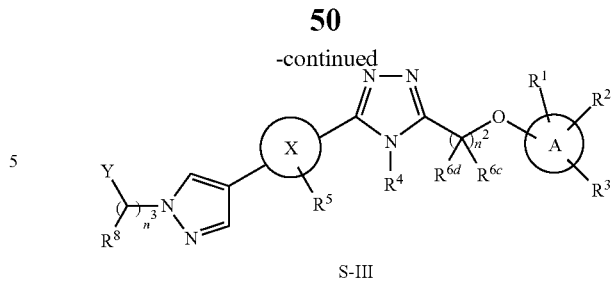

wherein the symbols used in the formula are the same as defined above. L represents a leaving group.

(Step S1) Step of Converting Hydroxyl Group into Leaving Group

This is a step of producing a compound (S-II) by reacting a compound (S-I) (equivalent to the compound (Q-VIII) that is used in Method Q) with sulfonyl halide (such as methanesulfonyl chloride) in the presence of a base.

Examples of the base used include triethylamine, diisopropylethylamine, pyridine, and 4-dimethylaminopyridine (DMAP).

The solvents used are not particularly limited as long as they do not inhibit the reaction, and examples thereof include methanol, ethanol, tetrahydrofuran, 1,4-dioxane, acetonitrile, ethyl acetate, dichloromethane, chloroform, toluene and a mixture of these. The reaction temperature is usually about 0 to 100° C. and the reaction time is usually about 5 minutes to 24 hours.

(Step S2) Step of Etherification by Substitution Reaction

This is a step of producing the compound (S-III) by reacting the compound (S-II) in a solvent with the corresponding alcohol in basic conditions.

Examples of the base used include sodium methylate, potassium tert-butoxide, sodium hydride, potassium hydride, sodium bistrimethylsilylamide, and lithium bistrimethylsilylamide.

The solvents used are not particularly limited as long as they do not inhibit the reaction, and examples thereof include diethyl ether, tetrahydrofuran, toluene, hexane, N,N-dimethylformamide, dimethyl sulfoxide and a mixture of these. The reaction temperature is usually about 0 to 200° C. and the reaction time is usually about 5 minutes to 24 hours.

[Method T]

Method T is a method of producing a compound (T-IV) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 56]

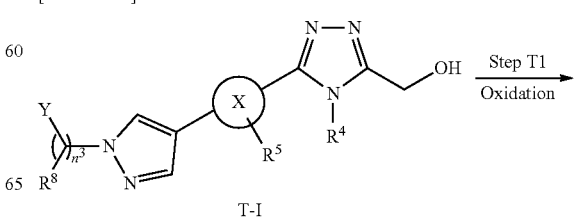

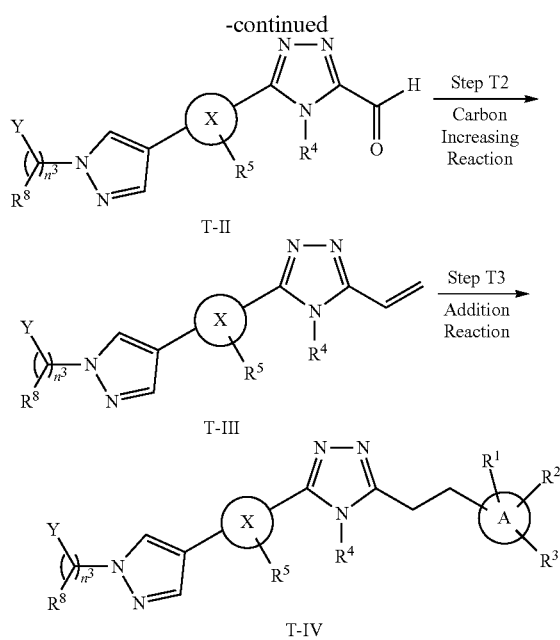

wherein the symbols used in the formula are as defined above. L represents a leaving group.

(Step T1) Step of Oxidizing Alcohol to Form Aldehyde

This is a step of producing a compound (T-II) by reacting a compound (T-I) (equivalent to the compound (Q-VIII) that is used in Method Q) with an oxidizing agent in a solvent under the same conditions as in Step M5 of Method M.

(Step T2) Step of Increasing Carbon in Aldehyde to Form Enol Ether

This is a step of producing a compound (T-III) by reacting the compound (T-II) with a phosphonate compound (such as methyl triphenylphosphonium bromide) in the presence of a base under the same conditions as in Step P1 of Method P.

(Step T3) Step of Conducting Addition Reaction

This is a step of producing a compound (T-IV) by reacting the compound (T-III) with the corresponding nucleophile (for example, 3-(trifluoromethyl)-2-pyridone) in a solvent.

The solvents used are not particularly limited as long as they do not inhibit the reaction, and examples thereof include tetrahydrofuran, 1,4-dioxane, acetonitrile, toluene, hexane, N,N-dimethylformamide, dimethyl sulfoxide, and a mixture of these. The reaction temperature is usually about 0 to 200° C. and the reaction time is usually about 5 minutes to 24 hours.

When the structure represented by J in the compound of the present invention is the following 1,3,4-oxadiazole:

[Formula 57]

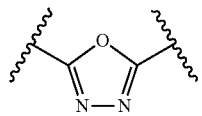

the compound (U-VII) of the present invention can be produced, for example, using the following Method U.

[Method U]

Method U is a method of producing the compound (U-VII) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 58]

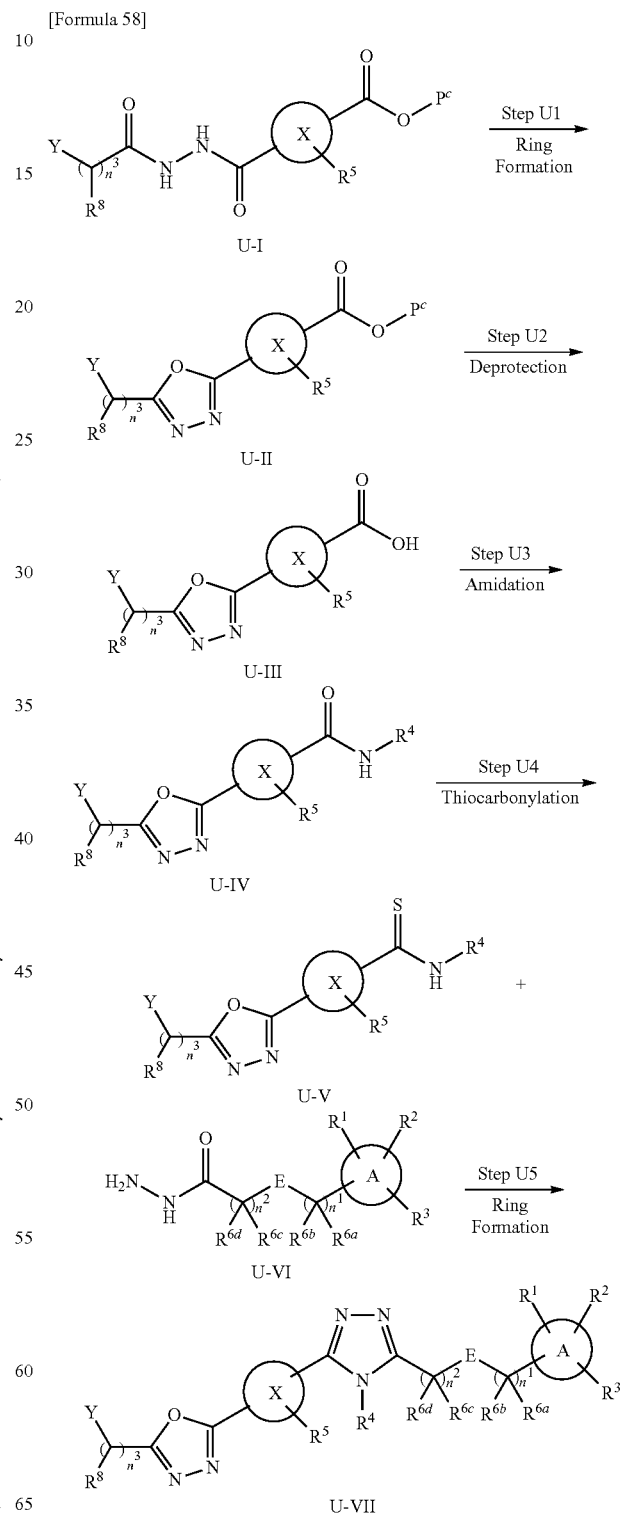

wherein the symbols used in the formula are as defined above. $P^c$ represents a carboxyl group-protecting group.

(Step U1) Step of Forming Oxadiazole Ring

This is a step of obtaining a compound (U-II) by reacting a compound (U-I) that is commercially available or can be synthesized by a known method, with a dehydrating reagent (for example, (methoxycarbonylsulfamoyl) triethylammonium hydroxide inner salt (Burgess reagent)) in a solvent.

The solvents used are not particularly limited as long as they do not inhibit the reaction, and examples thereof include tetrahydrofuran, 1,4-dioxane, acetonitrile, toluene, N,N-dimethylformamide, dichloromethane and a mixture of these. The reaction temperature is usually about 0 to 150° C. and the reaction time is usually about 5 minutes to 36 hours.

(Step U2) This is a step of obtaining a compound (U-III) by hydrolyzing the compound (U-II) in a solvent in the presence of a base.

Examples of the base used include sodium hydroxide and lithium hydroxide.

The solvents used are not particularly limited as long as they do not inhibit the reaction, and examples thereof include tetrahydrofuran, methanol, water, and a mixture of these. The reaction temperature is usually about 0 to 150° C. and the reaction time is usually about 5 minutes to 36 hours.

(Step U3) Step of Forming Amide by Condensation

This is a step of obtaining a compound (U-IV) from the compound (U-III) and a corresponding amine under the same conditions as in Step C1 of Method C.

(Step U4) Step of Thiocarbonylation

This is a step of obtaining a compound (U-V) by reacting the compound (U-IV) with a sulfurizing agent such as Lawesson's reagent in a solvent under the same conditions as in Step C2 of Method C.

(Step U5) Step of Forming Triazole Ring

This is a step of producing the compound (U-VII) by reacting the compound (U-V) with an alkylating agent such as methyl iodide to convert it into the corresponding thioimidate, and reacting the thioimidate with a compound (U-VI) (equivalent to the compound (D-II) that is used in Method D) under the same conditions as in Step B1 of Method B.

When the structure represented by J in the compound of the present invention is the following isoxazole:

[Formula 59]

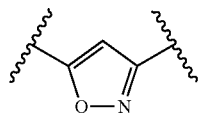

the compound (V-IV) of the present invention can be produced, for example, using the following Method V.

[Method V]

Method V is a method of producing the compound (V-IV) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 60]

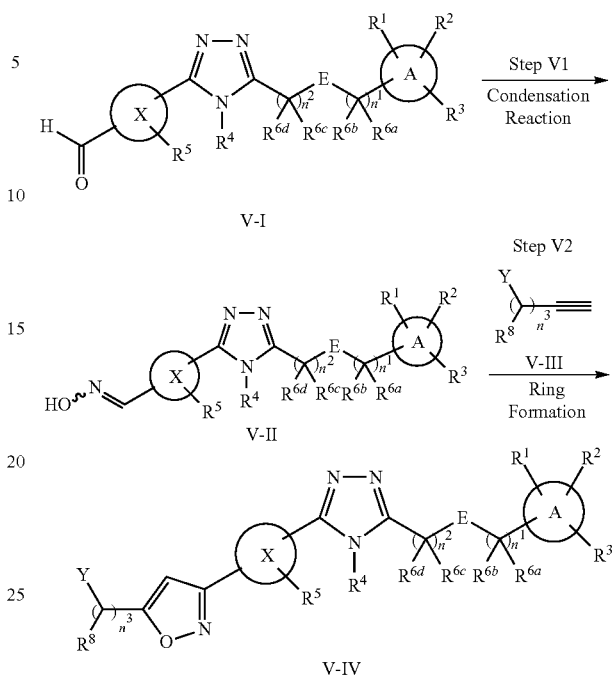

wherein the symbols used in the formula are as defined above. V-II represents a mixture of E and Z isomers.

(Step V1) Step to Forming Oxime

This is a step of producing a compound (V-II) by reacting the compound (V-I) (equivalent to the compound (M-VII) that is used in Method M) with hydroxylamine hydrochloride in the presence of a base.

Examples of the base used include triethylamine, pyridine, potassium hydrogen carbonate, sodium hydrogen carbonate, potassium carbonate, sodium carbonate, cesium carbonate, potassium hydroxide, sodium hydroxide, and sodium acetate.

The solvents used are not particularly limited as long as they do not inhibit the reaction, and examples thereof include water, methanol, ethanol, tetrahydrofuran, N,N-dimethylformamide, toluene, dichloromethane, and a mixture of these. The reaction temperature is usually about 0 to 150° C. and the reaction time is usually about 0.5 to 72 hours.

(Step V2) Step of Forming Isoxazole Ring by Cycloaddition Reaction

The is a step of producing the compound (V-IV) by reacting the compound (V-II) with N-chlorosuccinimide in the presence of a base, converting it into the corresponding nitrile oxide, and subjecting the nitrile oxide to a cycloaddition reaction with a compound (V-III).

Examples of the base used include triethylamine, pyridine, potassium hydrogen carbonate, sodium hydrogen carbonate, potassium carbonate, sodium carbonate, cesium carbonate, potassium hydroxide, and sodium hydroxide.

The solvents used are not particularly limited as long as they do not inhibit the reaction, and examples thereof include water, methanol, ethanol, tetrahydrofuran, N,N-dimethylformamide, toluene, dichloromethane, chloroform, and a mixture of these. The reaction temperature is usually about 0 to 100° C. and the reaction time is usually about 0.5 to 72 hours.

When the structure represented by J in the compound of the present invention is the following isoxazolidine:

[Formula 61]

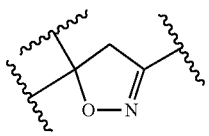

the compound (W-III) of the present invention can be produced, for example, using the following Method W.

[Method W]

Method W is a method of producing the compound (W-III) of the present invention. In this method, for convenience, the case where the structure represented by G in the compound of the general formula (1) of the present invention is 1,2,4-triazole is described as an example. However, even when the structure represented by G is another 5-membered aromatic heterocyclic compound, the target compound can be produced in the same manner by a method usually used in this field.

[Formula 62]

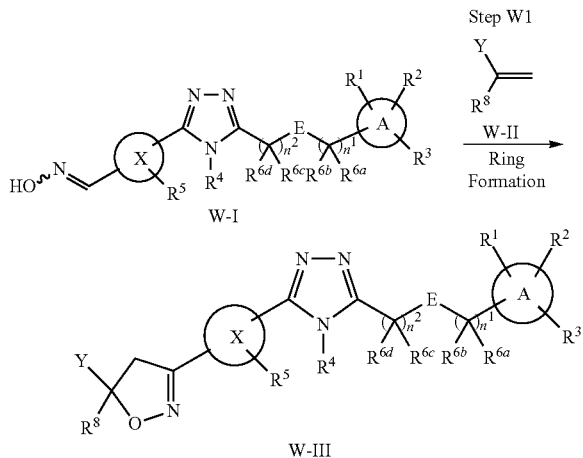

wherein the symbols used in the formula are the same as defined above. W-I indicates a mixture of E and Z isomers.

(Step W1) Step of Forming Isoxazole Ring by Cycloaddition Reaction

This is a step of producing the compound (W-III) by reacting a compound (W-I) (equivalent to the compound (V-II) that is used in Method V) with N-chlorosuccinimide in the presence of a base to convert it into the corresponding nitrile oxide, and subjecting the nitrile oxide to a cycloaddition reaction with a compound (W-II) under the same conditions as in Step V2 of Method V.

[Method X]

Method X is a method of producing a compound (X-II) (equivalent to a compound (A-IV) that is used in Method A, equivalent to a compound (E-VII) that is used in Method E, and equivalent to a compound (H-III) that is used in Method H).

[Formula 63]

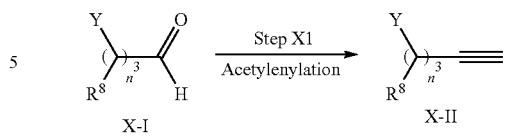

wherein the symbols used in the formula are the same as defined above.

(Step X1) Step of Increasing Carbon in Aldehyde to Form Alkyne

This is a step of producing the compound (X-II) by reacting a compound (X-I) that is commercially available or can be synthesized by a known method, with an α-diazophosphonate compound in the presence of a base under the same conditions as in Step M6 of Method M.

[Method Y]

Method Y is a method of producing a compound (Y-II) (equivalent to the compound (M-IX) that is used in Method M).

[Formula 64]

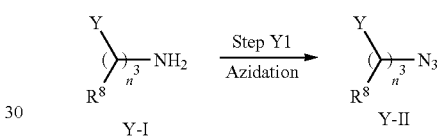

wherein the symbols used in the formula are the same as defined above.

(Step Y1) Step of Converting Amino Group into Azide Group

This is a step of obtaining a compound (Y-II) from a compound (Y-I) that is commercially available or can be synthesized by a known method, by converting an amino group into an azide group under the same conditions as in Step A2 of Method A.

The compounds produced by the above methods can be isolated and purified by a method known in the art, such as extraction, precipitation, distillation, chromatography, fractional recrystallization and recrystallization.

If a compound or an intermediate has an asymmetric carbon, it has optical isomers. These optical isomers can be isolated and purified by a conventional method such as fractional recrystallization (salt fractionation) using recrystallization via an appropriate salt, and column chromatography. For a method of fractionating an optical isomer from a racemic body, refer to the document: J. Jacques et al, "Enantiomers, Racemates and Resolution, John Wiley And Sons, Inc.".

(Dosage Form)

As an administration route, oral administration using a tablet, a pill, a capsule, a granule, a powder or a liquid; or parenteral administration using an injection such as intra-articular, intravenous or intramuscular injections, a suppository, an eye drop, an eye ointment, a transdermal liquid, an ointment, a transdermal patch, a transmucosal liquid, a transmucosal patch or an inhalant, may be employed.

As a solid composition for oral administration, tablets, powders, granules or the like are used. In such a solid composition, one or two or more active ingredients are mixed with at least one type of inactive excipient such as lactose, mannitol, dextrose, hydroxypropyl cellulose, microcrystalline cellulose, starch, polyvinylpyrrolidone and/or magnesium aluminometasilicate. In such a solid composition, an inactive additive such as a lubricant (for example, magnesium stearate), a disintegrant such as sodium carboxymethyl starch, a stabilizer and/or a solubilizer, may be added in accordance with a conventional method. Tablets or pills, if necessary, may be coated with sugar or a film soluble in the stomach or intestine.

As a liquid composition for oral administration, a pharmaceutically acceptable emulsion, solution, suspension, syrup, elixir, or the like are used. Such a liquid composition may contain an inactive diluent that is generally used, such as purified water or ethanol. The liquid composition may contain an additive such as a solubilizer, a wetting agent, a sweetener, a flavor, an aroma material or an antiseptic agent, other than the inactive diluent.

As an injection for parenteral administration, an aqueous or non-aqueous aseptic solution, suspension, emulsion, or the like are used. Examples of the aqueous solvent include distilled water for injection and physiological saline. Examples of the non-aqueous solvent include propylene glycol, polyethylene glycol, a vegetable oil such as olive oil, an alcohol such as ethanol and Polysorbate 80. Such a composition for injection may further contain a tonicity agent, a preservative, a wetting agent, an emulsifying agent, a dispersant, a stabilizer or a solubilizer. Such a composition for injection can be sterilized, for example, by filtration through a sterilization filter, addition of a disinfectant or irradiation. Alternatively, such a composition for injection can be produced as an aseptic solid composition, and dissolved or suspended in aseptic water or aseptic solvent for injection just before use and then put in use.

As an external formulation, an ointment, a plaster, a cream, a jelly, a cataplasm, a spray, a lotion, an eye drop, an eye ointment, and the like are used. Such an external formulation contains an ointment base, a lotion base, an aqueous or non-aqueous solution, a suspension, an emulsion, or the like that is generally used. Examples of the ointment or lotion base include polyethylene glycol, propylene glycol, white petrolatum, beeswax, polyoxyethylene hydrogenated castor oil, glyceryl monostearate, stearyl alcohol, cetyl alcohol, lauromacrogol and sorbitan sesquioleate.

As an inhalation and a transmucosal agent such as a transnasal agent, a solid, liquid or semi-solid composition is used and can be produced by a method known in the art. Such an agent may appropriately contain, for example, an excipient known in the art, further, a pH adjuster, a preservative, a surfactant, a lubricant, a stabilizer or a thickener. For these transmucosal agents, an appropriate device for inhalation or insufflation can be used in the administration method. For example, using a device known in the art such as a metered dose inhalation device or a spray, a compound (of the invention) may be administered alone or as a composition, in the form of powder; or used in combination with a pharmaceutically acceptable carrier in the form of a solution or suspension. An inhaler such as a dry powder inhaler may be used for single administration or multiple administrations. A dry powder or a powder-containing capsule can be used. Alternatively, an appropriate propellant can be used. For example, the inhaler may be a pressurized aerosol spray using a suitable gas such as chlorofluoroalkane, hydrofluoroalkane or carbon dioxide.

(Dosage Amount)

In the case of oral administration, the proper dosage amount per day per weight is generally about 0.001-100 mg/kg, preferably 0.1-30 mg/kg, and more preferably 0.1-10 mg/kg. This is administered in a single dose or in two or more doses. In the case of intravenous administration, the proper dosage amount per day per weight is about 0.0001-10 mg/kg and administered in a single dose per day or in a plurality of doses. In the case of a transmucosal agent, the dosage amount per weight is about 0.001-100 mg/kg, which is administered in a single dose or in a plurality of doses. The dosage amount is appropriately and individually determined in consideration of the symptoms, age and sex of the individual.

(Combined Use)

In the present invention, the compound of the invention can be used in combination with various types of therapeutic agents or prophylactic agents expected to have an effect on a disease. The agent to be used in combination may be administered simultaneously or sequentially or intermittently at desired time intervals. The formulations to be simultaneously administered may be a combination drug or separate drugs.

(Formulation Example 1) Powdered Medicine

The compound of the present invention or a salt thereof (5 g), lactose (895 g) and corn starch (100 g) were mixed in a blender to obtain a powdered medicine.

(Formulation Example 2) Granule

The compound of the present invention or a salt thereof (5 g), lactose (865 g) and low substituted hydroxypropyl cellulose (100 g) were mixed and then a 10% aqueous solution of hydroxypropyl cellulose (300 g) was added thereto. The mixture was kneaded, granulated by an extrusion granulator, and dried to obtain granules.

(Formulation Example 3) Tablet

The compound of the present invention or a salt thereof (5 g), lactose (90 g), corn starch (34 g), crystalline cellulose (20 g) and magnesium stearate (1 g) were mixed in a blender and compressed into tablets by a tableting machine to obtain tablets.

Pharmacological activity of the compound of the present invention or a pharmacologically acceptable salt thereof was checked by the following test.

(Test Example) Measurement of IL-10 Increase Rate

A test substance was suspended in a 0.5% (w/v) methyl cellulose and orally administered to mice at a dose of 100 mg/kg. One hour later, a lipopolysaccharide (LPS, Sigma-Aldrich, L2630 (trade name)) (0.4 mg/kg) was intraperitoneally administered to induce inflammation. One hour after administration of LPS, blood was taken from the vena cava under anesthesia with isoflurane, placed in a tube containing a serum separating agent, allowed to stand still at room temperature for 20-30 minutes and centrifuged at 4° C. at 12,000 rpm for 5 minutes to obtain the serum. Thereafter, the amount of the IL-10 in the serum was measured by using Mouse IL-10 Quantikine ELISA Kit (R&D systems, M1000B (trade name)) or Mouse IL-10 Immunoassay kit (PerkinElmer, AL502 (trade name)) in accordance with the protocol of the kit. The serum was diluted 10 times with the dilution solution contained in the kit and put in use. IL-10 increase rate (% control ratio) of the compound was calculated in accordance with the following expression:

IL-10 increase rate (% control ratio) (IL10 amount in compound administration group)×100/(IL-10 amount in 0.5% (w/v) methyl cellulose administration group)

TABLE 1

| Example No. | IL10 Increase Rate (%) |
| --- | --- |
| 1 | 146 |
| 2 | 220 |
| 3 | 179 |
| 4 | 131 |
| 5 | 206 |
| 6 | 243 |
| 7 | 113 |
| 8 | 197 |
| 9 | 182 |
| 10 | 390 |
| 11 | 180 |
| 12 | 177 |
| 13 | 156 |
| 14 | 216 |
| 15 | 227 |
| 16 | 170 |
| 17 | 334 |
| 18 | 157 |
| 19 | 227 |
| 20 | 176 |
| 21 | 312 |
| 22 | 113 |
| 23 | 232 |
| 24 | 257 |
| 25 | 216 |
| 26 | 231 |
| 27 | 255 |
| 28 | 113 |
| 29 | 111 |
| 30 | 141 |
| 31 | 222 |
| 32 | 202 |
| 33 | 144 |
| 34 | 202 |
| 35 | 184 |
| 36 | 230 |

From this test result, it was shown that the compound of the present invention or a pharmacologically acceptable salt thereof is useful for preventing and/or treating an inflammatory disease.

EXAMPLES

Now, the present invention will be more specifically described by way of Examples. However, the present invention is not limited by these.

In the following Examples, nuclear magnetic resonance (hereinafter referred to as $^1$H NMR) spectra were obtained by using tetramethylsilane as a standard substance and chemical shift values were expressed by S values (ppm). In a splitting pattern, a singlet was represented by s, a doublet d, a triplet t, a quartet q, a multiplet m and a broad br.

Example 1

1-Methyl-4-{1-[4-(4-methyl-5-{[3-(trifluoromethyl)phenoxy]methyl}-4H-1,2,4-triazol-3-yl)phenyl]-1H-1,2,3-triazol-4-yl}piperidine (1a)

2-[3-(Trifluoromethyl)phenoxy]acetohydrazide

Methyl 2-[3-(Trifluoromethyl)phenoxy]acetate (CAS Registry Number: 588-26-1, WO2008078291) (3 g, 13 mmol) was dissolved in ethanol (15 mL). To this, hydrazine monohydrate (9.7 g, 192 mmol) was added, and the mixture was stirred under heating to reflux for 8 hours.

After the reaction temperature had returned to room temperature, the residue obtained by concentration under reduced pressure was purified by silica gel column chromatography [elution solvent: methanol/ethyl acetate] to obtain the title compound (1.2 g (yield: 40%)) as a white solid.

(1b)

tert-Butyl N-[4-(methylcarbamothioyl)phenyl]carbamate tert-Butyl N-[4-(methylcarbamoyl)phenyl]carbamate (CAS Registry Number: 179625-42-4, WO1996013485) (1 g, 4 mmol) was dissolved in tetrahydrofuran (20 mL). To this, Lawesson's reagent (1.8 g, 4.4 mmol) was added, and the mixture was stirred at room temperature for 4 hours.

To this, a 1N aqueous sodium hydroxide solution was added, and the reaction mixture was extracted with dichloromethane. The organic layer was washed with saturated saline, and dried over anhydrous sodium sulfate. The resultant was concentrated under reduced pressure and triturated with diethyl ether to obtain the title compound (800 mg (yield: 80%)) as a yellowish white solid.

(1c)

tert-Butyl N-[4-[4-methyl-5-[[3-(trifluoromethyl)phenoxy]methyl]-1,2,4-triazol-3-yl]phenyl]carbamate The compound of Example 1(1b): tert-butyl N-[4-(methylcarbamothioyl)phenyl]carbamate (200 mg, 0.75 mmol) was dissolved in tetrahydrofuran (1 mL). To this, methyl iodide (0.93 mL, 15 mmol) was added and the mixture was stirred at room temperature for 3 hours.

The resultant was concentrated under reduced pressure, then the residue was dissolved in ethanol (3 mL). To this, the compound of Example 1(1a): 2-[3-(trifluoromethyl)phenoxy]acetohydrazide (352 mg, 1.5 mmol) was added, and the mixture was stirred at 100° C. for 6 hours.

After the reaction temperature had returned to room temperature, insoluble matters were filtered and concentrated under reduced pressure. The residue was triturated with dichloromethane to obtain the title compound (230 mg (yield: 68%)) as a yellowish white solid.

(1d)

4-[4-Methyl-5-[[3-(trifluoromethyl)phenoxy]methyl]-1,2,4-triazol-3-yl]aniline

The compound of Example 1(1c): tert-butyl N-[4-[4-methyl-5-[[3-(trifluoromethyl)phenoxy]methyl]-1,2,4-triazol-3-yl]phenyl]carbamate (230 mg, 0.51 mmol) was dissolved in 2N hydrochloric acid-methanol (3 mL) and the mixture was stirred at room temperature for 18 hours.

After the resultant was concentrated under reduced pressure, an aqueous potassium carbonate solution was added, and the reaction mixture was extracted with ethyl acetate. The organic layer was washed with saturated saline, and dried over anhydrous sodium sulfate. The dried product was concentrated under reduced pressure to obtain the title compound (170 mg (yield: 95%)) as a white solid.

(1e)

3-(4-Azidophenyl)-4-methyl-5-{[3-(trifluoromethyl)phenoxy]methyl}-4H-1,2,4-triazole The compound of Example 1(1d): 4-[4-methyl-5-[[3-(trifluoromethyl)phenoxy]methyl]-1,2,4-triazol-3-yl]aniline (1.5 g, 4.3 mmol) was dissolved in acetonitrile (8.6 mL). To this, tert-butyl nitrite (1.3 g, 13 mmol) was added under ice-cooling, and the mixture was stirred for 5 minutes. To the reaction solution, trimethylsilylazide (0.99 g, 8.6 mmol) was added, and the mixture was stirred under ice-cooling for 10 minutes. To this, trifluoroacetic acid (0.49 g, 4.3 mmol) was then added, and the mixture was stirred at room temperature for 3.5 hours.

The resultant was concentrated under reduced pressure, and the resultant residue was diluted with ethyl acetate. To the reaction mixture, water was added, and the reaction mixture was extracted with ethyl acetate. The organic layer was washed with saturated saline, and dried over anhydrous sodium sulfate. The resultant was concentrated under reduced pressure to obtain the title compound (303 mg (yield: 95%)) as a light yellow solid.

(1f)

tert-Butyl 4-{1-[4-(4-methyl-5-{[3-(trifluoromethyl) phenoxy]methyl}-4H-1,2,4-triazol-3-yl)phenyl]-1H-1,2,3-triazol-4-yl}piperidine-1-carboxylate The compound of Example 1(1e): 3-(4-azidophenyl)-4-methyl-5-{[3-(trifluoromethyl)phenoxy]methyl}-4H-1,2,4-triazole (500 mg, 0.975 mmol) and tert-butyl 4-ethynylpiperidine-1-carboxylate (CAS Registry Number: 287192-97-6, WO2000044728) (0.031 g, 0.17 mmol) were dissolved in tetrahydrofuran (9.8 mL). To this, diisopropylethylamine (0.254 mL, 1.46 mmol) and copper (I) iodide (279 mg, 1.47 mmol) were added, and the mixture was stirred at room temperature for 1 hour and allowed to stand still overnight.

To the reaction mixture, water was added, and the reaction mixture was extracted with ethyl acetate. The organic layer was washed with water and saturated saline and dried over anhydrous sodium sulfate. The residue obtained by concentration under reduced pressure was purified by silica gel column chromatography [elution solvent: methanol/ethyl acetate=0/1-1/9 (V/V)] to obtain the title compound (670 mg (yield: 100%)) as a white solid.

(1g)

4-{1-[4-(4-Methyl-5-{[3-(trifluoromethyl)phenoxy] methyl}-4H-1,2,4-triazol-3-yl)phenyl]-1H-1,2,3-triazol-4-yl}piperidine tert-Butyl 4-{1-[4-(4-methyl-5-{[3-(trifluoromethyl)phenoxy]methyl}-4H-1,2,4-triazol-3-yl)phenyl]-1H-1,2,3-triazol-4-yl}piperidine-1-carboxylate of Example 1(1f) (0.57 g, 0.98 mmol) was dissolved in dichloromethane (3.9 mL). To this, trifluoroacetic acid (2.2 mL) was added, and the mixture was stirred at room temperature for 2 hours.

To the residue obtained by concentration under reduced pressure, saturated aqueous sodium bicarbonate was added, and the mixture was extracted with chloroform. The organic layer was washed with saturated saline, and dried over anhydrous sodium sulfate. The residue obtained by concentration under reduced pressure was triturated with ethyl acetate to obtain the title compound (120 mg (yield: 25%)) as a white solid.

(1h)

1-Methyl-4-{1-[4-(4-methyl-5-{[3-(trifluoromethyl) phenoxy]methyl}-4H-1,2,4-triazol-3-yl)phenyl]-1H-1,2,3-triazol-4-yl}piperidine The compound of Example 1(1g): 4-{1-[4-(4-methyl-5-{[3-(trifluoromethyl)phenoxy]methyl}-4H-1,2,4-triazol-3-yl)phenyl]-1H-1,2,3-triazol-4-yl}piperidine (0.11 g, 0.23 mmol) was dissolved in dichloromethane (0.9 mL). To this, a formaldehyde solution (37%) (0.05 mL, 0.68 mmol) was added, and the mixture was stirred at room temperature for 5 minutes. Then to the reaction mixture, sodium triacetoxyborohydride (95%) (0.24 g, 1.1 mmol) was added, and the mixture was stirred at room temperature for 1 hour.

To the reaction mixture, saturated aqueous sodium bicarbonate was added, and the mixture was extracted with dichloromethane. The organic layer was washed with saturated saline, and dried over anhydrous sodium sulfate. To the residue obtained by concentration under reduced pressure, ethyl acetate was added, and the precipitated solid was collected by filtration and then dried to obtain the title compound (86 mg, yield: 53%)) as a light yellow solid.

Example 2

5-[4-(1-Methylpiperidin-4-yl)-1H-1,2,3-triazol-1-yl]-2-(4-methyl-5-{[3-(propan-2-yl)phenoxy]methyl}-4H-1,2,4-triazol-3-yl)pyridine (2a)

Methyl 2-(3-isopropylphenoxy)acetate

3-Isopropylphenol (Combi-Blocks Inc., Catalog Number: YF-6400) (10 g, 73 mmol) was dissolved in N,N-dimethylformamide (100 mL). To this, potassium carbonate (20 g, 147 mmol) and methyl bromoacetate (Tokyo Chemical Industry Co., Ltd., Catalog Number: B0533) (7.4 mL, 81 mmol) were added, and the mixture was allowed to stand still at room temperature for 3 days.

The reaction mixture was poured into water and extracted with ethyl acetate. The organic layer was washed with water and saturated saline and dried over anhydrous sodium sulfate. The residue obtained by concentration under reduced pressure was purified by silica gel column chromatography [elution solvent: hexane/ethyl acetate=1/0-7/3 (V/V)] to obtain the title compound (14.4 g (yield: 94%)) as a white solid.

(2b)

2-(3-Isopropylphenoxy)acetohydrazide

Methyl 2-(3-isopropylphenoxy) acetate (14.4 g, 69.1 mmol) from Example 2(2a) was dissolved in ethanol (150 mL). To this, hydrazine monohydrate (10.4 g, 207 mmol) was added, and the mixture was stirred for 3 hours.

The reaction solution was concentrated to approximately half. To this, water (200 mL) was added, and the precipitated solid was collected by filtration and washed with water. The resultant solid was dried to obtain the title compound (12.6 g (yield: 63%)) as a white solid.

(2c)

tert-Butyl N-[6-(methylcarbamoyl)-3-pyridyl]carbamate

Methyl 5-(tert-butoxycarbonylamino)pyridine-2-carboxylate (CAS Registry Number: 131052-40-9, WO2016033445) (0.9 g, 3.6 mmol) was dissolved in a 40% methylamine-methanol solution (about 9.8 mol/L) (30 mL, 290 mmol) and the mixture was stirred at 80° C. for 3 hours.

After the reaction temperature had returned to room temperature, the solid obtained by concentration under reduced pressure was washed with a mixture solvent of ethyl acetate and hexane to obtain the title compound (600 mg (yield: 70%)) as a white solid.

(2d)

tert-Butyl N-[6-(methylcarbamothioyl)-3-pyridyl]carbamate

The compound of Example 2(2c): tert-butyl N-[6-(methylcarbamoyl)-3-pyridyl]carbamate (0.6 g, 2.4 mmol) was dissolved in tetrahydrofuran (10 mL). To this, Lawesson's reagent (1.1 g, 2.6 mmol) was added, and the mixture was allowed to stand still at room temperature overnight. Further Lawesson's reagent (1.1 g, 2.6 mmol) was added and the mixture was allowed to stand still at room temperature overnight. Further Lawesson's reagent (1.06 g, 2.6 mmol) was added, and the mixture was allowed to stand still at room temperature for 4 days.

The reaction mixture was poured into water and extracted with ethyl acetate. The organic layer was washed with water and saturated saline and dried over anhydrous sodium sulfate. The residue obtained by concentration under reduced pressure was purified by silica gel column chromatography [elution solvent: hexane/ethyl acetate=10/0-7/3 (V/V)] to obtain the title compound (480 mg (yield: 75%)) as a white solid.

(2e)

tert-Butyl N-[6-[5-[(3-isopropylphenoxy)methyl]-4-methyl-1,2,4-triazol-3-yl]-3-pyridyl]carbamate The compound of Example 2(2d): tert-butyl N-[6-(methylcarbamothioyl)-3-pyridyl]carbamate (1.7 g, 6.4 mmol) was dissolved in tetrahydrofuran (40 mL). To this, methyl iodide (4 mL, 64 mmol) and potassium carbonate (0.88 g, 6.4 mmol) were added and the mixture was stirred at room temperature for 5 hours.

The crude product obtained by removing insoluble matters by filtration and concentrating the mother liquid was dissolved in 1,4-dioxane (20 mL). To this, the compound of Example 2(2b): 2-(3-isopropylphenoxy) acetohydrazide (1.5 g, 7.0 mmol) was added, and the mixture was stirred at 100° C. for 6 hours.

After the reaction temperature had returned to room temperature, the residue obtained by concentration under reduced pressure was purified by silica gel column chromatography [elution solvent: hexane/ethyl acetate=4/1-0/1 (V/V)] to obtain the title compound (360 mg (yield: 13%)) as a light yellow solid.

(2f)

6-[5-[(3-Isopropylphenoxy)methyl]-4-methyl-1,2,4-triazol-3-yl]pyridin-3-amine The compound of Example 2(2e): tert-butyl N-[6-[5-[(3-isopropylphenoxy)methyl]-4-methyl-1,2,4-triazol-3-yl]-3-pyridyl]carbamate (0.36 g, 0.85 mmol) was dissolved in dichloromethane (4.5 mL). To this, trifluoroacetic acid (0.5 mL) was added, and the mixture was stirred at room temperature for 3 hours.

The reaction mixture was neutralized with saturated aqueous sodium bicarbonate and extracted with dichloromethane. The organic layer was washed with saturated saline, and dried over anhydrous sodium sulfate. The residue obtained by concentration under reduced pressure was purified by NH silica gel column chromatography [elution solvent: methanol/ethyl acetate=0/1-1/20 (V/V)] to obtain the title compound (120 mg (yield: 44%)) as a light yellow solid.

(2g)

tert-Butyl 4-{1-[6-(4-methyl-5-{[3-(propan-2-yl)phenoxy]methyl}-4H-1,2,4-triazol-3-yl)pyridin-3-yl]-1H-1,2,3-triazol-4-yl}piperidine-1-carboxylate The compound of Example 2(2f): 6-[5-[(3-isopropylphenoxy)methyl]-4-methyl-1,2,4-triazol-3-yl]pyridin-3-amine (0.3 g, 0.93 mmol) was dissolved in tetrahydrofuran (10 mL). To this, 2-azido-1,3-dimethylimidazolinium hexafluorophosphate (0.52 g, 1.86 mmol) and 4-dimethylaminopyridine (0.34 g, 2.8 mmol) were added and the mixture was stirred at 50° C. for 7 hours.

The reaction mixture was poured into saturated aqueous sodium bicarbonate and extracted with ethyl acetate. The organic layer was washed with water and saturated saline and dried over anhydrous sodium sulfate. 5-Azido-2-[5-[(3-isopropylphenoxy)methyl]-4-methyl-1,2,4-triazol-3-yl]pyridine obtained by concentration under reduced pressure (300 mg, 0.86 mmol) was dissolved in tetrahydrofuran (9 mL). To this, copper (I) iodide (196 mg, 1.03 mmol), N,N-diisopropylethylamine (0.22 mL, 1.3 mmol) and tert-butyl 4-ethynylpiperidine-1-carboxylate (CAS Registry Number: 287192-97-6, WO2000044728) (216 mg, 1.03 mmol) were added, and the mixture was allowed to stand still at room temperature overnight.

To the reaction mixture, saturated ammonium chloride water was added, and the reaction mixture was extracted with ethyl acetate. The organic layer was washed with water and saturated saline and dried over anhydrous sodium sulfate. The solid obtained by concentration under reduced pressure was triturated with ethyl acetate and hexane to obtain the title compound (165 mg (yield: 34%)) as a yellow solid.

(2h)

2-(4-Methyl-5-{[3-(propan-2-yl)phenoxy]methyl}-4H-1,2,4-triazol-3-yl)-5-[4-(piperidin-4-yl)-1H-1,2,3-triazol-1-yl]pyridine The compound of Example 2(2g): tert-butyl 4-{1-[6-(4-methyl-5-{[3-(propan-2-yl)phenoxy]methyl}-4H-1,2,4-triazol-3-yl)pyridin-3-yl]-1H-1,2,3-triazol-4-yl}piperidine-1-carboxylate (0.17 g, 0.30 mmol) was dissolved in dichloromethane (8 mL). To this, trifluoroacetic acid (2.0 mL, 26 mmol) was added, and the mixture was stirred at room temperature for 3 hours.

To the reaction mixture, saturated aqueous sodium bicarbonate was added, and the reaction mixture was extracted with dichloromethane. The organic layer was washed with saturated saline, and dried over anhydrous sodium sulfate. The residue obtained by concentration under reduced pressure was purified by NH silica gel column chromatography [elution solvent: methanol/ethyl acetate=1/10-3/7 (V/V)] to obtain the title compound (121 mg (yield: 89%)) as a yellow solid.

(2i)

5-[4-(1-Methylpiperidin-4-yl)-1H-1,2,3-triazol-1-yl]-2-(4-methyl-5-{[3-(propan-2-yl)phenoxy]methyl}-4H-1,2,4-triazol-3-yl)pyridine The compound of Example 2(2h): 2-(4-methyl-5-{[3-(propan-2-yl)phenoxy]methyl}-4H-1,2,4-triazol-3-yl)-5-[4-(piperidin-4-yl)-1H-1,2,3-triazol-1-yl]pyridine (0.12 g, 0.26 mmol) was dissolved in ethanol (3 mL). To this, a formaldehyde solution (37%) (0.097 mL, 1.32 mmol), acetic acid (0.158 g, 2.64 mmol) and sodium triacetoxyborohydride (0.17 g, 0.79 mmol) were added and the mixture was stirred at room temperature for 3 hours.

The reaction mixture was poured into water and extracted with ethyl acetate. The organic layer was washed with saturated saline, and dried over anhydrous sodium sulfate. The residue obtained by concentration under reduced pressure was purified by NH silica gel column chromatography [elution solvent: methanol/ethyl acetate=0/1-1/9 (V/V)] to obtain the title compound (63 mg (yield: 50%)) as a yellow solid.

Example 3

4-Fluoro-1-methyl-4-{1-[trans-4-(4-methyl-5-{[3-(propan-2-yl)phenoxy]methyl}-4H-1,2,4-triazol-3-yl)cyclohexyl]-1H-1,2,3-triazol-4-yl}piperidine (3a)

tert-Butyl N-[trans-4-(methylcarbamothioyl)cyclohexyl]carbamate tert-Butyl N-[trans-4-(methylcarbamoyl)cyclohexyl]carbamate (CAS Registry Number: 1013111-97-1, WO2015103453) (2.16 g, 8.26 mmol) was dissolved in tetrahydrofuran (40 mL). To this, Lawesson's reagent (3.67 g, 9.08 mmol) was added, and the mixture was stirred at 80° C. for 6 hours.

After the reaction temperature had returned to room temperature, the residue obtained by concentration under reduced pressure was purified by silica gel column chromatography [elution solvent: hexane/ethyl acetate=7/3-3/7 (V/V)] to obtain the title compound (1.54 g (yield: 69%)) as a pale gray solid.

(3b)

Methyl trans-4-(tert-butoxycarbonylamino)-N-methyl-cyclohexanecarboximidothioate The compound of Example 3(3a): tert-butyl N-[trans-4-(methylcarbamothioyl)cyclohexyl]carbamate (1.5 g, 5.7 mmol) was dissolved in tetrahydrofuran (30 mL). To this, potassium carbonate (1.6 g, 11 mmol) and methyl iodide (1.2 g, 8.5 mmol) were added, and the mixture was stirred for 8 hours under reflux with heating.

After the reaction temperature had returned to room temperature, the reaction mixture was filtered and concentrated under reduced pressure to obtain the title compound (1.6 g (yield: 96%)) as a white solid.

(3c)

tert-Butyl [trans-4-(4-methyl-5-{[3-(propan-2-yl)phenoxy]methyl}-4H-1,2,4-triazol-3-yl)cyclohexyl]carbamate The compound of Example 3(3b): methyl trans-4-(tert-butoxycarbonylamino)-N-methyl-cyclohexanecarboximidothioate (0.2 g, 0.7 mmol) was dissolved in N,N-dimethylformamide (3 mL). To this, the compound of Example 2(2b): 2-(3-isopropylphenoxy) acetohydrazide (164 mg, 0.7 mmol) was added and the mixture was stirred at 110° C. for 8 hours.

After the reaction temperature had returned to room temperature, the reaction mixture was poured into water and extracted with ethyl acetate. The organic layer was washed with water and saturated saline and dried over anhydrous magnesium sulfate. The residue obtained by concentration under reduced pressure was purified by silica gel column chromatography [elution solvent: hexane/ethyl acetate=1/1-0/1, ethyl acetate/methanol=7/3 (V/V)] to obtain the title compound (216 mg (yield: 68%)) as a white solid.

(3d)

trans-4-(4-Methyl-5-{[3-(propan-2-yl)phenoxy] methyl}-4H-1,2,4-triazol-3-yl)cyclohexanamine The compound of Example 3(3c): tert-butyl [trans-4-(4-methyl-5-{[3-(propan-2-yl)phenoxy]methyl}-4H-1,2,4-triazol-3-yl)cyclohexyl]carbamate (216 mg, 0.48 mmol) was dissolved in dichloromethane (3 mL). To this, trifluoroacetic acid (3 mL, 39 mmol) was added, and the mixture was stirred at room temperature for 27 hours.

The residue obtained by concentration under reduced pressure was dissolved in methanol (5 mL) and desalted with Amberlyst A-26 (OH) (Sigma-Aldrich, Catalog Number: 542571). The eluate was filtered and then concentrated under reduced pressure to obtain the title compound (160 mg (yield: 95%)) as a colorless oily substance.

(3e)

3-(trans-4-Azidocyclohexyl)-4-methyl-5-{[3-(propan-2-yl)phenoxy]methyl}-4H-1,2,4-triazole The compound of Example 3(3d): trans-4-(4-methyl-5-{[3-(propan-2-yl)phenoxy]methyl}-4H-1,2,4-triazol-3-yl)cyclohexanamine (0.31 g, 0.96 mmol) was dissolved in dichloromethane (8 mL). To this, triethylamine (0.66 ml, 4.8 mmol) and 2-azido-1,3-dimethylimidazolinium hexafluorophosphate (0.33 g, 1.2 mmol) were added and the mixture was stirred at room temperature for 1 hour.

To the reaction mixture, saturated aqueous sodium bicarbonate was added, and the mixture was extracted with ethyl acetate. The combined organic layer was dried over anhydrous magnesium sulfate. The residue obtained by concentration under reduced pressure was purified by silica gel column chromatography [elution solvent: ethyl acetate alone] to obtain the title compound (304 mg (yield: 90%)) as a white solid.

(3f)

tert-Butyl 4-hydroxy-4-{1-[trans-4-(4-methyl-5-{[3-(propan-2-yl)phenoxy]methyl}-4H-1,2,4-triazol-3-yl)cyclohexyl]-1H-1,2,3-triazol-4-yl}piperidine-1-carboxylate The compound of Example 3(3e): 3-(trans-4-azidocyclohexyl)-4-methyl-5-{[3-(propan-2-yl)phenoxy]methyl}-4H-1,2,4-triazole (0.5 g, 1.41 mmol) was dissolved in tetrahydrofuran (7 mL). To this, copper (I) iodide (381 mg, 1.69 mmol), N,N-diisopropylethylamine (0.37 mL, 2.1 mmol) and tert-butyl 4-ethynyl-4-hydroxypiperidine-1-carboxylate (CAS Registry Number: 275387-83-2, WO2000035908) (381 mg, 1.69 mmol) were added, and the mixture was stirred at room temperature for 24 hours.

The residue obtained by concentrating the reaction mixture under reduced pressure was purified by NH silica gel column chromatography [elution solvent: methanol/ethyl acetate=0/1-3/7 (V/V)] to obtain the title compound (785 mg (yield: 96%)) as a white solid.

(3g)

tert-Butyl 4-fluoro-4-{1-[trans-4-(4-methyl-5-{[3-(propan-2-yl)phenoxy]methyl}-4H-1,2,4-triazol-3-yl)cyclohexyl]-1H-1,2,3-triazol-4-yl}piperidine-1-carboxylate The compound of Example 3(3f): tert-butyl 4-hydroxy-4-{1-[trans-4-(4-methyl-5-{[3-(propan-2-yl)phenoxy] methyl}-4H-1,2,4-triazol-3-yl)cyclohexyl]-1H-1,2,3-triazol-4-yl}piperidine-1-carboxylate (360 mg, 0.62 mmol) was dissolved in dichloromethane (15 mL). To this, bis(2-methoxyethyl)aminosulfur trifluoride (0.2 mL, 0.93 mmol) was added under ice-cooling, and the mixture was stirred for 2 hours.

To the reaction mixture, saturated aqueous sodium bicarbonate was added under ice-cooling, and the reaction mixture was extracted with dichloromethane. The organic layer was washed with saturated saline and dried over anhydrous magnesium sulfate. The residue obtained by concentration under reduced pressure was purified by NH silica gel column chromatography [elution solvent: ethyl acetate/hexane=9/1, ethyl acetate alone, ethyl acetate/methanol=9/1 (V/V)] to obtain the title compound (191 mg (yield: 53%)) as a white solid.

(3h)

4-Fluoro-1-methyl-4-{1-[trans-4-(4-methyl-5-{[3-(propan-2-yl)phenoxy]methyl}-4H-1,2,4-triazol-3-yl)cyclohexyl]-1H-1,2,3-triazol-4-yl}piperidine The compound of Example 3(3g): tert-butyl 4-fluoro-4-{1-[trans-4-(4-methyl-5-{[3-(propan-2-yl)phenoxy] methyl}-4H-1,2,4-triazol-3-yl)cyclohexyl]-1H-1,2,3-triazol-4-yl}piperidine-1-carboxylate (0.55 g, 0.95 mmol) was dissolved in dichloromethane (10 mL). To this, trifluoroacetic acid (3 mL) was added, and the mixture was stirred at room temperature for 3 hours.

The residue obtained by concentrating the reaction mixture under reduced pressure was dissolved in tetrahydrofuran (2 mL). To this, a formaldehyde solution (37%) (0.36 mL, 4.9 mmol), acetic acid (0.29 g, 4.9 mmol) and sodium triacetoxyborohydride (0.62 g, 2.9 mmol) were added at room temperature, and the mixture was stirred for 18 hours.

The residue obtained by concentrating the reaction mixture was purified by NH silica gel column chromatography [elution solvent: methanol/ethyl acetate=0/1-1/4 (V/V)] to obtain the title compound (320 mg (yield: 66%)) as a white solid.

Example 4

4-Fluoro-1-methyl-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine (4a)

(2R)-2-[3-(Propan-2-yl)phenoxy]propanehydrazide

Methyl (2R)-2-[(3-propan-2-yl)phenoxy]propanoate (CAS Registry Number: 1704955-34-9, (commercially available) Aurora Fine Chemicals LLC, Catalog Number: A27.074.107) (4.19 g, 18.9 mmol) was dissolved in ethanol (50 mL). To this, hydrazine monohydrate (5 mL, 103 mmol) was added and the mixture was stirred for 2.5 hours.

To the residue obtained by concentrating the reaction mixture, dichloromethane and water were added, and the mixture was extracted with dichloromethane. The organic layer was washed with water and dried over anhydrous magnesium sulfate. The resultant was concentrated under reduced pressure to obtain the title compound (4.25 g (yield: 100%)) as a colorless oil.

(4b)

tert-Butyl [trans-4-(4-methyl-5-{(1R)-1-[3-(propan-2-yl)phenoxy]ethyl}-4H-1,2,4-triazol-3-yl)cyclohexyl]carbamate The compound of Example 3(3b): methyl trans-4-(tert-butoxycarbonylamino)-N-methyl-cyclohexanecarboximidothioate (4.25 g, 19.1 mmol) was dissolved in ethanol (50 mL). To this, the compound of Example 4(4a): (2R)-2-[3-(propan-2-yl)phenoxy] propane hydrazide (4.25 g, 19.1 mmol) was added, and the mixture was stirred at 100° C. for 4 hours.

The residue obtained by concentration under reduced pressure was purified by NH silica gel column chromatography [elution solvent: hexane/ethyl acetate=1/1-0/1, ethyl acetate alone, ethyl acetate/methanol=9/1 (V/V)]] to obtain the title compound (6.05 g (yield: 72%)) as a white solid.

(4c)

trans-4-(4-Methyl-5-{(1R)-1-[3-(propan-2-yl)phenoxy]ethyl}-4H-1,2,4-triazol-3-yl)cyclohexanamine The compound of Example 4(4b): tert-butyl [trans-4-(4-methyl-5-{(1R)-1-[3-(propan-2-yl)phenoxy]ethyl}-4H-1,2,4-triazol-3-yl)cyclohexyl]carbamate (8.84 g, 20 mmol) was dissolved in dichloromethane (50 mL). To this, trifluoroacetic acid (10 mL, 131 mmol) was added, and the mixture was stirred at room temperature for 3 hours.

The residue obtained by concentration under reduced pressure was purified by NH silica gel column chromatography [elution solvent: methanol/ethyl acetate=0/1-3/2 (V/V)] to obtain the title compound (6.69 g (yield: 98%)) as a white solid.

(4d)

3-(trans-4-Azidocyclohexyl)-4-methyl-5-{(1R)-1-[3-(propan-2-yl)phenoxy]ethyl}-4H-1,2,4-triazole The compound of Example 4(4c): trans-4-(4-methyl-5-{(1R)-1-[3-(propan-2-yl)phenoxy]ethyl}-4H-1,2,4-triazol-3-yl)cyclohexanamine (1.14 g, 3 mmol) was dissolved in acetonitrile (15 mL). To this, triethylamine (2.08 mL, 15 mmol) and 2-azido-1,3-dimethylimidazolinium hexafluorophosphate (1.03 g, 3.59 mmol) were added, and the mixture was stirred at room temperature for 2 hours.

To the reaction mixture, saturated aqueous sodium bicarbonate was added, and the reaction mixture was extracted with ethyl acetate. The combined organic layer was dried over anhydrous magnesium sulfate. The residue obtained by concentration under reduced pressure was purified by NH silica gel column chromatography [elution solvent: hexane/ethyl acetate=7/3, ethyl acetate alone, ethyl acetate/methanol=9/1 (V/V)] to obtain the title compound (881 mg (yield: 80%)) as a white solid.

(4e)

tert-Butyl 4-hydroxy-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine-1-carboxylate The compound of Example 4(4d): 3-(trans-4-azidocyclohexyl)-4-methyl-5-{(1R)-1-[3-(propan-2-yl)phenoxy]ethyl}-4H-1,2,4-triazole (220 mg, 0.6 mmol) was dissolved in tetrahydrofuran (6 mL). To this, copper (I) iodide (136 mg, 0.72 mmol), N,N-diisopropylethylamine (0.16 mL, 0.9 mmol) and tert-butyl 4-ethynyl-4-hydroxypiperidine-1-carboxylate (CAS Registry Number: 275387-83-2, WO2000035908) (161 mg, 0.72 mmol) were added, and the mixture was stirred at room temperature overnight.

The residue obtained by concentrating the reaction mixture under reduced pressure was purified by NH silica gel column chromatography [elution solvent: methanol/ethyl acetate=0/1-3/7 (V/V)] to obtain the title compound (353 mg (yield: 100%)) as a white solid.

(4f)

tert-Butyl 4-fluoro-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine-1-carboxylate The compound of Example 4(4e): tert-butyl 4-hydroxy-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine-1-carboxylate (6.38 g, 10.7 mmol) was dissolved in dichloromethane (100 mL). To this, bis(2-methoxyethyl) aminosulfate (3.46 mL, 16.1 mmol) was added at −50° C. and the mixture was stirred for 40 minutes while warming to 0° C.

To the reaction mixture, saturated aqueous sodium bicarbonate was added under ice-cooling, and the reaction mixture was extracted with dichloromethane. The organic layer was washed with saturated saline and dried over anhydrous magnesium sulfate. The residue obtained by concentration under reduced pressure was purified by NH silica gel column chromatography [elution solvent: hexane/ethyl acetate=9/1, ethyl acetate alone, ethyl acetate/methanol=19/1 (V/V)]. To the obtained crude product, ethyl acetate was added, and the precipitated solid was collected by filtration to obtain the title compound (3.3 g (yield: 52%)) as a white solid.

(4g)

4-Fluoro-1-methyl-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine The compound of Example 4(4f): tert-butyl 4-fluoro-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine-1-carboxylate (174 mg, 0.29 mmol) was dissolved in dichloromethane (3 mL). To this, trifluoroacetic acid (1 mL, 13 mmol) was added, and the mixture was stirred at room temperature for 2 hours.

The residue obtained by concentrating the reaction mixture under reduced pressure was dissolved in tetrahydrofuran (3 mL). To this, a formaldehyde solution (37%) (0.11 mL, 1.45 mmol), acetic acid (0.08 ml, 4.9 mmol) and sodium triacetoxyborohydride (184 mg, 0.87 mmol) were added at room temperature and the mixture was stirred for 1 hour.

The residue obtained by concentrating the reaction mixture was purified by NH silica gel column chromatography [elution solvent: ethyl acetate/methanol=1/0-4/1 (V/V)] to obtain the title compound (110 mg (yield: 74%)) as a white solid.

Example 5

4-{1-[trans-4-(5-{[4-Chloro-3-(trifluoromethyl)phenoxy]methyl}-4-methyl-4H-1,2,4-triazol-3-yl)cyclohexyl]-1H-1,2,3-triazol-4-yl}-4-fluoro-1-methylpiperidine (5a)

2-{[tert-butyl(diphenyl)silyl]oxy}acetohydrazide

Methyl 2-{[tert-butyl(diphenyl)silyl]oxy}acetate (CAS Registry Number: 154698-92-7, WO2015192817) (47.1 g, 129 mmol) was dissolved in ethanol (200 mL). To this, hydrazine monohydrate (61.9 g, 1.24 mol) was added, and the reaction mixture was stirred at room temperature for 30 minutes.

To the residue obtained by concentration under reduced pressure, dichloromethane and water were added, and the mixture was extracted with dichloromethane. The organic layer was dried over anhydrous magnesium sulfate. The resultant was concentrated under reduced pressure to obtain the title compound (46.3 g (Yield: 100%)) as a white solid.

(5b)

tert-Butyl {trans-4-[5-({[tert-butyl(diphenyl)silyl]oxy}methyl)-4-methyl-4H-1,2,4-triazol-3-yl]cyclohexyl}carbamate The compound of Example 3(3b): methyl trans-4-(tert-butoxycarbonylamino)-N-methyl-cyclohexanecarboximidothioate (7.62 g, 26.6 mmol) was dissolved in ethanol (100 mL). To this, the compound of Example 5(5a): 2-{[tert-butyl(diphenyl)silyl]oxy}acetohydrazide (8.74 g, 26.6 mmol) was added, and the mixture was stirred at 80° C. for 1 hour.

After the reaction temperature had returned to room temperature, the residue obtained by concentration under reduced pressure was purified by silica gel column chromatography [elution solvent: hexane/ethyl acetate=1/1-0/1, ethyl acetate/methanol=9/1 (V/V)] to obtain the title compound (5.74 g (yield: 39%)) as a white solid.

(5c)

3-(trans-4-Azidocyclohexyl)-5-({[tert-butyl(diphenyl)silyl]oxy}methyl)-4-methyl-4H-1,2,4-triazole The compound of Example 5(5b): tert-butyl {trans-4-[5-({[tert-butyl(diphenyl)silyl]oxy}methyl)-4-methyl-4H-1,2,4-triazol-3-yl]cyclohexyl}carbamate (5.74 g, 10.5 mmol) was dissolved in dichloromethane (50 mL). To this, trifluoroacetic acid (10 ml, 131 mmol) was added under ice-cooling, and the mixture was stirred at room temperature for 2 hours.

The residue obtained by concentration under reduced pressure was purified by NH silica gel column chromatography [elution solvent: ethyl acetate/methanol=1/0-2/3 (V/V)] to obtain the crude product trans-4-[5-({[tert-butyl(diphenyl)silyl]oxy}methyl)-4-methyl-4H-1,2,4-triazol-3-yl]cyclohexaneamine (5.73 g).

The obtained crude product was dissolved in trans-4-[5-({[tert-butyl(diphenyl)silyl]oxy}methyl)-4-methyl-4H-1,2,4-triazol-3-yl]cyclohexanamine (5.73 g) in acetonitrile (50 mL). To this, triethylamine (7.26 mL, 52.4 mmol) and 2-azido-1,3-dimethylimidazolinium hexafluorophosphate (3.58 g, 12.6 mmol) was added and the mixture was stirred at 50° C. for 2 hours.

To the reaction mixture, saturated aqueous sodium bicarbonate was added, and the reaction mixture was extracted with ethyl acetate. The combined organic layer was dried over anhydrous magnesium sulfate. The residue obtained by concentration under reduced pressure was purified by NH silica gel column chromatography [elution solvent: hexane/ethyl acetate=4/1-0/1 (V/V)] to obtain the title compound (997 mg (yield: 20%)) as a colorless oil.

(5d)

4-(1-{trans-4-[5-({[tert-Butyl(diphenyl)silyl]oxy}methyl)-4-methyl-4H-1,2,4-triazol-3-yl]cyclohexyl}-1H-1,2,3-triazol-4-yl)-4-fluoropiperidine

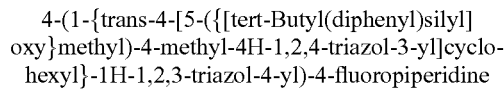

tert-Butyl 4-ethynyl-4-fluoropiperidine-1-carboxylate (CAS Registry Number: 191327-86-3, WO1997018202) (1.0 g, 4.4 mmol) was dissolved in dichloromethane (10 mL). To this, trifluoroacetic acid (3 mL, 39 mmol) was added under ice-cooling, and the mixture was stirred at room temperature for 2.5 hours.

The residue obtained by concentration under reduced pressure was dissolved in tetrahydrofuran (10 mL). To this, the compound of Example 5(5c)): 3-(trans-4-azidocyclohexyl)-5-({[tert-butyl (diphenyl)silyl]oxy}methyl)-4-methyl-4H-1,2,4-triazole (818 mg, 1.72 mmol) and triethylamine (0.549 mL, 3.96 mmol) in Example 5(5c) were added, and then a solution of tris[(1-benzyl-1H-1,2,3-triazol-4-yl)methyl]amine (91 mg, 0.17 mmol) and tetrakis(acetonitrile) copper (I) hexafluorophosphate (64 mg, 0.17 mmol) in a mixture of tetrahydrofuran (1 mL) and water (0.2 mL) was added at room temperature, and the mixture was stirred for 3 hours.

The residue obtained by concentration under reduced pressure was purified by NH silica gel column chromatography [elution solvent: methanol/ethyl acetate=0/1-1/9 (V/V)] to obtain the title compound (297 mg (yield: 29%)) as a light yellow solid.

(5e)

4-(1-{trans-4-[5-({[tert-Butyl(diphenyl)silyl]oxy}methyl)-4-methyl-4H-1,2,4-triazol-3-yl]cyclohexyl}-1H-1,2,3-triazol-4-yl)-4-fluoro-1-methylpiperidine

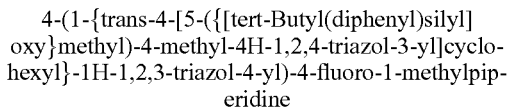

The compound of Example 5(5d): 4-(1-{trans-4-[5-({[tert-butyl (diphenyl)silyl]oxy}methyl)-4-methyl-4H-1,2,4-triazol-3-yl]cyclohexyl}-1H-1,2,3-triazol-4-yl)-4-fluoropiperidine (297 mg, 0.49 mmol) was dissolved in tetrahydrofuran (5 mL). To this, a formaldehyde solution (37%) (0.18 mL, 2.5 mmol) and sodium triacetoxyborohydride (314 mg, 1.48 mmol) were added at room temperature and the mixture was stirred for 4 hours.

The residue obtained by concentration under reduced pressure was purified by NH silica gel column chromatography [elution solvent: ethyl acetate/methanol=1/0-4/1 (V/V)] to obtain the title compound (300 mg (yield: 98%)) as a colorless oil.

(5f)

(5-{trans-4-[4-(4-Fluoro-1-methylpiperidin-4-yl)-1H-1,2,3-triazol-1-yl]cyclohexyl}-4-methyl-4H-1,2,4-triazol-3-yl)methanol

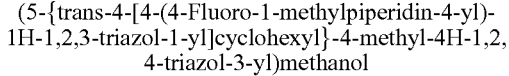

The compound of Example 5(5e): 4-(1-{trans-4-[5-({[tert-butyl (diphenyl)silyl]oxy}methyl)-4-methyl-4H-1,2,4-triazol-3-yl]cyclohexyl}-1H-1,2,3-triazol-4-yl)-4-fluoro-1-methylpiperidine (340 mg, 0.55 mmol) was dissolved in tetrahydrofuran (5 mL). To this, tetrabutylammonium fluoride (202 mg, 0.662 mmol) was added under ice-cooling, and the mixture was stirred for 2.5 hours.

The residue obtained by concentration under reduced pressure was purified by silica gel column chromatography [elution solvent: ethyl acetate/methanol=1/0-4/1 (V/V)] to obtain the title compound (197 mg (yield: 66%)) as a light yellow oily substance.

(5g)

4-{1-[trans-4-(5-{[4-Chloro-3-(trifluoromethyl)phenoxy]methyl}-4-methyl-4H-1,2,4-triazol-3-yl)cyclohexyl]-1H-1,2,3-triazol-4-yl}-4-fluoro-1-methylpiperidine

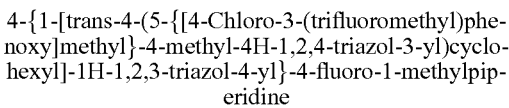

The compound of Example 5(5f): (5-{trans-4-[4-(4-fluoro-1-methylpiperidin-4-yl)-1H-1,2,3-triazol-3-yl]cyclohexyl}-4-methyl-4H-1,2,4-triazol-3-yl)methanol (100 mg, 0.19 mmol) was dissolved in 1,4-dioxane (3 mL). To this, 2-chloro-5-hydroxybenzotrifluoride (Tokyo Chemical Industry Co., Ltd., Catalog Number: F0754) (780 mg, 5.7 mmol) and cyanomethylene tributylphosphorane (109 mg, 0.56 mmol) were added and the mixture was stirred at 100° C. for 10 hours. To the reaction mixture, cyanomethylene tributylphosphorane (109 mg, 0.56 mmol) was added, and the mixture was stirred at 100° C. for 6 hours. To the reaction mixture, N,N-dimethylformamide (1 mL) was added, and the mixture was stirred at 100° C. for 20 hours.

After the reaction temperature had returned to room temperature, the residue obtained by concentration under reduced pressure was purified by NH silica gel column chromatography [elution solvent: methanol/ethyl acetate=0/1-3/7 (V/V)] to obtain the title compound (10 mg (yield: 10%)) as a light yellow solid.

Example 6

4-{4-[(1R)-1-(Azetidin-1-yl)ethyl]phenyl}-1-[trans-4-(4-methyl-5-{[3-(propan-2-yl)phenoxy]methyl}-4H-1,2,4-triazol-3-yl)cyclohexyl]-1H-1,2,3-triazole (6a)

Methyl 4-[(1R)-1-(azetidin-1-yl)ethyl]benzoate

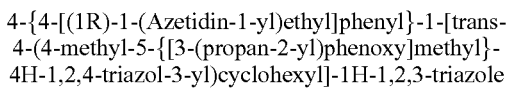

(R)-Methyl 4-(1-aminoethyl)benzoate (CAS Registry Number: (912342-10-0, WO2011106632) (1.5 g, 8.4 mmol) was dissolved in acetonitrile (40 mL). To this, diisopropylethylamine (3.6 mL, 21 mmol), tetrabutylammonium iodide (0.15 g, 0.42 mmol) and 1,3-dibromopropane (Tokyo Chemical Industry Co., Ltd., Catalog Number: D0202) (0.85 mL, 8.4 mmol) were added at room temperature, and the mixture was stirred at 100° C. for 9 hours.

After the reaction temperature had returned to room temperature, saturated aqueous sodium bicarbonate was added to the reaction mixture, and the obtained reaction mixture was extracted with dichloromethane. The organic layer was dried over anhydrous magnesium sulfate. The residue obtained by concentration under reduced pressure was purified by NH silica gel column chromatography [elution solvent: hexane/ethyl acetate=1/1-1/0 (V/V)] to obtain the title compound (1.65 g (yield: 90%)) as a yellow oily substance.

(6b)

{4-[(1R)-1-(Azetidin-1-yl)ethyl]phenyl}methanol

The compound of Example 6(6a): methyl 4-[(1R)-1-(azetidin-1-yl)ethyl]benzoate (1.35 g, 6.16 mmol) was dissolved in tetrahydrofuran (30 mL). To this, a lithium aluminium hydride-tetrahydrofuran solution (2.5 M, 2.5 mL) was added under ice-cooling, and the mixture was stirred at room temperature for 1 hour.

To the reaction mixture, water (0.25 mL), a 15% aqueous sodium hydroxide solution (0.25 mL), and water (0.75 mL) were sequentially added, and the mixture was stirred at room temperature for 10 minutes.

The reaction mixture was diluted with ethyl acetate, and filtered with celite. The filtrate was concentrated under reduced pressure to obtain the title compound (1.06 g (yield: 90%)) as a yellow oily substance.

(6c)

1-[(1R)-1-(4-Ethynylphenyl)ethyl]azetidine

The compound of Example 6(6b): {4-[(1R)-1-(azetidin-1-yl)ethyl]phenyl}methanol (1.06 g, 5.54 mmol) was dissolved in 1,4-dioxane (25 mL), and manganese dioxide (IV) (723 mg, 8.31 mmol) at room temperature, and the mixture was stirred at 80° C. for 2 hours. To the reaction mixture, manganese dioxide (IV) (723 mg, 8.31 mmol) was added at room temperature, and the mixture was stirred at 80° C. for 9 hours.

After the reaction temperature had returned to room temperature, the reaction mixture was filtered with celite. The filtrate was concentrated under reduced pressure and the resultant residue was dissolved in methanol (25 mL). To this, potassium carbonate (1.06 g, 11.1 mmol) and dimethyl(1-diazo-2-oxopropyl)phosphonate (0.83 mL, 5.54 mmol) were added under ice-cooling, and the mixture was stirred at room temperature for 3 hours.

The reaction mixture was diluted with dichloromethane and water and then extracted with dichloromethane. The organic layer was dried over anhydrous magnesium sulfate. The residue obtained by concentration under reduced pressure was purified by silica gel column chromatography [elution solvent: hexane/ethyl acetate=9/1-1/1 (V/V)] to obtain the title compound (740 mg (yield: 72%)) as a light yellow oily substance.

(6d)

4-{4-[(1R)-1-(Azetidin-1-yl)ethyl]phenyl}-1-[trans-4-(4-methyl-5-{[3-(propan-2-yl)phenoxy]methyl}-4H-1,2,4-triazol-3-yl)cyclohexyl]-1H-1,2,3-triazole The compound of Example 3(3e): 3-(trans-4-azidocyclohexyl)-4-methyl-5-{[3-(propan-2-yl)phenoxy]methyl}-4H-1,2,4-triazole (50 mg, 0.14 mmol) was dissolved in tetrahydrofuran (3 mL). To this, the compound of Example 6(6c): 1-[(1R)-1-(4-ethynylphenyl) ethyl]azetidine (31 mg, 0.17 mmol), N,N-diisopropylethylamine (0.074 mL, 0.42 mmol) and copper(I) iodide (32 mg, 0.17 mmol) were added at room temperature, and the mixture was stirred at room temperature for 24 hours.

The residue obtained by concentration under reduced pressure was purified by NH silica gel column chromatography [elution solvent: methanol/ethyl acetate=0/1-1/4 (V/V)] to obtain the title compound (66 mg (yield: 87%)) as a white solid.

Example 7

4-{4-[(1R)-1-(Azetidin-1-yl)ethyl]phenyl}-1-[4-(4-methyl-5-{(1S)-1-[3-(propan-2-yl)phenoxy]ethyl}-4H-1,2,4-triazol-3-yl)bicyclo[2.2.2]oct-1-yl]-1H-1,2,3-triazole (7a)

tert-Butyl [4-(methylcarbamoyl)bicyclo[2.2.2]oct-1-yl]carbamate

4-[(tert-Butoxycarbonyl)amino]bicyclo[2.2.2]octane-1-carboxylic acid (CAS Registry Number: (863304-76-1, WO2009152133) (2.00 g, 7.43 mmol) was dissolved in dichloromethane (20 mL). To this, methylamine hydrochloride (462 mg, 6.84 mmol), triethylamine (3.09 mL, 22.3 mmol) and O-(7-azabenzotriazol-1-yl)-N,N,N',N'-tetramethyluronium hexafluorophosphate (3.39 g, 8.92 mmol) were added, and the mixture was stirred at 30° C. for 15 hours.

The reaction mixture was diluted with dichloromethane and water, and then extracted with dichloromethane. The organic layer was dried over anhydrous sodium sulfate. The residue obtained by concentration under reduced pressure was purified by silica gel column chromatography [elution solvent: methanol/dichloromethane=1/100-1/50 (V/V)] to obtain the title compound (1.9 g (yield: 91%)) as a white solid.

(7b)

tert-Butyl[4-(methylcarbamothioyl)bicyclo[2.2.2]oct-1-yl]carbamate

The compound of Example 7(7a): tert-Butyl [4-(methylcarbamoyl)bicyclo[2.2.2]oct-1-yl]carbamate (1.9 g, 6.73 mmol) was dissolved in tetrahydrofuran (20 mL). To this, Lawesson's reagent (2.86 g, 7.07 mmol) was added, and the mixture was stirred at 90° C. for 12 hours.

The reaction mixture was diluted with water, and then extracted with ethyl acetate. The organic layer was washed with saturated saline, and dried over anhydrous sodium sulfate. The residue obtained by concentration under reduced pressure was purified by silica gel column chromatography [elution solvent: ethyl acetate/petroleum ether=1/10-1/1 (V/V)] to obtain the title compound (1.4 g (yield: 70%)) as a white solid.

(7c)

Methyl(2S)-2-[3-(propan-2-yl)phenoxy]propanoate

3-Isopropylphenol (20 g, 147 mmol) was dissolved in tetrahydrofuran (200 mL). To this, methyl (2R)-2-hydroxypropanoate (CAS Registry Number: 17392-83-5, Journal of Organic Chemistry (1987), 52(22), 4978-84) (15.3 g, 147 mmol), triphenylphosphine (42.4 g, 162 mmol) and diethyl azodicarboxylate (28.1 g, 162 mmol) were added under ice-cooling, and the mixture was stirred at 50° C. for 15 hours.

To the reaction mixture, water was added, and the mixture was extracted with ethyl acetate. The organic layer was washed with saturated saline, and dried over anhydrous sodium sulfate. The residue obtained by concentration under reduced pressure was purified by silica gel column chromatography [elution solvent: ethyl acetate/petroleum ether=1/500-1/100 (V/V)] to obtain the title compound (22 g (yield: 67%)) as a white solid.

(7d)

(2S)-2-[3-(Propan-2-yl)phenoxy]propanehydrazide

The compound of Example 7(7c): methyl (2S)-2-[3-(propan-2-yl)phenoxy]propanoate (22 g, 99 mmol) was dissolved in ethanol (220 mL). To this, hydrazine monohydrate (19.8 g, 396 mmol) was added, and the mixture was stirred at 50° C. for 13 hours.

After the reaction temperature had returned to room temperature, the mixture was concentrated under reduced pressure to obtain the title compound (16.9 g (yield: 77%)) as a colorless oily substance.

(7e)

4-{4-[(1R)-1-(Azetidin-1-yl)ethyl]phenyl}-1-[4-(4-methyl-5-{(1S)-1-[3-(propan-2-yl)phenoxy]ethyl}-4H-1,2,4-triazol-3-yl)bicyclo[2.2.2]oct-1-yl]-1H-1,2,3-triazole

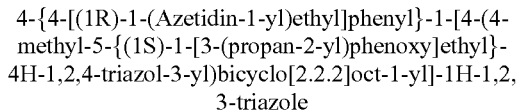

The compound of Example 7(7b): tert-butyl [4-(methylcarbamothioyl)bicyclo[2.2.2]octa-1-yl]carbamate (900 mg, 3.02 mmol) was dissolved in tetrahydrofuran (2 mL). To this, methyl iodide (3.38 mL, 54.4 mmol) and potassium carbonate (1.25 g, 9.06 mmol) were added and the mixture was stirred at 80° C. for 15 hours.

To the reaction mixture, water was added, and the mixture was extracted with ethyl acetate. The organic layer was washed with saturated saline, and dried over anhydrous sodium sulfate. The residue obtained by concentration under reduced pressure was dissolved in tert-butanol (20 mL). To this, the compound of Example 7(7d): (2S)-2-[3-(propan-2-yl)phenoxy] propane hydrazide (1.07 g, 4.80 mmol) was added and the mixture was stirred at 120° C. for 60 hours.

After the reaction temperature had returned to room temperature, the residue obtained by concentration under reduced pressure was purified by silica gel column chromatography [elution solvent: methanol/dichloromethane=1/100-1/40 (V/V)] to obtain tert-butyl [4-(4-methyl-5-{(1S)-1-[3-(propan-2-yl)phenoxy]ethyl}-4H-1,2,4-triazol-3-yl)bicyclo[2.2.2]octa-1-yl]carbamate as a yellow oily substance.

The obtained tert-butyl[4-(4-methyl-5-{(1S)-1-[3-(propan-2-yl)phenoxy]ethyl}-4H-1,2,4-triazol-3-yl)bicyclo[2.2.2]octa-1-yl]carbamate (800 mg, 1.71 mmol) was dissolved in ethyl acetate (5 mL). To this, 4N hydrochloric acid-ethyl acetate (2.14 mL, 8.56 mmol) was added under ice-cooling and the mixture was stirred at 30° C. for 1 hour.

The residue obtained by concentration under reduced pressure was dissolved in dichloromethane (5 mL). To this, triethylamine (1.37 mL, 9.88 mmol) and 2-azido-1,3-dimethylimidazolinium hexafluorophosphate (676 mg, 2.37 mmol) were added and the mixture was stirred at 50° C. for 12 hours.

To the reaction mixture, water was added, and the mixture was extracted with dichloromethane. The organic layer was washed with saturated saline, and dried over anhydrous sodium sulfate. Of 800 mg of the residue obtained by concentration under reduced pressure, 400 mg of the residue was dissolved in tetrahydrofuran (5 mL). To this, copper (I) iodide (192 mg, 1.01 mmol), N,N-diisopropylethylamine (0.27 mL, 1.5 mmol) and the compound of Example 6(6c):

1-[(1R)-1-(4-ethynylphenyl)ethyl] azetidine (187 mg, 1.01 mmol) were added, and the mixture was stirred at 30° C. for 12 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: methanol/dichloromethane=1/50-1/10 (V/V)] to obtain the title compound (200 mg (yield: 24%)) as a yellow solid.

Example 8

(3R,6S)—N,N-Dimethyl-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine (8a)

tert-Butyl [(3R,6S)-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-yl]carbamate

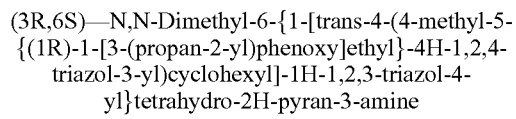

The compound of Example 4(4d): 3-(trans-4-azidocyclohexyl)-4-methyl-5-{(1R)-1-[3-(propan-2-yl)phenoxy]ethyl}-4H-1,2,4-triazole (210 mg, 0.57 mmol) was dissolved in N,N-dimethylformamide (10 mL) and water (1 mL). To this, tert-Butyl [(3R,6S)-6-ethynyltetrahydro-2H-pyran-3-yl]carbamate (CAS Registry Number: 881657-41-6, WO2006032466) (141 mg, 0.62 mmol), sodium ascorbate (45.5 mg, 0.23 mmol) and copper (II) sulfate pentahydrate (28 mg, 0.11 mmol) were added, and the mixture was stirred at room temperature for 18 hours.

To the reaction mixture, methanol was added, and the precipitated solid was dissolved and ethyl acetate and saturated aqueous sodium bicarbonate were added. The mixture was extracted with ethyl acetate. The organic layer was washed with water, then with saturated saline, and then dried over anhydrous sodium sulfate. The residue obtained by concentration under reduced pressure was purified by silica gel column chromatography [elution solvent: hexane/ethyl acetate=3/2-0/1 (V/V), methanol/ethyl acetate=1/3 (V/V)] to obtain the title compound (252 mg (yield: 74%)) as a white solid.

(8b)

(3R,6S)—N,N-Dimethyl-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine The compound of Example 8(8a): tert-butyl [(3R,6S)-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-yl]carbamate (249 mg, 0.42 mmol) was dissolved in methanol (4 mL). To this, 4N hydrochloric acid-1,4-dioxane (8 mL, 32 mmol) was added and the mixture was stirred at room temperature for 1 hour.

The residue obtained by concentrating the reaction mixture under reduced pressure was purified by NH silica gel column chromatography [elution solvent: methanol/ethyl acetate=0/1-1/1 (V/V)]. To the obtained crude product, acetonitrile was added, and the precipitated solid was collected by filtration to obtain (3R,6S)-6-{1-[trans-4-(4- methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine (179 mg) as a white solid.

The obtained (3R,6S)-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine (83 mg, 0.17 mmol) was dissolved in dichloromethane (8 mL). To this, a formaldehyde solution (37%) (0.28 mL, 3.7 mmol), acetic acid (0.06 mL, 3.7 mmol) and sodium triacetoxyborohydride (760 mg, 3.6 mmol) were added at room temperature and the mixture was stirred for 2 hours.

To the reaction mixture, methanol, dichloromethane and saturated aqueous sodium bicarbonate were added, and the mixture was extracted with dichloromethane. The organic layer was dried over anhydrous sodium sulfate. The residue obtained by concentration under reduced pressure was purified by NH silica gel column chromatography [elution solvent: hexane/ethyl acetate=3/2-1/0, methanol/ethyl acetate=15/85 (V/V)]. To the obtained crude product, acetonitrile was added, and the precipitated solid was collected by filtration to obtain the title compound (93 mg (yield: 46%)) as a white solid.

Example 9

N,N-Dimethyl-1-{1-[trans-4-(4-methyl-5-{[3-(trifluoromethyl)phenoxy]methyl}-4H-1,2,4-triazol-3-yl)cyclohexyl]-1H-1,2,3-triazol-4-yl}-2-oxabicyclo[2.2.2]octan-4-amine (9a)

tert-Butyl (1-ethynyl-2-oxabicyclo[2.2.2]oct-4-yl)carbamate tert-Butyl (1-formyl-2-oxabicyclo[2.2.2]oct-4-yl)carbamate (PharmaBlock, Inc., Catalog Number: PBJL0125) (500 mg, 1.96 mmol) was dissolved in methanol (7.8 mL). To this, potassium carbonate (541 mg, 3.92 mmol) and dimethyl (1-diazo-2-oxopropyl)phosphonate (0.35 mL, 2.35 mmol) were added under ice-cooling, and the mixture was stirred at room temperature for 3 hours.

The reaction mixture was diluted with dichloromethane and water, and then extracted with dichloromethane. The organic layer was washed with a saturated aqueous ammonium chloride solution and dried over anhydrous sodium sulfate. To the residue obtained by concentration under reduced pressure, water was added, and the precipitated solid was collected by filtration to obtain the title compound (474 mg (yield: 96%)) as a white solid.

(9b)

tert-Butyl N-[trans-4-[4-methyl-5-[[3-(trifluoromethyl)phenoxy]methyl]-1,2,4-triazol-3-yl]cyclohexyl]carbamate The compound of Example 3(3b): methyl trans-4-(tert-butoxycarbonylamino)-N-methyl-cyclohexane carboxyimidothioate (200 mg, 0.70 mmol) was dissolved in N,N-dimethylformamide (3 mL). To this, the compound of Example 1(1a): 2-[3-(trifluoromethyl)phenoxy]acetohydrazide (164 mg, 0.70 mmol) of Example 1 (1a) was added and the mixture was stirred at 110° C. for 8 hours.

After the reaction temperature had returned to room temperature, the reaction mixture was poured into water and extracted with ethyl acetate. The organic layer was washed with water and saturated saline and dried over anhydrous magnesium sulfate. The residue obtained by concentration under reduced pressure was purified by silica gel column chromatography [elution solvent: hexane/ethyl acetate=1/1-0/1, ethyl acetate/methanol=7/3 (V/V)] to obtain the title compound (216 mg (yield: 68%)) as a white solid.

(9c)

trans-4-[4-Methyl-5-[[3-(trifluoromethyl)phenoxy]methyl]-1,2,4-triazol-3-yl]cyclohexanamine The compound of Example 9(9b): tert-butyl N-[trans-4-[4-methyl-5-[[3-(trifluoromethyl)phenoxy]methyl]-1,2,4-triazol-3-yl]cyclohexyl]carbamate (216 mg, 0.48 mmol) was dissolved in dichloromethane (3 mL). To this, trifluoroacetic acid (3 mL, 39 mmol) was added, and the mixture was stirred at room temperature for 27 hours.

The residue obtained by concentration under reduced pressure was dissolved in methanol (5 mL) and desalted with Amberlyst A-26 (OH) (Sigma-Aldrich, Catalog Number: 542571). The eluate was filtered and then concentrated under reduced pressure to obtain the title compound (160 mg (yield: 95%)) as a colorless oily substance.

(9d)

3-(trans-4-Azidocyclohexyl)-4-methyl-5-{[3-(trifluoromethyl)phenoxy]methyl}-4H-1,2,4-triazole The compound of Example 9(9c): trans-4-[4-methyl-5-[[3-(trifluoromethyl)phenoxy]methyl]-1,2,4-triazol-3-yl]cyclohexaneamine (300 mg, 0.85 mmol) was dissolved in dichloromethane (8 mL). To this, triethylamine (0.59 mL, 4.2 mmol) and 2-azido-1,3-dimethylimidazolinium hexafluorophosphate (0.29 g, 1 mmol) were added and the mixture was stirred at 30° C. for 1 hour.

To the reaction mixture, saturated aqueous sodium bicarbonate was added, and the reaction mixture was extracted with dichloromethane. The combined organic layer was dried over anhydrous magnesium sulfate. The residue obtained by concentration under reduced pressure was purified by NH silica gel column chromatography [elution solvent: ethyl acetate alone] to obtain the title compound (283 mg (yield: 88%)) as a white solid.

(9e)

tert-Butyl (1-{1-[trans-4-(4-methyl-5-{[3-(trifluoromethyl)phenoxy]methyl}-4H-1,2,4-triazol-3-yl)cyclohexyl]-1H-1,2,3-triazol-4-yl}-2-oxabicyclo[2.2.2]oct-4-yl)carbamate The compound of Example 9(9d): 3-(trans-4-azidocyclohexyl)-4-methyl-5-{[3-(trifluoromethyl)phenoxy]methyl}-4H-1,2,4-triazole (500 mg, 1.31 mmol) was dissolved in tetrahydrofuran (7 mL). To this, the compound of Example 9 (9a): tert-butyl (1-ethynyl-2-oxabicyclo [2.2.2] octa-4-yl) carbamate (363 mg, 1.45 mmol) was added, and then a solution of tris[(1-benzyl-1H-1,2,3-triazol-4-yl)methyl]amine (140 mg, 0.26 mmol) and tetrakis(acetonitrile)copper (I) hexafluorophosphate (98 mg, 0.26 mmol) in tetrahydrofuran (1 mL) and water (0.2 mL) was added, and the mixture was stirred for 2 hours, and then allowed to stand still for 12 hours.

To the reaction mixture, methanol and dichloromethane were added, and the reaction mixture was extracted with dichloromethane. The combined organic layer was washed with saturated aqueous sodium bicarbonate and dried over anhydrous sodium sulfate. To the residue obtained by concentration under reduced pressure, ethyl acetate was added, and the precipitated solid was collected by filtration to obtain the title compound (756 mg (yield: 91%)) as a white solid.

(9f)

N,N-Dimethyl-1-{1-[trans-4-(4-methyl-5-{[3-(trifluoromethyl)phenoxy]methyl}-4H-1,2,4-triazol-3-yl)cyclohexyl]-1H-1,2,3-triazol-4-yl}-2-oxabicyclo[2.2.2]octan-4-amine

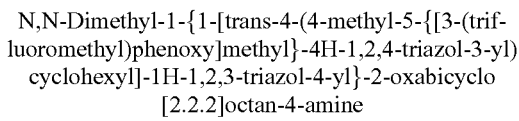

The compound of Example 9(9e): tert-butyl (1-{1-[trans-4-(4-methyl-5-{[3-(trifluoromethyl)phenoxy]methyl}-4H-1,2,4-triazol-3-yl)cyclohexyl]-1H-1,2,3-triazol-4-yl}-2-oxabicyclo [2.2.2]octa-4-yl)carbamate (750 mg, 1.19 mmol) was dissolved in dichloromethane (3 mL). To this, trifluoroacetic acid (0.91 mL, 11.9 mmol) was added, and the mixture was stirred at room temperature for 3 hours.

After the mixture was concentrated under reduced pressure and azeotropically concentrated with toluene, the residue was dissolved in dichloromethane (5 mL) and methanol (2 mL). To this, a formaldehyde solution (37%) (0.55 mL, 7.4 mmol) was added, and the mixture was stirred at room temperature for 5 minutes. To the reaction mixture, sodium triacetoxyborohydride (2.1 g, 9.9 mmol) was added, and the mixture was stirred at room temperature for 1 hour and allowed to stand still for 12 hours.

To the reaction mixture, saturated aqueous sodium bicarbonate was added, and the reaction mixture was extracted with dichloromethane. The organic layer was washed with saturated saline, and dried over anhydrous sodium sulfate. The residue obtained by concentration under reduced pressure was purified by NH silica gel column chromatography [elution solvent: methanol/dichloromethane=0/1-1/9 (V/V)]. To the obtained residue, ethyl acetate and hexane were added, and the precipitated solid was collected by filtration to obtain the title compound (320 mg (yield: 46%)) as a white solid.

Example 10

4-[4-(Azetidin-1-ylmethyl)bicyclo[2.2.2]oct-1-yl]-1-[trans-4-(4-methyl-5-{[3-(trifluoromethyl)phenoxy]methyl}-4H-1,2,4-triazol-3-yl)cyclohexyl]-1H-1,2,3-triazole

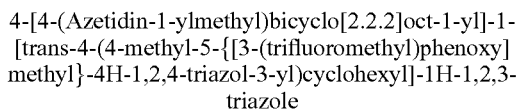

(10a)

Methyl 4-(azetidin-1-ylcarbonyl)bicyclo[2.2.2]octane-1-carboxylate

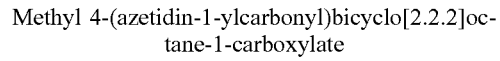

4-(Methoxycarbonyl)bicyclo[2.2.2]octane-1-carboxylic acid (CAS Registry Number: 18720-35-9, WO2001034610) (3 g, 14.1 mmol) was dissolved in N,N-dimethylformamide (50 mL). To this, azetidine hydrochloride (1.22 g, 13.0 mmol), triethylamine (5.88 ml, 42.4 mmol) and O-(7-azabenzotriazol-1-yl)-N,N,N',N'-tetramethyluronium hexafluorophosphate (6.45 g, 17.0 mmol) were added, and the mixture was stirred at 30° C. for 15 hours.

The reaction mixture was filtered and the filtrate was concentrated under reduced pressure. The resultant residue was purified by high performance liquid chromatography to obtain the title compound (2.3 g (yield: 65%)) as a white solid.

(10b)

Azetidin-1-yl[4-(hydroxymethyl)bicyclo[2.2.2]oct-1-yl]methanone

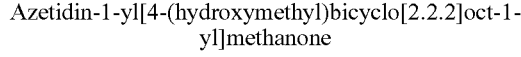

Lithium aluminium hydride (453 mg, 11.9 mmol) was added to tetrahydrofuran (30 mL). To this, a solution of the compound of Example 10(10a): methyl 4-(azetidin-1-ylcarbonyl)bicyclo[2.2.2]octane-1-carboxylate (1 g, 3.98 mmol) in tetrahydrofuran (10 mL) was added, and the mixture was stirred at 30° C. for 30 minutes.

To the reaction mixture, water (1 mL), 15% aqueous sodium hydroxide solution (1 mL), and water (1 mL) were sequentially added. The reaction mixture was filtered, and the filtrate was concentrated under reduced pressure to obtain the title compound (820 mg (yield: 99%)) as a light yellow oily substance.

(10c)

4-(Azetidin-1-ylcarbonyl)bicyclo[2.2.2]octane-1-carbaldehyde

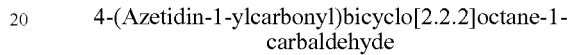

Dimethylsulfoxide (269 mg, 3.44 mmol) was dissolved in dichloromethane (5 mL). To this, a solution of oxalyl chloride (546 mg, 4.31 mmol) in dichloromethane (5 mL) was added dropwise at −78° C., and the mixture was stirred for 5 minutes. To the reaction mixture, a solution of Example 10(10b): azetidin-1-yl [4-(hydroxymethyl)bicyclo [2.2.2]oct-1-yl]methanone (600 mg, 2.87 mmol) in dichloromethane (5 mL) was added dropwise and the mixture was stirred at −78° C. for 30 minutes. To the reaction mixture, triethylamine (3 mL) was added, and the mixture was stirred at the same temperature for 15 minutes, and gradually warmed to room temperature, and then stirred for 10 minutes.

The reaction mixture was diluted with dichloromethane. To this, water was added, and the mixture was extracted with dichloromethane. The organic layer was washed with water and dried over anhydrous sodium sulfate. The resultant was concentrated under reduced pressure to obtain the title compound (550 mg (yield: 71%)) as a light yellow oily substance.

(10d)

Azetidin-1-yl(4-ethynylbicyclo[2.2.2]oct-1-yl)methanone

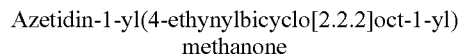

The compound of Example 10(10c): 4-(azetidin-1-ylcarbonyl)bicyclo[2.2.2]octane-1-carbaldehyde (550 mg, 2.65 mmol) was dissolved in methanol (15 ml). To this, potassium carbonate (1.10 g, 7.95 mmol) and dimethyl(1-diazo-2-oxopropyl)phosphonate (763 mg, 3.98 mmol) were added and the mixture was stirred at room temperature for 1.5 hours.

To the reaction mixture, water (20 mL) was added, and the reaction mixture was extracted with dichloromethane. The residue obtained by concentration under reduced pressure was purified by silica gel column chromatography [elution solvent: methanol/ethyl acetate=1/5 (V/V)] to obtain the title compound (280 mg (yield: 52%)) as a white solid.

(10e)

4-[4-(Azetidin-1-ylmethyl)bicyclo[2.2.2]oct-1-yl]-1-[trans-4-(4-methyl-5-{[3-(trifluoromethyl)phenoxy]methyl}-4H-1,2,4-triazol-3-yl)cyclohexyl]-1H-1,2,3-triazole

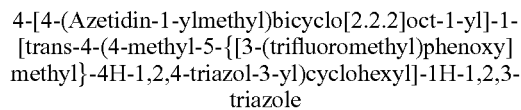

The compound of Example 10(10d): azetidin-1-yl(4-ethynylbicyclo[2.2.2]oct-1-yl)methanone (260 mg, 1.28 mmol) and Example 9(9d): 3-(trans-4-azidocyclohexyl)-4-methyl- 5-{[3-(trifluoromethyl)phenoxy]methyl}-4H-1,2,4-triazole (486 mg, 1.28 mmol) were dissolved in tetrahydrofuran (5 mL) and water (5 mL). To this, sodium ascorbate (51 mg, 0.26 mmol) and copper (II) sulfate pentahydrate (32 mg, 0.13 mmol) were added and the mixture was stirred at 60° C. for 15 hours.

To the reaction mixture, water (30 mL) was added, and the reaction mixture was extracted with dichloromethane. The organic layer was dried over anhydrous sodium sulfate. The residue obtained by concentration under reduced pressure was purified by silica gel column chromatography [elution solvent: methanol/dichloromethane=1/15 (V/V)] to obtain the title compound (321 mg (yield: 44%)) as a white solid.

Example 11

N,N-Dimethyl-4-{1-[trans-4-(4-methyl-5-{[3-(trifluoromethyl)phenoxy]methyl}-4H-1,2,4-triazol-3-yl)cyclohexyl]-1H-1,2,3-triazol-4-yl}bicyclo[2.2.2]octan-1-amine 4-Ethynyl-N,N-dimethylbicyclo[2.2.2]octane-i-amine (CAS Registry Number: 96454-76-1, J. Org. Chem. 1985, 50, 2551-2557) (100 mg, 0.56 mmol) was dissolved in tetrahydrofuran (5 mL) and water (5 mL). To this, the compound of Example 9(9d): 3-(trans-4-azidocyclohexyl)-4-methyl-5-{[3-(trifluoromethyl)phenoxy]methyl}-4H-1,2,4-triazole (215 mg, 0.56 mmol), sodium ascorbate (11 mg, 0.56 mmol) and copper(II) sulfate pentahydrate (18 mg, 0.11 mmol) were added, and the mixture was further stirred at 60° C. for 3 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: methanol/dichloromethane=0/1-1/1 (V/V), 0.1% ammonia water] to obtain the title compound (96 mg (yield: 30%)) as a yellow solid.

Example 12

N,N-Dimethyl-3-{1-[trans-4-(4-methyl-5-{[3-(trifluoromethyl)phenoxy]methyl}-4H-1,2,4-triazol-3-yl)cyclohexyl]-1H-1,2,3-triazol-4-yl}bicyclo[1.1.1]pentan-1-amine tert-Butyl (3-ethynylbicyclo[1.1.1]pent-1-yl)carbamate (CAS Registry Number: 1638761-54-2, WO2015141616) (150 mg, 0.72 mmol) was dissolved in tert-butanol (4 mL) and water (4 mL). To this, the compound of Example 9(9d): 3-(trans-4-azidocyclohexyl)-4-methyl-5-{[3-(trifluoromethyl)phenoxy]methyl}-4H-1,2,4-triazole (303 mg, 0.8 mmol), sodium ascorbate (29 mg, 0.15 mmol) and copper (II) sulfate pentahydrate (18 mg, 0.07 mmol) were added, and the mixture was stirred at 60° C. for 24 hours.

The reaction mixture was extracted with ethyl acetate. The organic layer was washed with saturated saline, and dried over anhydrous sodium sulfate. The residue obtained by concentration under reduced pressure was purified by thin layer silica gel chromatography [developing solvent: methanol/dichloromethane=1/1 (V/V)] to obtain tert-butyl (3-{1-[trans-4-(4-methyl-5-{[3-(trifluoromethyl)phenoxy]methyl}-4H-1,2,4-triazol-3-yl)cyclohexyl]-1H-1,2,3-triazol-4-yl}bicyclo[1.1.1]pent-1-yl)carbamate (220 mg) as a white solid.

The obtained tert-butyl (3-{1-[trans-4-(4-methyl-5-{[3-(trifluoromethyl)phenoxy]methyl}-4H-1,2,4-triazol-3-yl)cyclohexyl]-1H-1,2,3-triazol-4-yl}bicyclo[1.1.1]pent-1-yl)carbamate (220 mg) was dissolved in ethyl acetate (2 mL). To this, 4N hydrochloric acid-ethyl acetate (2 mL, 8 mmol) was added under ice-cooling, and the mixture was stirred at room temperature for 20 hours.

The residue obtained by concentrating the reaction mixture under reduced pressure was dissolved in methanol (8 mL). To this, a formaldehyde solution (37%) (0.32 mL, 1.2 mmol), acetic acid (0.011 mL, 0.19 mmol) and sodium cyanoborohydride (95.9 mg, 1.53 mmol) were added at room temperature and the mixture was stirred for 2.5 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: ethyl acetate/petroleum ether=1/50-1/10 (V/V)] to obtain the title compound (157 mg (yield: 80%)) as a white solid.

Example 13

4-Fluoro-1-methyl-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine (13a)

tert-Butyl N-[(3R,6S)-6-(methylcarbamothioyl)tetrahydropyran-3-yl]carbamate tert-Butyl N-[(3R,6S)-6-(methylcarbamoyl)tetrahydropyran-3-yl]carbamate (CAS Registry Number: 1398570-72-3, WO2012121361) (914 mg, 3.5 mmol) was added to tetrahydrofuran (20 mL). To this, Lawesson's reagent (1.6 g, 3.9 mmol) was added, and the mixture was stirred at 80° C. for 15 hours.

After the reaction temperature had returned to room temperature, the residue obtained by concentration under reduced pressure was purified by silica gel column chromatography [elution solvent: hexane/ethyl acetate=7/3-3/7 (V/V)] to obtain the title compound (580 mg (yield: 59%)) as a white solid.

(13b)

tert-Butyl N-[(3R,6S)-6-[5-[(3-isopropylphenoxy)methyl]-4-methyl-1,2,4-triazol-3-yl]tetrahydropyran-3-yl]carbamate The compound of Example 13(13a): tert-butyl N-[(3R,6S)-6-(methylcarbamothioyl)tetrahydropyran-3-yl]carbamate (580 mg, 2.1 mmol) was dissolved in tetrahydrofuran (15 mL). To this, potassium carbonate (351 mg, 2.5 mmol) and methyl iodide (600 mg, 4.2 mmol) were added and the mixture was stirred for 23 hours under reflux with heating.

After the reaction temperature had returned to room temperature, the reaction mixture was filtered and concentrated under reduced pressure. The resultant residue was dissolved in 1,4-dioxane (20 mL) and to the solution 2-(3-isopropylphenoxy)acetohydrazide (441 mg, 2.1 mmol) was added, and the mixture was stirred at 110° C. for 30 minutes.

After cooling, the residue obtained by concentration under reduced pressure was purified by silica gel column chromatography [elution solvent: methanol/ethyl acetate=0/

1-1/9 (V/V)] to obtain the title compound (499 mg (yield: 63%)) as a colorless oily substance.
(13c)

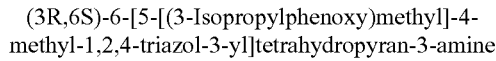

(3R,6S)-6-[5-[(3-Isopropylphenoxy)methyl]-4-methyl-1,2,4-triazol-3-yl]tetrahydropyran-3-amine The compound of Example 13(13b): tert-Butyl N-[(3R,6S)-6-[5-[(3-isopropylphenoxy)methyl]-4-methyl-1,2,4-triazol-3-yl]tetrahydropyran-3-yl]carbamate (499 mg, 1.6 mmol) was dissolved in dichloromethane (5 mL). To this, trifluoroacetic acid (5 mL) was added, and the mixture was stirred at room temperature for 1 hour.

The residue obtained by concentration under reduced pressure was purified by NH silica gel column chromatography [elution solvent: methanol/ethyl acetate=0/1-4/6 (V/V)] to obtain the title compound (377 mg (yield: 98%)) as a colorless oil.
(13d)

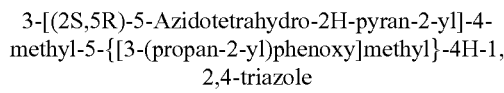

3-[(2S,5R)-5-Azidotetrahydro-2H-pyran-2-yl]-4-methyl-5-{[3-(propan-2-yl)phenoxy]methyl}-4H-1,2,4-triazole The compound of Example 13(13c): (3R, 6S)-6-[5-[(3-isopropylphenoxy)methyl]-4-methyl-1,2,4-triazol-3-yl]tetrahydropyran-3-amine (300 mg, 0.91 mmol) was dissolved in acetonitrile (50 mL). To this, triethylamine (0.63 mL, 4.5 mmol) and 2-azido-1,3-dimethylimidazolinium hexafluorophosphate (0.31 g, 1.1 mmol) were added, and the mixture was stirred at 50° C. for 2 hours.

To the reaction mixture, saturated aqueous sodium bicarbonate was added, and the reaction mixture was extracted with ethyl acetate. The combined organic layer was dried over anhydrous sodium sulfate. The residue obtained by concentration under reduced pressure was purified by NH silica gel column chromatography [elution solvent: methanol/ethyl acetate=0/1-1/9 (V/V)] to obtain the title compound (295 mg (yield: 91%)) as a colorless oil.
(13e)

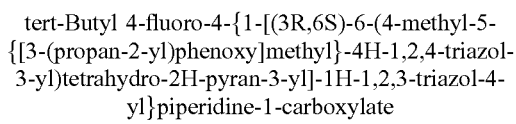

tert-Butyl 4-fluoro-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine-1-carboxylate The compound of Example 13(13d): 3-[(2S,5R)-5-azidotetrahydro-2H-pyran-2-yl]-4-methyl-5-{[3-propan-2-yl)phenoxy]methyl}-4H-1,2,4-triazole (200 mg, 0.56 mmol) was dissolved in tetrahydrofuran (7 mL). To this, tert-butyl 4-ethynyl-4-fluoropiperidine-1-carboxylate (CAS Registry Number: 191327-86-3, WO1997018202) (140 mg, 0.62 mmol) was added, then a solution of tris[(1-benzyl-1H-1,2,3-triazol-4-yl)methyl]amine (59.6 mg, 0.11 mmol) and tetrakis (acetonitrile) copper (I) hexafluorophosphate (41.8 mg, 0.11 mmol) in tetrahydrofuran (1 mL) and water (0.2 mL) was added, and the mixture was stirred for 2 hours, and allowed to stand still for 12 hours.

To the reaction mixture, methanol, dichloromethane and 1N hydrochloric acid were added, and the mixture was extracted with dichloromethane. The combined organic layer was washed with saturated aqueous sodium bicarbonate and dried over anhydrous sodium sulfate. To the residue obtained by concentration under reduced pressure, ethyl acetate was added, and the precipitated solid was collected by filtration to obtain the title compound (565 mg (yield: 100%)) as a white solid.
(13f)

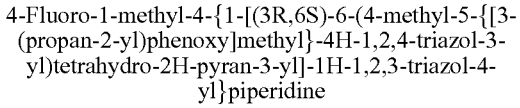

4-Fluoro-1-methyl-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine The compound of Example 13(13e): tert-butyl 4-fluoro-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine-1-carboxylate (400 mg, 0.55 mmol) was dissolved in dichloromethane (1.4 mL). To this, trifluoroacetic acid (0.42 mL, 5.48 mmol) was added and the mixture was stirred at room temperature for 3 hours.

After the resultant was concentrated under reduced pressure and azeotropically concentrated with toluene, the residue was dissolved in dichloromethane (2 mL) and methanol (2 mL). To this, a formaldehyde solution (37%) (0.2 mL, 2.7 mmol) was added, and the mixture was stirred at room temperature for 5 minutes. To the reaction mixture, sodium triacetoxyborohydride (698 mg, 3.29 mmol) was added, and the mixture was stirred at room temperature for 2 hours.

To the reaction mixture, saturated aqueous sodium bicarbonate was added, and the reaction mixture was extracted with dichloromethane. The organic layer was washed with saturated saline, and dried over anhydrous sodium sulfate. The residue obtained by concentration under reduced pressure was purified by NH silica gel column chromatography [elution solvent: methanol/ethyl acetate=0/1-1/9 (V/V)] to obtain the title compound (15 mg (yield: 5.5%)) as a white solid.

Example 14

3-{trans-4-[4-(4-Fluoro-1-methylpiperidin-4-yl)-1H-1,2,3-triazol-1-yl]cyclohexyl}-8-[3-(propan-2-yl) benzyl]-5,6-dihydro-8H-[1,2,4]triazolo[3,4-c][1,4] oxazine (14a)

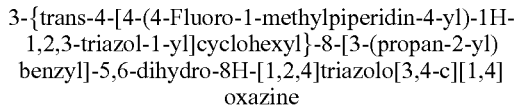

4-(4-Methoxybenzyl)-2-[3-(propan-2-yl)benzyl]morpholin-3-one 4-(4-methoxybenzyl)morpholin-3-one (CAS Registry Number: 570398-19-5, WO2003061652) (6 g, 27.1 mmol) was dissolved in tetrahydrofuran (100 mL). To this, a lithium diisopropylamine-tetrahydrofuran solution (2M, 17.6 ml) was added dropwise at −78° C. and the mixture was stirred for 30 minutes. To this, 1-(bromomethyl)-3-isopropylbenzene (CAS Registry Number: 75369-42-5, J. Am. Chem. Soc. 2014, 136, 642-645) (7.51 g, 35.3 mmol) was then added, and the mixture was stirred at 25° C. for 2.5 hours.

To the reaction mixture, a saturated aqueous ammonium chloride solution was added, and the mixture was extracted with ethyl acetate. The combined organic layer was washed with saturated saline and dried over anhydrous sodium sulfate. The residue obtained by concentration under reduced pressure was purified by high performance liquid chromatography to obtain the title compound (5 g (yield: 52%)) as a yellow solid.
(14b)

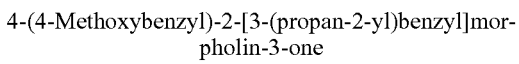

2-[3-(Propan-2-yl)benzyl]morpholin-3-one

To the compound of Example 14(14a) 4-(4-methoxybenzyl)-2-[3-(propan-2-yl)benzyl]morpholin-3-one (5 g, 14.1 mmol), trifluoroacetic acid (100 mL, 1.31 mol) was added, and the mixture was stirred at 120° C. for 36 hours.

To the residue obtained by concentration under reduced pressure, saturated aqueous sodium bicarbonate was added, and the mixture was extracted with dichloromethane. The organic layer was washed with saturated saline, and dried over anhydrous sodium sulfate. The residue obtained by concentration under reduced pressure was purified by silica gel column chromatography [elution solvent: ethyl acetate/petroleum ether=1/10-1/1 (V/V)] to obtain the title compound (3 g (yield: 91%)) as a colorless oil.

(14c)

2-[3-(Propan-2-yl)benzyl]morpholine-3-thione

The compound of Example 14(14b): 2-[3-(propan-2-yl)benzyl]morpholin-3-one (3 g, 12.9 mmol) was dissolved in toluene (30 mL). To this, Lawesson's reagent (3.12 g, 7.72 mmol) was added and the mixture was stirred at 90° C. for 12 hours.

The residue obtained by concentrating the reaction mixture under reduced pressure was purified by silica gel column chromatography [elution solvent: ethyl acetate/petroleum ether=1/10-1/5 (V/V)] to obtain the title compound (1.7 g (yield: 53%)) as a white solid.

(14d)

Methyl trans-4-azidocyclohexanecarboxylate

Methyl trans 4-aminocyclohexane carboxylate hydrochloride (CAS Registry Number: 61367-07-5, WO2003082847) (8 g, 41 mmol) was dissolved in dichloromethane (100 mL). To this, triethylamine (28.6 mL, 207 mmol) and 2-azido-1,3-dimethylimidazolinium hexafluorophosphate (13 g, 45.4 mmol) were added and the mixture was stirred at 50° C. for 12 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: ethyl acetate/petroleum ether=1/10-1/5 (V/V)]] to obtain the title compound (5 g (yield: 66%)) as a white solid.

(14e)

tert-Butyl 4-hydroxy-4-{1-[trans-4-(methoxycarbonyl)cyclohexyl]-1H-1,2,3-triazol-4-yl}piperidine-1-carboxylate tert-Butyl 4-ethynyl-4-hydroxypiperidine-1-carboxylate (CAS Registry Number: 275387-83-2, WO2000035908) (7.38 g, 32.8 mmol) was dissolved in tert-butanol (60 mL) and water (60 mL). The compound of Example 14(14d) methyl trans-4-azidocyclohexane carboxylate (5 g, 27.3 mmol), sodium ascorbate (541 mg, 2.73 mmol) and copper (II) sulfate pentahydrate (341 mg, 1.36 mmol) were added, and the mixture was stirred at room temperature for 12 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: ethyl acetate/petroleum ether=1/10-1/3 (V/V)]] to obtain the title compound (10 g (yield: 90%)) as a yellow solid.

(14f)

tert-Butyl 4-fluoro-4-{1-[trans-4-(methoxycarbonyl)cyclohexyl]-1H-1,2,3-triazol-4-yl}piperidine-1-carboxylate The compound of Example 14(14e): tert-butyl 4-hydroxy-4-{1-[trans-4-(methoxycarbonyl)cyclohexyl]-1H-1,2,3-triazol-4-yl}piperidine-1-carboxylate (10 g, 24.5 mmol) was dissolved in dichloromethane (80 mL). To this, (diethylamino)sulfur trifluoride (3.23 mL, 24.5 mmol) was added at −78° C. and the mixture was stirred at −78° C. for 1 hour, then warmed to room temperature and stirred for 2 hours.

To the reaction mixture, water was added. The reaction mixture was extracted with ethyl acetate. The organic layer was washed with a saturated aqueous potassium carbonate solution and saturated saline and dried over anhydrous sodium sulfate. The residue obtained by concentration under reduced pressure was purified by NH silica gel column chromatography [elution solvent: ethyl acetate/petroleum ether=1/5-1/1 (V/V)]] to obtain the title compound (7 g (yield: 70%)) as a yellow solid.

(14g)

tert-Butyl 4-fluoro-4-{1-[trans-4-(hydrazinylcarbonyl)cyclohexyl]-1H-1,2,3-triazol-4-yl}piperidine-1-carboxylate The compound of Example 14(14f): tert-butyl 4-fluoro-4-{1-[trans-4-(methoxycarbonyl)cyclohexyl]-1H-1,2,3-triazol-4-yl}piperidine-1-carboxylate (3 g, 7.31 mmol) was dissolved in ethanol (20 mL). To this, hydrazine monohydrate (1.81 mL, 36.5 mmol) was added, and the mixture was stirred at 90° C. for 12 hours.

The solvent was mostly distilled off from the reaction mixture under reduced pressure, and the precipitated solid was collected by filtration to obtain the title compound (2.8 g (yield: 93%)) as a white solid.

(14h)

3-{trans-4-[4-(4-Fluoro-1-methylpiperidin-4-yl)-1H-1,2,3-triazol-1-yl]cyclohexyl}-8-[3-(propan-2-yl)benzyl]-5,6-dihydro-8H-[1,2,4]triazolo[3,4-c][1,4]oxazine The compound of Example 14(14c): 2-[3-(propan-2-yl)benzyl]morpholine-3-thione (800 mg, 3.2 mmol) was dissolved in tetrahydrofuran (10 mL). To this, methyl iodide (1 mL, 16 mmol) and potassium carbonate (0.67 g, 4.8 mmol) were added, and the mixture was stirred at 90° C. for 3 hours.

Of 800 mg of the crude product obtained by removing insoluble matters by filtration and concentrating the mother liquid, 400 mg of the crude product was dissolved in isopropyl alcohol (10 mL) and the compound of Example 14(14g): tert-butyl 4-fluoro-4-{1-[trans-4-(hydrazinylcarbonyl)cyclohexyl]-1H-1,2,3-triazol-4-yl}piperidine-1-carboxylate (400 mg, 0.97 mmol) was added and the mixture was stirred at 90° C. for 2 hours.

The reaction mixture was poured into water and extracted with ethyl acetate. The organic layer was dried over anhydrous sodium sulfate. The residue obtained by concentration under reduced pressure was purified by silica gel column chromatography [elution solvent: methanol/dichloromethane=1/100-1/50 (V/V)] to obtain tert-butyl 4-fluoro-4-[1-(trans-4-{8-[3-(propan-2-yl)benzyl]-5,6-dihydro-8H-[1,2,4]

triazolo[3,4-c][1,4]oxazin-3-yl}cyclohexyl)-1H-1,2,3-triazol-4-yl]piperidine-1-carboxylate (350 mg) as a yellow solid.

The obtained tert-butyl 4-fluoro-4-[1-(trans-4-{8-[3-(propan-2-yl)benzyl]-5,6-dihydro-8H-[1,2,4]triazolo[3,4-c][1,4]oxazin-3-yl}cyclohexyl)-1H-1,2,3-triazol-4-yl]piperidine-1-carboxylate (300 mg, 0.49 mmol) was dissolved in methanol (3 mL). To this, 4N hydrochloric acid-methanol (1.2 mL, 4.8 mmol) was added, and the mixture was stirred at room temperature for 2 hours.

The residue obtained by concentrating the reaction mixture under reduced pressure was dissolved in methanol (10 mL). To this, a formaldehyde solution (37%) (0.12 mL, 1.7 mmol), triethylamine (0.21 mL, 1.5 mmol), acetic acid (0.09 ml, 1.5 mmol) and sodium cyanoborohydride (74 mg, 1.2 mmol) were added, and the mixture was stirred at room temperature for 12 hours.

The residue obtained by concentration under reduced pressure was purified by high performance liquid chromatography to obtain the title compound (116 mg (yield: 22%)) as a white solid.

Example 15

3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro[1,2,4]triazolo[4,3-a]pyridine (15a)

3-[3-(Trifluoromethyl)phenoxy]piperidin-2-one 3-(Trifluoromethyl)phenol (CAS Registry Number: 98-17-9, WO2000053611) (640 mg, 3.95 mmol) was dissolved in tetrahydrofuran (15 mL). To this, 3-hydroxypiperidin-2-one (CAS Registry Number: 19365-08-3, Journal of Organic Chemistry (1994), 59 (17), 5084-7) (500 mg, 4.34 mmol), triphenylphosphine (1.14 g, 4.34 mmol) and diethyl azodicarboxylate (756 mg, 4.34 mmol) were added under ice-cooling, and the mixture was stirred at room temperature for 3 hours.

Water was added to the reaction mixture, and it was extracted with ethyl acetate. The organic layer was washed with saturated saline, and dried over anhydrous sodium sulfate. The residue obtained by concentration under reduced pressure was purified by silica gel column chromatography [elution solvent: ethyl acetate/petroleum ether=1/1-1/2 (V/V)] to obtain the title compound (0.72 g (yield: 70%)) as a colorless oily substance.

(15b)

3-[3-(Trifluoromethyl)phenoxy]piperidine-2-thione

The compound of Example 15(15a): 3-[3-(trifluoromethyl)phenoxy]piperidin-2-one (700 mg, 2.7 mmol) was dissolved in toluene (20 mL). To this, Lawesson's reagent (1.1 g, 2.7 mmol) was added, and the mixture was stirred at 110° C. for 2 hours.

To the reaction mixture, water was added, and the mixture was extracted with ethyl acetate. The organic layer was washed with saturated saline, and dried over anhydrous sodium sulfate. The residue obtained by concentration under reduced pressure was purified by silica gel column chromatography [elution solvent: ethyl acetate/petroleum ether=1/10-1/2 (V/V)]] to obtain the title compound (400 mg (yield: 54%)) as a white solid.

(15c)

tert-Butyl 4-fluoro-4-[1-(trans-4-{8-[3-(trifluoromethyl)phenoxy]-5,6,7,8-tetrahydro[1,2,4]triazolo[4,3-a]pyridin-3-yl}cyclohexyl)-1H-1,2,3-triazol-4-yl]piperidine-1-carboxylate The compound of Example 15(15b): 3-[3-(trifluoromethyl)phenoxy]piperidine-2-thione (200 mg, 0.73 mmol) was dissolved in tetrahydrofuran (5 mL). To this, methyl iodide (0.45 mL, 7.27 mmol) and potassium carbonate (0.30 g, 2.2 mmol) were added, and the mixture was stirred at 66° C. for 2 hours.

The residue obtained by concentration under reduced pressure was added to a solution of the compound of Example 14(14g): tert-butyl 4-fluoro-4-{1-[trans-4-(hydrazinylcarbonyl)cyclohexyl]-1H-1,2,3-triazol-4-yl}piperidine-1-carboxylate (500 mg, 1.2 mmol) and triethylamine (0.51 mL, 3.7 mmol) in isopropyl alcohol (5 mL), and the mixture was stirred at 120° C. for 12 hours.

The residue obtained by concentration under reduced pressure was purified by silica gel column chromatography [elution solvent: methanol/dichloromethane=1/100-1/60 (V/V)] to obtain the title compound (380 mg (yield: 49%)) as a white solid.

(15d)

3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro[1,2,4]triazolo[4,3-a]pyridine The compound of Example 15(15c): tert-butyl 4-fluoro-4-[1-(trans-4-{8-[3-(trifluoromethyl)phenoxy]-5,6,7,8-tetrahydro[1,2,4]triazolo[4,3-a]pyridin-3-yl}cyclohexyl)-1H-1,2,3-triazol-4-yl]piperidine-1-carboxylate (380 mg, 0.6 mmol) was dissolved in ethyl acetate (5 mL). To this, 4N hydrochloric acid-ethyl acetate (0.75 mL, 3 mmol) was added, and the mixture was stirred at 15° C. for 10 hours.

The residue obtained by concentrating the reaction mixture under reduced pressure was dissolved in methanol (5 mL). To this, a formaldehyde solution (37%) (0.08 mL, 1.1 mmol), triethylamine (0.29 mL, 2.1 mmol), and acetic acid (0.06 ml, 1.1 mmol) were added and the mixture was stirred at 15° C. for 30 minutes. To the reaction mixture, sodium cyanoborohydride (88 mg, 1.4 mmol) was added, and the mixture was stirred at 15° C. for 2.5 hours.

To the reaction mixture, water was added, and the mixture was extracted with dichloromethane. The organic layer was washed with saturated saline, and dried over anhydrous sodium sulfate. The residue obtained by concentration under reduced pressure was purified by high performance liquid chromatography [developing solvent: ethyl acetate] to obtain the title compound (58 mg (yield: 15%)) as a yellow solid.

Example 16

1-Methyl-4-{1-[4-(4-methyl-5-{[3-(trifluoromethyl)phenoxy]methyl}-4H-1,2,4-triazol-3-yl)phenyl]-1H-pyrazol-4-yl}piperidine (16a)

4-Iodo-N-methylbenzenecarbothioamide

4-Iodo-N-methylbenzenamide (CAS Registry Number: 89976-43-2, WO2009016253) (21.3 g, 81.4 mmol) and Lawesson's reagent (34.6 g, 85.5 mmol) were dissolved in toluene (400 mL) and the mixture was stirred at 130° C. for 4 hours.

The reaction mixture was purified by NH silica gel column chromatography [elution solvent: dichloromethane alone]. The obtained crude product was washed by adding hexane to obtain the title compound (21.8 g (yield: 97%)) as a light yellow solid.

(16b)

3-(4-Iodophenyl)-4-methyl-5-{[3-(trifluoromethyl)phenoxy]methyl}-4H-1,2,4-triazole The compound of Example 16(16a): 4-iodo-N-methyl-benzenecarbothioamide (21.8 g, 78.7 mmol) was dissolved in acetone (450 mL). To this, methyl iodide (24.5 mL, 393 mmol) was added, and the mixture was stirred at room temperature for 66.5 hours.

After the resultant was concentrated under reduced pressure and azeotropically concentrated with toluene, ethyl acetate and saturated aqueous sodium bicarbonate were added to the residue, and the mixture was extracted with ethyl acetate. The organic layer was washed with a 10% aqueous sodium thiosulfate solution and saturated saline, and the mixture was dried over anhydrous magnesium sulfate. The residue obtained by concentration under reduced pressure was dissolved in ethanol (500 mL), and 2-[3-(trifluoromethyl)phenoxy]acetohydrazide (12.3 g, 52.4 mmol) of Example 1(1a) was added, and the mixture was stirred at 110° C. for 21 hours.

After the reaction temperature had returned to room temperature, diisopropyl ether was added to the residue obtained by concentration under reduced pressure, and the precipitated solid was collected by filtration to obtain the title compound (23 g (yield: 95%)) as a white solid.

(16c)

3-[4-(4-Bromo-1H-pyrazol-1-yl)phenyl]-4-methyl-5-{[3-(trifluoromethyl)phenoxy]methyl}-4H-1,2,4-triazole The compound of Example 16(16b): 3-(4-iodophenyl)-4-methyl-5-{[3-(trifluoromethyl)phenoxy]methyl}-4H-1,2,4-triazole (1.04 g, 2.26 mmol), 4-bromo-1H-pyrazole (CAS Registry Number: 2075-45-8, WO2003016275) (434 mg, 2.95 mmol) and potassium phosphate (1.44 g, 6.78 mmol) were dissolved in N,N-dimethylformamide (12 mL). To this, copper (I) iodide (110 mg, 0.58 mmol) was added, and the mixture was stirred at 160° C. for 2 hours under a nitrogen atmosphere and microwave irradiation.

To the reaction mixture, concentrated ammonia water and water were added, and the reaction mixture was extracted with ethyl acetate. The organic layer was washed with water and saturated saline and dried over anhydrous magnesium sulfate. The residue obtained by concentration under reduced pressure was purified by silica gel column chromatography [elution solvent: hexane/ethyl acetate=1/1-0/1, tetrahydrofuran/ethyl acetate=2/3 (V/V)] to obtain the title compound (529 mg (yield: 49%)) as a light yellow solid.

(16d)

1-Methyl-4-{1-[4-(4-methyl-5-{[3-(trifluoromethyl)phenoxy]methyl}-4H-1,2,4-triazol-3-yl)phenyl]-1H-pyrazol-4-yl}-1,2,3,6-tetrahydropyridine The compound of Example 16(16c): 3-[4-(4-bromo-1H-pyrazol-1-yl)phenyl]-4-methyl-5-{[3-(trifluoromethyl)phenoxy]methyl}-4H-1,2,4-triazole (519 mg, 1.11 mmol), 1-methyl-4-(4,4,5,5-tetramethyl-1,3,2-dioxaboran-2-yl)-1,2,3,6-tetrahydropyridine (CAS Registry Number: 1462950-11-2, US 20130261106) (574 mg, 2.21 mmol) and [1,1'-bis(di-tert-butylphosphino)ferrocene]palladium(II) dichloride (72 mg, 0.11 mmol) were dissolved in 1,4-dioxane (20 mL). To this, a 2N aqueous sodium carbonate solution (2.21 mL, 4.42 mmol) was added, and the mixture was stirred at 100° C. for 17 hours under a nitrogen atmosphere.

After the reaction temperature had returned to room temperature, the reaction mixture was extracted with ethyl acetate, then the organic layer was washed with saturated saline and dried over anhydrous sodium sulfate. The residue obtained by concentration under reduced pressure was purified by polyethylenimine (PEI) silica gel column chromatography [elution solvent: tetrahydrofuran/ethyl acetate=1/1 (V/V)]. The obtained crude product was washed by adding isopropyl alcohol. The obtained crude product was purified by diamine (DNH) silica gel column chromatography [elution solvent: hexane/ethyl acetate=7/3-0/1), tetrahydrofuran/ethyl acetate=1/1 (V/V)]. To the obtained crude product, isopropyl alcohol was added, and the precipitated solid was collected by filtration to obtain the title compound (361 mg (yield: 66%)) as an off-white solid.

(16e)

1-Methyl-4-{1-[4-(4-methyl-5-{[3-(trifluoromethyl)phenoxy]methyl}-4H-1,2,4-triazol-3-yl)phenyl]-1H-pyrazol-4-yl}piperidine The compound of Example 16(16d): 1-methyl-4-{1-[4-(4-methyl-5-{[3-(trifluoromethyl)phenoxy]methyl}-4H-1,2,4-triazol-3-yl)phenyl]-1H-pyrazol-4-yl}-1,2,3,6-tetrahydropyridine (315 mg, 0.637 mmol) and 10% palladium on carbon catalyst (50 mg) were added to ethanol (12 mL), and the mixture was stirred at room temperature for 2 hours under a hydrogen atmosphere. Then the temperature was raised to 70° C., and the mixture was stirred for 3 hours.

The palladium-carbon was filtered off, and the filtrate was washed with ethanol and concentrated under reduced pressure, and the resultant residue was purified by high performance liquid chromatography. After acetonitrile was distilled off under reduced pressure, potassium carbonate was added to the resultant residue to adjust the pH to about 8. Then, sodium chloride was added to saturate the aqueous solution, and the mixture was extracted with ethyl acetate. The organic layer was washed with saturated saline and dried over anhydrous magnesium sulfate. To the residue concentrated under reduced pressure, hexane/isopropyl alcohol (1/1 (V/V)) was added, and the precipitated solid was collected by filtration to obtain the title compound (223 mg (yield: 71%)) as a light yellow solid.

Example 17

3-(trans-4-{4-[trans-4-(Azetidin-1-yl)cyclohexyl]-1H-pyrazol-1-yl}cyclohexyl)-4-methyl-5-{[3-(trifluoromethyl)phenoxy]methyl}-4H-1,2,4-triazole (17a)

Methyl trans-4-(4-bromo-1H-pyrazol-1-yl)cyclohexanecarboxylate

Methyl cis-4-[(methylsulfonyl)oxy]cyclohexane carboxylate (CAS Registry Number: 1959557-93-7, US 20160185785) (70 g, 296 mmol) was dissolved in N,N- dimethylformamide (12 mL). To this, 4-bromo-1H-pyrazole (CAS Registry Number: 2075-45-8, WO2003016275) (47.9 g, 326 mmol) and potassium carbonate (81.9 g, 592 mmol) were added, and the mixture was stirred at 80° C. for 16 hours.

To the reaction mixture, water was added, and the mixture was extracted with ethyl acetate. The organic layer was dried over anhydrous sodium sulfate. The residue obtained by concentration under reduced pressure was purified by silica gel column chromatography [elution solvent: ethyl acetate/ petroleum ether=1/100-1/10 (V/V)]] to obtain the title compound (32 g (yield: 38%)) as a white solid.
(17b)

trans-4-(4-Bromo-1H-pyrazol-1-yl)cyclohexanecarbohydrazide

The compound of Example 17(17a): methyl trans-4-(4-bromo-1H-pyrazol-1-yl)cyclohexanecarboxylate (8 g, 27.9 mmol) was dissolved in ethanol (80 mL). To this, hydrazine monohydrate (14.2 g, 279 mmol) was added and the mixture was stirred at 100° C. for 10 hours.

After the reaction temperature had returned to room temperature, the mixture was concentrated under reduced pressure, and the precipitated solid was collected by filtration to obtain the title compound (6.5 g (yield: 81%)) as a white solid.
(17c)

N-Methyl-2-[3-(trifluoromethyl)phenoxy]ethanethioamide

N-Methyl-2-[3-(trifluoromethyl)phenoxy] acetamide (CAS Registry Number: 87964-42-9, JP58134048) (300 g, 1.29 mol) was dissolved in tetrahydrofuran (1.5 L). To this, Lawesson's reagent (313 g, 774 mmol) was added, and the mixture was stirred at 80° C. for 12 hours. After the reaction temperature had returned to room temperature, the residue obtained by concentration under reduced pressure was purified by silica gel column chromatography [elution solvent: ethyl acetate/petroleum ether=1/25-1/15 (V/V)] to obtain the title compound (220 g (yield: 68%)) as a white solid.
(17d)

Methyl N-methyl-2-[3-(trifluoromethyl)phenoxy] ethanimidothioate

The compound of Example 17(17c): N-methyl-2-[3-(trifluoromethyl)phenoxy]ethanethioamide (210 g, 843 mmol) and potassium carbonate (233 g, 1.69 mol) were dissolved in tetrahydrofuran (2 L). To this, methyl iodide (262 mL, 4.21 mol) was added, and the mixture was stirred at 80° C. for 12 hours.

The reaction mixture was filtered to remove insoluble matters, and the filtrate was concentrated under reduced pressure to obtain the title compound (220 g (yield: 99%)) as a yellow oily substance.
(17e)

3-[trans-4-(4-Bromo-1H-pyrazol-1-yl)cyclohexyl]-4-methyl-5-{[3-(trifluoromethyl)phenoxy]methyl}-4H-1,2,4-triazole The compound of Example 17(17b): trans-4-(4-bromo-1H-pyrazol-1-yl)cyclohexane carbohydrazide (6.5 g, 22.6 mmol) was dissolved in isopropyl alcohol (100 mL). To this, the compound of Example 17(17d): methyl N-methyl-2-[3-(trifluoromethyl)phenoxy]ethanamidothioate (5.96 g, 22.6 mmol) was added and the mixture was stirred at 100° C. for 20 hours.

The residue obtained by concentration under reduced pressure was purified by silica gel column chromatography [elution solvent: ethyl acetate/petroleum ether=1/20-1/1 (V/V)] to obtain the title compound (5 g (yield: 46%)) as a white solid.
(17f)

tert-Butyl (4-{1-[trans-4-(4-methyl-5-{[3-(trifluoromethyl)phenoxy]methyl}-4H-1,2,4-triazol-3-yl) cyclohexyl]-1H-pyrazol-4-yl}cyclohex-3-en-1-yl) carbamate The compound of Example 17(17e): 3-[trans-4-(4-bromo-1H-pyrazol-1-yl)cyclohexyl]-4-methyl-5-{[3-(trifluoromethyl)phenoxy]methyl}-4H-1,2,4-triazole (2.50 g, 5.16 mmol), tert-butyl[4-(4,4,5,5-tetramethyl-1,3,2-dioxoboran-2-yl)cyclohex-3-en-1-yl)carbamate (CAS Registry Number: 1251732-64-5, WO2010118207) (2.50 g, 7.74 mmol) and cesium carbonate (5.05 g, 15.5 mmol) were dissolved in 1,4-dioxane (50 mL). To this, [1,1'-bis(diphenylphosphino) ferrocene] palladium (II) dichloride (302 mg, 0.41 mmol) was added at 10° C., and the mixture was stirred at 120° C. for 12 hours under a nitrogen atmosphere.

To the reaction mixture, water was added. The reaction mixture was extracted with ethyl acetate. The organic layer was washed with saturated saline, and dried over anhydrous sodium sulfate. The residue obtained by concentration under reduced pressure was purified by silica gel column chromatography [elution solvent: tetrahydrofuran/ethyl acetate=1/1 (V/V)]. The resulting crude product was washed by adding isopropyl alcohol. The resulting crude product was purified by diamine (DNH) silica gel column chromatography [elution solvent: methanol/dichloromethane=0/1-1/100 (V/V)] to obtain the title compound (2.1 g (yield: 68%)) as a white solid.
(17g)

tert-Butyl (trans-4-{1-[trans-4-(4-methyl-5-{[3-(trifluoromethyl)phenoxy]methyl}-4H-1,2,4-triazol-3-yl) cyclohexyl]-1H-pyrazol-4-yl}cyclohexyl)carbamate 10% palladium carbon catalyst (500 mg) was suspended in ethanol (100 mL). To this, the compound of Example 17(17f): tert-butyl (4-{1-[trans-4-(4-methyl-5-{[3-(trifluoromethyl)phenoxy]methyl}-4H-1,2,4-triazol-3-yl)cyclohexyl]-1H-pyrazol-4-yl}cyclohex-3-en-1-yl)carbamate (2.1 g, 3.5 mmol) was added at 10° C., and the mixture was stirred at 40° C. for 12 hours under a hydrogen atmosphere.

After purging with nitrogen, the palladium-carbon was filtered off. The residue obtained by concentration under reduced pressure was triturated with petroleum ether/ethyl acetate (10/1 (V/V)) to obtain the title compound (960 mg (yield: 46%)) as a white solid.
(17h)

3-(trans-4-{4-[trans-4-(Azetidin-1-yl)cyclohexyl]-1H-pyrazol-1-yl}cyclohexyl)-4-methyl-5-{[3-(trifluoromethyl)phenoxy]methyl}-4H-1,2,4-triazole The compound of Example 17(17g): tert-Butyl (trans-4-{1-[trans-4-(4-methyl-5-{[3-(trifluoromethyl)phenoxy] methyl}-4H-1,2,4-triazol-3-yl)cyclohexyl]-1H-pyrazol-4-yl}cyclohexyl) carbamate (860 mg, 1.43 mmol) was dissolved in dichloromethane (5 mL). To this, 4N hydrochloric acid-ethyl acetate (5 mL, 20 mmol) was added at 10° C. and the mixture was stirred at 10° C. for 2 hours.

The residue concentrated under reduced pressure was dissolved in ethanol (80 mL). To this, 1,3-dibromopropane (Tokyo Chemical Industry Co., Ltd., Catalog Number: D0202) (270 mg, 1.34 mmol) and diisopropylethylamine (203 mg, 2.01 mmol) were added, and the mixture was stirred at 80° C. for 12 hours.

The residue obtained by concentration under reduced pressure was purified by high performance liquid chromatography to obtain the title compound (110 mg (yield: 61%)) as a white solid.

Example 18

1-Methyl-4-{1-[4-(4-methyl-5-{[3-(trifluoromethyl)phenoxy]methyl}-4H-1,2,4-triazol-3-yl)phenyl]-1H-imidazol-4-yl}piperidine (18a)

N,N-Dimethyl-4-(1-methyl-1,2,3,6-tetrahydropyridin-4-yl)-1H-imidazole-1-sulfonamide 4-Iodo-N,N-dimethyl-1H-imidazole-1-sulfonamide (CAS Registry Number: 135773-25-0, WO2009023179) (234 mg, 0.78 mmol) was dissolved in 1,4-dioxane (5 mL) and water (1 mL). To this, 1-methyl-4-(4,4,5,5-tetramethyl-1,3,2-dioxaboran-2-yl)-1,2,3,6-tetrahydropyridine (CAS Registry Number: 1462950-11-2, US 20130261106) (300 mg, 1.34 mmol), potassium carbonate (270 mg, 1.95 mmol) and bis(triphenylphosphine)palladium(II) dichloride (60 mg, 0.09 mmol) were added and the mixture was stirred at 130° C. for 30 minutes under microwave irradiation.

To the reaction mixture, ethyl acetate was added, then the mixture was filtered. The filtrate was washed with water, and the organic layer was dried over anhydrous magnesium sulfate. The residue obtained by concentration under reduced pressure was purified by NH silica gel column chromatography [elution solvent: methanol/ethyl acetate=3/2-1/1 (V/V)]. The resultant crude product was purified by silica gel column chromatography [elution solvent: methanol/ethyl acetate=0/1-3/97, methanol/dichloromethane=1/9 (V/V)] to obtain the title compound (550 mg (yield: 62%)) as a white solid.

(18b)

4-(1H-Imidazol-4-yl)-1-methyl-1,2,3,6-tetrahydropyridine dihydrochloride

To the compound of Example 18(18a): N,N-dimethyl-4-(1-methyl-1,2,3,6-tetrahydropyridin-4-yl)-1H-imidazole-1-sulfonamide (550 mg, 2.0 mmol), concentrated hydrochloric acid (excess amount) was added, and the mixture was stirred at 95° C. for 15 hours.

The residue obtained by concentrating the reaction mixture under reduced pressure was washed by adding diethyl ether to obtain the title compound (500 mg (quantitative)) as a white solid.

(18c)

4-(1H-Imidazol-4-yl)-1-methylpiperidine dihydrochloride

The compound of Example 18(18b): 4-(1H-imidazol-4-yl)-1-methyl-1,2,3,6-tetrahydropyridine hydrochloride (500 mg, 3.0 mmol) was dissolved in methanol (25 mL) and water (1 mL). To this, a 20% palladium hydroxide carbon catalyst (50 mg) was added and the mixture was stirred under a hydrogen atmosphere at room temperature for 4 hours.

Palladium-carbon was filtered off and the filtrate was concentrated under reduced pressure to obtain the title compound (460 mg (quantitative)) as a white solid.

(18d)

1-Methyl-4-{1-[4-(4-methyl-5-{[3-(trifluoromethyl)phenoxy]methyl}-4H-1,2,4-triazol-3-yl)phenyl]-1H-imidazol-4-yl}piperidine The compound of Example 18(18c): 4-(1H-imidazol-4-yl)-1-methylpiperidine hydrochloride (460 mg, 2.28 mmol), and the compound of Example 16(16b): 3-(4-iodophenyl)-4-methyl-5-{[3-(trifluoromethyl)phenoxy]methyl}-4H-1,2,4-triazole (838 mg, 1.82 mmol) were dissolved in N,N-dimethylformamide (5 mL). To this, copper (I) iodide (173 mg, 0.91 mmol) and potassium phosphate (1.9 g, 8.96 mmol) were added, and the mixture was stirred at 160° C. for 2 hours under microwave irradiation, under a nitrogen atmosphere.

To the reaction mixture, ethyl acetate and water were added, and the mixture was extracted with ethyl acetate. The residue obtained by concentration under reduced pressure was purified by NH silica gel column chromatography [elution solvent: methanol/ethyl acetate=0/1-5/95 (V/V)] to obtain the title compound (100 mg (yield: 9%)) as a white solid.

Example 19

1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol (19a)

Methyl trans-4-(methylcarbamoyl)cyclohexanecarboxylate trans-4-(Methoxycarbonyl)cyclohexane carboxylic acid (Tokyo Chemical Industry Co., Ltd., Catalog Number: M2526) (25.3 g, 136 mmol) was dissolved in dichloromethane (400 mL). To this, triethylamine (56.6 mL, 408 mmol), methylamine hydrochloride (Tokyo Chemical Industry Co., Ltd., Catalog Number: M0138) (18.4 g, 272 mmol), 3H-1,2,3-triazolo[4,5-b]pyridin-3-ol (0.93 g, 130 mmol), 1-ethyl-3-(3-dimethylaminopropyl)carbodiimide hydrochloride (29.5 g, 154 mmol) were added and the mixture was stirred at room temperature for 70 hours.

To the reaction mixture, water and 1N hydrochloric acid was added, and the reaction mixture was extracted with dichloromethane. The organic layer was dried over anhydrous magnesium sulfate. The resultant was concentrated under reduced pressure and the precipitated solid were diluted with hexane and the solid was collected by filtration to obtain the title compound (25.7 g (yield: 95%)) as a white solid.

(19b)

Methyl trans-4-(methylcarbamothioyl)cyclohexanecarboxylate

The compound of Example 19(19a): methyl trans-4-(methylcarbamoyl)cyclohexanecarboxylate (19 g, 95.5 mmol) was dissolved in toluene (400 mL). To this, Lawesson's reagent (21.3 g, 52.5 mmol) was added, and the mixture was stirred at 90° C. for 8 hours.

To the reaction mixture, saturated aqueous sodium bicarbonate was added, and the reaction mixture was extracted with ethyl acetate. The organic layer was washed with saturated saline and dried over anhydrous magnesium sulfate. The residue obtained by concentration under reduced pressure was purified by NH silica gel column chromatography [elution solvent: dichloromethane/ethyl acetate=9/1-1/1 (V/V)] to obtain the title compound (20.6 g (yield: 100%)) as a white solid.

(19c)

Methyl trans-4-[(methylimino)(methylsulfanyl)methyl]cyclohexanecarboxylate

The compound of Example 19(19b): methyl trans-4-(methylcarbamothioyl)cyclohexane carboxylate (1.5 g, 5.7 mmol) was dissolved in acetone (400 mL). To this, potassium carbonate (26.5 g, 192 mmol) and methyl iodide (15.9 ml, 256 mmol) were added and the mixture was stirred for 5 hours under reflux with heating.

After the reaction temperature had returned to room temperature, dichloromethane was added to the residue obtained by concentration under reduced pressure, and the precipitated solid was collected by filtration to obtain the title compound 29.4 g (yield: 100%)) as a white solid.

(19d)

Methyl trans-4-(4-methyl-5-{[3-(trifluoromethyl)phenoxy]methyl}-4H-1,2,4-triazol-3-yl)cyclohexanecarboxylate The compound of Example 19(19c): methyl trans-4-[(methylimino)(methylsulfanyl)methyl]cyclohexanecarboxylate (0.2 g, 0.7 mmol) was dissolved in ethanol (200 mL). The compound of Example 1(1a): 2-[3-(trifluoromethyl)phenoxy]acetohydrazide (10.5 g, 44.9 mmol) was added and the mixture was stirred at 90° C. for 4 hours.

After the reaction temperature had returned to room temperature, dichloromethane and 1N hydrochloric acid were added to the residue obtained by concentration under reduced pressure. The mixture was extracted with dichloromethane, and the organic layer was dried over anhydrous magnesium sulfate. The residue obtained by concentration under reduced pressure was dissolved in ethyl acetate. To this, hexane was added, and the precipitated solid was collected by filtration to obtain the title compound (12.3 g (yield: 69%)) as a white solid.

(19e)

[trans-4-(4-Methyl-5-{[3-(trifluoromethyl)phenoxy]methyl}-4H-1,2,4-triazol-3-yl)cyclohexyl]methanol To a suspension of the compound of Example 19(19d) of methyl trans-4-(4-methyl-5-{[3-(trifluoromethyl)phenoxy]methyl}-4H-1,2,4-triazol-3-yl)cyclohexanecarboxylate (4.97 g, 12.5 mmol) in tetrahydrofuran (120 mL), a lithium aluminium hydride-tetrahydrofuran solution (2.5 M, 7.5 mL) was added under ice-cooling and the mixture was stirred at room temperature for 15 minutes.

To the reaction mixture, water (0.33 mL), a 15% aqueous sodium hydroxide solution (0.34 mL), and water (1 mL) were sequentially added under ice-cooling, and the mixture was diluted with ethyl acetate and then filtered with celite. The filtrate was concentrated under reduced pressure to obtain the title compound (4.9 g (quantitative)) as a white solid.

(19f)

trans-4-(4-Methyl-5-{[3-(trifluoromethyl)phenoxy]methyl}-4H-1,2,4-triazol-3-yl)cyclohexanecarbaldehyde The compound of Example 19(19e): [trans-4-(4-methyl-5-{[3-(trifluoromethyl)phenoxy]methyl}-4H-1,2,4-triazol-3-yl)cyclohexyl] methanol (4.9 g, 13.3 mmol) was dissolved in dichloromethane (130 mL). To this, Dess-Martin periodinane (6.75 g, 15.9 mmol) was added under ice-cooling, and the mixture was stirred for 1 hour, and then the reaction temperature was raised to room temperature and the mixture was stirred for 1 hour.

To the reaction solution, saturated aqueous sodium bicarbonate was added, and the mixture was extracted with dichloromethane. The combined organic layer was dried over magnesium sulfate. The residue obtained by concentration under reduced pressure was purified by silica gel column chromatography [elution solvent: hexane/ethyl acetate=1/1, ethyl acetate alone, methanol/ethyl acetate=1/4 (V/V)] to obtain the title compound (4.3 g (yield: 88%)) as a yellow oily substance.

(19g)

3-(trans-4-Ethynylcyclohexyl)-4-methyl-5-{[3-(trifluoromethyl)phenoxy]methyl}-4H-1,2,4-triazole The compound of Example 19(19f): trans-4-(4-methyl-5-{[3-(trifluoromethyl)phenoxy]methyl}-4H-1,2,4-triazol-3-yl)cyclohexanecarbaldehyde (4.8 g, 13 mmol) was dissolved in methanol (100 mL). To this, potassium carbonate (3.5 g, 26 mmol) and dimethyl (1-diazo-2-oxopropyl)phosphonate (3 g, 16 mmol) were added under ice-cooling, and the mixture was stirred at room temperature for 2 hours.

The reaction mixture was neutralized with 1N hydrochloric acid, and then methanol was distilled off under reduced pressure. The reaction mixture was extracted with dichloromethane. The organic layer was dried over anhydrous sodium sulfate. The residue obtained by concentration under reduced pressure was purified by silica gel column chromatography [elution solvent: hexane/ethyl acetate=3/2-0/1 (V/V)] to obtain the title compound (4.5 g (yield: 93%)) as a white solid.

(19h)

1,5-Anhydro-2-azido-6-O-[tert-butyl(dimethyl)silyl]-2,3,4-trideoxy-D-erythro-hexitol 2,6-Anhydro-1-O-[tert-butyl(dimethyl)silyl]-3,4-dideoxy-D-threo-hexitol (CAS Registry Number: 216098-97-4, Journal of Organic Chemistry (1998), 63 (23), 8133-8144) (3.86 g, 15.7 mmol) was dissolved in pyridine (10 mL). To this, para-toluenesulfonyl chloride (3.6 g, 18.8 mmol) and a catalytic amount of N,N-dimethyl-4-aminopyridine were added, and the mixture was stirred at room temperature for 20 hours.

To the reaction mixture, water was added, and the reaction mixture was stirred and extracted with ethyl acetate. The organic layer was washed with water, saturated aqueous sodium bicarbonate and saturated saline and dried over anhydrous sodium sulfate. The residue obtained by concentration under reduced pressure was purified by silica gel column chromatography [elution solvent: hexane/ethyl acetate=9/1-1/1 (V/V)] to obtain 2,6-anhydro-1-O-[tert-butyl(dimethyl)silyl]-3,4-dideoxy-5-O-[(4-methylphenyl)sulfonyl]-D-threo-hexitol (1.5 g) was obtained as a colorless oily substance.

The obtained 2,6-anhydro-1-O-[tert-butyl(dimethyl)silyl]-3,4-dideoxy-5-O-[(4-methylphenyl)sulfonyl]-D-threo-hexitol (4.89 g, 12.2 mmol) was dissolved in N,N-dimethylformamide (80 mL). To this, sodium azide (2.49 g, 38.3 mmol) was added, and the mixture was stirred at 80° C. for 1 hour. Then the reaction temperature was raised to 100° C., and the mixture was stirred for 3 hours.

To the reaction mixture, 1N hydrochloric acid was added, and the reaction mixture was extracted with ethyl acetate. The organic layer was washed with saturated aqueous sodium bicarbonate and saturated saline and dried over anhydrous sodium sulfate. The residue obtained by concentration under reduced pressure was purified by silica gel column chromatography [elution solvent: hexane/ethyl acetate=3/2 (V/V)] to obtain the title compound (1.5 g (yield: 40%)) as a colorless oily substance.
(19i)

1,5-Anhydro-6-O-[tert-butyl(dimethyl)silyl]-2,3,4-trideoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol The compound of Example 19(19g): 3-(trans-4-ethynylcyclohexyl)-4-methyl-5-{[3-(trifluoromethyl)phenoxy]methyl}-4H-1,2,4-triazole (2 g, 5.5 mmol) was dissolved in N,N-dimethylformamide (30 mL) and water (5 mL). To this, the compound of Example 19(19h): 1,5-anhydro-2-azido-6-O-[tert-butyl(dimethyl)silyl]-2,3,4-trideoxy-D-erythro-hexitol (1.8 g, 6.1 mmol), sodium ascorbate (0.22 g, 1.1 mmol) and copper(II) sulfate pentahydrate (0.14 g, 0.55 mmol) were added and the mixture was stirred at room temperature for 18 hours.

The reaction mixture was diluted with tetrahydrofuran and ethyl acetate, and neutralized with 1N hydrochloric acid. The reaction mixture was extracted with ethyl acetate. The organic layer was washed with water and saturated saline and dried over anhydrous sodium sulfate. The residue obtained by concentration under reduced pressure was purified by silica gel column chromatography [elution solvent: hexane/ethyl acetate=7/3-0/1 (V/V)] to obtain the title compound (2.6 g (yield: 76%)) as a white solid.
(19j)

1,5-Anhydro-2,3,4-trideoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol The compound of Example 19(19i): 1,5-anhydro-6-O-[tert-butyl (dimethyl)silyl]-2,3,4-trideoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol (2.6 g, 4.2 mmol) was dissolved in tetrahydrofuran (30 mL). To this, a tetrabutylammonium fluoride-tetrahydrofuran solution (1 M, 6.3 mL) was added, and the mixture was stirred at room temperature for 1 hour.

To the reaction mixture, water and dichloromethane were added, and the mixture was extracted with dichloromethane. The combined organic layer was dried over sodium sulfate. The residue obtained by concentration under reduced pressure was purified by silica gel column chromatography [elution solvent: hexane/ethyl acetate=7/3-0/1, methanol/ethyl acetate=25/75 (V/V)] to obtain the title compound (2.1 g (yield: 95%)) as a white solid.
(19k)

1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol The compound of Example 19(19j): 1,5-anhydro-2,3,4-trideoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-D-erythro-hexitol (1 g, 1.9 mmol) and lutidine (0.41 g, 3.9 mmol) were dissolved in dichloromethane (25 mL). To this, trifluoromethanesulfonic anhydride (0.68 g, 2.4 mmol) was added dropwise at −78° C. The mixture was stirred at −78° C. for 1 hour, and then the temperature was raised to −40° C. To this, azetidine (1.1 g, 19 mmol) was added, and the mixture was stirred at −40° C. for 30 minutes. The mixture was stirred for 1 hour while warming to room temperature.

The residue obtained by concentration under reduced pressure was purified by silica gel column chromatography [elution solvent: hexane/ethyl acetate=7/3-0/1, methanol/ethyl acetate=15/85 (V/V)] to obtain the title compound (0.61 g (yield: 57%)) as a white solid.

Example 20

2-({5-[trans-4-(1-{trans-4-[3-(Fluoromethyl)azetidin-1-yl]cyclohexyl}-1H-1,2,3-triazol-4-yl)cyclohexyl]-4-methyl-4H-1,2,4-triazol-3-yl}methoxy)-4-(trifluoromethyl)pyridine (20a)

Methyl trans-4-[5-({[tert-butyl(diphenyl)silyl]oxy}methyl)-4-methyl-4H-1,2,4-triazol-3-yl]cyclohexanecarboxylate The compound of Example 19(19c): methyl trans-4-[(methylimino) (methylsulfanyl)methyl]cyclohexanecarboxylate (18 g, 78.4 mmol) was dissolved in ethanol (200 mL). To this, the compound of Example 5(5a): 2-{[tert-butyl (diphenyl)silyl]oxy}acetohydrazide (25.7 g, 78.4 mmol) was added and the mixture was stirred at 90° C. for 16 hours.

After the reaction temperature had returned to room temperature, the residue obtained by concentration under reduced pressure was diluted with dichloromethane. To this, 1N hydrochloric acid was added, and the mixture was extracted with dichloromethane. The combined organic layer was dried over magnesium sulfate. The residue obtained by concentration under reduced pressure was purified by silica gel column chromatography [elution solvent: hexane/ethyl acetate=1/1-0/1 (V/V), ethyl acetate/methanol=9/1 (V/V)] to obtain the title compound (32 g (yield: 83%)) as a colorless oily substance.
(20b)

{trans-4-[5-({[tert-Butyl(diphenyl)silyl]oxy}methyl)-4-methyl-4H-1,2,4-triazol-3-yl]cyclohexyl}methanol The compound of Example 20(20a): methyl trans-4-[5-({[tert-butyl(diphenyl)silyl]oxy}methyl)-4-methyl-4H-1,2,4-triazol-3-yl]cyclohexanecarboxylate (24.9 g, 50.6 mmol) was dissolved in tetrahydrofuran (300 mL). To this, a lithium aluminium hydride-tetrahydrofuran solution (2.5 M, 20 mL) was added under ice-cooling, and the mixture was stirred for 5 minutes under ice-cooling and then stirred at room temperature for 20 minutes.

To the reaction mixture, water (2 mL), a 15% aqueous sodium hydroxide solution (2 mL), and water (6 mL) were sequentially added under ice-cooling, and the mixture was diluted with ethyl acetate and then filtered with celite. The filtrate was concentrated under reduced pressure to obtain the title compound (23.4 g (yield: 99%)) as a white solid.
(20c)

trans-4-[5-({[tert-Butyl(diphenyl)silyl]oxy}methyl)-4-methyl-4H-1,2,4-triazol-3-yl]cyclohexanecarbaldehyde The compound of Example 20(20b):{trans-4-[5-({[tert-butyl(diphenyl)silyl]oxy}methyl)-4-methyl-4H-1,2,4-triazol-3-yl]cyclohexyl}methanol (18.8 g, 40.5 mmol) was dissolved in dichloromethane (250 mL). To this, Dess Martin periodinane (19 g, 44.6 mmol) was added under ice-cooling, and the mixture was stirred at room temperature for 1 hour.

To the reaction solution, a 1N aqueous sodium hydroxide solution (250 mL) was added under ice-cooling and the mixture was stirred. To this, dichloromethane, and 10% aqueous sodium thiosulfate were further added sequentially, and the mixture was filtered with celite. The reaction solution was extracted with dichloromethane, and the organic layer was dried over anhydrous sodium sulfate. After filtration, the filtrate was concentrated under reduced pressure to obtain the title compound (19.5 g (quantitative)) as a light yellow solid.
(20d)

3-({[tert-Butyl (diphenyl)silyl]oxy}methyl)-5-(trans-4-ethynylcyclohexyl)-4-methyl-4H-1,2,4-triazole The compound of Example 20(20c): trans-4-[5-({[tert-butyl (diphenyl)silyl]oxy}methyl)-4-methyl-4H-1,2,4-triazol-3-yl]cyclohexanecarbaldehyde (5.03 g, 10.9 mmol) was dissolved in methanol (50 mL). To this, potassium carbonate (3.01 g, 21.8 mmol) and dimethyl(1-diazo-2-oxopropyl)phosphonate (1.64 mL, 10.9 mmol) were added under ice-cooling, and the mixture was stirred at room temperature for 1 hour.

The reaction mixture was diluted with dichloromethane. To this, water was added, and the mixture was extracted with dichloromethane. The organic layer was dried over anhydrous sodium sulfate. The residue obtained by concentration under reduced pressure was purified by silica gel column chromatography [elution solvent: hexane/ethyl acetate=9/1-1/1 (V/V)] to obtain the title compound (4.93 g (yield: 99%)) as a light yellow oily substance.
(20e)

[5-(trans-4-Ethynylcyclohexyl)-4-methyl-4H-1,2,4-triazol-3-yl]methanol

The compound of Example 20(20d): 3-({[tert-butyl (diphenyl)silyl]oxy}methyl)-5-(trans-4-ethynylcyclohexyl)-4-methyl-4H-1,2,4-triazole (4.93 g, 10.8 mmol) was dissolved in tetrahydrofuran (50 mL). To this, tetrabutyl ammonium fluoride hydrate (3.61 g, 12.9 mmol) was added and the mixture was stirred at room temperature for 30 minutes.

To the reaction mixture, a saturated aqueous ammonium chloride solution was added, and the mixture was extracted with ethyl acetate. The organic layer was washed with a saturated aqueous ammonium chloride solution and saturated saline and then dried over anhydrous magnesium sulfate. To the residue obtained by concentration under reduced pressure, ethyl acetate was added, and the precipitated solid was collected by filtration and washed with ethyl acetate to obtain the title compound (504 mg (yield: 21%)) as a white solid.
(20f)

2-{[5-(trans-4-Ethynylcyclohexyl)-4-methyl-4H-1,2,4-triazol-3-yl]methoxy}-4-(trifluoromethyl)pyridine To a suspension of the compound of Example 20(20e): [5-(trans-4-ethynylcyclohexyl)-4-methyl-4H-1,2,4-triazol-3-yl]methanol (504 mg, 2.30 mmol) in tetrahydrofuran (10 mL), sodium hydride (63%) (105 mg, 2.76 mmol) and 2-fluoro-4-(trifluoromethyl)pyridine (455 mg, 2.76 mmol) were added under ice-cooling and the mixture was stirred at 60° C. for 2 hours.

The reaction solution was ice-cooled, and a saturated aqueous ammonium chloride solution was added, then the mixture was extracted with dichloromethane. The combined organic layer was dried over anhydrous magnesium sulfate. The residue obtained by concentration under reduced pressure was purified by silica gel column chromatography [elution solvent: hexane/ethyl acetate=7/3, ethyl acetate alone, ethyl acetate/methanol=9/1 (V/V)] to obtain the title compound (715 mg (yield: 85%)) as a white solid.
(20g)

tert-Butyl {trans-4-[3-(fluoromethyl)azetidin-1-yl] cyclohexyl}carbamate 2-(Fluoromethyl)propane-1,3-diol (CAS Registry Number: 1036393-01-7, WO2008078424) (6.06 g, 56.1 mmol) was dissolved in dichloromethane (400 mL). To this, N,N-diisopropylethylamine (97.6 mL, 561 mmol) was added. Then, the mixture was cooled to −78° C. and trifluoromethanesulfonic acid anhydride (19.8 mL, 118 mmol) was added dropwise thereto, and the mixture was stirred while warming to −20° C. To this, tert-butyl (trans-4-aminocyclohexyl) carbamate (Angene Chemical Private Limited, Catalog Number: AGN-PC-0051A3) (12 g, 56.1 mmol) was added at −20° C., and the mixture was stirred at room temperature for 7 hours.

To the reaction mixture, water was added, and the mixture was extracted with dichloromethane. The combined organic layer was dried over magnesium sulfate. The residue obtained by concentration under reduced pressure was dissolved in dichloromethane, then diluted with ethyl acetate. The precipitated solid was filtered and washed with ethyl acetate, and insoluble matters were filtered off. The residue obtained by concentration under reduced pressure was purified by NH silica gel column chromatography [elution solvent: [elution solvent: hexane/ethyl acetate=7/3, ethyl acetate alone, methanol/ethyl acetate=9/1 (V/V)] to obtain the title compound (8.09 g (yield: 50%)) as a light yellow solid.
(20h)

trans-4-[3-(Fluoromethyl)azetidin-1-yl]cyclohexanamine dihydrochloride

The compound of Example 20(20g): tert-butyl {trans-4-[3-(fluoromethyl) azetidin-1-yl] cyclohexyl} carbamate (22.2 g, 77.5 mmol) was dissolved in ethanol (100 mL). To this, 5N hydrochloric acid (200 mL) was added at room temperature, and the mixture was stirred for 1 hour.

The residue obtained by concentrating the reaction solution under reduced pressure was dissolved in ethanol. To this, diethyl ether was added dropwise, and the resulting solid was collected by filtration to obtain the title compound (20 g (yield: 97%)) as a white solid.

(20i)

2-({5-[trans-4-(1-{trans-4-[3-(Fluoromethyl)azetidin-1-yl]cyclohexyl}-1H-1,2,3-triazol-4-yl)cyclohexyl]-4-methyl-4H-1,2,4-triazol-3-yl}methoxy)-4-(trifluoromethyl)pyridine

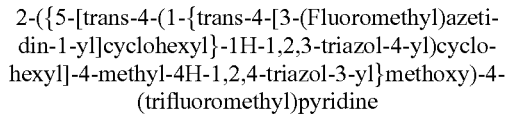

Tris[(1-benzyl-1H-1,2,3-triazol-4-yl)methyl]amine (40.9 mg, 0.0772 mmol) and tetrakis(acetonitrile) copper (I) hexafluorophosphate (28.8 mg, 0.0772 mmol) were dissolved in tetrahydrofuran (1 mL) and water (0.1 mL) to prepare a catalyst solution.

To a suspension of the compound of Example 20(20h): trans-4-[3-(fluoromethyl)azetidin-1-yl]cyclohexane amine hydrochloride (100 mg, 0.386 mmol) in acetonitrile (4 mL), N,N-diisopropylethylamine (0.47 mL, 2.7 mmol) and water (0.5 mL) were sequentially added. Upon dissolution, 2-azido-1,3-dimethylimidazolinium hexafluorophosphate (110 mg, 0.39 mmol) was added at room temperature. The mixture was stirred at room temperature for 1 hour, and then the compound of Example 20(20f): (2-{[5-(trans-4-ethynylcyclohexyl)-4-methyl-4H-1,2,4-triazol-3-yl]methoxy}-4-(trifluoromethyl)pyridine (169 mg, 0.46 mmol) and the aforementioned catalyst solution were added at room temperature and the mixture was stirred for 24 hours.

The reaction mixture was purified by NH silica gel column chromatography [elution solvent: ethyl acetate alone, methanol/ethyl acetate=1/4 (V/V)] to obtain the title compound (168 mg (yield: 76%)) as a white solid.

Example 21

3-(trans-4-{1-[trans-4-(Azetidin-1-yl)cyclohexyl]-1H-pyrazol-4-yl}cyclohexyl)-4-methyl-5-{[3-(trifluoromethyl)phenoxy]methyl}-4H-1,2,4-triazole (21a)

Ethyl 4-[1-(tetrahydro-2H-pyran-2-yl)-1H-pyrazol-4-yl]cyclohex-3-ene-1-carboxylate Ethyl 4-(4,4,5,5-tetramethyl-1,3,2-dioxaborolan-2-yl)cyclohex-3-ene-1-carboxylate (CAS Registry Number: 10490004-32-1, WO2008099221) (200 g, 714 mmol) and 4-bromo-1-(tetrahydro-2H-pyran-2-yl)-1H-pyrazole (CAS Registry Number: 82099-98-7, WO2008092891) (150 g, 649 mmol) were dissolved in 1,4-dioxane (900 mL). To this, [1,1'-bis(diphenylphosphino)ferrocene] palladium (II) dichloride (23.8 g, 32.5 mmol) and an aqueous cesium carbonate (423 g, 1.3 mol) solution (100 mL) were added at room temperature, and the mixture was stirred at 90° C. for 12 hours under a nitrogen atmosphere.

The reaction solution was concentrated under reduced pressure, diluted with ethyl acetate, and then washed with saturated saline. The aqueous layer was extracted with ethyl acetate, and then the combined organic layer was dried over anhydrous sodium sulfate. The residue obtained by concentration under reduced pressure was purified by silica gel column chromatography [elution solvent: ethyl acetate/petroleum ether=1/20-1/15 (V/V)] to obtain the title compound (160 g (yield: 81%)) as a yellow oily substance.

(21b)

trans-4-[1-(Tetrahydro-2H-pyran-2-yl)-1H-pyrazol-4-yl]cyclohexanecarbohydrazide

10% Palladium on carbon catalyst (24 g) was suspended in ethanol (1.5 L). To this, the compound of Example 21(21a): ethyl 4-[1-(tetrahydro-2H-pyran-2-yl)-1H-pyrazol-4-yl]cyclohex-3-ene-1-carboxylate (160 g, 526 mmol) was added, and the mixture was stirred at room temperature for 12 hours under a hydrogen atmosphere.

After purging with nitrogen, the palladium-carbon was filtered off. The residue obtained by concentration under reduced pressure was dissolved by adding tetrahydrofuran (1.5 L). To the obtained solution, sodium hydride (60%) (41.8 g, 1.04 mol) was added under ice-cooling and the mixture was stirred at 50° C. for 1.5 hours under a nitrogen atmosphere.

To the reaction solution, a saturated aqueous ammonium chloride solution was added, and the mixture was extracted with ethyl acetate. The organic layer was dried over anhydrous sodium sulfate. To the residue obtained by concentration under reduced pressure, hydrazine monohydrate (500 g, 9.79 mol) was added, and the mixture was stirred at 90° C. for 12 hours.

The residue obtained by concentration under reduced pressure was purified by high performance liquid chromatography to obtain the title compound (45 g (yield: 39%)) as a white solid.

(21c)

4-Methyl-3-[trans-4-(1H-pyrazol-4-yl)cyclohexyl]-5-{[3-(trifluoromethyl)phenoxy]methyl}-4H-1,2,4-triazole The compound of Example 21(21b): trans-4-[1-(tetrahydro-2H-pyran-2-yl)-1H-pyrazol-4-yl]cyclohexane carbohydrazide (45 g, 154 mmol) was dissolved in isopropyl alcohol (500 mL). To this, the compound of Example 17(17d): methyl N-methyl-2-[3-(trifluoromethyl)phenoxy]ethaneimidothioate (60.8 g, 185 mmol) was added, and the mixture was stirred at 100° C. for 36 hours.

The reaction mixture was concentrated under reduced pressure. The resultant residue was purified by silica gel column chromatography [elution solvent: methanol/dichloromethane=1/100-1/50 (V/V)]. The obtained residue was then dissolved in ethyl acetate (400 mL)-methanol (100 mL). To this, 4N hydrochloric acid-ethyl acetate (400 mL, 1.6 mol) was added at room temperature, and the mixture was stirred for 12 hours.

The residue obtained by concentrating the reaction mixture was dissolved by adding dichloromethane and methanol, and washed with saturated aqueous sodium bicarbonate, and the aqueous layer was extracted with dichloromethane. The combined organic layer was dried over anhydrous sodium sulfate. The residue obtained by concentration under reduced pressure was triturated with ethyl acetate and petroleum ether to obtain the title compound (30.5 g (yield: 92%)) as a white solid.

(21d)

3-(trans-4-{1-[trans-4-(Azetidin-1-yl)cyclohexyl]-1H-pyrazol-4-yl}cyclohexyl)-4-methyl-5-{[3-(trifluoromethyl)phenoxy]methyl}-4H-1,2,4-triazole cis-4-[(tert-Butoxycarbonyl) amino] cyclohexyl methanesulfonate (CAS Registry Number: 1007306-61-7, WO2011086053) (4.05 g, 21.1 mmol) and the compound of Example 21(21c): 4-methyl-3-[trans-4-(1H-pyrazol-4-yl)cyclohexyl]-5-{[3-(trifluoromethyl)phenoxy]methyl}-4H-1,2,4-triazole (4 g, 9.87 mmol) were dissolved in N,N-dimethylformamide (20 mL). To this, sodium hydride (60%) (789 mg, 19.7 mmol) was added at room temperature, and the mixture was stirred at 50° C. for 12 hours.

To the reaction mixture, water was added, and the mixture was extracted with dichloromethane. The organic layer was washed with saturated saline, and dried over anhydrous sodium sulfate. The residue obtained by concentration under reduced pressure was purified by silica gel column chromatography [elution solvent: methanol/dichloromethane=1/60-1/20 (V/V)]. The obtained tert-butyl (trans-4-{4-[trans-4-(4-methyl-5-{[3-(trifluoromethyl)phenoxy]methyl}-4H-1,2,4-triazol-3-yl)cyclohexyl]-1H-pyrazol-1-yl}cyclohexyl) carbamate (850 mg) was dissolved by adding dichloromethane. To the obtained solution, 4N hydrochloric acid-ethyl acetate (10 mL, 40 mol) was added at room temperature, and the mixture was stirred for 12 hours.

The reaction mixture was concentrated under reduced pressure, and the obtained residue was dissolved by adding acetonitrile (50 mL). To the obtained solution, 1,3-dibromopropane (1.7 mL, 16.7 mmol) and N,N-diisopropylethylamine (3.13 mL, 22.3 mmol)) were added at room temperature, and the mixture was stirred at 70° C. for 12 hours under a nitrogen atmosphere.

The residue obtained by concentrating the reaction mixture under reduced pressure was purified by high performance liquid chromatography to obtain the title compound (600 mg (yield: 2.8%)) as a yellow solid.

Example 22

1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-pyrazol-1-yl}-D-erythro-hexitol (22a)

1,5-Anhydro-2-[(tert-butoxycarbonyl)amino]-6-O-[tert-butyl(diphenyl)silyl]-2,3,4-trideoxy-D-erythro-hexitol 1,5-Anhydro-2-[(tert-butoxycarbonyl)amino]-2,3,4-trideoxy-D-erythro-hexitol (CAS Registry Number: 603130-12-7, WO2006125974) (3 g, 13.0 mmol) and imidazole (1.77 g, 25.9 mmol) were dissolved in N,N-dimethylformamide (25 mL). To this, tert-butyldiphenylchlorosilane (3.74 g, 13.6 mmol) was added dropwise at room temperature, and the mixture was stirred at room temperature for 55 hours.

To the reaction mixture, ethyl acetate and water were added, and the mixture was extracted with ethyl acetate. The organic layer was washed with water and saturated saline and dried over anhydrous magnesium sulfate. The residue obtained by concentration under reduced pressure was purified by silica gel column chromatography [elution solvent: hexane/ethyl acetate=19/1-7/3 (V/V)] to obtain the title compound (6.72 g (yield: 100%)) as a colorless oily substance.

(22b)

2-Amino-1,5-anhydro-6-O-[tert-butyl(diphenyl)silyl]-2,3,4-trideoxy-D-erythro-hexitol The compound of Example 22(22a): 1,5-anhydro-2-[(tert-butoxycarbonyl)amino]-6-O-[tert-butyl(diphenyl)silyl]-2,3, 4-trideoxy-D-erythro-hexitol (6.72 g, 13 mmol) was dissolved in dichloromethane (30 mL). To this, trifluoroacetic acid (10 mL) was added under ice-cooling, and the mixture was stirred for 30 minutes.

The residue obtained by concentration under reduced pressure was purified by NH silica gel column chromatography [elution solvent: ethyl acetate alone, ethyl acetate/methanol=4/1 (V/V)] to obtain the title compound (4.53 g (yield: 94%)) as a colorless oily substance.

(22c)

1,5-Anhydro-2-[2-(tert-butoxycarbonyl)hydrazinyl]-6-O-[tert-butyl(diphenyl)silyl]-2,3,4-trideoxy-D-erythro-hexitol The compound of Example 22(22b): 2-amino-1,5-anhydro-6-O-[tert-butyl(diphenyl)silyl]-2,3,4-trideoxy-D-erythro-hexitol (2.49 g, 6.74 mmol) was dissolved in dichloromethane (60 mL). To this, a solution of tert-butyl 3-(trichloromethyl)oxadiridine-2-carboxylate (CAS Registry Number: 219547-77-0, WO2012074067) (1.15 g, 4.38 mmol) in dichloromethane (5 mL) was added at −60° C. and the mixture was stirred for 1 hour while warming.

The reaction temperature was raised to room temperature. The residue obtained by concentration under reduced pressure was purified by NH silica gel column chromatography [elution solvent: hexane/ethyl acetate=9/1, ethyl acetate alone, methanol/ethyl acetate=3/7 (V/V)] to obtain the title compound (1.72 g (yield: 81%)) as a colorless oily substance.

(22d)

[trans-4-(4-Methyl-5-{[3-(trifluoromethyl)phenoxy]methyl}-4H-1,2,4-triazol-3-yl)cyclohexyl]acetaldehyde To a suspension of (methoxymethyl)triphenylphosphonium chloride (3.38 g, 9.85 mmol) in tetrahydrofuran (15 mL), tert-butoxypotassium (1.11 g, 9.85 mmol) was added under ice-cooling, and the mixture was stirred for 15 minutes. This solution was added dropwise using a cannula to a solution of the compound of Example 19(19f): trans-4-(4-methyl-5-{[3-(trifluoromethyl)phenoxy]methyl}-4H-1,2,4-triazol-3-yl)cyclohexanecarbaldehyde (1.81 g, 4.93 mmol) in tetrahydrofuran (25 mL) under ice-cooling and the mixture was stirred for 2 hours.

To the reaction mixture, water was added, and the mixture was extracted with ethyl acetate. The organic layer was dried over anhydrous magnesium sulfate. The residue obtained by concentration under reduced pressure was dissolved by adding tetrahydrofuran (40 mL). To this, 1N hydrochloric acid (10 mL) was added, and the mixture was stirred at room temperature for 30 minutes and then allowed to stand still for 13 hours in a refrigerator.

The reaction mixture was concentrated, and diluted with ethyl acetate. To this, saturated aqueous sodium bicarbonate was added, and the mixture was stirred for 10 minutes. The reaction mixture was extracted with ethyl acetate, and the organic layer was washed with water and saturated saline and dried over anhydrous magnesium sulfate. The residue obtained by concentration under reduced pressure was purified by silica gel column chromatography [elution solvent: ethyl acetate alone, methanol/ethyl acetate=1/4 (V/V)] to obtain the title compound (1.32 g (yield: 71%)) as a colorless oily substance.

(22e)

2-[trans-4-(4-Methyl-5-{[3-(trifluoromethyl)phenoxy]methyl}-4H-1,2,4-triazol-3-yl)cyclohexyl] prop-2-enal The compound of Example 22(22d): trans-4-(4-methyl-5-{[3-(trifluoromethyl)phenoxy]methyl}-4H-1,2,4-triazol-3-yl)cyclohexyl]acetaldehyde (1.32 g, 3.46 mmol) was dissolved in N,N-dimethylformamide (7 mL). To this, formaldehyde solution (37%) (0.47 mL, 17.3 mmol) and L-proline (0.12 g, 1.04 mmol) were added, and the mixture was stirred at room temperature for 13 hours.

The reaction solution was diluted with ethyl acetate and washed with water and saturated saline. The organic layer was dried over anhydrous magnesium sulfate and then concentrated under reduced pressure to obtain the title compound (1.35 g (yield: 99%)) as a white solid.

(22f)

2-[trans-4-(4-Methyl-5-{[3-(trifluoromethyl)phenoxy]methyl}-4H-1,2,4-triazol-3-yl)cyclohexyl] oxirane-2-carbaldehyde Sodium methoxide (0.196 mL, 3.43 mmol) was added to aqueous hydrogen peroxide (30%) (0.65 mL, 6.86 mmol), and the resulting suspension was added dropwise to a solution of the compound of Example 22(22e): 2-[trans-4-(4-methyl-5-{[3-(trifluoromethyl)phenoxy]methyl}-4H-1,2,4-triazol-3-yl)cyclohexyl]prop-2-enal (1.32 g, 3.46 mmol) in methanol (15 mL) and the mixture was stirred at room temperature for 10 minutes.

To the reaction mixture, a 10% aqueous sodium thiosulfate solution was added, and the reaction mixture was extracted with ethyl acetate. The organic layer was dried over anhydrous magnesium sulfate and then concentrated under reduced pressure to obtain the title compound (1.25 g (yield: 89%)) as a colorless oily substance.

(22g)

1,5-Anhydro-2,3,4-trideoxy-2-{4-[trans-4-(4-methyl-5-{[3-(trifluoromethyl)phenoxy]methyl}-4H-1,2,4-triazol-3-yl)cyclohexyl]-1H-pyrazol-1-yl}-D-erythro-hexitol The compound of Example 22(22c): 1,5-anhydro-2-[2-tert-butoxycarbonyl)hydrazinyl]-6-O-[tert-butyl (diphenyl) silyl]-2,3,4-trideoxy-D-erythro-hexitol (1.72 g, 3.55 mmol) was dissolved in methanol (10 mL). To this, 5N hydrochloric acid (10 mL) was added, and the mixture was stirred at room temperature for 40 minutes. Then, the reaction temperature was raised to 60° C., and the mixture was stirred for 23 hours.

The reaction solution was concentrated, dissolved in methanol and diluted with diethyl ether. The resulting precipitate was filtered and the resulting solid was dissolved in methanol and concentrated again to obtain 1,5-anhydro-2,3,4-trideoxy-2-hydrazinyl-D-erythro-hexitol hydrochloride (658 mg) as a crude product.

The compound of Example 22(22f): 2-[trans-4-(4-methyl-5-{[3-(trifluoromethyl)phenoxy]methyl}-4H-1,2,4-triazol-3-yl)cyclohexyl]oxirane-2-carbaldehyde (1.25 g, 3.05 mmol) was dissolved in ethanol (15 mL). To this, sodium hydrogen carbonate (0.51 g, 6.1 mmol) was added at room temperature, then a solution of the above-mentioned crude product 1,5-anhydro-2,3,4-trideoxy-2-hydrazinyl-D-erythro-hexitol hydrochloride (623 mg) in ethanol (5 mL) was added dropwise, and the mixture was stirred at room temperature for 13 hours.

After the reaction mixture was diluted with dichloromethane, and insoluble matters were filtered, and the filtrate was concentrated. The resultant residue was purified by NH silica gel column chromatography [elution solvent: ethyl acetate alone, methanol/ethyl acetate=1/4 (V/V)] to obtain the title compound (1.41 g (yield: 89%)) as a white solid.

(22h)

1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-pyrazol-1-yl}-D-erythro-hexitol The compound of Example 22(22g): 1,5-anhydro-2,3,4-trideoxy-2-{4-[trans-4-(4-methyl-5-{[3-(trifluoromethyl)phenoxy]methyl}-4H-1,2,4-triazol-3-yl)cyclohexyl]-1H-pyrazol-1-yl}-D-erytro-hexitol (100 mg, 0.19 mmol) was dissolved in dichloromethane (4 mL). To this, 2,6-lutidine (0.0448 mL, 0.385 mmol) and trifluoromethanesulfonic acid anhydride (0.0388 mL, 0.231 mmol) were added at −30° C. and the mixture was stirred for 45 minutes. To the reaction mixture, azetidine (44 mg, 0.77 mmol) was added, and the mixture was stirred at 0° C. for 30 minutes and at room temperature for 2 hours, and then stirred at 50° C. with heating under reflux.

After the reaction temperature had returned to room temperature, the residue obtained by concentration under reduced pressure was purified by NH silica gel column chromatography [elution solvent: ethyl acetate alone, methanol/ethyl acetate=1/4 (V/V)] to obtain the title compound (49.7 mg (yield: 46%)) as a white solid.

Example 23

4-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]morpholine (23a)

tert-Butyl 2-[trans-4-(morpholin-4-yl)cyclohexyl] hydrazinecarboxylate 4-(Morpholin-4-yl)cyclohexanone (CAS Registry Number: 139025-93-7, WO2008095943) (6 g, 29.47 mmol) was dissolved in dichloroethane (40 mL). To this, acetic acid (0.51 mL, 8.84 mmol) and tert-butyl carbazate (Tokyo Chemical Industry Co., Ltd., Catalog Number: C0933) (4.01 g, 30.4 mmol) were added, and the mixture was stirred at 10° C. for 1 hour, then sodium borohydride (4.99 g, 132 mmol) was added and the mixture was stirred for 11 hours.

To the reaction solution, water was added, and the mixture was extracted with dichloromethane. The combined organic layer was washed with saturated saline and dried over anhydrous sodium sulfate. The residue obtained by concentration under reduced pressure was purified by silica gel column chromatography [elution solvent: dichloromethane/methanol=1/0-30/1, 0.1% ammonia water]. The obtained residue was purified by high performance liquid chromatography to obtain the title compound (700 mg (yield: 7.9%)) as a white solid.

(23b)

4-(trans-4-Hydrazinylcyclohexyl)morpholine hydrochloride

The compound of Example 23(23a): tert-butyl 2-[trans-4-(morpholin-4-yl)cyclohexyl]hydrazinecarboxylate (630 mg, 2 mmol) was dissolved in dichloromethane (15 mL). To this, 4N Hydrochloric acid-ethyl acetate (2 mL, 8 mmol) was added, and the mixture was stirred at 10° C. for 10 hours.

The resultant mixture was concentrated under reduced pressure to obtain the title compound (430 mg (yield: 89%)) as a white solid.

(23c)

Methyl{[4-(trifluoromethyl)pyridin-2-yl]oxy}acetate

Methyl glycolate (Tokyo Chemical Industry Co., Ltd., Catalog Number: G0199) (87 g, 969 mmol) was dissolved in tetrahydrofuran (1.47 L). To this, sodium hydride (63%) (23.3 g, 969 mmol) and 2-chloro-4-(trifluoromethyl)pyridine (Manchester, Catalog Number: S10181) were added at room temperature (80 g, 441 mmol) and the mixture was stirred at 90° C. for 4 hours.

The reaction mixture was diluted with ethyl acetate and washed with a saturated aqueous ammonium chloride solution. The organic layer was washed with saturated saline, and dried over anhydrous sodium sulfate. The residue obtained by concentration under reduced pressure was purified by silica gel column chromatography [elution solvent: hexane/ethyl acetate=1/0-3/1 (V/V)] to obtain the title compound (88.2 g (yield: 85%)) as a colorless oily substance.

(23d)

2-{[4-(Trifluoromethyl)pyridin-2-yl]oxy}acetohydrazide

The compound of Example 23(23c): methyl{[4-(trifluoromethyl)pyridin-2-yl]oxy}acetate (111 g, 472 mmol) was dissolved in ethanol (2.4 L). To this, hydrazine monohydrate (177 g, 3.54 mol) was added, and the mixture was stirred at 90° C. for 3 hours.

The resultant was concentrated under reduced pressure to obtain the title compound (106 g (yield: 95%)) as a white solid.

(23e)

Methyl trans-4-[4-methyl-5-({[4-(trifluoromethyl)pyridin-2-yl]oxy}methyl)-4H-1,2,4-triazol-3-yl]cyclohexanecarboxylate The compound of Example 19(19c): methyl trans-4-[(methylimino) (methylsulfanyl)methyl]cyclohexanecarboxylate (20 g, 87 mmol) was dissolved in ethanol (200 mL). To this, the compound of Example 23(23d): 2-{[4-(trifluoromethyl)pyridin-2-yl]oxy}acetohydrazide (20.5 g, 87 mmol) was added, and the mixture was stirred at 90° C. for 4 hours.

The residue obtained by concentration under reduced pressure was purified by silica gel column chromatography [elution solvent: methanol/dichloromethane=0/1-1/9 (V/V)] to obtain the title compound (19.7 g (yield: 57%)) as a white solid.

(23f)

{trans-4-[4-Methyl-5-({[4-(trifluoromethyl)pyridin-2-yl]oxy}methyl)-4H-1,2,4-triazol-3-yl]cyclohexyl}methanol The compound of Example 23(23e): methyl trans-4-[4-methyl-5-({[4-(trifluoromethyl)pyridin-2-yl]oxy}methyl)-4H-1,2,4-triazol-3-yl]cyclohexanecarboxylate (19.7 g, 49.4 mmol) was dissolved in tetrahydrofuran (250 mL). To this, a lithium aluminium hydride-tetrahydrofuran solution (2.5 M, 20 mL) was added under ice-cooling, and the mixture was stirred at room temperature for 25 minutes.

To the reaction mixture, water (1.9 mL), a 15% aqueous sodium hydroxide solution (1.9 mL), and water (5.7 mL) were sequentially added under ice-cooling, and the mixture was diluted with ethyl acetate and then filtered with celite. The filtrate was concentrated under reduced pressure to obtain the title compound (17.9 g (yield: 98%)) as a light yellow oily substance.

(23g)

trans-4-[4-Methyl-5-({[4-(trifluoromethyl)pyridin-2-yl]oxy}methyl)-4H-1,2,4-triazol-3-yl]cyclohexanecarbaldehyde The compound of Example 23(23f): {trans-4-[4-methyl-5-({[4-(trifluoromethyl)pyridin-2-yl]oxy}methyl)-4H-1,2,4-triazol-3-yl]cyclohexyl}methanol (17.9 g, 48.3 mmol) was dissolved in dichloromethane (300 mL). To this, Dess-Martin Periodinane (22.4 g, 52.8 mmol) was added under ice-cooling, and the mixture was stirred for 5 minutes under ice-cooling and at room temperature for 40 minutes.

The reaction solution was ice-cooled. To this, a 1N aqueous sodium hydroxide solution (230 mL) and a 10% aqueous sodium thiosulfate solution were added and stirred, and then the mixture was extracted with dichloromethane. The organic layer was dried over anhydrous sodium sulfate. The residue obtained by concentration under reduced pressure was purified by silica gel column chromatography [elution solvent: methanol/ethyl acetate=0/1-1/9 (V/V)] to obtain the title compound (11.6 g (yield: 65%)) as a white solid.

(23h)

{trans-4-[4-Methyl-5-({[4-(trifluoromethyl)pyridin-2-yl]oxy}methyl)-4H-1,2,4-triazol-3-yl]cyclohexyl}acetaldehyde (Methoxymethyl)triphenylphosphonium chloride (13.2 g, 38.4 mmol) was suspended in tetrahydrofuran (100 mL). To this, potassium tert-butoxide (4.31 g, 38.4 mmol) was added under ice-cooling and the mixture was stirred for 20 minutes. The resultant solution was added dropwise using a cannula to a solution of the compound of Example 23(23 g): trans-4-[4-methyl-5-({[4-(trifluoromethyl)pyridin-2-yl]oxy}methyl)-4H-1,2,4-triazol-3-yl]cyclohexanecarbaldehyde (9.44 g, 25.6 mmol) in tetrahydrofuran (150 mL). After 45 minutes, to a suspension of (methoxymethyl) triphenylphosphonium chloride (8.79 g, 25.6 mmol) in tetrahydrofuran (100 mL), potassium tert-butoxide (2.88 g, 25.6 mmol) was added under ice-cooling, and the mixture was stirred for 5 minutes. The obtained solution was added dropwise again to the reaction solution using a cannula.

After 10 minutes, water was added to the reaction solution, and the mixture was concentrated under reduced pressure and extracted with ethyl acetate. The organic layer was washed with saturated saline, and then dried over anhydrous sodium sulfate. After filtration, the residue obtained by concentration under reduced pressure was purified by silica gel column chromatography [elution solvent: ethyl acetate/hexane=1/1, ethyl acetate alone, methanol/ethyl acetate=1/9 (V/V)]. The obtained 2-[(5-{trans-4-[2-methoxyethenyl]cyclohexyl}-4-methyl-4H-1,2,4-triazol-3-yl)methoxy]-4-(trifluoromethyl)pyridine (10.7 g) was dissolved by adding tetrahydrofuran (100 mL), and 1N hydrochloric acid (70 mL) was added, then the mixture was stirred at room temperature for 2.5 hours.

The reaction solution was ice-cooled and 2N aqueous sodium hydroxide (35 mL) was added thereto and the mixture was extracted with ethyl acetate. The organic layer was washed with saturated saline, and then dried over anhydrous sodium sulfate. After filtration, the residue obtained by concentration under reduced pressure was purified by silica gel column chromatography [elution solvent: methanol/ethyl acetate=0/1-1/9 (V/V)] to obtain the title compound (6.87 g (yield: 70%)) as a colorless oily substance.

(23i)

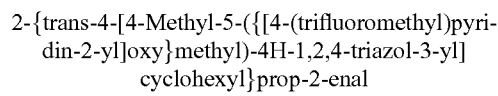

2-{trans-4-[4-Methyl-5-({[4-(trifluoromethyl)pyridin-2-yl]oxy}methyl)-4H-1,2,4-triazol-3-yl]cyclohexyl}prop-2-enal The compound of Example 23(23h): {trans-4-[4-methyl-5-({[4-(trifluoromethyl)pyridin-2-yl]oxy}methyl)-4H-1,2,4-triazol-3-yl] cyclohexyl} acetaldehyde (6.87 g, 18 mmol) was dissolved in N,N-dimethylformamide (40 mL). To this, a formaldehyde solution (37%) (6.6 mL, 89.8 mmol) and L-proline (618 mg, 5.39 mmol) were added, and the mixture was stirred at room temperature for 14 hours.

The reaction mixture was diluted with ethyl acetate and washed with water and saturated saline. The organic layer was dried over anhydrous sodium sulfate. After filtration, the residue obtained by concentration under reduced pressure was purified by silica gel column chromatography [elution solvent: ethyl acetate/hexane=1/2, ethyl acetate alone, methanol/ethyl acetate=1/9 (V/V)] to obtain the title compound (3.68 g (yield: 52%)) as a white solid.

(23j)

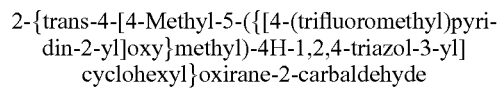

2-{trans-4-[4-Methyl-5-({[4-(trifluoromethyl)pyridin-2-yl]oxy}methyl)-4H-1,2,4-triazol-3-yl]cyclohexyl}oxirane-2-carbaldehyde The compound of Example 23(23i): 2-{trans-4-[4-methyl-5-({[4-(trifluoromethyl)pyridin-2-yl]oxy}methyl)-4H-1,2,4-triazol-3-yl] cyclohexyl} prop-2-enal (3.68 g, 9.33 mmol) was dissolved in methanol (60 mL). To this, a hydrogen peroxide solution (30%) (1.33 mL, 14 mmol) and a 5N aqueous sodium hydroxide solution (0.47 mL, 2.33 mmol) were sequentially added under ice-cooling and the mixture was stirred for 1 hour.

To the reaction mixture, a 10% aqueous sodium thiosulfate solution was added, and the reaction mixture was extracted with ethyl acetate. The organic layer was washed with saturated saline, and then dried over anhydrous sodium sulfate. The mixture was concentrated under reduced pressure, then dichloromethane was added. The mixture was azeotropically concentrated to obtain the title compound (3.4 g (yield: 89%)) as a white solid.

(23k)

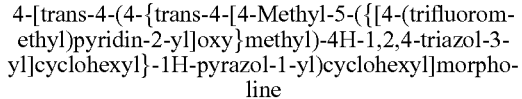

4-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]morpholine The compound of Example 23(23j): 2-{trans-4-[4-methyl-5-({[4-(trifluoromethyl)pyridin-2-yl]oxy}methyl)-4H-1,2,4-triazol-3-yl]cyclohexyl}oxirane-2-carbaldehyde (237 mg, 0.58 mmol) was dissolved in ethanol (29 mL). To this, a solution of the compound of Example 23(23b): 4-(trans-4-hydrazinylcyclohexyl) morpholine hydrochloride (150 mg, 0.64 mmol) in ethanol (5 mL) was added dropwise, and the mixture was stirred at room temperature for 2.5 hours, then stirred at 50° C. for 15.5 hours.

The residue obtained by concentration under reduced pressure was purified by silica gel column chromatography [elution solvent: hexane/ethyl acetate=1/4-0/1 (V/V)] to obtain the title compound (151 mg (yield: 46%)) as a white solid.

Example 24

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane (24a)

Benzyl 3-(trichloromethyl)oxaziridine-2-carboxylate

Benzyl (triphenyl-λ⁵-phosphanilidene) carbamate (CAS Registry Number: 81357-08-6, WO2012031298) (240 g, 583 mmol) was dissolved in toluene (600 mL). To this, 2,2,2-trichloroacetaldehyde (111 g, 758 mmol) was added, and the mixture was stirred at 110° C. for 1 hour.

The residue obtained by concentration under reduced pressure was dissolved in hexane (100 mL). The reaction solution was stirred for 30 minutes and insoluble matters were removed by filtration, then the filtrate was concentrated under reduced pressure to obtain benzyl(2,2,2-trichloroethylidene)carbamate (150 g) as a crude product.

The resultant crude product: benzyl (2,2,2-trichloroethylidene)carbamate (150 g) was dissolved in chloroform (3 L). To this, a solution of potassium carbonate (300 g, 2.17 mol) in water (3 L) and a solution of oxon (300 g, 488 mmol) in water (3 L) were added, and the mixture was stirred at 0° C. for 1 hour. The aqueous layer was separated, and freshly prepared solutions of potassium carbonate (300 g, 2.17 mol) in water (3 L) and of oxon (300 g, 488 mmol) in water (3 L) were added, and the mixture was stirred at 0° C. for 1 hour. This procedure was repeated 5 times, and then the reaction solution was extracted with chloroform. The combined organic layer was washed with saturated saline and dried over anhydrous sodium sulfate. The residue obtained by concentration under reduced pressure was purified by silica gel column chromatography [elution solvent: dichloromethane alone] to obtain the title compound (84 g (yield: 57%)) as a yellow oily substance.

(24b)

Benzyl [trans-4-(2-oxa-6-azaspiro[3.3]hept-6-yl)cyclohexyl]carbamate

Oxetane-3,3-diyldimethanol (Heat-Biochem, Catalog Number: HB-0630) (11.4 g, 96.6 mmol) was suspended in dichloromethane (200 mL). To this, N,N-diisopropylethylamine (140 mL, 805 mmol) was added and then trifluoromethanesulfonic acid anhydride (32.5 mL, 193 mmol) was added dropwise at −78° C. The mixture was stirred at −78° C. for 10 minutes, then the temperature was raised to ice-cooling and the mixture was stirred for 5 minutes. To the reaction mixture, a solution of benzyl(trans-4-aminocyclohexyl)carbamate (CAS Registry Number: 149423-77-8, WO1992021361) (20 g, 80.5 mmol) in acetonitrile (100 mL) was added, and the mixture was stirred for 15 minutes under ice-cooling, then the mixture was stirred at room temperature for 3 hours.

The reaction solution was diluted with dichloromethane and then extracted with dichloromethane. The organic layer was washed with water and saturated saline and dried over anhydrous sodium sulfate. To the residue obtained by concentration under reduced pressure, ethyl acetate and hexane were added, and the obtained solid was collected by filtration to obtain the title compound (14 g) as a white solid. Furthermore, the mother liquid was concentrated under reduced pressure and the obtained residue was purified by NH silica gel column chromatography [elution solvent: hexane/ethyl acetate=1/1-0/1 (V/V)] to obtain the title compound (2.5 g). Combined with the above-described obtained title compound, the title compound (16.5 g (yield: 62%)) was obtained as a white solid.

(24c)

trans-4-(2-Oxa-6-azaspiro[3.3]hept-6-yl)cyclohexanamine

The compound of Example 24(24b): benzyl [trans-4-(2-oxa-6-azaspiro [3.3] hept-6-yl)cyclohexyl]carbamate (14 g, 42.4 mmol) was dissolved in ethanol (200 mL). To this, 10% palladium carbon catalyst (1.4 g) was added and the mixture was stirred at room temperature for 2 hours under a hydrogen atmosphere.

To the reaction mixture, ethanol was added, then palladium-carbon was filtered off, and the filtrate was washed with ethanol. The resultant was concentrated under reduced pressure to obtain the title compound (8.2 g (yield: 100%)) as a white solid.

(24d)

Benzyl 2-[trans-4-(2-oxa-6-azaspiro[3.3]hept-6-yl) cyclohexyl]hydrazinecarboxylate The compound of Example 24(24c): trans-4-(2-oxa-6-azaspiro[3.3]hepta-6-yl)cyclohexanamine (8.2 g, 42 mmol) was dissolved in dichloromethane (80 mL). To this, a solution of the compound of Example 24(24a): benzyl 3-(trichloromethyl)oxaziridine-2-carboxylate (11 g, 29 mmol) in dichloromethane (80 mL) was added dropwise at −65° C. The mixture was stirred at −65° C. for 10 minutes, then the temperature was raised to ice-cooling.

To the reaction mixture, diisopropylamine (12 mL, 84 mmol) was added, and the mixture was stirred for 15 minutes. Then, a saturated aqueous ammonium chloride solution was added to separate liquids, and the organic layer was washed with saturated saline. The organic layer was dried over anhydrous sodium sulfate. The residue obtained by concentration under reduced pressure was purified by NH silica gel column chromatography [elution solvent: hexane/ethyl acetate=1/1-0/1 (V/V)] to obtain the title compound (5.8 g (yield: 40%)) as a white solid.

(24e)

6-(trans-4-Hydrazinylcyclohexyl)-2-oxa-6-azaspiro [3.3]heptane acetate

The compound of Example 24(24d): benzyl [trans-4-(2-oxa-6-azaspiro[3.3]hept-6-yl)cyclohexyl]hydrazine carboxylate (5.8 g, 17 mmol) was dissolved in ethanol (60 mL). To this, acetic acid (1.2 mL, 20 mmol) and 10% palladium carbon catalyst (0.6 g) were added and the mixture was stirred at room temperature for 1 hour under a hydrogen atmosphere. To the reaction mixture, acetic acid (1.2 mL, 20 mmol) was added, and the reaction mixture was stirred under a hydrogen atmosphere at room temperature for 1 hour. To the reaction mixture, acetic acid (2.3 mL, 40 mmol) was added, and the reaction mixture was stirred under a hydrogen atmosphere at room temperature for 2 hours.

To the reaction mixture, ethanol was added, then palladium-carbon was filtered off, and the filtrate was washed with ethanol. To this, toluene was added, and the mixture was azeotropically concentrated, and concentrated under reduced pressure to obtain the title compound (4.5 g (yield: 99%)) as a light yellow oily substance.

(24f)

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane The compound of Example 23(23j): 2-{trans-4-[4-methyl-5-({[4-(trifluoromethyl)pyridin-2-yl]oxy}methyl)-4H-1,2,4-triazol-3-yl]cyclohexyl}oxirane-2-carbaldehyde (6 g, 14.6 mmol) was dissolved in ethanol (25 mL). To this, the compound of Example 24(24e): 6-(trans-4-hydrazinylcyclohexyl)-2-oxa-6-azaspiro[3.3]heptane acetate (4.76 g, 17.5 mmol) was added, and the mixture was stirred at room temperature, and allowed to stand still overnight.

To this, toluene was added, and the reaction solvent was distilled away under reduced pressure and the resultant residue was purified by NH silica gel column chromatography [elution solvent: methanol/ethyl acetate=0/1-1/19 (V/V)] to obtain the title compound (4.1 g (yield: 48%)) as a white solid.

Example 25

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane (25a)

Benzyl [trans-4-(4-{trans-4-[4-methyl-5-({[4-(trifluoromethyl)pyridin-2-yl]oxy}methyl)-4H-1,2,4-triazol-3-yl]cyclohexyl}-1H-pyrazol-1-yl)cyclohexyl]carbamate Benzyl (trans-4-hydrozinylcyclohexyl)carbamate hydrochloride (CAS Registry Number: 1607494-41-6, WO2014064219) (442 mg, 1.47 mmol) was suspended in ethanol (10 mL). To this, the compound of Example 23(23j): 2-{trans-4-[4-methyl-5-({[4-(trifluoromethyl)pyridin-2-yl]oxy}methyl)-4H-1,2,4-triazol-3-yl] cyclohexyl}oxirane-2-carbaldehyde (504 mg, 1.23 mmol) was added and the mixture stirred at room temperature for 43 hours.

The solvent was distilled away under reduced pressure and the resultant residue was purified by NH silica gel column chromatography [elution solvent: hexane/dichloromethane/ethyl acetate=2/8/0-0/2/8 (V/V/V)]. The resultant crude product was washed with ethyl acetate to obtain the title compound (663 mg (yield: 85%)) as a white solid.
(25b)

trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexanamine The compound of Example 25(25a): benzyl [trans-4-(4-{trans-4-[4-methyl-5-({[4-(trifluoromethyl)pyridin-2-yl]oxy}methyl)-4H-1,2,4-triazol-3-yl]cyclohexyl}-1H-pyrazol-1-yl)cyclohexyl]carbamate (300 mg, 0.47 mmol) was dissolved in methanol (6 mL) and dichloromethane (1 mL). To this, acetic acid (0.14 mL, 2.4 mmol) and 10% palladium carbon catalyst (150 mg) were added at room temperature and the mixture was stirred at room temperature for 4 hours under a hydrogen atmosphere.

Palladium-carbon was filtered off, and the mixture was washed with dichloromethane. The resultant was concentrated under reduced pressure and the solvent was azeotropically concentrated with ethanol and toluene, and the resultant residue was purified by silica gel column chromatography [elution solvent: methanol/dichloromethane=0/1-1/19 (V/V)] to obtain the title compound (217 mg (yield: 92%)) as a white solid.
(25c)

Oxetane-2,2-diyldimethanol

Diethyl oxetane-2,2-dicarboxylate (CAS Registry Number: (1384465-73-9, Synthesis (2012), 44 (10), 1584-1590) (4 g, 19.8 mmol) and lithium chloride (2.52 g, 59.4 mmol) were dissolved in tetrahydrofuran (20 mL) and methanol (40 mL). To this, sodium borohydride (2.25 g, 59.4 mmol) was added under ice-cooling, and then the mixture was stirred at 0° C. for 30 minutes, then at 20° C. for 18.5 hours.

To the reaction mixture, an aqueous potassium sodium tartrate solution was added, and the mixture was stirred at 20° C. for 30 minutes, and then extracted with ethyl acetate and dichloromethane. The combined organic layer was dried over anhydrous sodium sulfate. The residue obtained by concentration under reduced pressure was purified by silica gel column chromatography [elution solvent: ethyl acetate/petroleum ether=1/2-1/1 (V/V), 5% methanol] to obtain the title compound. The aqueous layer was re-extracted with chloroform/isopropanol (4/1 (V/V)), and the combined organic layer was dried over anhydrous sodium sulfate. The residue obtained by concentration under reduced pressure was purified by silica gel column chromatography [elution solvent: ethyl acetate/petroleum ether=1/2-1/1 (V/V), 5% methanol] to obtain the title compound (1.75 g (yield: 75%)) as a colorless oily substance.
(25d)

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane The compound of Example 25(25c): oxetane-2,2-diyldimethanol (75 mg, 0.63 mmol) and N,N-diisopropylethylamine (0.72 mL, 4.23 mmol) were dissolved in dichloromethane (1.5 mL). The mixture was cooled to −78° C., then trifluoromethanesulfonic acid anhydride (0.21 mL, 1.27 mmol) was added dropwise thereto. The mixture was stirred at −78° C. for 15 minutes. To this, a solution of the compound of Example 25(25b): trans-4-(4-{trans-4-[4-methyl-5-({[4-(trifluoromethyl)pyridin-2-yl]oxy}methyl)-4H-1,2,4-triazol-3-yl]cyclohexyl}-1H-pyrazol-1-yl)cyclohexanamine (213 mg, 0.42 mmol) in dichloromethane (5 mL) was added at 0° C., and the mixture was stirred at 0° C. for 15 minutes and then stirred at room temperature for 18 hours.

The residue obtained by concentration under reduced pressure was purified by NH silica gel column chromatography [elution solvent: methanol/dichloromethane=0/1-1/99 (V/V)]. To the obtained crude product, diethyl ether was added, and the precipitated solid was collected by filtration to obtain of the title compound (76 mg (yield: 31%)) as a white solid.

Example 26

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.4]octane (26a)

Benzyl 2-(4-oxocyclohexyl)hydrazinecarboxylate

Benzyl 2-(1,4-dioxaspiro[4.5]dec-8-yl)hydrazine carboxylate (CAS Registry Number: 1630725-36-8, WO2014163146) (1.5 g, 4.9 mmol) was dissolved in tetrahydrofuran (9.8 mL). To this, 1N hydrochloric acid (9.8 mL, 9.8 mmol) was added and the mixture was stirred at room temperature for 1 hour and then stirred at 50° C. for 5 hours.

To the residue obtained by concentration under reduced pressure, ethyl acetate was added, and the mixture was neutralized by adding 1N sodium hydroxide (10 mL, 10 mmol). To the reaction mixture, water (20 ml) was added, and the reaction mixture was extracted with ethyl acetate. The organic layer was washed with saturated saline, and dried over anhydrous sodium sulfate. The resultant was concentrated under reduced pressure to obtain the title compound (1.27 g (yield: 99%)) as a white solid.
(26b)

Benzyl 2-[trans-4-(2-oxa-6-azaspiro[3.4]oct-6-yl)cyclohexyl]hydrazinecarboxylate 2-Oxa-6-azaspiro[3.4]octane (J&W-PharmLab, Catalog Number: 75R0364) (500 mg, 4.42 mmol) was dissolved in methanol/dichloromethane (1/1 (V/V)) (8.8 mL). To this, the compound of Example 26(26a): benzyl 2-(4-oxocyclohexyl)hydrazinecarboxylate (5.06 g, 30.5 mmol) was added at room temperature, and the mixture was stirred at room temperature for 15 minutes. To the reaction mixture, acetic acid (0.76 ml, 13.3 mmol) and sodium cyanoborohydride (2.34 g, 8.84 mmol) were added, and the mixture was stirred at room temperature for 16 hours.

To the reaction mixture, saturated aqueous sodium bicarbonate was added, and the reaction mixture was extracted with dichloromethane. The organic layer was washed with saturated saline, and then dried over anhydrous sodium sulfate. The residue obtained by concentration under reduced pressure was purified by NH silica gel column chromatography [elution solvent: hexane/ethyl acetate=7/3-

1/4 (V/V)]. To the obtained crude product, diisopropyl ether was added and trituration was performed to obtain the title compound (154 mg (yield: 10%)) as a white solid.

(26c)

6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.4]octane The compound of Example 26(26b)): benzyl 2-[trans-4-(2-oxa-6-azaspiro[3.4]octa-6-yl)cyclohexyl}]hydrazine carboxylate (150 mg, 0.42 mmol) was dissolved in ethanol (3 mL). To this, acetic acid (0.119 mL, 2.09 mmol) and 10% palladium on carbon catalyst (45 mg) were added, and the mixture was stirred at room temperature for 5 hours under a hydrogen atmosphere.

Palladium-carbon was filtered off, and the filtrate was washed with ethanol. The residue obtained by concentration under reduced pressure was dissolved in ethanol (15 mL). To this, the compound of Example 23(23j): 2-{trans-4-[4-methyl-5-({[4-(trifluoromethyl)pyridin-2-yl]oxy}methyl)-4H-1,2,4-triazol-3-yl]cyclohexyl}oxirane-2-carbaldehyde (119 mg, 0.42 mmol) in ethanol (6 mL) was added and the mixture was stirred at room temperature for 18.5 hours.

The residue obtained by concentration under reduced pressure was purified by NH silica gel column chromatography [elution solvent: ethyl acetate alone] to obtain the title compound (50 mg (yield: 20%)) as a white solid.

Example 27

2-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-6-oxa-2-azaspiro[3.4]octane (27a)

2-(1,4-Dioxaspiro[4.5]dec-8-yl)-6-oxa-2-azaspiro[3.4]octane

2-Benzyl-6-oxa-2-azaspiro[3.4]octane (CAS Registry Number: 1419590-34-3, WO2013011285) (2 g, 9.84 mmol) was dissolved in ethanol (40 mL). To this, acetic acid (2.81 mL, 49.2 mmol) and 10% palladium carbon catalyst (1 g) were added, and the mixture was stirred under a hydrogen atmosphere at room temperature for 23 hours.

Palladium-carbon was filtered off, and the filtrate was washed with ethanol. After concentration under reduced pressure, a crude product 6-oxa-2-azaspiro[3.4]octaneacetate (3.15 g) was obtained as a light brown oily substance.

The obtained crude product 6-oxa-2-azaspiro[3.4]octaneacetate (3.15 g) was dissolved in ethanol (40 mL). To this, 1,4-dioxaspiro [4.5] decan-8-one (Tokyo Chemical Industry Co., Ltd., Catalog Number: C1292) (1.54 g, 9.84 mmol) was added, and the mixture was stirred at room temperature for 20 minutes. To the reaction mixture, sodium cyanoborohydride (1.24 g, 19.7 mmol) was added, and the mixture was stirred at room temperature for 22 hours.

To the reaction mixture, saturated aqueous sodium bicarbonate was added, and the reaction mixture was extracted with dichloromethane. The organic layer was washed with saturated saline, and then dried over anhydrous sodium sulfate. The residue obtained by concentration under reduced pressure was purified by NH silica gel column chromatography [elution solvent: hexane/ethyl acetate=1/0-1/1 (V/V)] to obtain the title compound (2.36 g (yield: 95%)) as a white solid.

(27b)

4-(6-Oxa-2-azaspiro[3.4]oct-2-yl)cyclohexanone

The compound of Example 27(27a): 2-(1,4-dioxaspiro[4.5]deca-8-yl)-6-oxa-2-azaspiro[3.4]octane (1.01 g, 3.98 mmol) was dissolved in tetrahydrofuran (8 mL). To this, 1N hydrochloric acid (8 mL, 8 mmol) was added, and the mixture was stirred at 50° C. for 66 hours.

To the reaction mixture, saturated aqueous sodium bicarbonate was added, and the reaction mixture was extracted with dichloromethane. The organic layer was washed with saturated saline, and then dried over anhydrous sodium sulfate. The resultant was concentrated under reduced pressure to obtain the title compound (0.85 g (quantitative)) as a light brown oily substance.

(27c)

Benzyl 2-[trans-4-(6-oxa-2-azaspiro[3.4]oct-2-yl)cyclohexyl]hydrazinecarboxylate The compound of Example 27(27b): 4-(6-oxa-2-azaspiro[3.4]oct-2-yl)cyclohexanone (833 mg, 3.98 mmol) was dissolved in methanol (16 mL). To this, benzyl carbazate (Tokyo Chemical Industry Co., Ltd., Catalog Number: C1564) (661 mg, 3.98 mmol) was added at room temperature, and the mixture was stirred at room temperature for 20 minutes. To the reaction mixture, acetic acid (0.46 ml, 7.96 mmol) and sodium cyanoborohydride (500 g, 7.96 mmol) were added, and the mixture was stirred at room temperature for 17 hours.

To the reaction mixture, saturated aqueous sodium bicarbonate was added, and the reaction mixture was extracted with dichloromethane. The organic layer was washed with saturated saline, and then dried over anhydrous sodium sulfate. The residue obtained by concentration under reduced pressure was purified by NH silica gel column chromatography [elution solvent: hexane/ethyl acetate=65/35-0/1 (V/V)]. To the obtained crude product, diisopropyl ether was added, and trituration was performed to obtain the title compound (822 mg (yield: 58%)) as a white solid.

(27d)

2-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-6-oxa-2-azaspiro[3.4]octane The compound of Example 27(27c): benzyl 2-[trans-4-(6-oxa-2-azaspiro[3.4]octa-2-yl)cyclohexyl]hydrazine carboxylate (200 mg, 0.56 mmol) was dissolved in ethanol (4 mL). To this, acetic acid (0.159 mL, 2.78 mmol) and 10% palladium on carbon catalyst (100 mg) was added, and the mixture was stirred at room temperature for 4 hours under a hydrogen atmosphere.

Palladium-carbon was filtered off, and the filtrate was washed with ethanol. The residue obtained by concentration under reduced pressure was dissolved in ethanol (7 mL). To this, a solution of the compound of Example 23(23j): 2-{trans-4-[4-methyl-5-({[4-(trifluoromethyl)pyridin-2-yl]oxy}methyl)-4H-1,2,4-triazol-3-yl]cyclohexyl}oxirane-2-carbaldehyde (208 mg, 0.51 mmol) in ethanol (18 mL) was added, and the mixture was stirred at 50° C. for 16 hours.

The residue obtained by concentration under reduced pressure was purified by NH silica gel column chromatography [elution solvent: hexane/ethyl acetate=2/8-0/1 (V/V)] to obtain the title compound (92 mg (yield: 30%)) as a white solid.

Example 28

(1SR,2SR,4RS)-2-(Azetidin-1-yl)-4-(4-{trans-4-[4-methyl-5-({[4-(trifluoromethyl)pyridin-2-yl]oxy}methyl)-4H-1,2,4-triazol-3-yl]cyclohexyl}-1H-pyrazol-1-yl)cyclopentanol (28a)

2-[(1RS,3SR,4SR)-3-Azido-4-{[tert-butyl(diphenyl)silyl]oxy}cyclopentyl]-1H-isoindole-1,3(2H)-dione 2-[(1RS,3SR,4SR)-3-Azido-4-hydroxycyclopentyl]-1H-isoindol-1,3(2H)-dione (600 mg, 2.2 mmol) synthesized according to a reference document (Arch. Pharm. Chem. Life Sci. 2012, 345, 677-686) was dissolved in N,N-dimethylformamide (10 mL). To this, imidazole (0.39 g, 5.8 mmol) and tert-butyldiphenylchlorosilane (790 mg, 2.9 mmol) were added and the mixture was stirred at room temperature for 6 hours.

The reaction mixture was diluted with ethyl acetate and washed with water. The organic layer was washed with saturated saline, and dried over anhydrous sodium sulfate. The residue obtained by concentration under reduced pressure was purified by silica gel column chromatography [elution solvent: hexane/ethyl acetate=97/3-7/3 (V/V)] to obtain the title compound (0.95 g (yield: 84%)) as a light yellow solid.

(28b)

2-[(1RS,3SR,4SR)-3-Amino-4-{[tert-butyl(diphenyl)silyl]oxy}cyclopentyl]-1H-isoindole-1,3(2H)-dione The compound of Example 28(28a): 2-[(1RS,3SR,4SR)-3-azido-4-{[[tert-butyl(diphenyl)silyl]oxy}cyclopentyl]-1H-isoindole-1,3(2H)-dione (0.1 g, 0.2 mmol) was dissolved in ethanol (5 mL). To this, 10% palladium on carbon catalyst (0.1 g) was added, and the mixture was stirred at room temperature for 2 hours under a hydrogen atmosphere. Palladium-carbon was filtered off, and the filtrate was washed with ethanol and concentrated under reduced pressure to obtain the title compound (95 mg (quantitative)) as a light yellow oily substance.

(28c)

Benzyl [(1SR,2SR,4RS)-2-{[tert-butyl(diphenyl)silyl]oxy}-4-(1,3-dioxo-1,3-dihydro-2H-isoindol-2-yl)cyclopentyl]carbamate The compound of Example 28(28b): 2-[(1RS,3SR,4SR)-3-amino-4-{[tert-butyl(diphenyl)silyl]oxy}cyclopentyl]-1H-isoindole-1,3(2H)-dione (95 mg, 0.2 mmol) was dissolved in tetrahydrofuran (2 mL). To this, triethylamine (0.081 mL, 0.59 mmol) and benzyl chloroformate (0.034 mL, 0.24 mmol) were added, and the mixture was stirred at room temperature for 14 hours.

The reaction mixture was diluted with ethyl acetate and washed with water. The organic layer was washed with saturated saline, and dried over anhydrous sodium sulfate. The residue obtained by concentration under reduced pressure was purified by silica gel column chromatography [elution solvent: hexane/ethyl acetate=9/1-1/1 (V/V)] to obtain the title compound (70 mg (yield: 58%)) as a light yellow solid.

(28d)

Benzyl [(1SR,2SR,4RS)-4-amino-2-{[tert-butyl(diphenyl)silyl]oxy}cyclopentyl]carbamate The compound of Example 28 (28c): benzyl [(1SR,2SR,4RS)-2-{[tert-butyl(diphenyl)silyl]oxy}-4-(1,3-dioxo-1,3-dihydro-2H-isoindol-2-yl)cyclopentyl]carbamate (70 mg, 0.11 mmol) was dissolved in ethanol (2 mL). To this, hydrazine monohydrate (0.017 mL, 0.34 mmol) was added, and the mixture was stirred at 90° C. for 3 hours.

The residue obtained by concentrating the reaction mixture under reduced pressure was purified by silica gel column chromatography [elution solvent: methanol/ethyl acetate=0/1-1/9 (V/V)] to obtain the title compound (52 mg (yield: 94%)) as a light yellow oily substance.

(28e)

(1SR,2SR,4RS)-2-(Azetidin-1-yl)-4-(4-{trans-4-[4-methyl-5-({[4-(trifluoromethyl)pyridin-2-yl]oxy}methyl)-4H-1,2,4-triazol-3-yl]cyclohexyl}-1H-pyrazol-1-yl)cyclopentanol The compound of Example 28 (28d): benzyl [(1SR,2SR,4RS)-4-amino-2-{[tert-butyl(diphenyl)silyl]oxy}cyclopentyl]carbamate (837 mg, 1.71 mmol) was dissolved in tetrahydrofuran (20 mL) and dimethylacetamide (10 mL). To this, a solution of tert-butyl 3-(trichloromethyl)oxaziridine-2-carboxylate (CAS Registry Number: 219547-77-0, WO2012074067) (315 mg, 1.2 mmol) in tetrahydrofuran (3 mL) was added dropwise at −70° C. for 30 minutes. The mixture was stirred for 1.5 hours while warming to −20° C.

To this, dilute hydrochloric acid and ethyl acetate were added at −20° C., and the mixture was extracted with ethyl acetate. The organic layer was washed with water and saturated saline and dried over anhydrous sodium sulfate. The residue obtained by concentration under reduced pressure was purified by NH silica gel column chromatography [elution solvent: hexane/ethyl acetate=8/2-6/4 (V/V)] to obtain the crude product of tert-butyl 2-[(1RS,3SR,4SR)-3-{[(benzyloxy)carbonyl]amino}-4-{[tert-butyl(diphenyl)silyl]oxy}cyclopentyl]hydrazine carboxylate (650 mg) as a colorless oily substance.

Similarly, the compound of Example 28(28d): benzyl [(1SR,2SR,4RS)-4-amino-2-{[tert-butyl(diphenyl)silyl]oxy}cyclopentyl]carbamate (330 mg, 0.675 mmol) was dissolved in tetrahydrofuran (8 mL) and dimethylacetamide (4 mL). To this, a solution of tert-butyl 3-(trichloromethyl)oxadiridine-2-carboxylate (CAS Registry Number: 219547-77-0, WO2012074067) (124 mg, 0.472 mmol) in tetrahydrofuran (1 mL) was added dropwise at −60° C. for 30 minutes. The mixture was stirred for 1 hour while warming to −20° C.

To the reaction mixture, dilute hydrochloric acid and ethyl acetate was added at −20° C., and the mixture was extracted with ethyl acetate. The organic layer was washed with water and saturated saline and dried over anhydrous sodium sulfate. The residue obtained by concentration under reduced pressure was combined with the above-described crude product, and the mixture was purified by NH silica gel column chromatography [elution solvent hexane/ethyl acetate=9/1-7/3 (V/V)] to obtain tert-butyl 2-[(1RS,3SR,4SR)-3-{[(benzyloxy)carbonyl]amino}-4-{[tert-butyl(diphenyl)silyl]oxy}cyclopentyl]hydrazinecarboxylate (518 mg) as a colorless oily substance.

The obtained tert-butyl 2-[(1RS,3SR,4SR)-3-{[(benzyloxy)carbonyl]amino}-4-{[tert-butyl(diphenyl) silyl] oxy}cyclopentyl]hydrazinecarboxylate (518 mg, 0.86 mmol) was dissolved in ethanol (15 mL). To this, a 10% palladium carbon catalyst (100 mg) was added, and the mixture was stirred under a hydrogen atmosphere at room temperature for 2 hours and then stirred at 60° C. for 2 hours.

Palladium-carbon was filtered off, and the filtrate was washed with ethyl acetate. The residue obtained by concentration under reduced pressure was dissolved in tetrahydrofuran (15 mL). To this, a 10% palladium carbon catalyst (100 mg) was added, and the mixture was stirred under a hydrogen atmosphere at room temperature for 18 hours and then stirred at 60° C. for 32 hours.

Palladium-carbon was filtered off, and the filtrate was washed with ethyl acetate. The residue obtained by concentration under reduced pressure was purified by NH silica gel column chromatography [elution solvent: hexane/ethyl acetate=9/1-2/8 (V/V)] to obtain tert-butyl 2-[(1RS,3SR,4SR)-3-amino-4-{[tert-butyl(diphenyl)silyl]oxy}cyclopentyl]hydrazinecarboxylate (215 mg) as a colorless oily substance.

The obtained tert-butyl 2-[(1RS,3SR,4SR)-3-amino-4-{[tert-butyl (diphenyl)silyl]oxy}cyclopentyl]hydrazine carboxylate (212 mg, 0.451 mmol) was dissolved in acetonitrile (10 mL). To this, potassium carbonate (310 mg, 2.24 mmol) and 1,3-dibromopropane (Tokyo Chemical Industry Co., Ltd., Catalog Number: D0202) (145 mg, 0.718 mmol) were added and the mixture was stirred at 90° C. for 4.5 hours.

The residue obtained by concentrating the reaction mixture under reduced pressure was subjected to NH silica gel column chromatography [elution solvent: hexane/ethyl acetate=9/1-4/6 (V/V)] to obtain tert-butyl 2-[(1RS,3SR, 4SR)-3-(azetidin-1-yl)-4-{[tert-butyl (diphenyl)silyl] oxy}cyclopentyl]hydrazinecarboxylate (163 mg) as a colorless oily substance.

The obtained tert-butyl 2-[(1RS,3SR,4SR)-3-(azetidin-1-yl)-4-{[tert-butyl (diphenyl)silyl]oxy}cyclopentyl]hydrazinecarboxylate (160 mg, 0.314 mmol) was dissolved in methanol (2 mL). To this, 4N hydrochloric acid-1,4-dioxane (4 mL, 16 mmol) was added, and the mixture was stirred at room temperature for 2 hours.

To the residue obtained by concentrating the reaction mixture under reduced pressure, ethanol was added, and the mixture was azeotropically concentrated to obtain 1-[(1SR, 2SR,4RS)-2-{[tert-butyl(diphenyl)silyl]oxy}-4-hydrazinylcyclopentyl]azetidine hydrochloride (176 mg) as a colorless oily substance.

The obtained 1-[(1SR,2SR,4RS)-2-{[tert-butyl(diphenyl) silyl]oxy}-4-hydrozinylcyclopentyl]azetidine hydrochloride (176 mg, 0.429 mmol) and the compound of Example 23(23j): 2-{trans-4-[4-methyl-5-({[4-(trifluoromethyl)pyridin-2-yl]oxy}methyl)-4H-1,2,4-triazol-3-yl] cyclohexyl}oxirane-2-carbaldehyde (117 mg, 0.285 mmol) were dissolved in ethanol (15 mL) and the mixture was stirred at room temperature for 18 hours.

The residue obtained by concentration under reduced pressure was purified by NH silica gel column chromatography [elution solvent hexane/ethyl acetate=9/1-0/1 (V/V)] to obtain 2-{[5-(trans-4-{1-[(1RS,3SR,4SR)-3-(azetidin-1-yl)-4-{[tert-butyl (diphenyl)silyl]oxy}cyclopentyl]-1H-pyrazol-4-yl}cyclohexyl)-4-methyl-4H-1,2,4-triazol-3-yl] methoxy}-4-(trifluoromethyl)pyridine (52 mg) as an colorless oily substance.

The obtained 2-{[5-(trans-4-{1-[(1RS,3SR,4SR)-3-(azetidin-1-yl)-4-{[tert-butyl(diphenyl)silyl]oxy}cyclopentyl]-1H-pyrazol-4-yl}cyclohexyl)-4-methyl-4H-1,2,4-triazol-3-yl] methoxy}-4-(trifluoromethyl)pyridine (52 mg, 0.066 mmol) was dissolved in tetrahydrofuran (2 mL). To this, a 1M tetrabutylammonium fluoride-tetrahydrofuran solution (0.2 mL, 0.2 mmol) was added and the mixture was stirred at 70° C. for 3 hours.

The reaction mixture was diluted with ethyl acetate and washed with water. The organic layer was washed with saturated saline, and dried over anhydrous sodium sulfate. The residue obtained by concentration under reduced pressure was azeotropically concentrated with acetonitrile, then ethyl acetate was added. The mixture was filtered and then washed with ethyl acetate. The obtained crude product was purified by NH silica gel column chromatography [elution solvent: hexane/ethyl acetate=7/3-0/1 (V/V)] to obtain the title compound (20.1 mg (yield: 2.4%)) as a white solid.

Example 29

{1-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]azetidine-3,3-diyl}dimethanol The compound of Example 24(24f): 6-[trans-4-(4-{trans-4-[4-methyl-5-({[4-(trifluoromethyl)pyridin-2-yl] oxy}methyl)-4H-1,2,4-triazol-3-yl]cyclohexyl}-1H-pyrazol-1-yl)cyclohexyl]-2-oxa-6-azaspiro[3.3]heptane (100 mg, 0.17 mmol) was dissolved in 1,4-dioxane (4 mL). To this, sulfuric acid (0.57 mL, 10.6 mmol) was added and the mixture was stirred at 70° C. for 2 hours. To the reaction mixture, water (4 mL) was added, and the mixture was stirred at 70° C. for 3 hours.

To the reaction mixture, dichloromethane and saturated aqueous sodium bicarbonate were added under ice-cooling, and the mixture was extracted with dichloromethane. The organic layer was washed with saturated saline, and dried over anhydrous sodium sulfate. The residue obtained by concentration under reduced pressure was purified by thin layer silica gel chromatography [developing solvent: dichloromethane/methanol=3/1 (V/V)] to obtain the title compound (13 mg (yield: 12%)) as a white solid.

Example 30

Methyl 3-{[5-(trans-4-{1-[trans-4-(azetidin-1-yl) cyclohexyl]-1H-pyrazol-4-yl}cyclohexyl)-4-methyl-4H-1,2,4-triazol-3-yl]methoxy}benzoate (30a)

4-(Azetidin-1-yl)cyclohexanone 4-aminocyclohexanone hydrochloride (CAS Registry Number: 675112-40-0, WO2004024728) (40 g, 267 mmol) was dissolved in acetonitrile. To this, potassium carbonate (180 g, 1.3 mol) and 1,3-dibromopropane (27 mL, 265 mmol) were added, and the mixture was stirred at 70° C. for 10 hours.

The reaction mixture was filtered and the filtrate was concentrated under reduced pressure. The resultant residue was purified by silica gel column chromatography [elution solvent: methanol/dichloromethane=0/1-1/40 (V/V), 0.1% ammonia water] to obtain the title compound (13 g (yield: 29%)) as a yellow oily substance.

(30b)

tert-Butyl 2-[trans-4-(azetidin-1-yl)cyclohexyl]hydrazinecarboxylate

The compound of Example 30(30a): 4-azetidin-1-yl)cyclohexanone (12 g, 78.3 mmol) was dissolved in methanol (100 mL). To this, sodium carbonate (45 g, 317 mmol) and tert-butyl carbazate (10.5 g, 79.1 mmol) were added, and the mixture was stirred at 15° C. for 1 hour.

The residue obtained by concentrating the reaction mixture under reduced pressure was dissolved in a mixed solvent of dichloromethane (24 mL) and methanol (6 mL). To this, sodium borohydride (7.22 g, 190.74 mmol) was added and the mixture was stirred at 15° C. for 12 hours.

To the reaction mixture, water was added, and the mixture was extracted with ethyl acetate. The combined organic layer was washed with saturated saline and dried over anhydrous sodium sulfate. The residue obtained by concentration under reduced pressure was dissolved in a mixed solvent of methanol/ethyl acetate (1/20 (V/V), 42 mL). To this, petroleum ether was added, and the precipitated solid was collected by filtration to obtain a crude product. The obtained crude product was purified by high performance liquid chromatography to obtain the title compound (3.1g (yield: 17%)) as a white solid.

(30c)

1-(trans-4-Hydrazinylcyclohexyl)azetidine hydrochloride

The compound of Example 30(30b): tert-butyl 2-[trans-4-azetidin-1-yl)cyclohexyl]hydrazine carboxylate (2.9 g, 10.2 mmol) was dissolved in dichloromethane (35 mL). To this, 4N hydrochloric acid-ethyl acetate (14.5 mL, 58 mmol) was added, and the mixture was stirred at 15° C. for 10 hours.

The reaction mixture was concentrated under reduced pressure to obtain the title compound (2.43 g (yield: 98%)) as a white solid.

(30d)

{trans-4-[5-({[tert-Butyl(diphenyl)silyl]oxy}methyl)-4-methyl-4H-1,2,4-triazol-3-yl]cyclohexyl}acetaldehyde (Methoxymethyl)triphenylphosphonium chloride (27.8 g, 81 mmol) was suspended by adding tetrahydrofuran (200 mL). To this, potassium tert-butoxide (9.12 g, 81 mmol) was added under ice-cooling and the mixture was stirred for 10 minutes. The obtained solution was added dropwise while stirring, using a cannula, to a solution of the compound of Example 20(20c): trans-4-[5-({[tert-butyl(diphenyl)silyl]oxy}methyl)-4-methyl-4H-1,2,4-triazol-3-yl]cyclohexanecarbaldehyde (18.7 g, 40.5 mmol) in tetrahydrofuran (200 mL) under ice-cooling. The mixture was stirred for 10 minutes under ice-cooling.

To the reaction solution, water was added, and the mixture was concentrated to about half volume under reduced pressure, then extracted with ethyl acetate, and dried over anhydrous sodium sulfate. The residue obtained by concentration under reduced pressure was purified by silica gel column chromatography [elution solvent dichloromethane/ ethyl acetate=1/0-0/1 (V/V)]. The obtained residue was dissolved in toluene (200 mL). To this, magnesium chloride (11.6 g, 122 mmol) was added and the mixture was stirred at 60° C. for 1.5 hours. After the mixture was cooled to room temperature, insoluble matters were filtered. The residue obtained by concentration under reduced pressure was dissolved by adding tetrahydrofuran (160 mL). To this, 1N hydrochloric acid (80 mL) was added under ice-cooling, and the mixture was stirred for 8 hours.

The mixture was ice-cooled, and neutralized by adding a 1N aqueous sodium hydroxide solution (80 mL) dropwise, and extracted with ethyl acetate. The organic layer was washed with saturated saline, and then dried over anhydrous sodium sulfate. The residue obtained by concentration under reduced pressure was purified by silica gel column chromatography [elution solvent: ethyl acetate/hexane=1/1, ethyl acetate alone, methanol/ethyl acetate=9/1 (V/V)] to obtain the title compound (9.44 g (yield: 55%)) as a white solid.

(30e)

2-{trans-4-[5-({[tert-Butyl(diphenyl)silyl]oxy}methyl)-4-methyl-4H-1,2,4-triazol-3-yl]cyclohexyl}prop-2-enal The compound of Example 30(30d): {trans-4-[5-({[tert-butyl(diphenyl)silyl]oxy}methyl)-4-methyl-4H-1,2,4-triazol-3-yl]cyclohexyl}acetaldehyde (9.44 g, 19.8 mmol) was dissolved in N,N-dimethylformamide (50 mL). To this, a formaldehyde solution (37%) (7.3 mL, 99.2 mmol) and L-proline (685 mg, 5.95 mmol) were added and the mixture was stirred at room temperature for 16 hours.

The reaction solution was diluted with ethyl acetate, and sequentially washed with saline, water and saturated saline, and dried over anhydrous sodium sulfate. The residue obtained by concentration under reduced pressure was purified by silica gel column chromatography [elution solvent: ethyl acetate/hexane=1/1, ethyl acetate alone, methanol/ ethyl acetate=1/9 (V/V)] to obtain the title compound (8.52 g (yield: 88%)) as a white solid.

(30f)

2-{trans-4-[5-({[tert-Butyl(diphenyl)silyl]oxy}methyl)-4-methyl-4H-1,2,4-triazol-3-yl]cyclohexyl}oxirane-2-carbaldehyde The compound of Example 30(30e): 2-{trans-4-[5-({[tert-butyl(diphenyl)silyl]oxy}methyl)-methyl-4H-1,2,4-triazol-3-yl]cyclohexyl}prop-2-enal (8.52 g, 17.5 mmol) was dissolved in methanol (80 mL). To this, hydrogen peroxide (30%) (2.5 mL, 26.2 mmol) and sodium hydroxide (380 mg, 8.73 mmol) were added under ice-cooling, and the mixture was stirred for 30 minutes under ice-cooling.

To the reaction mixture, a 10% aqueous sodium thiosulfate solution was added, and the reaction mixture was extracted with ethyl acetate. The organic layer was washed with saturated saline, and then dried over anhydrous sodium sulfate. To the residue obtained by concentration under reduced pressure, dichloromethane was added, and the mixture was azeotropically concentrated to obtain the title compound (8.51 g (yield: 97%)) as a white solid.

(30g)

3-(trans-4-{1-[trans-4-(Azetidin-1-yl)cyclohexyl]-1H-pyrazol-4-yl}cyclohexyl)-5-({[tert-butyl(diphenyl)silyl]oxy}methyl)-4-methyl-4H-1,2,4-triazole The compound of Example 30(30f): 2-{trans-4-[5-({[tert-butyl (diphenyl)silyl]oxy}methyl)-4-methyl-4H-1,2,4-triazol-3-yl]cyclohexyl}oxirane-2-carbaldehyde (800 mg, 1.59 mmol) was dissolved in ethanol (80 mL). To this, the compound of Example 30(30c): 1-(trans-4-hydradinylcyclohexyl)azetidine hydrochloride (392 mg, 1.91 mmol) was added, and the mixture was stirred at room temperature for 17 hours.

The residue obtained by concentrating the reaction mixture under reduced pressure was purified by NH silica gel column chromatography [elution solvent: methanol/ethyl acetate=0/1-1/19 (V/V)] to obtain the title compound (732 mg (yield: 72%)) as a light brown solid.

(30h)

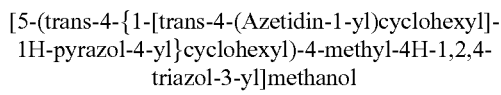

[5-(trans-4-{1-[trans-4-(Azetidin-1-yl)cyclohexyl]-1H-pyrazol-4-yl}cyclohexyl)-4-methyl-4H-1,2,4-triazol-3-yl]methanol The compound of Example 30(30g): 3-(trans-4-{1-[trans-4-(azetidin-1-yl)cyclohexyl]-1H-pyrazol-4-yl}cyclohexyl)-5-({[tert-butyl(diphenyl)silyl]oxy}methyl)-4-methyl-4H-1,2,4-triazole (728 mg, 1.14 mmol) was dissolved in 1,4-dioxane (15 mL). To this, fluoride, polymer-supported (Sigma-Aldrich, Catalog Number: 387789) (1.83 g, 4.12 mmol) was added, and the mixture was stirred at 100° C. for 25 hours.

The reaction mixture was filtered and the filtrate was concentrated under reduced pressure. The obtained residue was purified by NH silica gel column chromatography [elution solvent: methanol/ethyl acetate=1/9-15/85 (V/V)] to obtain the title compound (334 mg (yield: 73%)) as a light brown solid.

(30i)

Methyl 3-{[5-(trans-4-{1-[trans-4-(azetidin-1-yl)cyclohexyl]-1H-pyrazol-4-yl}cyclohexyl)-4-methyl-4H-1,2,4-triazol-3-yl]methoxy}benzoate The compound of Example 30(30h): [5-(trans-4-{1-[trans-4-(azetidin-1-yl)cyclohexyl]-1H-pyrazol-4-yl}cyclohexyl)-4-methyl-4H-1,2,4-triazol-3-yl]methanol (25 mg, 0.06 mmol) and methyl 3-hydroxybenzoate (Tokyo Chemical Industry Co., Ltd., Catalog Number: H0215) (104 mg, 0.681 mmol) was suspended in 1,4-dioxane (0.5 mL). To this, cyanomethylene tributylphosphorane (0.049 mL, 0.19 mmol) was added, and the mixture was stirred at 130° C. for 1 hour under microwave irradiation.

Similarly, the compound of Example 30(30h): [5-(trans-4{1-[trans-4-(-azetidin-1-yl)cyclohexyl]-1H-pyrazol-4-yl}cyclohexyl)-4-methyl-4H-1,2,4-triazol-3-yl]methanol (150 mg, 0.38 mmol) and methyl 3-hydroxybenzoate (Tokyo Chemical Industry Co., Ltd., Catalog Number: H0215) (172 mg, 1.13 mmol) was suspended in 1,4-dioxane (3 mL). To this, cyanomethylene tributylphosphorane (0.296 mL, 1.13 mmol) was added, and the mixture was stirred at 130° C. for 1 hour under microwave irradiation.

The resultant was combined with the reaction mixture in which the reaction was performed previously, then the residue obtained by concentration under reduced pressure was purified by NH silica gel column chromatography [elution solvent: hexane/ethyl acetate/methanol=2/8/0-0/97.5/2.5 (V/V/V)] twice. To the obtained crude product, diethyl ether was added, and the precipitated solid was collected by filtration to obtain the title compound (86 mg (yield: 43%)) as a light brown solid.

Example 31

Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate (31a)

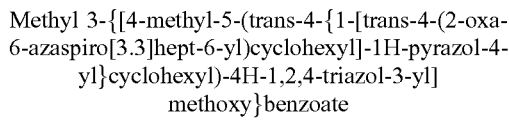

6-[trans-4-(4-{trans-4-[5-({[tert-Butyl(diphenyl)silyl]oxy}methyl)-4-methyl-4H-1,2,4-triazol-3-yl]cyclohexyl}-1H-pyrazol-1-yl)cyclohexyl]-2-oxa-6-azaspiro[3.3]heptane The compound of Example 30(30f): 2-trans-4-[5-{[tert-butyl(diphenyl)silyl]oxy}methyl)-4-methyl-4H-1,2,4-triazol-3-yl]cyclohexyl}oxirane-2-carbaldehyde (730 mg, 1.43 mmol) was dissolved in ethanol (7 mL). The compound of Example 24(24e): 6-(trans-4-hydrazinylcyclohexyl)-2-oxa-6-azaspiro[3.3]heptane acetate (512 mg, 1.43 mmol) was added, and the mixture was stirred at room temperature for 16 hours.

The residue obtained by concentrating the reaction mixture under reduced pressure was purified by NH silica gel column chromatography [elution solvent: methanol/ethyl acetate=0/1-1/4 (V/V)] to obtain the title compound (635 mg (yield: 65%)) as a white solid.

(31b)

[4-Methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methanol The compound of Example 31(31a): 6-[trans-4-(4-{trans-4-[5-({[tert-butyl(diphenyl)silyl]oxy}methyl)-4-methyl-4H-1,2,4-triazol-3-yl]cyclohexyl}-1H-pyrazol-1-yl)cyclohexyl]-2-oxa-6-azaspiro[3.3]heptane (2.54 g, 3.74 mmol) was dissolved in tetrahydrofuran (30 mL) and water (15 mL). To this, fluoride, polymer-supported (Sigma-Aldrich, Catalog Number: 387789) (6 g, 15 mmol) was added, and the mixture was stirred at 80° C. for 9 hours, and then the reaction solution was cooled to room temperature and allowed to stand still for 12 hours. After stirring again at 80° C. for 12 hours, the reaction solution was cooled to room temperature and allowed to stand still for 12 hours. This procedure was repeated 3 times.

The reaction mixture was filtered, and the residue obtained by concentration under reduced pressure was purified by NH silica gel column chromatography [elution solvent: methanol/ethyl acetate=0/1-3/7 (V/V)] to obtain the title compound (632 mg (yield: 38%)) as a light yellow solid.

(31c)

Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate The compound of Example 31(31b): [4-methyl-5-(trans-4-{1-[trans-4-(2-oxa-6-azaspiro[3.3]hepta-6-yl)cyclohexyl]-1H-pyrazol-4-yl}cyclohexyl)-4H-1,2,4-triazol-3-yl]methanol (100 mg, 0.227 mmol) was suspended in 1,4-dioxane (4 mL). To this, methyl 3-hydroxybenzoate (Tokyo Chemical Industry Co., Ltd., Catalog Number: H0215) (104 mg, 0.681 mmol) and cyanomethylene tributylphosphorane (164 mg, 0.681 mmol) were added and the mixture was stirred at 130° C. for 1 hour under microwave irradiation.

The reaction mixture was cooled to room temperature, and then purified by NH silica gel column chromatography [elution solvent methanol/ethyl acetate=0/1-1/9 (V/V)], and then further purified by silica gel column chromatography [elution solvent methanol/ethyl acetate=0/1-4/6 (V/V)]. After the obtained crude product was dissolved in dichloromethane, diethyl ether was added. Then, the precipitated solid was collected by filtration to obtain the title compound (66 mg (yield: 51%)) as a white solid.

Example 32

2-[trans-4-(4-{trans-4-[4-Methyl-5-({[3-(trifluoromethyl)cyclohexyl]oxy}methyl)-4H-1,2,4-triazol-3-yl]cyclohexyl}-1H-pyrazol-1-yl)cyclohexyl]-6-oxa-2-azaspiro[3.4]octane (32a)

2-[trans-4-(4-{trans-4-[5-({[tert-Butyl(diphenyl)silyl]oxy}methyl)-4-methyl-4H-1,2,4-triazol-3-yl]cyclohexyl}-1H-pyrazol-1-yl)cyclohexyl]-6-oxa-2-azaspiro[3.4]octane The compound of Example 27(27c): benzyl 2-[trans-4-(6-oxa-2-azaspiro[3.4]oct-2-yl)cyclohexyl]hydrazine carboxylate (5 g, 13.9 mmol) was dissolved in ethanol (100 mL). To this, acetic acid (3.98 mL, 69.6 mmol) and a 10% palladium carbon catalyst (1.5 g) were added and the mixture was stirred at room temperature for 17 hours under a hydrogen atmosphere.

Palladium-carbon was filtered off, and the filtrate was washed with ethanol. The residue concentrated under reduced pressure was dissolved in ethanol (80 mL). To this, a solution of the compound of Example 30(30f): 2-{trans-4-[5-({[tert-butyl(diphenyl)silyl]oxy}methyl)-4-methyl-4H-1,2,4-triazol-3-yl]cyclohexyl}oxirane-2-carbaldehyde (5.84 g, 11.6 mmol) in ethanol (20 mL) was added, and the mixture was stirred at room temperature for 19 hours, and then stirred at 80° C. for 1 hour.

The reaction mixture was cooled to room temperature, then the residue obtained by concentration under reduced pressure was purified by NH silica gel column chromatography [elution solvent: hexane/ethyl acetate/methanol=2/8/0-0/95/5(V/V/V)] to obtain the title compound (6.19 g (yield: 77%)) as a light brown solid.
(32b)

[4-Methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazol-3-yl]methanol The compound of Example (32a): 2-[trans-4-(4-{trans-4-[5-({[tert-butyl(diphenyl)silyl]oxy}methyl)-4-methyl-4H-1,2,4-triazol-3-yl]cyclohexyl}-1H-pyrazol-1-yl)cyclohexyl]-6-oxa-2-azaspiro[3.4]octane (6.19 g, 8.93 mmol) was dissolved in 1,4-dioxane (90 mL) and methanol (30 mL). To this, fluoride, polymer-supported (Sigma-Aldrich Corporation, Catalog Number: 387789) (14.3 g, 35.5 mmol) was added, and the mixture was stirred at 100° C. for 88 hours.

The reaction mixture was filtered, then the residue obtained by concentration under reduced pressure was purified by silica gel column chromatography [elution solvent: methanol/dichloromethane=1/9 (V/V)] to obtain the title compound (3.76 g (yield: 93%)) as a light brown solid.
(32c)

2-[trans-4-(4-{trans-4-[4-Methyl-5-({[3-(trifluoromethyl)cyclohexyl]oxy}methyl)-4H-1,2,4-triazol-3-yl]cyclohexyl}-1H-pyrazol-1-yl)cyclohexyl]-6-oxa-2-azaspiro[3.4]octane The compound of Example 32(32b): [4-methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazol-3-yl]methanol (150 mg, 0.33 mmol) and triethylamine (0.091 mL, 0.662 mmol) were dissolved in dichloromethane (5 mL). To this, methanesulfonyl chloride (0.038 mL, 0.498 mmol) was added under ice-cooling, and the mixture was stirred under ice-cooling for 1 hour.

To the reaction mixture, saturated aqueous sodium bicarbonate was added, and the mixture was extracted with dichloromethane. The organic layer was washed with saturated saline, and dried over anhydrous sodium sulfate. The resultant was concentrated under reduced pressure to obtain 181 mg of [4-methyl-5-(trans-4-{1-[trans-4-(6-oxa-2-azaspiro[3.4]octa-2-yl)cyclohexyl]-1H-pyrazol-4-yl}cyclohexyl)-4H-1,2,4-triazol-3-yl]methyl methanesulfonate as a light brown solid.

3-(Trifluoromethyl)cyclohexanol (Enamine Ltd., Catalog Number: EN300-62207) (83 mg, 0.494 mmol) was dissolved in N,N-dimethylformamide (4 mL). To this, sodium hydride (55%) (22 mg, 0.504 mmol) was added under ice-cooling, and the mixture was stirred at room temperature for 30 minutes. To the reaction mixture, a suspension of the obtained [4-methyl-5-(trans-4-{1-[trans-4-(6-oxa-2-azaspiro[3.4]octa-2-yl)cyclohexyl]-1H-pyrazol-4-yl}cyclohexyl)-4H-1,2,4-triazol-3-yl]methyl methanesulfonate (176 mg) in N,N-dimethylformamide (3 mL) was added under ice-cooling and the mixture was stirred at room temperature for 1 hour.

Ice was added to the reaction mixture and the mixture was extracted with dichloromethane. The organic layer was washed with saturated saline, and then dried over anhydrous sodium sulfate. After filtration, the resultant was concentrated under reduced pressure. The obtained residue was purified by NH silica gel column chromatography [elution solvent: methanol/ethyl acetate=0/1-1/99 (V/V)], then by silica gel column chromatography [elution solvent: methanol/dichloromethane=15/85 (V/V)] to obtain the title compound (77 mg (yield: 39%)) as a white solid.

Example 33

1-{2-[4-Methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazol-3-yl]ethyl}-3-(trifluoromethyl)pyridin-2(1H)-one (33a)

4-Methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazole-3-carbaldehyde The compound of Example 32(32b): [4-methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazol-3-yl] methanol (1 g, 2.2 mmol) was dissolved in dichloromethane (20 mL). To this, Dess-Martin periodinane (1.4 g, 3.3 mmol)

was added under ice-cooling and the mixture was stirred at room temperature for 17.5 hours.

To the reaction mixture, saturated aqueous sodium bicarbonate and sodium thiosulfate were sequentially added to the reaction mixture, and the mixture was stirred and extracted with dichloromethane. The organic layer was washed with saturated saline and then dried over anhydrous sodium sulfate. The resultant was concentrated under reduced pressure to obtain the title compound (1.01 g (quantitative)) as a light brown solid.

(33b)

2-(trans-4-{4-[trans-4-(5-Ethenyl-4-methyl-4H-1,2,4-triazol-3-yl)cyclohexyl]-1H-pyrazol-1-yl}cyclohexyl)-6-oxa-2-azaspiro[3.4]octane Methyltriphenylphosphonium bromide (Tokyo Chemical Industry Co., Ltd., Catalog Number: M0779) (1.1 g, 3.09 mmol) was suspended in tetrahydrofuran (7 mL). To this, potassium tert-butoxide (347 mg, 3.09 mmol) was added under ice-cooling and the mixture was stirred for 20 minutes. To the reaction mixture, a solution of the compound of Example 33(33a): 4-methyl-5-(trans-4-{1-[trans-4-(6-oxa-2-azaspiro[3.4]octa-2-yl)cyclohexyl]-1H-pyrazol-4-yl}cyclohexyl)-4H-1,2,4-triazole-3-carbaldehyde (699 mg, 1.54 mmol) in tetrahydrofuran (21 mL) was added dropwise under ice-cooling and the mixture was stirred at 0° C. for 1.5 hours.

Water was added to the reaction solution to stop the reaction. Then, to the residue obtained by concentration under reduced pressure, water was added, and the mixture was extracted with dichloromethane. The organic layer was washed with saturated saline and then dried over anhydrous sodium sulfate. After filtration, the residue obtained by concentration under reduced pressure was purified by NH silica gel column chromatography [elution solvent: hexane/dichloromethane/methanol=3/7/0-0/99/1 (V/V/V)] to obtain the title compound (647 mg (yield: 93%)) as a light brown solid.

(33c)

1-{2-[4-Methyl-5-(trans-4-{1-[trans-4-(6-oxa-2-azaspiro[3.4]oct-2-yl)cyclohexyl]-1H-pyrazol-4-yl}cyclohexyl)-4H-1,2,4-triazol-3-yl]ethyl}-3-(trifluoromethyl)pyridin-2(1H)-one The compound of Example 33(33b): 2-(trans-4-{4-[trans-4-(5-ethenyl-4-methyl-4H-1,2,4-triazol-3-yl)cyclohexyl]-1H-pyrazol-1-yl}cyclohexyl)-6-oxa-2-azaspiro[3.4]octane (25 mg, 0.06 mmol) and 3-(trifluoromethyl)pyridin-2(1H)-one (CAS Registry Number: 22245-83-6, WO2007126765) (45 mg, 0.28 mmol) were suspended by adding acetonitrile (1 mL). The mixture was stirred at 120° C. for 1 hour under microwave irradiation.

The residue obtained by concentrating the reaction mixture under reduced pressure was purified by silica gel column chromatography [elution solvent: methanol/ethyl acetate=8/92-1/9 (V/V)] to obtain the crude product (25 mg).

Similarly, the compound of Example 33(33b): 2-(trans-4-{4-[trans-4-(5-ethenyl-4-methyl-4H-1,2,4-triazol-3-yl)cyclohexyl]-1H-pyrazol-1-yl}cyclohexyl)-6-oxa-2-azaspiro[3.4]octane (100 mg, 0.22 mmol) and 3-(trifluoromethyl)pyridin-2(1H)-one (CAS Registry Number: 22245-83-6, WO2007126765) (181 mg, 1.11 mmol) were added to acetonitrile (4 mL) and suspended. The mixture was stirred at 120° C. for 1 hour under microwave irradiation.

The residue obtained by concentrating the reaction mixture under reduced pressure was purified by silica gel column chromatography [elution solvent: methanol/ethyl acetate=8/92-1/9 (V/V)]. The obtained crude product was combined with the previously obtained crude product (25 mg) and triturated with ethyl acetate to obtain the title compound (131 mg (yield: 77%)) as a white solid.

Example 34

1-Methyl-4-{5-[4-(4-methyl-5-{[3-(trifluoromethyl)phenoxy]methyl}-4H-1,2,4-triazol-3-yl)phenyl]-1,3,4-oxadiazol-2-yl}piperidine (34a)

tert-Butyl 4-{5-[4-(methoxycarbonyl)phenyl]-1,3,4-oxadiazol-2-yl}piperidine-1-carboxylate tert-Butyl 4-({2-[4-(methoxycarbonyl)benzoyl]hydrazinyl}carbonyl)piperidine-1-carboxylate (CAS Registry Number: 208537-78-4, WO199823637) (500 mg, 1.23 mmol) was dissolved in tetrahydrofuran (5 mL). To this, (methoxycarbonylsulfamoyl)triethylammonium hydroxide inner salt (Tokyo Chemical Industry Co., Ltd., Catalog Number: M1279) (647 mg, 2.71 mmol) was added, and the mixture was stirred at 120° C. for 15 minutes under microwave irradiation.

To the reaction mixture, water was added, and the mixture was extracted with ethyl acetate. The organic layer was washed with saturated saline and then dried over anhydrous sodium sulfate. To the residue obtained by concentration under reduced pressure, ethyl acetate and hexane were added, and the precipitated solid was collected by filtration to obtain the title compound (380 mg (yield: 79%)) as a white solid.

(34b)

4-{5-[1-(tert-Butoxycarbonyl)piperidin-4-yl]-1,3,4-oxadiazol-2-yl}benzoic acid

The compound of Example 34(34a): tert-Butyl 4-{5-[4-(methoxycarbonyl)phenyl]-1,3,4-oxadiazol-2-yl}piperidine-1-carboxylate (300 mg, 0.77 mmol) was dissolved in methanol (1.5 mL) and tetrahydrofuran (1.5 mL). To this, a solution of sodium hydroxide (155 mg, 3.87 mmol) in water (1.5 mL) was added under ice-cooling, and the mixture was stirred at room temperature for 2 hours.

After concentration under reduced pressure, the mixture was acidified with 1N hydrochloric acid and extracted with dichloromethane. The organic layer was washed with saturated saline and then dried over anhydrous sodium sulfate. The resultant was concentrated under reduced pressure to obtain the title compound (250 mg (yield: 86%)) as a white solid.

(34c)

tert-Butyl 4-{5-[4-(methylcarbamoyl)phenyl]-1,3,4-oxadiazol-2-yl}piperidine-1-carboxylate The compound of Example 34(34b): 4-{5-[1-(tert-Butoxycarbonyl)piperidin-4-yl]-1,3,4-oxadiazol-2-yl}benzoic acid (240 mg, 0.64 mmol) was dissolved in N,N-dimethylformamide (0.6 mL). To this, triethylamine (0.27 mL, 1.93 mmol), methylamine hydrochloride (Tokyo Chemical Industry Co., Ltd., Catalog Number: M0138) (52 mg, 0.77 mmol), 3H-1,2,3-triazolo[4,5-b]pyridin-3-ol (44 mg, 0.32 mmol), 1-ethyl-3-(3-dimethylaminopropyl) carbodiimide hydrochloride (185 mg, 0.96 mmol) were added and the mixture was stirred at room temperature for 4 hours.

The reaction mixture was diluted with dichloromethane. To this, saturated aqueous sodium bicarbonate was added, and the mixture was extracted with dichloromethane. The organic layer was dried over anhydrous sodium sulfate. The residue obtained by concentration under reduced pressure was purified by silica gel column chromatography [elution solvent: methanol/dichloromethane=0/1-1/9 (V/V)] to obtain the title compound (250 mg (yield: 100%)) as a white solid.

(34d)

tert-Butyl 4-{5-[4-(methylcarbamothioyl)phenyl]-1, 3,4-oxadiazol-2-yl}piperidine-1-carboxylate The compound of Example 34(34c): tert-butyl 4-{5-[4-(methylcarbamoyl)phenyl]-1,3,4-oxadiazol-2-yl}piperidine-1-carboxylate (240 mg, 0.621 mmol) was dissolved in tetrahydrofuran (6.2 mL). To this, Lawesson's reagent (276 mg, 0.683 mmol) was added, and the mixture was stirred at room temperature for 1 hour and allowed to stand still overnight.

The residue obtained by concentration under reduced pressure was purified by silica gel column chromatography [elution solvent: methanol/dichloromethane=0/1-1/9 (V/V)] to obtain the title compound (246 mg (yield: 98%)) as a light yellow solid.

(34e)

tert-Butyl 4-{5-[4-(4-methyl-5-{[3-(trifluoromethyl) phenoxy]methyl}-4H-1,2,4-triazol-3-yl)phenyl]-1,3, 4-oxadiazol-2-yl}piperidine-1-carboxylate The compound of Example 34(34d): tert-Butyl 4-{5-[4-(methylcarbamothioyl)phenyl]-1,3,4-oxadiazol-2-yl}piperidine-1-carboxylate (230 mg, 0.571 mmol) was dissolved in tetrahydrofuran (1.1 mL). To this, methyl iodide (122 mg, 0.857 mmol) and potassium carbonate (158 mg, 1.14 mmol) were added, and the mixture was stirred at room temperature for 1 hour and then at 50° C. for 1 hour.

Insoluble matters were removed by filtration, and the filtrate was concentrated under reduced pressure. The obtained residue was dissolved by adding tetrahydrofuran (1.1 mL). To this, methyl iodide (811 mg, 5.71 mmol) was added, and the mixture was stirred at 70° C. for 3 hours.

Insoluble matters were removed by filtration, and the filtrate was concentrated under reduced pressure to obtain the crude product of tert-butyl 4-(5-{4-[(methylimino) (methylsulfanyl)methyl]phenyl}-1,3,4-oxadiazol-2-yl)piperidine-1-carboxylate (275 mg).

The obtained crude product (130 mg) was dissolved in ethanol (0.62 mL) and the compound of Example 1(1a): 2-[3-(trifluoromethyl)phenoxy]acetohydrazide (87.7 mg, 0.375 mmol) was added and the mixture was stirred at 90° C. for 3 hours. To the reaction mixture, the compound of Example 1(1a): 2-[3-(trifluoromethyl)phenoxy]acetohydrazide (87.7 mg, 0.375 mmol) was added and the mixture was stirred at 90° C. for 3 hours.

The reaction mixture was diluted with dichloromethane. To this, a saturated aqueous ammonium chloride solution was added, and the mixture was extracted with dichloromethane. The organic layer was washed with saturated aqueous sodium bicarbonate and then dried over anhydrous sodium sulfate. The residue obtained by concentration under reduced pressure was purified by silica gel column chromatography [elution solvent: methanol/dichloromethane=0/1-1/19 (V/V)] to obtain the title compound (40 mg (yield: 22%)) as a white solid.

(34f)

4-{5-[4-(4-Methyl-5-{[3-(trifluoromethyl)phenoxy] methyl}-4H-1,2,4-triazol-3-yl)phenyl]-1,3,4-oxadiazol-2-yl}piperidine To a solution of the compound of Example 34(34e): tert-butyl 4-{5-[4-(4-methyl-5-{[3-(trifluoromethyl)phenoxy]methyl}-4H-1,2,4-triazol-3-yl)phenyl]-1,3,4-oxadiazol-2-yl}piperidine-1-carboxylate (40 mg, 0.0684 mmol) in dichloromethane (0.27 mL), trifluoroacetic acid (0.157 mL, 2.05 mmol) was added, and the mixture was stirred at room temperature for 2 hours.

To the residue obtained by concentration under reduced pressure, saturated aqueous sodium bicarbonate was added, and the mixture was extracted with chloroform. The organic layer was washed with saturated saline, and dried over anhydrous sodium sulfate. The resultant was concentrated under reduced pressure to obtain the title compound (30 mg (yield: 90%)) as a white solid.

(34g)

1-Methyl-4-{5-[4-(4-methyl-5-{[3-(trifluoromethyl) phenoxy]methyl}-4H-1,2,4-triazol-3-yl)phenyl]-1,3, 4-oxadiazol-2-yl}piperidine To a solution of the compound of Example 34(34f) 4-{5-[4-(4-methyl-5-{[3-(trifluoromethyl)phenoxy] methyl}-4H-1,2,4-triazol-3-yl)phenyl]-1,3,4-oxadiazol-2-yl}piperidine (25 mg, 0.0516 mmol) in dichloromethane (0.21 mL), a formaldehyde solution (37%) (0.011 mL, 0.155 mmol) was added, and the mixture was stirred at room temperature for 5 minutes. To the reaction mixture, sodium triacetoxyborohydride (95%) (54.7 mg, 0.258 mmol) was added, and the mixture was stirred at room temperature for 1 hour.

To the reaction mixture, saturated aqueous sodium bicarbonate was added, and the reaction mixture was extracted with dichloromethane. The organic layer was washed with saturated saline, and dried over anhydrous sodium sulfate. To the crude product obtained by concentration under reduced pressure, ethyl acetate was added, and the precipitated solid was collected by filtration to obtain the title compound (15 mg (yield: 58%)) as a light yellow solid.

Example 35

3-(trans-4-{5-[(2S,5R)-5-(Azetidin-1-yl)tetrahydro-2H-pyran-2-yl]-1,2-oxazol-3-yl}cyclohexyl)-5-[(3-chlorophenoxy)methyl]-4-methyl-4H-1,2,4-triazole (35a)

Methyl trans-4-{5-[(3-chlorophenoxy)methyl]-4-methyl-4H-1,2,4-triazol-3-yl}cyclohexanecarboxylate The compound of Example 19(19c): methyl trans-4-[(methylimino) (methylsulfanyl)methyl]cyclohexane carboxylate (10.1 g, 44 mmol) was dissolved in ethanol (50 mL). To this, 2-(3-chlorophenoxy)acetohydrazide (CAS Registry Number: 52094-93-6, Bioorganic & Medicinal Chemistry 19 (2011) 211-220) (8.41 g, 41.9 mmol) was added and the mixture was stirred at 100° C. for 5 hours.

To the residue obtained by concentration under reduced pressure, isopropyl alcohol was added, and the precipitated solid was collected by filtration to obtain the title compound (9.55 g (yield: 63%)) as a white solid.

(35b)

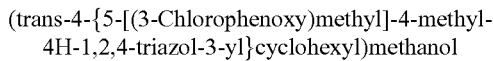

(trans-4-{5-[(3-Chlorophenoxy)methyl]-4-methyl-4H-1,2,4-triazol-3-yl}cyclohexyl)methanol The compound of Example 35(35a): methyl trans-4-{5-[(3-chlorophenoxy)methyl]-4-methyl-4H-1,2,4-triazol-3-yl}cyclohexanecarboxylate (9.55 g, 26.3 mmol) was dissolved in tetrahydrofuran (160 mL). To this, a lithium aluminium hydride-tetrahydrofuran solution (2.5 M, 8 mL) was added under ice-cooling, and the mixture was stirred at room temperature for 1 hour and then at 60° C. for 1 hour.

To the reaction mixture, water (1 mL), a 1N aqueous sodium hydroxide solution (3 mL), and water (1 mL) were sequentially added under ice-cooling. The residue obtained by concentration under reduced pressure was purified by silica gel column chromatography [elution solvent: hexane/ethyl acetate=3/2-0/1, methanol/ethyl acetate=1/1 (V/V)] to obtain the title compound (5.5 g (yield: 62%)) as a white solid.

(35c)

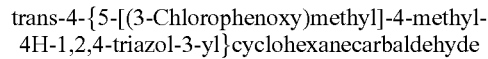

trans-4-{5-[(3-Chlorophenoxy)methyl]-4-methyl-4H-1,2,4-triazol-3-yl}cyclohexanecarbaldehyde The compound of Example 35(35b): (trans-4-{5-[(3-chlorophenoxy)methyl]-4-methyl-4H-1,2,4-triazol-3-yl}cyclohexyl)methanol (1 g, 2.98 mmol) was dissolved in dichloromethane (10 mL) and dimethyl sulfoxide (10 mL). To this, diisopropylethylamine (2.2 mL, 12.6 mmol) and pyridine-sulfur-trioxide complex (2.07 g, 13 mmol) were added under ice-cooling and the mixture was stirred for 1.5 hours.

To the reaction mixture, dichloromethane and water were added, the mixture was extracted with dichloromethane. The organic layer was washed with water and dried over anhydrous sodium sulfate. The resultant was concentrated under reduced pressure to obtain the title compound (1.3 g (quantitative)) as a colorless oily substance.

(35d)

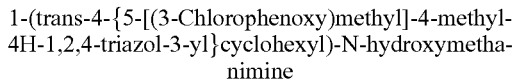

1-(trans-4-{5-[(3-Chlorophenoxy)methyl]-4-methyl-4H-1,2,4-triazol-3-yl}cyclohexyl)-N-hydroxymethanimine The compound of Example 35(35c): trans-4-{5-[(3-chlorophenoxy)methyl]-4-methyl-4H-1,2,4-triazol-3-yl}cyclohexanecarbaldehyde (1.3 g, 2.98 mmol) was dissolved in methanol (15 mL). To this, hydroxylamine hydrochloride (620 mg, 8.92 mmol) and sodium acetate (740 mg, 9.02 mmol) were added and the mixture was stirred at room temperature for 2 hours.

To the reaction mixture, ethyl acetate and water were added, and the mixture was extracted with ethyl acetate. The organic layer was washed with water and saturated saline and dried over anhydrous sodium sulfate. The residue obtained by concentration under reduced pressure, isopropyl alcohol was added, and the precipitated solid was filtered to obtain the title compound (1.1 g (quantitative)) as a white solid.

(35e)

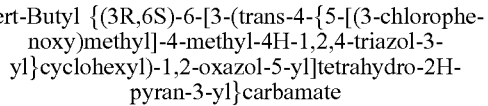

tert-Butyl {(3R,6S)-6-[3-(trans-4-{5-[(3-chlorophenoxy)methyl]-4-methyl-4H-1,2,4-triazol-3-yl}cyclohexyl)-1,2-oxazol-5-yl]tetrahydro-2H-pyran-3-yl}carbamate The compound of Example 35(35d): 1-trans-4-{5-[3-chlorophenoxy)methyl]-4-methyl-4H-1,2,4-triazol-3-yl}cyclohexyl)-N-hydroxymethanaimine (430 mg, 1.23 mmol) was dissolved in N,N-dimethylformamide (10 mL). To this, N-chlorosuccinimide (180 mg, 1.35 mmol) was added and stirred at 50° C. for 1.5 hours. To the reaction mixture, a solution of tert-butyl [(3R,6S)-6-ethynyltetrahydro-2H-pyran-3-yl]carbamate (CAS Registry Number: 881657-41-6, WO2006032466) (8.41 g, 41.9 mmol) and triethylamine (1.7 mL, 12.2 mmol) in N,N-dimethylformamide (3 mL) was added, and the mixture was stirred at room temperature for 30 minutes and then at 60° C. for 1.5 hours.

To the reaction mixture, ethyl acetate and tetrahydrofuran were added, and the mixture was extracted with ethyl acetate. The organic layer was washed with diluted hydrochloric acid, water and saturated saline, and the mixture was dried over anhydrous sodium sulfate. The residue obtained by concentration under reduced pressure was purified by silica gel column chromatography [elution solvent: ethyl acetate/dichloromethane=3/7-1/0 (V/V)] to obtain the title compound (180 mg (yield: 25%)) as a white solid.

(35f)

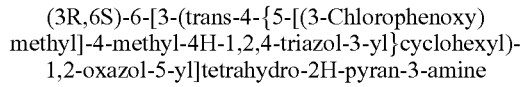

(3R,6S)-6-[3-(trans-4-{5-[(3-Chlorophenoxy)methyl]-4-methyl-4H-1,2,4-triazol-3-yl}cyclohexyl)-1,2-oxazol-5-yl]tetrahydro-2H-pyran-3-amine The compound of Example 35(35e): tert-butyl{(3R,6S)-6-[3-(trans-4-{5-[(3-chlorophenoxy)methyl]-4-methyl-4H-1,2,4-triazol-3-yl}cyclohexyl)-1,2-oxazol-5-yl]tetrahydro-2H-pyran-3-yl}carbamate (180 mg, 0.315 mmol) was dissolved in methanol (2 mL). To this, 4N hydrochloric acid-1,4-dioxane (4 mL, 16 mmol) was added, and the mixture was stirred at room temperature for 1 hour.

The residue obtained by concentration under reduced pressure was purified by NH silica gel column chromatography [elution solvent: methanol/ethyl acetate=0/1-3/7 (V/V)] to obtain the title compound (134 mg (yield: 90%)) as a white solid.

(35g)

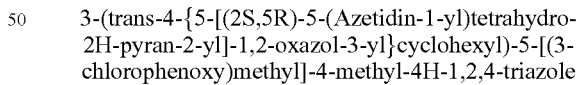

3-(trans-4-{5-[(2S,5R)-5-(Azetidin-1-yl)tetrahydro-2H-pyran-2-yl]-1,2-oxazol-3-yl}cyclohexyl)-5-[(3-chlorophenoxy)methyl]-4-methyl-4H-1,2,4-triazole The compound of Example 35(35f): (3R,6S)-6-[3-(trans-4-{5-[(3-chlorophenoxy)methyl]-4-methyl-4H-1,2,4-triazol-3-yl}cyclohexyl)-1,2-oxazol-5-yl]tetrahydro-2H-pyran-3-amine (134 mg, 0.284 mmol) was dissolved in acetonitrile (15 mL). To this, 1,3-dibromopropane (Tokyo Chemical Industry Co., Ltd., Catalog Number: D0202) (229 mg, 1.13 mmol) and potassium carbonate (152 mg, 1.1 mmol) were added, and the mixture was stirred at 90° C. for 3 hours, and then at 80° C. for 17 hours.

The residue obtained by concentration under reduced pressure was purified by NH silica gel column chromatography [elution solvent: methanol/ethyl acetate=0/1-15/85 (V/V)] to obtain the title compound (41.3 mg (yield: 28%)) as a white solid.

Example 36

8-Methyl-3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-ene

(36a)

tert-Butyl 3-[trans-4-(methylcarbamoyl)cyclohexyl]-1-oxa-2,8-diazaspiro[4.5]dec-2-ene-8-carboxylate

Methyl trans-4-[chloro(hydroxyimino)methyl]cyclohexanecarboxylate (CAS Registry Number: 1346450-09-6, WO2013050334) (1.5 g, 6.83 mmol) was dissolved in dichloromethane (50 mL). To this, tert-butyl 4-methylidenepiperidine-1-carboxylate (Wako Pure Chemical Industries, Ltd. Catalog Number: 353-23543) (2.02 g, 10.3 mmol) and sodium hydrogen carbonate (1.15 g, 13.7 mmol) were added, and the mixture was stirred at 30° C. for 16 hours.

The reaction mixture was filtered, and concentrated under reduced pressure. The obtained residue was purified by silica gel column chromatography [elution solvent: ethyl acetate/petroleum ether=1/30 (V/V)] to obtain tert-Butyl 3-[trans-4-(methoxycarbonyl)cyclohexyl]-1-oxa-2,8-diazaspiro[4.5]dec-2-ene-8-carboxylate (2 g) as a white solid.

To a solution of the obtained tert-butyl 3-[trans-4-(methoxycarbonyl)cyclohexyl]-1-oxa-2,8-diazaspiro[4.5]dec-2-ene-8-carboxylate (1 g, 2.63 mmol) in methanol (10 mL)/water (2 mL), lithium hydroxide monohydrate (221 mg, 5.26 mmol) was added, and the mixture was stirred at 30° C. for 16 hours.

To the residue obtained by concentration under reduced pressure, water was added, and the mixture was extracted with ethyl acetate. The aqueous layer was adjusted with 2N hydrochloric acid to about pH=6 and extracted with ethyl acetate. The combined organic layer was dried over anhydrous sodium sulfate. The resultant was concentrated under reduced pressure to obtain trans-4-[8-(tert-butoxycarbonyl)-1-oxa-2,8-diazaspiro[4.5]dec-2-en-3-yl]cyclohexanecarboxylic acid (950 mg) as a white solid.

To a solution of the obtained trans-4-[8-(tert-butoxycarbonyl)-1-oxa-2,8-diazaspiro[4.5]dec-2-en-3-yl]cyclohexanecarboxylic acid (1.7 g, 4.64 mmol) and methylamine hydrochloride (849 mg, 12.6 mmol) in dichloromethane (20 mL), diisopropylethylamine (1.8 g, 13.9 mmol) and methylamine hydrochloride (1.76 g, 4.64 mmol) were added, and the mixture was stirred at 30° C. for 16 hours.

To the reaction mixture, water was added, and the mixture was extracted with ethyl acetate. The organic layer was washed with saturated saline, and dried over anhydrous sodium sulfate. The residue obtained by concentration under reduced pressure was purified by silica gel chromatography [elution solvent: ethyl acetate/petroleum ether=1/10-1/1, methanol/dichloromethane=1/10 (V/V)], and triturated with petroleum ether (30 mL) to obtain the title compound (2.3 g (yield: 76%)) as a white solid.

(36b)

8-Methyl-3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-ene

The compound of Example 36(36a): tert-butyl 3-[trans-4-(methylcarbamoyl)cyclohexyl]-1-oxa-2,8-diazaspiro[4.5]dec-2-ene-8-carboxylate (1.8 g, 4.74 mmol) was dissolved in tetrahydrofuran (40 mL). To this, Lawesson's reagent (2.88 g, 7.11 mmol) was added and the mixture was stirred at 60° C. for 10 hours.

After the reaction temperature had returned to room temperature, the residue obtained by concentration under reduced pressure was purified by silica gel column chromatography [elution solvent: methanol/dichloromethane=1/100-1/30 (V/V)], then purified by thin layer silica gel chromatography [developing solvent: methanol/dichloromethane=1/20 (V/V)] to obtain tert-butyl 3-[trans-4-(methylcarbamothioyl)cyclohexyl]-1-oxa-2,8-diazaspiro[4.5]dec-2-ene-8-carboxylate (410 mg) as a white solid.

To a solution of the obtained tert-butyl 3-[trans-4-(methylcarbamothioyl)cyclohexyl]-1-oxa-2,8-diazaspiro[4.5]dec-2-ene-8-carboxylate (260 mg, 0.657 umol) in tetrahydrofuran (10 mL), potassium carbonate (273 mg, 1.97 mmol) and methyl iodide (933 mg, 6.57 mmol) were added, and the mixture was stirred at 80° C. for 16 hours.

To the residue obtained by concentration under reduced pressure, water was added, and the mixture was extracted with dichloromethane. The organic layer was washed with saturated saline, and dried over anhydrous sodium sulfate. The resultant was concentrated under reduced pressure to obtain tert-butyl 3-{trans-4-[(methylimino) (methylsulfanyl)methyl]cyclohexyl}-1-oxa-2,8-diazaspiro[4.5]dec-2-en-8-carboxylate (300 mg) as a crude product.

The obtained crude product of tert-butyl 3-{trans-4-[(methylimino) (methylsulfanyl)methyl]cyclohexyl}-1-oxa-2,8-diazaspiro[4.5]dec-2-en-8-carboxylate (200 mg) was dissolved in ethanol (5 mL). To this, the compound of Example 4(4a): (2R)-2-[3-(propan-2-yl)phenoxy]propanehydrazide (163 mg, 0.732 mmol) was added, and the mixture was stirred at 80° C. for 16 hours.

The residue obtained by concentration under reduced pressure was purified by high performance liquid chromatography to obtain tert-butyl 3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-ene-8-carboxylate (140 mg, (yield: 51%)) as a white solid.

To a solution of the obtained tert-butyl 3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-en-8-carboxylate (140 mg, 0.247 mmol) in dichloromethane (4 mL), 4N hydrochloric acid-1,4-dioxane (0.5 mL, 2 mmol) was added, and the mixture was stirred at 30° C. for 2 hours.

The resultant was concentrated under reduced pressure to obtain 3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-ene (124 mg) as a crude product.

The obtained crude product of 3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro [4.5] dec-2-ene (124 mg) was dissolved in tetrahydrofuran (4 mL) and N,N-dimethylformamide (2 mL). To this, sodium bicarbonate (62.2 mg, 0.741 mmol) and a formaldehyde solution (37%) (111 mg, 1.23 mmol) was added and the mixture was stirred at 30° C. for 1 hour. To this, triacetoxyborohydride (157 mg, 0.741 mmol) was added and the mixture was stirred at 30° C. for 15 hours.

The residue obtained by concentration under reduced pressure was purified by high performance liquid chromatography to obtain the title compound (44.7 mg (yield: 8.3%)) as a white solid.

The analysis results of the compounds of Examples by powder X-ray diffraction are shown below.

Analysis Conditions:

Machine model: Rigaku Rint TTR-III

Sample holder: Non-reflective sample holder

Samples: Appropriate amount

X-ray generation conditions: 50 kV, 300 mA

Wavelength: 1.54 Å (Copper Kα Ray)

Scan Speed: 20°/min

Scan Range: 2-40°

Sampling width: 0.020

Analysis procedures: Several mg of the test substance was collected with a spatula, placed on a non-reflective sample holder, and flattened with medicine wrapping paper. Thereafter, the peak pattern was analyzed under the above conditions.

Example 4

Table 2 shows peaks of relative intensity 4 or more when the maximum peak intensity is 100 in the diffraction pattern of powder X-ray diffraction (CuKα, λ=1.54 Å, scanning speed=20°/min) in FIG. 1.

TABLE 2

| Peak Number | 2θ | d Value | Relative Intensity |
|---|---|---|---|
| 1 | 3.94 | 22.41 | 97 |
| 2 | 4.10 | 21.53 | 100 |
| 3 | 8.34 | 10.59 | 17 |
| 4 | 12.58 | 7.03 | 4 |
| 5 | 16.20 | 5.47 | 13 |
| 6 | 18.42 | 4.81 | 13 |
| 7 | 19.46 | 4.56 | 11 |
| 8 | 22.32 | 3.98 | 7 |

Example 8

Table 3 shows peaks of relative intensity 4 or more when the maximum peak intensity is 100 in the diffraction pattern of powder X-ray diffraction (CuKα, λ=1.54 Å, scanning speed=20°/min) in FIG. 2.

TABLE 3

| Peak Number | 2θ | d Value | Relative Intensity |
|---|---|---|---|
| 1 | 3.80 | 23.23 | 100 |
| 2 | 16.38 | 5.41 | 22 |
| 3 | 18.02 | 4.92 | 41 |
| 4 | 18.56 | 4.78 | 36 |
| 5 | 19.76 | 4.49 | 21 |
| 6 | 21.18 | 4.19 | 19 |
| 7 | 22.74 | 3.91 | 20 |

Example 20

Table 4 shows peaks of relative intensity 4 or more when the maximum peak intensity is 100 in the diffraction pattern of powder X-ray diffraction (CuKα, λ=1.54 Å, scanning speed=20°/min) in FIG. 3.

TABLE 4

| Peak Number | 2θ | d Value | Relative Intensity |
|---|---|---|---|
| 1 | 13.52 | 6.54 | 20 |
| 2 | 15.74 | 5.63 | 29 |
| 3 | 17.18 | 5.16 | 40 |
| 4 | 17.78 | 4.98 | 38 |
| 5 | 18.16 | 4.88 | 72 |
| 6 | 19.16 | 4.63 | 89 |
| 7 | 20.40 | 4.35 | 100 |
| 8 | 20.76 | 4.28 | 53 |
| 9 | 21.96 | 4.04 | 26 |
| 10 | 27.22 | 3.27 | 18 |

Example 24

Table 5 shows peaks of relative intensity 4 or more when the maximum peak intensity is 100 in the diffraction pattern of powder X-ray diffraction (CuKα, λ=1.54 Å, scanning speed=20°/min) in FIG. 4.

TABLE 5

| Peak Number | 2θ | d Value | Relative Intensity |
|---|---|---|---|
| 1 | 3.30 | 26.75 | 42 |
| 2 | 13.36 | 6.62 | 16 |
| 3 | 15.46 | 5.73 | 23 |
| 4 | 16.84 | 5.26 | 29 |
| 5 | 17.54 | 5.05 | 30 |
| 6 | 17.90 | 4.95 | 38 |
| 7 | 18.88 | 4.70 | 54 |
| 8 | 20.44 | 4.34 | 100 |
| 9 | 21.78 | 4.08 | 17 |
| 10 | 26.90 | 3.31 | 17 |

Example 25

Table 6 shows peaks of relative intensity 4 or more when the maximum peak intensity is 100 in the diffraction pattern of powder X-ray diffraction (CuKα, λ=1.54 Å, scanning speed=20°/min) in FIG. 5.

TABLE 6

| Peak Number | 2θ | d Value | Relative Intensity |
|---|---|---|---|
| 1 | 13.16 | 6.72 | 20 |
| 2 | 15.80 | 5.60 | 24 |
| 3 | 16.48 | 5.37 | 30 |
| 4 | 17.76 | 4.99 | 69 |
| 5 | 18.08 | 4.90 | 55 |
| 6 | 19.00 | 4.67 | 88 |
| 7 | 20.26 | 4.38 | 100 |
| 8 | 20.82 | 4.26 | 47 |
| 9 | 21.38 | 4.15 | 22 |
| 10 | 27.86 | 3.20 | 25 |

Example 27

Table 7 shows peaks of relative intensity 4 or more when the maximum peak intensity is 100 in the diffraction pattern of powder X-ray diffraction (CuKα, λ=1.54 Å, scanning speed=20°/min) in FIG. 6.

TABLE 7

| Peak Number | 2θ | d Value | Relative Intensity |
|---|---|---|---|
| 1 | 14.16 | 6.25 | 58 |
| 2 | 16.72 | 5.30 | 59 |
| 3 | 17.36 | 5.10 | 43 |
| 4 | 18.22 | 4.87 | 75 |
| 5 | 18.64 | 4.76 | 51 |
| 6 | 19.48 | 4.55 | 100 |
| 7 | 19.96 | 4.44 | 51 |
| 8 | 20.88 | 4.25 | 57 |
| 9 | 21.58 | 4.11 | 42 |
| 10 | 21.82 | 4.07 | 43 |

Example 31

Table 8 shows peaks of relative intensity 4 or more when the maximum peak intensity is 100 in the diffraction pattern of powder X-ray diffraction (CuKα, λ=1.54 Å, scanning speed=20°/min) in FIG. 7.

TABLE 8

| Peak Number | 2θ | d Value | Relative Intensity |
|---|---|---|---|
| 1 | 15.38 | 5.76 | 26 |
| 2 | 17.64 | 5.02 | 49 |

TABLE 8-continued

| Peak Number | 2θ | d Value | Relative Intensity |
|---|---|---|---|
| 3 | 17.92 | 4.95 | 36 |
| 4 | 18.36 | 4.83 | 27 |
| 5 | 18.66 | 4.75 | 36 |
| 6 | 19.18 | 4.62 | 100 |
| 7 | 20.18 | 4.40 | 39 |
| 8 | 20.70 | 4.29 | 30 |
| 9 | 22.96 | 3.87 | 42 |
| 10 | 23.76 | 3.74 | 32 |

In the following tables, the structural formula of the compounds described in the Examples and physicochemical data thereof are collectively shown.

The abbreviations listed below are used.

Bn: benzyl group
Et: ethyl group
Me: methyl group
iPr: i-propyl group
tBu: t-butyl group
Ph: phenyl group
Cbz: benzyloxycarbonyl group
Boc: t-butoxycarbonyl group
TBDMS: t-butyldimethylsilyl group
TBDPS: t-butyldiphenylsilyl group

TABLE 9

| Example No. | Structural formula | Physicochemical data |
|---|---|---|
| 1(1a) | [structure] | 1H NMR (CDCl₃) δ(ppm) 3.94 (br s, 2H) 4.62 (s, 2H) 7.09 (dd, J = 8.5, 2.7 Hz, 1H) 7.16 (s, 1H) 7.31 (d, J = 7.8 Hz, 1H) 7.46 (t, J = 8.1 Hz, 1H) 7.69 (br s, 1H). |
| 1(1b) | [structure] | 1H NMR (CDCl₃) δ(ppm) 1.53 (s, 9H) 3.36 (d, J = 4.9 Hz, 3H) 6.62 (br s, 1H) 7.39 (d, J = 8.3 Hz, 2H) 7.64 (br s, 1H) 7.75 (d, J = 8.6 Hz, 2H). |
| 1(1c) | [structure] | 1H NMR (CDCl₃) δ(ppm) 1.54 (s, 9H) 3.76 (s, 3H) 5.37 (s, 2H) 6.65 (s, 1H) 7.27-7.32 (m, 3H) 7.45 (t, J = 7.3 Hz, 1H) 7.51-7.55 (m, 2H) 7.58-7.63 (m, 2H). |
| 1(1d) | [structure] | 1H NMR (CDCl₃) δ(ppm) 3.75 (s, 3H) 3.94 (br s, 2H) 5.36 (s, 2H) 6.76-6.79 (m, 2H) 7.25-7.32 (m, 3H) 7.42-7.47 (m, 3H). |

TABLE 9-continued

| Example No. | Structural formula | Physicochemical data |
|---|---|---|
| 1(1e) | | 1H NMR (CDCl₃) δ(ppm) 3.85 (s, 3H) 5.45 (s, 2H) 7.20-7.35 (m, 5H) 7.48 (t, J = 7.9 Hz, 1H) 7.68 (d, J = 8.5 Hz, 2H). |
| 1(1f) | | 1H NMR (DMSO-d₆) δ(ppm) 1.42 (s, 9H) 1.47-1.62 (m, 2H) 1.96-2.04 (m, 2H) 2.86-3.03 (m, 4H) 3.80 (s, 3H) 3.97-4.05 (m, 1H) 5.53 (s, 2H) 7.38 (d, J = 7.9 Hz, 1H) 7.44-7.51 (m, 2H) 7.60 (t, J = 7.9 Hz, 1H) 7.99 (d, J = 8.5 Hz, 2H) 8.10 (d, J = 8.5 Hz, 2H) 8.79 (s, 1H). |
| 1(1g) | | 1H NMR (CDCl₃) δ(ppm) 1.23-1.27 (m, 1H) 1.62-1.75 (m, 2H) 2.09-2.16 (m, 2H) 2.77-2.85 (m, 2H) 2.97-3.06 (m, 1H) 3.18-3.24 (m, 2H) 3.84 (s, 3H) 5.41 (s, 2H) 7.28-7.33 (m, 3H) 7.46 (t, J = 7.9 Hz, 1H) 7.79 (s, 1H) 7.86 (d, J = 8.5 Hz, 2H) 7.94 (d, J = 8.5 Hz, 2H). |
| 1(1h) | | 1H NMR (CDCl₃) δ(ppm) 1.52-1.60 (m, 2H) 1.78-1.89 (m, 2H) 2.10-2.19 (m, 3H) 2.36 (s, 3H) 2.83-3.03 (m, 2H) 3.84 (s, 3H) 5.41 (s, 2H) 7.28-7.33 (m, 3H) 7.46 (t, J = 7.9 Hz, 1H) 7.79 (s, 1H) 7.85 (d, J = 8.5 Hz, 2H) 7.93 (d, J = 7.6 Hz, 2H). MS (APCI) m/z: 498 [M + H]⁺. |
| 2(2a) | | 1H NMR (CDCl₃) δ(ppm) 1.24 (d, J = 6.8 Hz, 6H) 2.80-2.93 (m, 1H) 3.81 (s, 3H) 4.64 (s, 2H) 6.69 (dd, J = 8.1, 2.7 Hz, 1H) 6.82 (t, J = 2.2 Hz, 1H) 6.85-6.90 (m, 1H) 7.21 (t, J = 7.8 Hz, 1H). |

TABLE 10

| Example No. | Structural formula | Physicochemical data |
|---|---|---|
| 2(2b) | | 1H NMR (CDCl₃) δ(ppm) 1.25 (d, J = 6.8 Hz, 6H) 2.85-2.94 (m, 1H) 3.93 (br s, 2H) 4.59 (s, 2H) 6.71 (d, J = 7.8 Hz, 1H) 6.79 (br d, J = 2.0 Hz, 1H) 6.92 (br d, J = 7.8 Hz 1H) 7.22-7.31 (m, 1H) 7.76 (br s, 1H). |

TABLE 10-continued

| Example No. | Structural formula | Physicochemical data |
|---|---|---|
| 2(2c) | | 1H NMR (CDCl₃) δ(ppm) 1.45 (s, 9H) 3.02 (d, J = 5.4 Hz, 3H) 6.77 (br s, 1H) 7.85 (br s, 1H) 8.00 (br d, J = 7.8 Hz, 1H) 8.14 (d, J = 8.8 Hz, 1H) 8.46 (d, J = 2.4 Hz, 1H). |
| 2(2d) | | 1H NMR (CDCl₃) δ(ppm) 1.54 (s, 9H) 3.38 (d, J = 5.4 Hz, 3H) 6.67 (br s, 1H) 7.92 (dd, J = 8.8, 2.4 Hz, 1H) 8.45 (d, J = 2.4 Hz, 1H) 8.65 (d, J = 8.8 Hz, 1H) 10.00 (br s, 1H). |
| 2(2e) | | 1H NMR (CDCl₃) δ(ppm) 1.24 (d, J = 6.8 Hz, 6H) 1.55 (s, 9H) 2.82-2.98 (m, 1H) 4.13 (s, 3H) 5.33 (s, 2H) 6.64 (s, 1H) 6.86-6.95 (m, 3H) 7.24 (t, J = 7.5 Hz, 1H) 8.01 (br d, J = 7.3 Hz, 1H) 8.24 (d, J = 8.8 Hz, 1H) 8.59 (d, J = 2.4 Hz, 1H). |
| 2(2f) | | 1H NMR (CDCl₃) δ(ppm) 1.24 (d, J = 7.3 Hz, 6H) 2.83-2.95 (m, 1H) 3.92 (br s, 2H) 4.10 (s, 3H) 5.31 (s, 2H) 6.84-6.94 (m, 3H) 7.03-7.13 (m, 1H) 7.21-7.25 (m, 1H) 8.04-8.12 (m, 2H). |
| 2(2g) | | 1H NMR (CDCl₃) δ(ppm) 1.25 (d, J = 6.8 Hz, 6H) 1.49 (s, 9H) 1.50-1.55 (m, 2H) 1.64-1.75 (m, 2H) 2.08-2.15 (m, 2H) 2.86-2.98 (m, 3H) 3.02-3.10 (m, 1H) 4.22 (s, 3H) 5.37 (s, 2H) 6.91-6.93 (m, 3H) 7.22-7.27 (m, 1H) 7.80-7.82 (m, 1H) 8.18-8.23 (m, 1H) 8.53 (d, J = 8.8 Hz, 1H) 9.09-9.12 (m, 1H). |
| 2(2h) | | 1H NMR (CDCl₃) δ(ppm) 1.25 (d, J = 7.3 Hz, 6H) 1.63-1.75 (m, 2H) 2.09-2.16 (m, 2H) 2.78-2.85 (m, 2H) 2.87-2.93 (m, 1H) 2.98-3.06 (m, 1H) 3.17-3.24 (m, 2H) 4.21 (s, 3H) 5.37 (s, 2H) 6.89-6.95 (m, 3H) 7.23-7.27 (m, 1H) 7.80 (s, 1H) 8.18-8.22 (m, 1H) 8.51-8.54 (m, 1H) 9.10-9.13 (m, 1H). |
| 2(2i) | | 1H NMR (CDCl₃) δ(ppm) 1.25 (d, J = 6.8 Hz, 6H) 1.76-1.87 (m, 2H) 2.09-2.18 (m, 4H) 2.34 (s, 3H) 2.84-3.00 (m, 4H) 4.21 (s, 3H) 5.37 (s, 2H) 6.87-6.97 (m, 3H) 7.22-7.29 (m, 1H) 7.80 (s, 1H) 8.20-8.21 (m, 1H) 8.51-8.53 (m, 1H) 9.11 (s, 1H). MS (APCI) m/z: 473 [M + H]⁺. |
| 3(3a) | | 1H NMR (CDCl₃) δ(ppm) 1.13-1.21 (m, 2H) 1.44 (s, 9H) 1.68-1.76 (m, 1H) 1.92-2.02 (m, 2H) 2.08-2.16 (m, 2H) 2.46-2.51 (m, 1H) 3.19 (d, J = 4.9 Hz, 3H) 3.42-3.46 (m, 1H) 3.79-3.90 (m, 1H) 4.38 (br s, 1H) 7.30 (br s, 1H). |

TABLE 11

| Example No. | Structural formula | Physicochemical data |
|---|---|---|
| 3(3b) | | 1H NMR (CDCl₃) δ(ppm) 1.08-1.21 (m, 2H) 1.44 (s, 9H) 1.52-1.92 (m, 3H) 2.13-2.16 (m, 2H) 2.17-2.26 (m, 1H) 2.42 (s, 3H) 2.72-2.82 (m, 0.3H) 3.17 (s, 2H) 3.26 (s, 1H) 3.34-3.50 (m, 1H) 3.77-3.91 (m, 0.7H) 4.29-4.43 (m, 1H). |
| 3(3c) | | 1H NMR (CDCl₃) δ(ppm) 1.19-1.30 (m, 8H) 1.46 (s, 9H) 1.83-1.94 (m, 2H) 1.98-2.06 (m, 2H) 2.19 (br d, J = 12.2 Hz, 2H) 2.59 (tt, J = 12.0, 3.4 Hz, 1H) 2.82-2.94 (m, 1H) 3.45-3.60 (m, 1H) 3.65 (s, 3H) 4.43 (br s, 1H) 5.24 (s, 2H) 6.84-6.91 (m, 3H) 7.23 (t, J = 7.6 Hz, 1H). |
| 3(3d) | | 1H NMR (CDCl₃) δ(ppm) 1.23 (d, J = 6.8 Hz, 6H) 1.33-1.42 (m, 2H) 1.78-1.87 (m, 2H) 1.98-2.05 (m, 2H) 2.06-2.13 (m, 2H) 2.45-2.68 (m, 3H) 2.84-2.99 (m, 2H) 3.65 (s, 3H) 5.22 (s, 2H) 6.83-6.90 (m, 3H) 7.21-7.25 (m, 1H). |
| 3(3e) | | 1H NMR (CDCl₃) δ(ppm) 1.24 (d, J = 6.8 Hz, 6H) 1.48 (dq, J = 2.8, 12.8 Hz, 2H) 1.85-1.91 (m, 2H) 2.07-2.10 (m, 2H) 2.20 (dd, J = 13.2, 2.9 Hz, 2H) 2.63-2.65 (m, 1H) 2.86-2.91 (m, 1H) 3.42-3.44 (m, 1H) 3.66 (s, 3H) 5.24 (s, 2H) 6.87-6.88 (m, 3H) 7.23 (t, J = 7.6 Hz, 1H). |
| 3(3f) | | 1H NMR (CDCl₃) δ(ppm) 1.24 (d, J = 6.8 Hz, 6H) 1.47 (s, 9H) 1.90-1.92 (m, 2H) 2.00-2.09 (m, 7H) 2.21-2.22 (m, 2H) 2.42-2.43 (m, 2H) 2.76-2.85 (m, 1H) 2.85-2.93 (m, 1H) 3.36-3.38 (m, 2H) 3.70 (s, 3H) 3.87-3.89 (m, 2H) 4.51-4.55 (m, 1H) 5.26 (s, 2H) 6.87-6.89 (m, 3H) 7.23-7.24 (m, 1H) 7.50 (s, 1H). |
| 3(3g) | | 1H NMR (CDCl₃) δ(ppm) 1.24 (d, J = 6.8 Hz, 6H) 1.48 (s, 9H) 2.00-2.25 (m, 10H) 2.43-2.44 (m, 2H) 2.77-2.80 (m, 1H) 2.85-2.93 (m, 1H) 3.27 (s, 2H) 3.69 (s, 3H) 3.99-4.01 (m, 2H) 4.52-4.56 (m, 1H) 5.26 (s, 2H) 6.87-6.89 (m, 3H) 7.23-7.24 (m, 1H) 7.60 (s, 1H). |
| 3(3h) | | 1H NMR (CDCl₃) δ(ppm) 1.24 (d, J = 6.3 Hz, 6H) 2.01-2.09 (m, 4H) 2.19-2.34 (m, 6H) 2.35 (s, 3H) 2.42-2.48 (m, 4H) 2.72-2.80 (m, 3H) 2.85-2.93 (m, 1H) 3.69 (s, 3H) 4.52-4.54 (m, 1H) 5.26 (s, 2H) 6.87-6.89 (m, 3H) 7.23-7.26 (m, 1H) 7.58 (s, 1H). MS (APCI) m/z: 496 [M + H]⁺. |
| 4(4a) | | 1H NMR (CDCl₃) δ(ppm) 1.24 (d, J = 6.8 Hz, 6H) 1.59 (d, J = 6.8 Hz, 3H) 2.83-2.92 (m, 1H) 3.85 (d, J = 4.4 Hz, 2H) 4.78 (q, J = 6.8 Hz, 1H) 6.68 (dd, J = 8.3, 2.4 Hz, 1H) 6.76-6.78 (m, 1H) 6.89 (d, J = 8.3 Hz, 1H) 7.22 (t, J = 7.8 Hz, 1H) 7.63 (br s, 1H). |

TABLE 12

| Example No. | Structural formula | Physicochemical data |
|---|---|---|
| 4(4b) | (structure) | 1H NMR (CDCl₃) δ(ppm) 1.20-1.24 (m ,9H) 1.45 (s, 9H) 1.78 (d, J = 6.8 Hz, 3H) 1.83-2.02 (m, 4H) 2.15-2.18 (m, 2H) 2.51-2.54 (m, 1H) 2.81-2.85 (m, 1H) 3.61 (s, 3H) 4.41 (br s, 1H) 5.72 (q, J = 6.7 Hz, 1H) 6.80-6.83 (m, 3H) 7.16 (t, J = 8.1 Hz, 1H). |
| 4(4c) | (structure) | 1H NMR (CDCl₃) δ(ppm) 1.20 (d, J = 6.8 Hz, 3H) 1.21 (d, J = 7.3 Hz, 3H) 1.22 (m, 2H) 1.78 (d, J = 6.8 Hz, 3H) 1.80-1.86 (m, 1H) 1.92-2.00 (m, 5H) 2.50-2.53 (m, 1H) 2.76-2.87 (m, 2H) 3.62 (s, 3H) 5.73 (q, J =6.7 Hz, 1H) 6.79-6.84 (m, 3H) 7.16 (t, J = 8.1 Hz, 1H). |
| 4(4d) | (structure) | 1H NMR (CDCl₃) δ(ppm) 1.20 (d, J = 6.7 Hz, 3H) 1.21 (d, J = 6.7 Hz, 3H) 1.40-1.51 (m, 2H) 1.60-1.64 (m, 1H) 1.79 (d, J = 6.8 Hz, 3H) 1.81-1.88 (m, 1H) 1.98-2.06 (m, 2H) 2.14-2.20 (m, 2H) 2.57 (tt, J = 11.7, 3.5 Hz, 1H) 2.82-2.85 (m, 1H) 3.41 (tt, J = 11.2, 4.1 Hz, 1H) 3.62 (s, 3H) 5.72 (q, J = 6.7 Hz, 1H) 6.79-6.81 (m, 1H) 6.84-6.85 (m, 2H) 7.17 (t, J = 7.8 Hz, 1H). |
| 4(4e) | (structure) | 1H NMR (CDCl₃) δ(ppm) 1.19-1.23 (m, 6H) 1.47 (s, 9H) 1.58-1.61 (m, 2H) 1.80 (d, J = 6.8 Hz, 3H) 1.89-1.91 (m, 2H) 1.99-2.05 (m, 4H) 2.13-2.20 (m, 2H) 2.39-2.41 (m, 2H) 2.48-2.54 (m, 1H) 2.71-2.73 (m, 1H) 2.84-2.86 (m, 1H) 3.35-3.37 (m, 2H) 3.66 (s, 3H) 3.87 (br s, 2H) 4.50-4.52 (m, 1H) 5.74 (q, J = 6.8 Hz, 1H) 6.81-6.85 (m, 3H) 7.18 (t, J = 8.3 Hz, 1H) 7.47 (s, 1H). |
| 4(4f) | (structure) | 1H NMR (CDCl₃) δ(ppm) 1.19-1.22 (m, 6H) 1.47 (s, 9H) 1.59-1.65 (m, 2H) 1.80 (d, J = 6.8 Hz, 3H) 1.94-2.29 (m, 8H) 2.36-2.46 (m, 2H) 2.69-2.76 (m, 1H) 2.81-2.89 (m, 1H) 3.21-3.33 (m, 2H) 3.66 (s, 3H) 3.92-4.05 (m, 2H) 4.49-4.56 (m, 1H) 5.75 (q, J = 6.7 Hz, 1H) 6.79-6.87 (m, 3H) 7.18 (t, J = 8.3 Hz, 1H) 7.59 (s, 1H). |
| 4(4g) | (structure) | 1H NMR (CDCl₃) δ(ppm) 1.21 (d, J = 6.8 Hz, 6H) 1.80 (d, J = 6.8 Hz, 3H) 2.02-2.03 (m, 4H) 2.12-2.31 (m, 6H) 2.34 (s, 3H) 2.43-2.46 (m, 4H) 2.71 (s, 3H) 2.82-2.88 (m, 1H) 3.66 (s, 3H) 4.51 (s, 1H) 5.74 (q, J = 6.5 Hz, 1H) 6.81-6.85 (m, 3H) 7.17-7.18 (m, 1H) 7.57 (s, 1H). MS (APCI) m/z: 510 [M + H]⁺. |
| 5(5a) | (structure) | 1H NMR (CDCl₃) δ(ppm) 1.09 (s, 9H) 3.90 (d, J = 4.4 Hz, 2H) 4.20 (s, 2H) 7.38-7.43 (m, 4H) 7.45-7.47 (m, 2H) 7.60-7.61 (m, 4H) 7.88 (br s, 1H). |

TABLE 13

| Example No. | Structural formula | Physicochemical data |
|---|---|---|
| 5(5b) | (structure) | 1H NMR (CDCl₃) δ(ppm) 1.05 (s, 9H) 1.20-1.27 (m, 2H) 1.46 (s, 9H) 1.84-1.94 (m, 2H) 2.01-2.04 (m, 2H) 2.17-2.20 (m, 2H) 2.54-2.59 (m, 1H) 3.53-3.55 (m, 1H) 3.59 (s, 3H) 4.43 (br s, 1H) 4.86 (s, 2H) 7.38-7.40 (m, 4H) 7.43-7.46 (m, 2H) 7.64-7.66 (m, 4H). |

TABLE 13-continued

| Example No. | Structural formula | Physicochemical data |
|---|---|---|
| 5(5c) | | 1H NMR (CDCl₃) δ(ppm) 1.06 (s, 9H) 1.43-1.52 (m, 2H) 1.83-1.88 (m, 2H) 2.05-2.09 (m, 2H) 2.18-2.20 (m, 2H) 2.61 (tt, J = 11.7, 3.7 Hz, 1H) 3.42 (tt, J = 11.2, 4.1 Hz, 1H) 3.61 (s, 3H) 4.87 (s, 2H) 7.39-7.40 (m, 4H) 7.44-7.46 (m, 2H) 7.64-7.66 (m, 4H). |
| 5(5d) | | 1H NMR (CDCl₃) δ(ppm) 1.06 (s, 9H) 1.96-2.27 (m, 11H) 2.39-2.47 (m, 2H) 2.72-2.79 (m, 1H) 2.96-3.03 (m, 2H) 3.05-3.12 (m, 2H) 3.64 (s, 3H) 4.49-4.56 (m, 1H) 4.88 (s, 2H) 7.38-7.48 (m, 6H) 7.58 (s, 1H) 7.65-7.68 (m, 4H). |
| 5(5e) | | 1H NMR (CDCl₃) δ(ppm) 1.06 (s, 9H) 2.03-2.04 (m, 5H) 2.22-2.25 (m, 5H) 2.33-2.35 (m, 1H) 2.35 (s, 3H) 2.38-2.49 (m, 3H) 2.74-2.76 (m, 3H) 3.64 (s, 3H) 4.51-4.53 (m, 1H) 4.88 (s, 2H) 7.40-7.46 (m, 6H) 7.59 (s, 1H) 7.66-7.66 (m, 4H). |
| 5(5f) | | 1H NMR (CDCl₃) δ(ppm) 1.95-2.01 (m, 5H) 2.16-2.21 (m, 5H) 2.25-2.31 (m, 1H) 2.31 (s, 3H) 2.39-2.44 (m, 4H) 2.71-2.74 (m, 3H) 3.70 (s, 3H) 4.49-4.52 (m, 1H) 4.76 (s, 2H) 7.56 (s, 1H). |
| 5(5g) | | 1H NMR (CDCl₃) δ(ppm) 1.99-2.13 (m, 4H) 2.17-2.34 (m, 6H) 2.35 (s, 3H) 2.41-2.50 (m, 4H) 2.71-2.84 (m, 3H) 3.71 (s, 3H) 4.49-4.58 (m, 1H) 5.30 (s, 2H) 7.22 (dd, J = 8.8, 3.4 Hz, 1H) 7.33 (d, J = 3.4 Hz, 1H) 7.42 (d, J = 8.8 Hz, 1H) 7.59 (s, 1H). MS (APCI) m/z: 556 [M + H]⁺. |
| 6(6a) | | 1H NMR (CDCl₃) δ(ppm) 1.20 (d, J = 6.3 Hz, 3H) 2.00-2.06 (m, 2H) 3.05-3.11 (m, 2H) 3.14-3.20 (m, 2H) 3.28-3.34 (m, 1H) 3.90 (s, 3H) 7.38 (d, J = 8.3 Hz, 2H) 7.97 (d, J = 8.3 Hz, 2H). |
| 6(6b) | | 1H NMR (CDCl₃) δ(ppm) 1.19 (d, J = 6.3 Hz, 3H) 1.99-2.04 (m, 2H) 3.06 (q, J = 7.0 Hz, 2H) 3.17 (q, J = 7.0 Hz, 2H) 3.25 (q, J = 6.3 Hz, 1H) 4.67 (s, 2H) 7.29-7.33 (m, 4H). |

TABLE 14

| Example No. | Structural formula | Physicochemical data |
|---|---|---|
| 6(6c) | | 1H NMR (CDCl₃) δ(ppm) 1.18 (d, J = 6.8 Hz, 3H) 1.99-2.04 (m, 2H) 3.03-3.08 (m, 3H) 3.16 (q, J = 7.0 Hz, 2H) 3.24 (q, J = 6.5 Hz, 1H) 7.26 (d, J = 8.3 Hz, 2H) 7.43 (d, J = 8.3 Hz, 2H). |

TABLE 14-continued

| Example No. | Structural formula | Physicochemical data |
|---|---|---|
| 6(6d) | | 1H NMR (CDCl₃) δ(ppm) 1.22 (d, J = 6.8 Hz, 3H) 1.24 (d, J = 7.3 Hz, 6H) 2.02-2.10 (m, 6H) 2.23-2.24 (m, 2H) 2.46-2.48 (m, 2H) 2.80-2.82 (m, 1H) 2.86-2.92 (m, 1H) 3.09 (q, J = 7.0 Hz, 2H) 3.20 (q, J = 7.0 Hz, 2H) 3.28 (q, J = 6.5 Hz, 1H) 3.70 (s, 3H) 4.58 (s, 1H) 5.27 (s, 2H) 6.86-6.91 (m, 3H) 7.24 (t, J = 8.5 Hz, 1H) 7.37 (d, J = 7.8 Hz, 2H) 7.77-7.78 (m, 3H). MS (APCI) m/z: 540 [M + H]⁺. |
| 7(7a) | | 1H NMR (DMSO-d₆) δ(ppm) 1.36 (s, 9H) 1.64-1.75 (m, 12H) 2.71 (s, 3H) 6.40 (br s, 1H) 7.31-7.33 (m, 1H). |
| 7(7b) | | 1H NMR (DMSO-d₆) δ(ppm) 1.36 (s, 9H) 1.69-1.80 (m, 6H) 1.80-1.88 (m, 6H) 2.94 (d, J = 4.8 Hz, 3H) 6.43 (br s, 1H) 9.25 (d, J = 4.0 Hz, 1H). |
| 7(7c) | | 1H NMR: (CDCl₃) δ 1.23-1.25 (m, 6H) 1.63 (d, J = 6.8 Hz, 3H) 2.82-2.94 (m, 1H) 3.77 (s, 3H) 4.80 (q, J = 6.8 Hz, 1H) 6.68-6.69 (m, 1H) 6.80-6.82 (m, 1H) 6.86 (dd, J = 7.7, 0.6 Hz, 1H) 7.18-7.22 (m, 1H). |
| 7(7d) | | 1H NMR (CDCl₃) δ(ppm) 1.22-1.24 (m, 6H) 1.55-1.59 (m, 3H) 2.84-2.91 (m, 1H) 3.89 (br s, 2H) 4.74-4.79 (m, 1H) 6.67-6.69 (m, 1H) 6.78 (s, 1H) 6.87-6.89 (m, 1H) 7.18-7.21 (m, 1H) 7.82-8.06 (m, 1H). |
| 7(7e) | | 1H NMR (CDCl₃) δ(ppm) 1.14-1.17 (m, 9H) 1.74 (d, J = 6.8 Hz, 3H) 1.92-2.01 (m, 2H) 2.21-2.34 (m, 12H) 2.77-2.84 (m, 1H) 3.02-3.26 (m, 5H) 3.75 (s, 3H) 5.66 (q, J = 6.8 Hz, 1H) 6.74-6.80 (m, 3H) 7.12 (t, J = 8.0 Hz, 1H) 7.30 (d, J = 8.0 Hz, 2H) 7.68-7.71 (m, 3H). MS (ESI) m/z: 580 [M + H]⁺. |
| 8(8a) | | 1H NMR (CDCl₃) δ(ppm) 1.23 (d, J = 6.9 Hz, 3H) 1.24 (d, J = 6.9 Hz, 3H) 1.48 (s, 9H) 1.50-2.25 (m, 11H) 1.82 (d, J = 6.9 Hz, 3H) 2.38-2.45 (m, 2H) 2.69-2.75 (m, 1H) 2.84-2.90 (m, 1H) 3.23 (t, J = 10.7 Hz, 1H) 3.68 (s, 3H) 4.17-4.23 (m, 1H) 4.35-4.50 (m, 1H) 4.51-4.58 (m, 2H) 5.77 (q, J = 6.9 Hz, 1H) 6.83-6.88 (m, 3H) 7.18-7.22 (m, 1H) 7.55 (s, 1H). |

TABLE 15

| Example No. | Structural formula | Physicochemical data |
| --- | --- | --- |
| 8(8b) | (structure) | i-Pr 1H NMR (DMSO-d₆) δ(ppm) 1.16 (d, J = 6.8 Hz, 3H) 1.17 (d, J = 6.8 Hz, 3H) 1.31-2.40 (m, 14H) 1.67 (d, J = 6.5 Hz, 3H) 2.50 (s, 6H) 2.80-2.93 (m, 2H) 3.58 (s, 3H) 4.00-4.03 (m, 1H) 4.38 (dd, J = 11.5, 2.0 Hz, 1H) 4.54-4.69 (m, 1H) 5.76 (q, J = 6.5 Hz, 1H) 6.84-6.87 (m, 3H) 7.20 (t, J = 7.9 Hz, 1H) 8.04 (s, 1H). MS (APCI) m/z: 522 [M + H]⁺. |
| 9(9a) | (structure) | 1H NMR (CDCl₃) δ(ppm) 1.42 (s, 9H) 1.79-1.89 (m, 2H) 1.94-2.04 (m, 2H) 2.07-2.17 (m, 2H) 2.26-2.36 (m, 2H) 2.45 (s, 1H) 4.00 (s, 2H) 4.28 (br s, 1H). |
| 9(9b) | (structure) | 1H NMR (CDCl₃) δ(ppm) 1.20-1.33 (m, 2H) 1.45 (s, 9H) 1.83-1.95 (m, 2H) 1.99-2.07 (m, 2H) 2.20 (br d, J = 12.2 Hz, 2H) 2.60 (tt, J = 12.1, 3.5 Hz, 1H) 3.48-3.60 (m, 1H) 3.66 (s, 3H) 4.43 (br s, 1H) 5.28 (s, 2H) 7.22-7.31 (m, 3H) 7.42 (t, J = 7.9 Hz, 1H). |
| 9(9c) | (structure) | 1H NMR (CDCl₃) δ(ppm) 1.18-1.29 (m, 2H) 1.79-1.91 (m, 2H) 1.96-2.07 (m, 4H) 2.54-2.65 (m, 1H) 2.76-2.86 (m, 1H) 3.66 (s, 3H) 5.28 (s, 2H) 7.22-7.29 (m, 3H) 7.39-7.43 (m, 1H). |
| 9(9d) | (structure) | 1H NMR (CDCl₃) δ(ppm) 1.48-1.58 (m, 2H) 1.80-1.89 (m, 2H) 2.09-2.13 (m, 2H) 2.19-2.23 (m, 2H) 2.60-2.76 (m, 1H) 3.41-3.48 (m, 1H) 3.69 (s, 3H) 5.30 (s, 2H) 7.25-7.30 (m, 3H) 7.41-7.49 (m, 1H). |
| 9(9e) | (structure) | CF₃ 1H NMR (CDCl₃) δ(ppm) 1.44 (s, 9H) 1.88-2.10 (m, 6H) 2.16-2.32 (m, 8H) 2.35-2.44 (m, 2H) 2.72-2.81 (m, 1H) 3.69 (s, 3H) 4.12 (s, 2H) 4.33-4.38 (m, 1H) 4.46-4.55 (m, 1H) 5.31 (s, 2H) 7.24-7.31 (m, 3H) 7.43 (t, J = 7.6 Hz, 1H) 7.50 (s, 1H). |
| 9(9f) | (structure) | CF₃ 1H NMR (CDCl₃) δ(ppm) 1.77-2.10 (m, 8H) 2.14-2.29 (m, 6H) 2.26 (s, 6H) 2.36-2.44 (m, 2H) 2.72-2.81 (m, 1H) 3.70 (s, 3H) 3.94 (s, 2H) 4.48-4.56 (m, 1H) 5.31 (s, 2H) 7.23-7.31 (m, 3H) 7.43 (t, J = 7.9 Hz, 1H) 7.50 (s, 1H). MS (APCI) m/z: 560 [M + H]⁺. |

TABLE 15-continued

| Example No. | Structural formula | Physicochemical data |
| --- | --- | --- |
| 10(10a) | | 1H NMR (CDCl$_3$) δ(ppm) 1.81 (s, 12H) 2.21-2.29 (m, 2H) 3.65 (s, 3H) 4.00 (br s, 2H) 4.36 (br s, 2H). |

TABLE 16

| Example No. | Structural formula | Physicochemical data |
| --- | --- | --- |
| 10(10b) | | 1H NMR (CDCl$_3$) δ(ppm) 1.40 (s, 12H) 2.06-2.19 (m, 2H) 2.16 (s, 2H) 3.22-3.26 (m, 5H). |
| 10(10c) | | 1H NMR (CDCl$_3$) δ(ppm) 1.42-1.46 (m, 6H) 1.60-1.64 (m, 6H) 2.07-2.10 (m, 2H) 2.17 (s, 2H) 3.23 (t, J = 6.8 Hz, 2H) 9.44 (s, 1H). |
| 10(10d) | | 1H NMR (CDCl$_3$) δ(ppm) 1.29-1.33 (m, 6H) 1.65-1.69 (m, 6H) 1.99-2.01 (m, 3H) 2.05 (s, 2H) 3.15 (t, J = 7.2 Hz, 2H). |
| 10(10e) | | 1H NMR (CDCl$_3$) δ(ppm) 1.49-1.53 (m, 6H) 1.84-1.88 (m, 6H) 2.03-2.10 (m, 6H) 2.19 (br s, 4H) 2.41 (br s, 2H) 2.80 (br s, 1H) 3.24 (t, J = 6.8 Hz, 4H) 3.71 (s, 3H) 4.47-4.51 (m, 1H) 5.32 (s, 2H) 7.23-7.30 (m, 4H) 7.45 (t, J = 7.6 Hz, 1H). MS (ESI) m/z: 584 [M + H]$^+$. |
| 11 | | 1H NMR (CDCl$_3$) δ(ppm) 1.72-1.81 (m, 6H) 1.93-2.00 (m, 6H) 2.01-2.11 (m, 4H) 2.22 (d, J = 7.8 Hz, 2H) 2.32 (s, 6H) 2.42 (d, J = 7.2 Hz, 2H) 2.76-2.83 (m, 1H) 3.72 (s, 3H) 4.44-4.54 (m, 1H) 5.32 (s, 2H) 7.25-7.28 (m, 3H) 7.30 (s, 1H) 7.42-7.48 (m, 1H). MS (ESI) m/z: 558 [M + H]$^+$. |
| 12 | | 1H NMR (CDCl$_3$) δ(ppm) 1.88-2.00 (m, 4H) 2.05 (s, 6H) 2.09-2.17 (m, 2H) 2.22 (s, 6H) 2.28-2.39 (m, 2H) 2.63-2.81 (m, 1H) 3.63 (s, 3H) 4.37-4.48 (m, 1H) 5.24 (s, 2H) 7.16-7.23 (m, 4H) 7.32-7.40 (m, 1H). MS (ESI) m/z: 516 [M + H]$^+$. |
| 13(13a) | | 1H NMR (CDCl$_3$) δ(ppm) 1.32-1.50 (m, 11H) 2.08-2.18 (m, 1H) 2.55-2.65 (m, 1H) 3.07 (t, J = 10.6 Hz, 1H) 3.18 (d, J = 4.9 Hz, 3H) 3.46-3.73 (m, 1H) 4.02-4.14 (m, 1H) 4.15-4.33 (m, 2H) 8.42 (br s, 1H). |

TABLE 16-continued

| Example No. | Structural formula | Physicochemical data |
|---|---|---|
| 13(13b) | (BOC-NH-tetrahydropyran-triazole(Me)-CH2O-phenyl-i-Pr) | 1H NMR (CDCl$_3$) δ(ppm) 1.24 (d, J = 6.8 Hz, 6H) 1.43-1.49 (m, 9H) 1.52-1.62 (m, 1H) 2.22 (br s, 2H) 2.24-2.37 (m, 1H) 2.84-2.94 (m, 1H) 3.24 (t, J = 10.3 Hz, 1H) 3.73 (br s, 1H) 3.76 (s, 3H) 4.08-4.14 (m, 1H) 4.32-4.53 (m, 1H) 4.53-4.72 (m, 1H) 5.19-5.30 (m, 2H) 6.84-6.91 (m, 3H) 7.28-7.38 (m, 1H). |

TABLE 17

| Example No. | Structural formula | Physicochemical data |
|---|---|---|
| 13(13c) | (H$_2$N-tetrahydropyran-triazole(Me)-CH2O-phenyl-i-Pr) | 1H NMR (CDCl$_3$) δ(ppm) 1.24 (d, J = 6.8, 6H) 1.48-1.56 (m, 1H) 2.18-2.32 (m, 3H) 2.45-2.67 (m, 2H) 2.85-2.93 (m, 1H) 3.02-3.08 (m, 1H) 3.28-3.33 (m, 1H) 3.75 (s, 3H) 4.04-4.08 (m, 1H) 4.52-4.56 (m, 1H) 5.20-5.27 (m, 2H) 6.83-6.90 (m, 3H) 7.22 (t, J = 7.8 Hz, 1H). |
| 13(13d) | (N$_3$-tetrahydropyran-triazole(Me)-CH2O-phenyl-i-Pr) | 1H NMR (CDCl$_3$) δ(ppm) 1.24 (d, J = 6.7 Hz, 6H) 1.68-1.77 (m, 1H) 2.28-2.36 (m, 2H) 2.40-2.48 (m, 1H) 2.84-2.93 (m, 1H) 3.41 (dd, J = 11.2, 9.4 Hz, 1H) 3.54-3.62 (m, 1H) 3.75 (s, 3H) 3.99-4.04 (m, 1H) 4.56-4.61 (m, 1H) 5.25 (dd, J = 17.9, 12.5 Hz, 2H) 6.83-6.91 (m, 3H) 7.23 (t, J = 7.9 Hz, 1H). |
| 13(13e) | (BOC-N-piperidine(F)-triazole-tetrahydropyran-triazole(Me)-CH2O-phenyl-i-Pr) | 1H NMR (CDCl$_3$) δ(ppm) 1.24 (d, J = 6.7 Hz, 6H) 1.48 (s, 9H) 2.08-2.17 (m, 3H) 2.19-2.53 (m, 4H) 2.61-2.69 (m, 1H) 2.84-2.93 (m, 1H) 3.21-3.31 (m, 2H) 3.79 (s, 3H) 3.91-4.10 (m, 3H) 4.29-4.34 (m, 1H) 4.63-4.77 (m, 2H) 5.28 (dd, J = 17.9, 12.5 Hz, 2H) 6.84-6.91 (m, 2H) 7.19-7.25 (m, 1H) 7.32-73.8 (m, 1H) 7.64-7.69 (m, 1H). |
| 13(13f) | (Me-N-piperidine(F)-triazole-tetrahydropyran-triazole(Me)-CH2O-phenyl-i-Pr) | 1H NMR (CDCl$_3$) δ(ppm) 1.24 (d, J = 6.7 Hz, 6H) 2.05-2.53 (m, 9H) 2.35 (s, 3H) 2.60-2.68 (m, 1H) 2.70-2.78 (m, 2H) 2.84-2.93 (m, 1H) 3.79 (s, 3H) 3.94-4.01 (m, 1H) 4.29-4.34 (m, 1H) 4.63-4.77 (m, 2H) 5.27 (dd, J = 17.9, 12.5 Hz, 2H) 6.84-6.91 (m, 3H) 7.23 (t, J = 8.2 Hz, 1H) 7.68 (s, 1H). MS (APCI) m/z: 498 [M + H]$^+$. |
| 14(14a) | (MeO-phenyl-CH2-N-morpholinone-CH2-phenyl-i-Pr) | 1H NMR (CDCl$_3$) δ(ppm) 1.26 (d, J = 6.8 Hz, 6H) 2.89-2.91 (m, 1H) 2.95-3.01 (m, 1H) 3.07-3.12 (m, 1H) 3.35-3.39 (m, 2H) 3.65-3.73 (m, 1H) 3.82 (s, 3H) 3.93-3.97 (m, 1H) 4.45-4.60 (m, 3H) 6.83 (d, J = 8.4 Hz, 2H) 7.03 (d, J = 8.8 Hz, 2H) 7.15-7.24 (m, 4H). |
| 14(14b) | (HN-morpholinone-CH2-phenyl-i-Pr) | 1H NMR (CDCl$_3$) δ(ppm) 1.17 (d, J = 6.8 Hz, 6H) 2.82-2.96 (m, 2H) 3.07-3.15 (m, 1H) 3.24-3.29 (m, 1H) 3.35-3.50 (m, 1H) 3.60-3.66 (m, 1H) 3.86-3.90 (m, 1H) 4.02-4.09 (m, 1H) 4.30 (d, J = 6.0 Hz, 1H) 7.04-7.19 (m, 4H). |
| 14(14c) | (HN-morpholinethione-CH2-phenyl-i-Pr) | 1H NMR (CDCl$_3$) δ(ppm) 1.27 (d, J = 6.8 Hz, 6H) 22.90-.92 (m, 1H) 3.11-3.17 (m, 1H) 3.31-3.46 (m, 2H) 3.76-3.80 (m, 2H) 4.04-4.06 (m, 1H) 4.69 (dd, J = 8.8, 2.8 Hz, 1H) 7.12-7.29 (m, 4H) 8.83-8.95 (m, 1H). |

TABLE 18

| Example No. | Structural formula | Physicochemical data |
|---|---|---|
| 14(14d) | | 1H NMR (CDCl₃) δ(ppm) 1.32-1.39 (m, 2H) 1.45-1.54 (m, 2H) 2.02-2.06 (m, 4H) 2.24-2.30 (m, 1H) 3.25-3.31 (m, 1H) 3.65 (s, 3H). |
| 14(14e) | | 1H NMR (CDCl₃) δ(ppm) 1.47 (s, 9H) 1.66-1.69 (m, 2H) 1.83-2.00 (m, 6H) 2.22 (d, J = 12.8 Hz, 2H) 2.32 (d, J = 11.2 Hz, 2H) 2.30-2.42 (m, 1H) 3.00-3.19 (m, 1H) 3.26-3.45 (m, 2H) 3.71 (s, 3H) 3.77-4.00 (m, 2H) 4.36-4.52 (m, 1H) 7.40-7.55 (br s, 1H). |
| 14(14f) | | 1H NMR (CDCl₃) δ(ppm) 1.40 (s, 9H) 1.59-1.62 (m, 2H) 1.76-1.80 (m, 2H) 2.04-2.07 (m, 3H) 2.13-2.16 (m, 3H) 2.24-2.38 (m, 3H) 3.10-3.26 (br s, 2H) 3.64 (s, 3H) 3.80-4.06 (br s, 2H) 4.35-4.42 (m, 1H), 7.49 (s, 1H). |
| 14(14g) | | 1H NMR (DMSO-d₆) δ(ppm) 1.41 (s, 9H) 1.61-1.64 (m, 2H) 1.77-1.85 (m, 4H) 1.91 (s, 2H) 1.97-2.22 (m, 7H) 3.64-3.68 (m, 2H) 4.47-4.53 (m, 1H) 8.39 (s, 1H) 9.04 (s, 1H). |
| 14(14h) | | 1H NMR (CDCl₃) δ(ppm) 1.18 (d, J = 6.8 Hz, 6H) 1.89-2.05 (m, 4H) 2.08-2.20 (m, 5H) 2.32 (s, 3H) 2.34-2.45 (m, 2H) 2.71-2.85 (m, 5H) 3.00-3.07 (m, 3H) 3.55-3.58 (m, 1H) 3.74-3.86 (m, 3H) 4.17-4.19 (m, 1H) 4.46-4.51 (m, 1H) 4.97-4.99 (dd, J = 9.6, 6.4 Hz, 1H) 7.04-7.19 (m, 4H) 7.52 (s, 1H). MS (ESI) m/z: 522 [M + H]⁺. |
| 15(15a) | | 1H NMR (CDCl₃) δ(ppm) 1.70-1.96 (m, 2H) 2.10-2.14 (m, 1H) 2.18-2.28 (m, 1H) 3.31-3.50 (m, 2H) 4.75 (dd, J = 7.6, 5.6 Hz, 1H) 6.33 (s, 1H) 7.22-7.29 (m, 2H) 7.37-7.44 (m, 1H) 7.55-7.59 (m, 1H). |
| 15(15b) | | 1H NMR (CDCl₃) δ(ppm) 1.84-1.97 (m, 1H) 2.07-2.24 (m, 3H) 3.33-3.58 (m, 2H) 5.06 (t, J = 4.4 Hz, 1H) 7.25-7.29 (m, 1H,) 7.32-7.38 (m, 2H) 7.39-7.47 (m, 1H) 8.75-9.10 (m, 1H). |

TABLE 18-continued

| Example No. | Structural formula | Physicochemical data |
|---|---|---|
| 15(15c) | (BOC-piperidine-F, triazole, cyclohexyl, triazolopyridine-O-phenyl-CF₃) | 1H NMR (CDCl₃) δ(ppm) 1.47-1.51 (m, 9H) 1.99-2.28 (m, 12H) 2.41-2.56 (m, 4H) 2.75-2.88 (m, 1H) 3.12-3.41 (m, 3H) 3.85 (d, J = 11.7, 5.1 Hz, 1H) 4.01 (s, 2H) 4.13-4.24 (m, 1H) 5.64-5.74 (m, 1H) 7.27 (d, J = 7.7 Hz, 1H) 7.39-7.48 (m, 2H) 7.50-7.55 (m, 1H) 7.62 (s, 1H). |

TABLE 19

| Example No. | Structural formula | Physicochemical data |
|---|---|---|
| 15(15d) | (H₃C-N-piperidine-F, triazole, cyclohexyl, triazolopyridine-O-phenyl-CF₃) | 1H NMR (CDCl₃) δ (ppm) 1.88-2.22 (m, 12H) 2.28 (s, 3H) 2.32-2.45 (m, 6H) 2.60-2.79 (m, 3H) 3.72-3.79 (m, 1H) 4.06-4.10 (m, 1H) 4.45 (s, 1H) 5.56-5.63 (m, 1H) 7.16-7.18 (m, 1H) 7.30-7.39 (m, 2H) 7.42-7.47 (m, 1H) 7.51 (s, 1H). MS (ESI) m/z: 548 [M + H]⁺. |
| 16(16a) | (4-iodo-N-methylbenzenethioamide) | 1H NMR (CDCl₃) δ (ppm) 3.35 (d, J = 4.6 Hz, 3H) 7.48 (d, J = 8.4 Hz, 2H) 7.62 (m, 1H) 7.73 (d, J = 8.4 Hz, 2H). |
| 16(16b) | (4-iodophenyl-triazole-CH₂-O-phenyl-CF₃) | 1H NMR (CDCl₃) δ (ppm) 3.78 (s, 3H) 5.38 (s, 2H) 7.28-7.31 (m, 3H) 7.39-7.47 (m, 3H) 7.88 (d, J = 8.4 Hz, 2H). |
| 16(16c) | (4-bromopyrazolyl-phenyl-triazole-CH₂-O-phenyl-CF₃) | 1H NMR (CDCl₃) δ (ppm) 3.82 (s, 3H) 5.40 (s, 2H) 7.29-7.32 (m, 3H) 7.44-7.47 (m, 1H) 7.72 (s, 1H) 7.79 (d, J = 9.2 Hz, 2H) 7.84 (d, J = 9.2 Hz, 2H) 8.03 (s, 1H). |
| 16(16d) | (Me-N-tetrahydropyridine-pyrazole-phenyl-triazole-CH₂-O-phenyl-CF₃) | 1H NMR (CDCl₃) δ (ppm) 2.51 (s, 3H) 2.59-2.64 (m, 2H) 2.79-2.84 (m, 2H) 3.22-3.27 (m, 2H) 3.82 (s, 3H) 5.40 (s, 2H) 6.03-6.06 (m, 1H) 7.28-7.32 (m, 3H) 7.44-7.48 (m, 1H) 7.77 (d, J = 9.2 Hz, 2H) 7.83 (s, 1H) 7.86 (d, J = 9.2 Hz, 2H) 7.93 (s, 1H). |
| 16(16e) | (Me-N-piperidine-pyrazole-phenyl-triazole-CH₂-O-phenyl-CF₃) | 1H NMR (CDCl₃) δ (ppm) 1.71-1.79 (m, 2H) 1.98 (d, J = 13.8 Hz, 2H) 2.08 (t, J = 11.5 Hz, 2H) 2.33 (s, 3H) 2.53-2.59 (m, 1H) 2.73 (d, J = 11.5 Hz, 2H) 3.81 (s, 3H) 5.39 (s, 2H) 7.28-7.32 (m, 3H) 7.43-7.47 (m, 1H) 7.64 (s, 1H) 7.74-7.79 (m, 3H) 7.84 (d, J = 9.2 Hz, 2H). MS (ESI) m/z: 497 [M + H]⁺. |
| 17(17a) | (4-bromopyrazolyl-cyclohexyl-C(O)OMe) | 1H NMR (CDCl₃) δ (ppm) 1.60-1.78 (m, 2H) 2.06-2.20 (m, 4H) 2.24-2.37 (m, 1H) 3.55-3.72 (m, 3H) 4.05-4.14 (m, 1H) 7.30-7.43 (m, 2H). |

TABLE 19-continued

| Example No. | Structural formula | Physicochemical data |
| --- | --- | --- |
| 17(17b) | | 1H NMR (DMSO-d$_6$) δ (ppm) 1.48-1.74 (m, 4H) 1.78 (d, J = 11.2 Hz, 2H) 1.95-2.17 (m, 3H) 4.02-4.25 (m, 3H) 7.51 (s, 1H) 8.00 (1H, s, 1H) 9.01 (s, 1H). |
| 17(17c) | | 1H NMR (CDCl$_3$) δ (ppm) 3.30 (d, J = 4.8 Hz, 3H) 4.82-5.06 (m, 2H) 7.08-7.12 (m, 1H) 7.20 (s, 1H) 7.26-7.33 (m, 1H) 7.41-7.48 (m, 1H) 8.17-8.69 (m, 1H). |

TABLE 20

| Example No. | Structural formula | Physicochemical data |
| --- | --- | --- |
| 17(17d) | | 1H NMR (CDCl$_3$) δ (ppm) 2.66 (s, 3H) 3.16 (s, 3H) 4.79 (s, 2H), 7.10 (s, 1H) 7.15-7.20 (m, 2H) 7.31-7.34 (m, 1H). |
| 17(17e) | | 1H NMR (CDCl$_3$) δ (ppm) 1.88-2.05 (m, 4H) 2.11-2.27 (m, 3H) 2.29-2.38 (m, 2H) 2.70-2.82 (m, 1H) 3.70 (s, 3H) 4.17-4.30 (m, 1H) 5.31 (s, 1H) 5.28-5.33 (m, 1H) 7.22-7.33 (m, 4H) 7.40-7.47 (m, 1H) 7.49 (d, J = 4.0 Hz, 2H). |
| 17(17f) | | 1H NMR (CDCl$_3$) δ (ppm) 1.47 (s, 9H) 1.68-1.76 (m, 1H) 1.95-2.08 (m, 6H) 2.15-2.23 (m, 2H) 2.28-2.46 (m, 4H) 2.48-2.58 (m, 1H) 2.71-2.82 (m, 1H) 3.70 (s, 3H) 3.81-3.92 (m, 1H) 4.16-4.26 (m, 1H) 4.56-4.65 (m, 1H) 5.32 (s, 2H) 5.91 (s, 1H) 7.24-7.32 (m, 3H) 7.40-7.46 (m, 2H) 7.59 (s, 1H). |
| 17(17g) | | 1H NMR (CDCl$_3$) δ (ppm) 1.18-1.28 (m, 2H) 1.38-1.47 (m, 11H) 1.93-2.21 (m, 10H) 2.28-2.36 (m, 2H) 2.41-2.48 (m, 1H) 2.71-2.81 (m, 1H) 3.40-3.54 (m, 1H) 3.70 (s, 3H) 4.14-4.23 (m, 1H) 4.38-4.48 (m, 1H) 5.31 (s, 2H) 7.23-7.29 (m, 4H) 7.37 (s, 1H) 7.44 (t, J = 7.6 Hz, 1H). |
| 17(17h) | | 1H NMR (CDCl$_3$) δ (ppm) 1.05-1.15 (m, 2H) 1.27-1.37 (m, 2H) 1.83-1.91 (m, 2H) 1.94-2.03 (m, 7H) 2.05-2.10 (m, 2H) 2.15-2.22 (m, 2H) 2.29-2.36 (m, 2H) 2.40-2.48 (m, 1H) 2.71-2.81 (m, 1H) 3.22 (t, J = 7.2 Hz, 4H) 3.70 (s, 3H) 4.13-4.22 (m, 1H) 5.31 (s, 2H) 7.23 (s, 1H) 7.26-7.29 (m, 3H) 7.38 (s, 1H) 7.44 (t, J = 8.0 Hz, 1H). MS (ESI) m/z: 543 [M + H]$^+$. |
| 18(18a) | | 1H NMR (CDCl$_3$) δ (ppm) 2.41 (s, 3H) 2.44-2.49 (m, 2H) 2.65 (t, J = 5.7 Hz, 2H) 2.86 (s, 6H) 3.12-3.15 (m, 2H) 6.50 (s, 1H) 7.07 (s, 1H) 7.83-7.85 (m, 1H). |

TABLE 20-continued

| Example No. | Structural formula | Physicochemical data |
|---|---|---|
| 18(18b) | | 1H NMR (DMSO-$d_6$) δ (ppm) 2.56-2.68 (m, 1H) 2.80 (s, 3H) 3.12-3.25 (m, 1H) 3.29-3.60 (m, 2H) 3.67-3.82 (m, 1H) 3.89-4.01 (m, 1H) 6.52 (s, 1H) 7.81 (s, 1H) 9.16 (s, 1H) 11.08 (br s, 1H). |
| 18(18c) | | 1H NMR (CD$_3$OD) δ (ppm) 1.94-2.05 (m, 2H) 2.25-2.35 (m, 2H) 2.91 (s, 3H) 3.10-3.24 (m, 4H) 3.61-3.66 (m, 2H) 7.46 (s, 1H) 8.90 (s, 1H). |
| 18(18d) | | 1H NMR (CDCl$_3$) δ (ppm) 1.68-1.80 (m, 2H) 2.04-2.15 (m, 4H) 2.32 (s, 3H) 2.58-2.67 (m, 1H) 2.93-2.98 (m, 2H) 3.83 (s, 3H) 5.40 (s, 2H) 7.06 (s, 1H) 7.28-7.34 (m, 3H) 7.46 (t, J = 8.0 Hz, 1H) 7.52-7.58 (m, 2H) 7.79 (s, 1H) 7.80 (s, 1H) 7.87 (s, 1H). MS (APCI) m/z: 497 [M + H]$^+$. |

TABLE 21

| Example No. | Structural formula | Physicochemical data |
|---|---|---|
| 19(19a) | | 1H NMR (CDCl$_3$) δ (ppm) 1.38-1.58 (m, 4H) 1.92-1.98 (m, 2H) 2.01-2.09 (m, 3H) 2.27-2.34 (m, 1H) 2.81 (d, J = 4.9 Hz, 3H) 3.67 (s, 3H) 5.40-5.48 (m, 1H). |
| 19(19b) | | 1H NMR (CDCl$_3$) δ (ppm) 1.44-1.54 (m, 2H) 1.69-1.79 (m, 2H) 1.93-1.98 (m, 2H) 2.07-2.12 (m, 2H) 2.31-2.38 (m, 1H) 2.41-2.48 (m, 1H) 3.19 (d, J = 4.9 Hz, 3H) 3.67 (s, 3H) 7.26-7.31 (m, 1H). |
| 19(19c) | | 1H NMR (CDCl$_3$) δ (ppm) 1.44-1.56 (m, 4H) 1.79-1.85 (m, 0.7H) 1.88-1.97 (m, 1.3H) 2.04-2.11 (m, 2H) 2.20 (s, 1H) 2.29-2.36 (m, 1H) 2.42 (s, 2H) 2.47-2.53 (m, 0.7H) 2.80-2.87 (m, 0.3H) 3.17 (s, 2H) 3.26 (s, 1H) 3.67 (s, 1.3H) 3.67 (s, 0.7H). |
| 19(19d) | | 1H NMR (CDCl$_3$) δ: 1.52-1.64 (m, 2H) 1.87-1.98 (m, 2H) 2.06-2.14 (m, 2H) 2.16-2.23 (m, 2H) 2.47 (dt, J = 12.2, 3.4 Hz, 1H) 2.75 (dt, J = 12.2, 3.4 Hz, 1H) 3.70 (s, 3H) 3.78 (s, 3H) 5.40 (s, 2H) 7.22-7.32 (m, 3H) 7.45 (t, J = 7.8 Hz, 1H). |

TABLE 21-continued

| Example No. | Structural formula | Physicochemical data |
|---|---|---|
| 19(19e) | | 1H NMR (CDCl₃) δ: 1.08-1.20 (m, 2H) 1.34 (d, J = 5.4 Hz, 1H) 1.55-1.72 (m, 1H) 1.76-1.89 (m, 2H) 1.94-2.11 (m, 4H) 2.62 (dt, J = 12.2, 3.4 Hz, 1H) 3.53 (t, J = 5.9 Hz, 2H) 3.66 (s, 3H) 5.29 (s, 2H) 7.22-7.29 (m, 3H) 7.42 (t, J = 7.8 Hz, 1H). |
| 19(19f) | | ¹H-NMR (CDCl₃) δ: 1.36-1.47 (m, 2H) 1.82-1.92 (m, 2H) 2.09-2.16 (m, 2H) 2.18-2.25 (m, 2H) 2.36-2.44 (m, 1H) 2.64 (dt, J = 12.2, 3.4 Hz, 1H) 3.67 (s, 3H) 5.30 (s, 2H) 7.22-7.31 (m, 3H) 7.43 (t, J = 7.8 Hz, 1H) 9.70 (s, 1H). |
| 19(19g) | | 1H NMR (CDCl₃) δ (ppm) 1.43-2.20 (m, 8H) 2.11 (s, 1H) 2.40-2.45 (m, 1H) 2.65-2.70 (m, 1H) 3.80 (s, 3H) 5.31 (s, 2H) 7.26-7.36 (m, 3H) 7.43-7.46 (m, 1H). |
| 19(19h) | | 1H NMR (CDCl₃) δ (ppm) 0.06 (s, 6H) 0.89 (s, 9H) 1.35-1.55 (m, 2H) 1.78-1.85 (m, 1H) 2.16-2.22 (m, 1H) 3.17 (t, J = 10.7 Hz, 1H) 3.28-3.33 (m, 1H) 3.37-3.45 (m, 1H) 3.51 (dd, J = 10.7, 5.4 Hz, 1H) 3.65 (dd, J = 10.7, 5.9 Hz, 1H) 4.00-4.04 (m, 1H). |
| 19(19i) | | 1H NMR (CDCl₃) δ (ppm) 0.08 (s, 6H) 0.91 (s, 9H) 1.53-2.40 (m, 12H) 2.69-2.78 (m, 1H) 2.83-2.91 (m, 1H) 3.47-3.51 (m, 1H) 3.57-3.61 (m, 1H) 3.64-3.69 (m, 1H) 3.68 (s, 3H) 3.72-3.75 (m, 1H) 4.25-4.28 (m, 1H) 4.50-4.56 (m, 1H) 5.30 (s, 2H) 7.24-7.28 (m, 4H) 7.41-7.44 (m, 1H). |

TABLE 22

| Example No. | Structural formula | Physicochemical data |
|---|---|---|
| 19(19j) | | 1H NMR (CDCl₃) δ (ppm) 1.61-2.36 (m, 12H) 2.40-2.44 (m, 1H) 2.72-2.78 (m, 1H) 2.87-2.93 (m, 1H) 3.60-3.77 (m, 4H) 3.71 (s, 3H) 4.32-4.38 (m, 1H) 4.54-4.61 (m, 1H) 5.32 (s, 2H) 7.27-7.32 (m, 4H) 7.42-7.47 (m, 1H). |
| 19(19k) | | 1H NMR (CDCl₃) δ (ppm) 1.48-2.15 (m, 11H) 2.23-2.27 (m, 2H) 2.34-2.39 (m, 1H) 2.45 (dd, J = 8.5, 4.0 Hz, 1H) 2.60 (dd, J = 7.4, 5.1 Hz, 1H) 2.69-2.75 (m, 1H) 2.84-2.89 (m, 1H) 3.22-3.29 (m, 4H) 3.38-3.42 (m, 1H) 3.61-3.67 (m, 1H) 3.67 (s, 3H) 4.24-4.27 (m, 1H) 4.48-4.54 (m, 1H) 5.30 (s, 2H) 7.24-7.27 (m, 4H) 7.42 (t, J = 7.9 Hz, 1H). MS (APCI) m/z: 560 [M + H]⁺. |
| 20(20a) | | 1H NMR (CDCl₃) δ (ppm) 1.05 (s, 9H) 1.52-1.64 (m, 2H) 1.76-1.87 (m, 2H) 2.01-2.11 (m, 2H) 2.12-2.22 (m, 2H) 2.39-2.47 (m, 1H) 2.57-2.65 (m, 1H) 3.60 (s, 3H) 3.70 (s, 3H) 4.87 (s, 2H) 7.36-7.48 (m, 6H) 7.62-7.68 (m, 4H). |
| 20(20b) | | 1H NMR (CDCl₃) δ (ppm) 1.03 (s, 9H) 1.08-1.14 (m, 1H) 1.56-1.65 (m, 1H) 1.72-1.87 (m, 3H) 1.92-2.02 (m, 5H) 2.51-2.59 (m, 1H) 3.47-3.51 (m, 2H) 3.57 (s, 3H) 4.84 (s, 2H) 7.35-7.39 (m, 4H) 7.40-7.44 (m, 2H) 7.62-7.65 (m, 4H). |

TABLE 22-continued

| Example No. | Structural formula | Physicochemical data |
|---|---|---|
| 20(20c) | | 1H NMR (CDCl$_3$) δ (ppm) 1.03 (s, 9H) 1.32-1.42 (m, 2H) 1.73-1.87 (m, 2H) 2.04-2.11 (m, 2H) 2.14-2.20 (m, 2H) 2.33-2.39 (m, 1H) 2.53-2.60 (m, 1H) 3.58 (s, 3H) 4.84 (s, 2H) 7.34-7.45 (m, 6H) 7.62-7.66 (m, 4H) 9.67 (s, 1H). |
| 20(20d) | | 1H NMR (CDCl$_3$) δ (ppm) 1.06 (s, 9H) 1.47-1.58 (m, 2H) 1.73-1.83 (m, 2H) 1.96-2.04 (m, 2H) 2.09 (d, J = 2.1 Hz, 1H) 2.14-2.22 (m, 2H) 2.34-2.44 (m, 1H) 2.57-2.65 (m, 1H) 3.60 (s, 3H) 4.86 (s, 2H) 7.37-7.48 (m, 6H) 7.62-7.68 (m, 4H). |
| 20(20e) | | 1H NMR (CDCl$_3$) δ (ppm) 1.47-1.58 (m, 2H) 1.68-1.79 (m, 2H) 1.94-2.03 (m, 2H) 2.09 (d, J = 2.0 Hz, 1H) 2.13-2.21 (m, 2H) 2.33-2.42 (m, 1H) 2.58-2.66 (m, 1H) 3.64 (s, 3H) 3.81 (br s, 1H) 4.77 (s, 2H). |
| 20(20f) | | 1H NMR (CDCl$_3$) δ (ppm) 1.48-1.60 (m, 2H) 1.75-1.88 (m, 2H) 1.98-2.06 (m, 2H) 2.09 (d, J = 2.4 Hz, 1H) 2.15-2.25 (m, 2H) 2.36-2.45 (m, 1H) 2.62-2.71 (m, 1H) 3.64 (s, 3H) 5.58 (s, 2H) 7.07 (s, 1H) 7.16 (d, J = 5.4 Hz, 1H) 8.36 (d, J = 5.4 Hz, 1H). |
| 20(20g) | | 1H NMR (CDCl$_3$) δ (ppm) 1.01-1.15 (m, 4H) 1.44 (s, 9H) 1.72-1.84 (m, 2H) 1.88-2.07 (m, 3H) 2.70-2.86 (m, 1H) 2.98 (t, J = 6.8 Hz, 2H) 3.30-3.46 (m, 3H) 4.35 (br s, 1H) 4.48 (dd, J = 7.4, 5.4 Hz, 2H). |

TABLE 23

| Example No. | Structural formula | Physicochemical data |
|---|---|---|
| 20(20h) | | 1H NMR (CD$_3$OD) δ (ppm) 1.27-1.59 (m, 4H) 2.10-2.24 (m, 4H) 3.05-3.23 (m, 2H) 4.04-4.20 (m, 2H) 4.20-4.81 (m, 5H). |
| 20(20i) | | 1H NMR (CDCl$_3$) δ (ppm) 1.16-1.29 (m, 2H) 1.60-1.72 (m, 2H) 1.75-1.87 (m, 2H) 1.90-2.04 (m, 4H) 2.06-2.18 (m, 4H) 2.20-2.33 (m, 4H) 2.69-2.93 (m, 3H) 3.06 (d, J = 7.3 Hz, 1H) 3.41 (t, J = 6.8 Hz, 2H) 3.66 (s, 3H) 4.34-4.44 (m, 1H) 4.45 (d, J = 5.4 Hz, 1H) 4.55 (d, J = 5.9 Hz, 1H) 5.59 (s, 2H) 7.02 (s, 1H) 7.16 (d, J = 4.9 Hz, 1H) 7.28 (s, 1H) 8.36 (d, J = 5.4 Hz, 1H). MS (APCI) m/z: 577 [M + H]$^+$. |
| 21(21a) | | 1H NMR (CDCl$_3$) δ (ppm) 1.23-1.28 (m, 3H) 1.56-1.82 (m, 4H) 2.02-2.12 (m, 2H) 2.18-2.29 (m, 2H) 2.32-2.45 (m, 4H) 2.51-2.64 (m, 1H) 3.68-3.70 (m, 2H) 4.03-4.18 (m, 2H) 5.32-5.34 (m, 1H) 5.96-5.99 (m, 1H) 7.53 (s, 1H) 7.60 (s, 1H). |

TABLE 23-continued

| Example No. | Structural formula | Physicochemical data |
|---|---|---|
| 21(2b) | | 1H NMR (CDCl₃) δ (ppm) 1.25-1.46 (m, 2H) 1.52-1.77 (m, 6H) 1.87-1.98 (m, 2H) 2.03-2.15 (m, 7H) 2.42-2.53 (m, 1H) 3.60-3.78 (m, 1H) 4.06-4.10 (m, 1H) 5.33 (dd, J = 9.6, 2.4 Hz, 1H) 7.10 (s, 1H) 7.39-7.41 (m, 2H). |
| 21(21c) | | 1H NMR (DMSO-d₆) δ (ppm) 1.35-1.55 (m, 2H) 1.60-1.77 (m, 2H) 1.91-2.10 (m, 4H) 2.54-2.57 (m, 1H) 2.79-2.92 (m, 1H) 3.64 (s, 3H) 5.37 (s, 2H) 7.36 (d, J = 7.6 Hz, 1H) 7.42 (d, J = 8.0 Hz, 1H) 7.46 (s, 3H) 7.54-7.60 (m, 1H). |
| 21(21d) | | 1H NMR (CDCl₃) δ (ppm) 1.05-1.13 (m, 2H) 1.38-1.45 (m, 2H) 1.68-1.84 (m, 2H) 1.84-1.87 (m, 4H) 1.97-2.10 (m, 9H) 2.52-2.70 (m, 2H) 3.14 (t, J = 7.2 Hz, 4H) 3.60 (s, 3H) 3.96-4.10 (m, 1H) 5.22 (s, 2H) 7.15-7.20 (m, 4H) 7.30-7.37 (m, 2H). MS (ESI) m/z: 543 [M + H]⁺. |

TABLE 24

| Example No. | Structural formula | Physicochemical data |
|---|---|---|
| 22(22a) | | 1H NMR (CDCl₃) δ (ppm) 1.05 (s, 9H) 1.19-1.30 (m, 1H) 1.36-1.50 (m, 10H) 1.77-1.84 (m, 1H) 2.06-2.15 (m, 1H) 2.97 (t, J = 10.7 Hz, 1H) 3.30-3.37 (m, 1H) 3.51-3.67 (m, 2H) 3.71 (dd, J = 10.7, 4.9 Hz, 1H) 4.05 (ddd, J = 10.7, 4.9, 2.0 Hz, 1H) 4.23 (br s, 1H) 7.33-7.45 (m, 6H) 7.63-7.69 (m, 4H). |
| 22(22b) | | 1H NMR (CDCl₃) δ (ppm) 1.05 (s, 9H) 1.15-1.28 (m, 1H) 1.31-1.41 (m, 1H) 1.53 (br s, 2H) 1.77-1.83 (m, 1H) 2.00-2.08 (m, 1H) 2.73-2.82 (m, 1H) 2.96 (t, J = 10.7 Hz, 1H) 3.30-3.38 (m, 1H) 3.53 (dd, J = 10.3, 5.9 Hz, 1H) 3.72 (dd, J = 10.7, 4.9 Hz, 1H) 3.91 (ddd, J = 10.7, 4.9, 2.4 Hz, 1H) 7.34-7.45 (m, 6H) 7.63-7.70 (m, 4H). |
| 22(22c) | | 1H NMR (CDCl₃) δ (ppm) 1.05 (s, 9H) 1.22-1.42 (m, 2H) 1.42-1.53 (m, 9H) 1.76-1.84 (m, 1H) 1.93-2.02 (m, 1H) 2.91-3.01 (m, 1H) 3.09 (t, J = 10.3 Hz, 1H) 3.31-3.38 (m, 1H) 3.53 (dd, J = 10.7, 5.9 Hz, 1H) 3.72 (dd, J = 10.3, 5.4 Hz, 1H) 3.83 (br s, 1H) 4.04 (ddd, J = 10.7, 4.4, 2.5 Hz, 1H) 5.94 (br s, 1H) 7.34-7.44 (m, 6H) 7.63-7.69 (m, 4H). |

TABLE 24-continued

| Example No. | Structural formula | Physicochemical data |
|---|---|---|
| 22(22d) | | 1H NMR (CDCl₃) δ (ppm) 1.03-1.25 (m, 2H) 1.50-1.62 (m, 1H) 1.72-1.91 (m, 2H) 1.91-2.09 (m, 4H) 2.38 (dd, J = 6.8, 2.0 Hz, 2H) 2.56-2.70 (m, 1H) 3.66 (s, 3H) 5.29 (s, 2H) 7.22-7.29 (m, 3H) 7.42 (t, J = 7.8 Hz, 1H) 9.70 (d, J = 2.0 Hz, 1H). |
| 22(22e) | | 1H NMR (CDCl₃) δ (ppm) 1.35-1.48 (m, 2H) 1.85-2.01 (m, 4H) 2.02-2.11 (m, 2H) 2.57-2.72 (m, 2H) 3.66 (s, 3H) 5.29 (s, 2H) 6.00 (s, 1H) 6.27 (s, 1H) 7.22-7.29 (m, 3H) 7.42 (t, J = 7.8 Hz, 1H) 9.55 (s, 1H). |
| 22(22f) | | 1H NMR (CDCl₃) δ (ppm) 1.30-1.42 (m, 1H) 1.44-1.57 (m, 1H) 1.75-1.96 (m, 4H) 2.00-2.15 (m, 3H) 2.57-2.67 (m, 1H) 3.01 (d, J = 4.0 Hz, 1H) 3.13 (d, J = 4.0 Hz, 1H) 3.65 (s, 3H) 5.29 (s, 2H) 7.20-7.29 (m, 3H) 7.42 (t, J = 7.5 Hz, 1H) 8.87 (s, 1H). |

TABLE 25

| Example No. | Structural formula | Physicochemical data |
|---|---|---|
| 22(22g) | | 1H NMR (CDCl₃) δ (ppm) 1.41-1.56 (m, 4H) 1.56-1.64 (m, 1H) 1.76-1.82 (m, 1H) 1.86-1.97 (m, 2H) 2.05-2.19 (m, 5H) 2.26-2.33 (m, 1H) 2.56-2.72 (m, 2H) 3.51-3.62 (m, 2H) 3.63-3.72 (m, 4H) 4.17-4.28 (m, 2H) 5.30 (s, 2H) 7.19-7.29 (m, 4H) 7.38-7.47 (m, 2H). |
| 22(22h) | | 1H NMR (CDCl₃) δ (ppm) 1.41-1.55 (m, 5H) 1.75-1.85 (m, 1H) 1.87-1.99 (m, 2H) 2.02-2.19 (m, 6H) 2.21-2.32 (m, 1H) 2.39-2.47 (m, 1H) 2.55-2.74 (m, 3H) 3.18-3.31 (m, 3H) 3.32-3.41 (m, 1H) 3.55-3.64 (m, 1H) 3.67 (s, 3H) 4.13-4.26 (m, 2H) 5.30 (s, 2H) 7.17-7.32 (m, 4H) 7.46-7.87 (m, 2H). MS (APCI) m/z: 559 [M + H]⁺. |
| 23(23a) | | 1H NMR (CDCl₃) δ (ppm) 1.11-1.17 (m, 2H) 1.24-1.32 (m, 2H) 1.48 (s, 9H) 1.94-1.97 (m, 4H) 2.20-2.23 (m, 1H) 2.50-2.63 (m, 4H) 2.57-2.77 (m, 1H) 3.72-3.75 (m, 4H) 3.97 (br s, 1H) 6.11 (br s, 1H). |
| 23(23b) | | 1H NMR (D₂O) δ (ppm) 1.32-1.38 (m, 2H) 1.47-1.54 (m, 2H) 2.15-2.20 (m, 4H) 3.05-3.14 (m, 4H) 3.16-3.17 (m, 2H) 3.69-3.72 (m, 2H) 3.99-4.03 (m, 2H). |

TABLE 25-continued

| Example No. | Structural formula | Physicochemical data |
|---|---|---|
| 23(23c) | | 1H NMR (CDCl₃) δ (ppm) 3.78 (s, 3H) 4.95 (s, 2H) 7.10-7.14 (m, 2H) 8.26 (d, J = 5.5 Hz, 1H). |
| 23(23d) | | 1H NMR (CDCl₃) δ (ppm) 3.51-4.26 (m, 2H) 4.96 (s, 2H) 7.07-7.09 (m, 1H) 7.17-7.20 (m, 1H) 7.51-7.65 (m, 1H) 8.32-8.34 (m, 1H). |
| 23(23e) | | 1H NMR (CDCl₃) δ (ppm) 1.53-1.73 (m, 2H) 1.78-1.91 (m, 2H) 2.04-2.12 (m, 2H) 2.14-2.23 (m, 2H) 2.39-2.50 (m, 1H) 2.61-2.70 (m, 1H) 3.64 (s, 3H) 3.70 (s, 3H) 5.58 (s, 2H) 7.00-7.02 (m, 1H) 7.15-7.18 (m, 1H) 8.36 (d, J = 5.5 Hz, 1H). |
| 23(23f) | | 1H NMR (CDCl₃) δ (ppm) 1.08-1.17 (m, 2H) 1.51-2.05 (m, 7H) 2.57-2.64 (m, 1H) 3.51 (t, J = 5.9 Hz, 2H) 3.62 (s, 3H) 5.55 (s, 2H) 6.98-6.99 (m, 1H) 7.13 (d, J = 5.4 Hz, 1H) 8.33 (d, J = 5.4 Hz, 1H). |
| 23(23g) | | 1H NMR (CDCl₃) δ (ppm) 1.37-1.48 (m, 2H) 1.70-2.51 (m, 7H) 2.60-2.69 (m, 1H) 3.65 (s, 3H) 5.59 (s, 2H) 7.01 (s, 1H) 7.16 (d, J = 4.9 Hz, 1H) 8.36 (d, J = 4.9 Hz, 1H) 9.71 (s, 1H). |

TABLE 26

| Example No. | Structural formula | Physicochemical data |
|---|---|---|
| 23(23h) | | 1H NMR (CDCl₃) δ (ppm) 1.13-1.22 (m, 2H) 1.61-2.06 (m, 7H) 2.36 (dd, J = 6.6, 2.2 Hz, 2H) 2.57-2.64 (m, 1H) 3.61 (s, 3H) 5.55 (s, 2H) 6.98-6.99 (m, 1H) 7.12-7.14 (m, 1H) 8.33 (d, J = 5.4 Hz, 1H) 9.76 (t, J = 2.2 Hz, 1H). |
| 23(23i) | | 1H NMR (CDCl₃) δ (ppm) 1.34-1.44 (m, 2H) 1.85-1.98 (m, 4H) 2.03-2.08 (m, 2H) 2.56-2.63 (m, 1H) 2.64-2.71 (m, 1H) 3.62 (s, 3H) 5.55 (s, 2H) 5.98 (s, 1H) 6.25 (s, 1H) 6.99 (s, 1H) 7.13 (d, J = 5.4 Hz, 1H) 8.33 (d, J = 5.4 Hz, 1H) 9.52 (s, 1H). |
| 23(23j) | | 1H NMR (CDCl₃) δ (ppm) 1.30-1.39 (m, 1H) 1.44-1.53 (m, 1H) 1.76-1.93 (m, 4H) 2.00-2.12 (m, 3H) 2.58-2.64 (m, 1H) 2.98 (d, J = 4.4 Hz, 1H) 3.10 (d, J = 4.4 Hz, 1H) 3.61 (s, 3H) 5.55 (s, 2H) 6.98-6.99 (m, 1H) 7.12-7.14 (m, 1H) 8.33 (d, J = 4.9 Hz, 1H) 8.85 (s, 1H). |

TABLE 26-continued

| Example No. | Structural formula | Physicochemical data |
|---|---|---|
| 23(23k) | | 1H NMR (CDCl₃) δ (ppm) 1.38-2.41 (m, 17H) 2.53-2.70 (m, 6H) 3.65 (s, 3H) 3.72-3.75 (m, 4H) 4.00-4.13 (m, 1H) 5.59 (s, 2H) 7.01 (s, 1H) 7.16 (d, J = 5.0 Hz, 1H) 7.22 (s, 1H) 7.38 (s, 1H) 8.36 (d, J = 5.0 Hz, 1H). MS (APCI) m/z: 574 [M + H]⁺. |
| 24(24a) | | 1H NMR (CDCl₃) δ (ppm) 5.03 (s, 1H) 5.34 (s, 2H) 7.38-7.44 (m, 5H). |
| 24(24b) | | 1H NMR (CDCl₃) δ (ppm) 1.02-1.14 (m, 4H) 1.71-1.78 (m, 2H) 1.78-1.87 (m, 1H) 1.96-2.07 (m, 2H) 3.33 (s, 4H) 3.39-3.50 (m, 1H) 4.73 (s, 4H) 5.08 (s, 2H) 7.27-7.40 (m, 5H). |
| 24(24c) | | 1H NMR (CDCl₃) δ (ppm) 0.96-1.11 (m, 4H) 1.70-1.76 (m, 2H) 1.80-1.87 (m, 3H) 2.58-2.67 (m, 1H) 3.33 (s, 4H) 4.73 (s, 4H). |
| 24(24d) | | 1H NMR (CDCl₃) δ (ppm) 0.92-1.13 (m, 4H) 1.70-1.79 (m, 2H) 1.80-1.92 (m, 3H) 2.73-2.85 (m, 1H) 3.33 (s, 4H) 3.98 (br s, 1H) 4.73 (s, 4H) 5.13 (s, 2H) 6.19 (br s, 1H) 7.32-7.40 (m, 5H). |
| 24(24e) | | 1H NMR (CDCl₃) δ (ppm) 1.04-1.28 (m, 4H) 1.76-1.87 (m, 2H) 2.00-2.21 (m, 6H) 2.56-2.63 (m, 1H) 3.48-3.79 (m, 4H) 4.71-4.79 (m, 4H) 5.57-5.93 (m, 3H). |

TABLE 27

| Example No. | Structural formula | Physicochemical data |
|---|---|---|
| 24(24f) | | 1H NMR (CDCl₃) δ (ppm) 1.09-1.23 (m, 2H) 1.42-1.54 (m, 2H) 1.69-1.81 (m, 2H) 1.85-2.20 (m, 11H) 2.64-2.66 (m, 2H) 3.37 (s, 4H) 3.65 (s, 3H) 3.98-4.06 (m, 1H) 4.75 (s, 4H) 5.59 (s, 2H) 7.01-7.02 (m, 1H) 7.15-7.17 (m, 1H) 7.21 (s, 1H) 7.37 (s, 1H) 8.36 (d, J = 5.4 Hz, 1H). MS (APCI) m/z: 586 [M + H]⁺. |

TABLE 27-continued

| Example No. | Structural formula | Physicochemical data |
|---|---|---|
| 25(25a) | | 1H NMR (CDCl$_3$) δ (ppm) 1.29-1.39 (m, 2H) 1.42-1.53 (m, 2H) 1.80-1.99 (m, 4H) 2.03-2.25 (m, 9H) 2.58-2.73 (m, 2H) 3.66 (s, 3H) 4.02-4.11 (m, 1H) 4.61-4.69 (m, 1H) 5.10 (s, 2H) 5.59 (s, 2H) 7.02 (s, 1H) 7.16 (d, J = 5.4 Hz, 1H) 7.22 (s, 1H) 7.30-7.39 (m, 6H) 8.36 (d, J = 5.4 Hz, 1H). |
| 25(25b) | | 1H NMR (CDCl$_3$) δ (ppm) 1.25-1.35 (m, 2H) 1.43-1.54 (m, 2H) 1.75-2.24 (m, 14H) 2.59-2.73 (m, 3H) 3.66 (s, 3H) 4.02-4.09 (m, 1H) 5.59 (s, 2H) 7.02 (s, 1H) 7.16 (d, J = 5.4 Hz, 1H) 7.23 (s, 1H) 7.38 (s, 1H) 8.36 (d, J = 5.4 Hz, 1H). |
| 25(25c) | | 1H NMR (CDCl$_3$) δ (ppm) 2.53-2.65 (m, 4H) 3.66 (s, 4H) 4.52 (t, J = 8.0 Hz, 2H). |
| 25(25d) | | 1H NMR (CDCl$_3$) δ (ppm) 1.16-1.26 (m, 2H) 1.42-1.53 (m, 2H) 1.70-1.80 (m, 2H) 1.89-2.19 (m, 11H) 2.58-2.72 (m, 2H) 2.88 (t, J = 7.5 Hz, 2H) 3.11-3.16 (m, 2H) 3.64-3.68 (m, 2H) 3.65 (s, 3H) 3.99-4.07 (m, 1H) 4.53 (t, J = 7.5 Hz, 2H) 5.59 (s, 2H) 7.01-7.02 (m, 1H) 7.15-7.17 (m, 1H) 7.21 (s, 1H) 7.37 (s, 1H) 8.36 (d, J = 5.1 Hz, 1H). MS (APCI) m/z: 586 [M + H]$^+$. |
| 26(26a) | | 1H NMR (CDCl$_3$) δ (ppm) 1.69-1.82 (m, 2H) 1.97-2.09 (m, 2H) 2.23-2.35 (m, 2H) 2.45-2.56 (m, 2H) 3.36-3.44 (m, 1H) 4.12 (br s, 1H) 5.16 (s, 2H) 6.34 (br s, 1H) 7.32-7.42 (m, 5H). |
| 26(26b) | | 1H NMR (CDCl$_3$) δ (ppm) 1.07-1.17 (m, 2H) 1.18-1.30 (m, 2H) 1.84-2.00 (m, 5H) 2.11 (t, J = 6.9 Hz, 2H) 2.57 (t, J = 7.3 Hz, 2H) 2.76-2.87 (m, 1H) 2.89 (s, 2H) 3.99 (br s, 1H) 4.61 (s, 4H) 5.13 (s, 2H) 6.22 (br s, 1H) 7.31-7.39 (m, 5H). |
| 26(26c) | | 1H NMR (CDCl$_3$) δ (ppm) 1.36-1.53 (m, 4H) 1.75-1.85 (m, 2H) 1.89-1.99 (m, 2H) 2.04-2.23 (m, 11H) 2.58-2.73 (m, 4H) 2.93 (s, 2H) 3.65 (s, 3H) 4.01-4.09 (m, 1H) 4.63 (s, 4H) 5.59 (s, 2H) 7.01-7.02 (m, 1H) 7.15-7.17 (m, 1H) 7.23 (s, 1H) 7.38 (s, 1H) 8.36 (d, J = 5.4 Hz, 1H). MS (APCI) m/z: 600 [M + H]$^+$. |

TABLE 28

| Example No. | Structural formula | Physicochemical data |
|---|---|---|
| 27(27a) | | 1H NMR (CDCl$_3$) δ (ppm) 1.33-1.42 (m, 2H) 1.44-1.52 (m, 2H) 1.62-1.69 (m, 2H) 1.74-1.80 (m, 2H) 2.01-2.06 (m, 1H) 2.07 (t, J = 6.9 Hz, 2H) 3.15-3.20 (m, 4H) 3.77 (t, J = 6.9 Hz, 2H) 3.81 (s, 2H) 3.92 (s, 4H). |
| 27(27b) | | 1H NMR (CDCl$_3$) δ (ppm) 1.63-1.72 (m, 2H) 1.83-1.90 (m, 2H) 2.10 (t, J = 7.3 Hz, 2H) 2.19-2.26 (m, 2H) 2.41-2.46 (m, 1H) 2.48-2.55 (m, 2H) 3.21-3.26 (m, 4H) 3.80 (t, J = 7.3 Hz, 2H) 3.83 (s, 2H). |

TABLE 28-continued

| Example No. | Structural formula | Physicochemical data |
|---|---|---|
| 27(27c) | | 1H NMR (CDCl₃) δ (ppm) 0.97-1.13 (m, 4H) 1.73-1.79 (m, 2H) 1.84-1.95 (m, 3H) 2.08 (t, J = 6.9 Hz, 2H) 2.76-2.84 (m, 1H) 3.16-3.22 (m, 4H) 3.77 (t, J = 6.9 Hz, 2H) 3.80 (s, 2H) 3.98 (br s, 1H) 5.13 (s, 2H) 6.22 (br s, 1H) 7.30-7.39 (m, 5H). |
| 27(27d) | | 1H NMR (CDCl₃) δ (ppm) 1.16-1.26 (m, 2H) 1.43-1.53 (m, 2H) 1.71-1.81 (m, 2H) 1.88-1.99 (m, 4H) 2.02-2.12 (m, 3H) 2.10 (t, J = 6.9 Hz, 2H) 2.13-2.20 (m, 4H) 2.58-2.73 (m, 2H) 3.21-3.26 (m, 4H) 3.65 (s, 3H) 3.79 (t, J = 6.9 Hz, 2H) 3.83 (s, 2H) 4.00-4.07 (m, 1H) 5.59 (s, 2H) 7.01-7.02 (m, 1H) 7.15-7.17 (m, 1H) 7.22 (s, 1H) 7.37 (s, 1H) 8.36 (d, J = 5.1 Hz, 1H). MS (APCI) m/z: 600 [M + H]⁺. |
| 28(28a) | | 1H NMR (CDCl₃) δ (ppm) 1.11 (s, 9H) 1.82-1.92 (m, 1H) 2.13 (dt, J = 15.1, 6.6 Hz, 1H) 2.18-2.27 (m, 1H) 2.38 (dt, J = 15.1, 6.6 Hz, 1H) 3.80 (td, J = 6.6, 4.9 Hz, 1H) 4.42-4.51 (m, 1H) 4.86-4.97 (m, 1H) 7.33-7.50 (m, 6H), 7.62-7.73 (m, 6H), 7.76-7.82 (m, 2H). |
| 28(28b) | | 1H NMR (CDCl₃) δ (ppm) 1.08 (s, 9H) 1.74-1.83 (m, 1H) 1.84-1.95 (m, 1H) 2.31-2.40 (m, 1H) 2.40-2.50 (m, 1H) 3.20 (td, J = 6.8, 3.9 Hz, 1H) 4.11-4.16 (m, 1H) 4.90-5.01 (m, 1H) 7.32-7.47 (m, 6H) 7.62-7.71 (m, 6H) 7.76-7.84 (m, 2H). |
| 28(28c) | | 1H NMR (CDCl₃) δ (ppm) 1.10 (s, 9H) 1.73-1.88 (m, 2H) 2.06-2.17 (m, 1H) 2.72-2.90 (m, 1H) 4.21-4.30 (m, 1H) 4.33 (s, 1H) 5.01-5.19 (m, 3H) 6.37 (d, J = 8.3 Hz, 1H) 7.28-7.46 (m, 11H) 7.64-7.77 (m, 6H) 7.77-7.85 (m, 2H). |

TABLE 29

| Example No. | Structural formula | Physicochemical data |
|---|---|---|
| 28(28d) | | 1H NMR (CDCl₃) δ (ppm) 1.00 (s, 9H) 1.20-1.33 (m, 1H) 1.41-1.56 (m, 1H) 1.80-1.90 (m, 1H) 2.27-2.41 (m, 1H) 3.57-3.71 (m, 1H) 4.00-4.13 (m, 1H) 4.18-4.26 (m, 1H) 5.04 (s, 2H) 5.56 (d, J = 7.3 Hz, 1H) 7.24-7.45 (m, 11H) 7.54-7.72 (m, 4H). |
| 28(28e) | | 1H NMR (CDCl₃) δ (ppm) 1.44-2.28 (m, 12H) 2.30-2.50 (m, 2H) 2.60-2.75 (m, 4H) 3.26 (t, J = 7.6 Hz, 4H) 3.65 (s, 3H) 4.15-4.18 (m, 1H) 4.82-4.95 (m, 1H) 5.58 (s, 2H) 7.02 (s, 1H) 7.16 (d, J = 5.4 Hz, 1H) 7.35 (s, 1H) 7.37 (s, 1H) 8.36 (d, J = 5.4 Hz, 1H). MS (APCI) m/z: 546 [M + H]⁺. |

TABLE 29-continued

| Example No. | Structural formula | Physicochemical data |
|---|---|---|
| 29 | (structure) | 1H NMR (CDCl₃) δ (ppm) 1.13-1.27 (m, 2H) 1.42-1.54 (m, 2H) 1.71-1.82 (m, 2H) 1.87-1.99 (m, 4H) 2.05-2.20 (m, 7H) 2.58-2.74 (m, 2H) 3.14 (s, 4H) 3.66 (s, 3H) 3.84 (s, 4H) 3.99-4.08 (m, 1H) 5.58 (s, 2H) 7.02 (d, J = 1.8 Hz, 1H) 7.17 (dd, J = 5.5, 1.8 Hz, 1H) 7.22 (s, 1H) 7.38 (s, 1H) 8.36 (d, J = 5.5 Hz, 1H). MS (APCI) m/z: 604 [M + H]⁺. |
| 30(30a) | (structure) | 1H NMR (CDCl₃) δ (ppm) 1.63-1.65 (m, 2H) 1.85-1.86 (m, 2H) 2.03-2.07 (m, 2H) 2.22-2.24 (m, 2H) 2.42-2.51 (m, 3H) 3.17-3.24 (m, 4H). |
| 30(30b) | (structure) | 1H NMR (CDCl₃) δ (ppm) 1.27-1.32 (m, 4H) 1.39 (s, 9H) 1.73-1.82 (m, 4H) 1.92-1.95 (m, 1H) 2.40-2.43 (m, 1H) 2.62-2.65 (m, 1H) 2.96 (s, 1H) 3.32 (s, 2H) 3.62-3.69 (m, 2H) 4.07-4.08 (m, 1H) 8.20 (br s, 1H). |
| 30(30c) | (structure) | 1H NMR (D₂O) δ (ppm) 1.19-1.31 (m, 4H) 2.08-2.47 (m, 6H) 3.04-3.11 (m, 2H) 4.04 (br s, 4H). |
| 30(30d) | (structure) | 1H NMR (CDCl₃) δ (ppm) 1.03 (s, 9H) 1.09-1.20 (m, 2H) 1.77-1.86 (m, 2H) 1.89-1.94 (m, 2H) 1.96-2.04 (m, 3H) 2.35 (dd, J = 6.8, 2.0 Hz, 2H) 2.51-2.59 (m, 1H) 3.57 (s, 3H) 4.84 (s, 2H) 7.35-7.39 (m, 4H) 7.40-7.44 (m, 2H) 7.61-7.65 (m, 4H) 9.76 (t, J = 2.2 Hz, 1H). |
| 30(30e) | (structure) | 1H NMR (CDCl₃) δ (ppm) 1.03 (s, 9H) 1.32-1.42 (m, 2H) 1.83-1.96 (m, 4H) 2.00-2.05 (m, 2H) 2.54-2.65 (m, 2H) 3.58 (s, 3H) 4.84 (s, 2H) 5.97 (s, 1H) 6.25 (s, 1H) 7.35-7.44 (m, 6H) 7.61-7.65 (m, 4H) 9.52 (s, 1H). |

TABLE 30

| Example No. | Structural formula | Physicochemical data |
|---|---|---|
| 30(30f) | (structure) | 1H NMR (CDCl₃) δ (ppm) 1.03 (s, 9H) 1.28-1.37 (m, 1H) 1.42-1.51 (m, 1H) 1.72-1.91 (m, 4H) 1.98-2.03 (m, 2H) 2.04-2.12 (m, 1H) 2.51-2.60 (m, 1H) 2.97 (d, J = 4.4 Hz, 1H) 3.09 (d, J = 4.4 Hz, 1H) 3.56 (s, 3H) 4.84 (s, 2H) 7.35-7.38 (m, 4H) 7.40-7.44 (m, 2H) 7.61-7.64 (m, 4H) 8.85 (s, 1H). |

TABLE 30-continued

| Example No. | Structural formula | Physicochemical data |
|---|---|---|
| 30(30g) | | 1H NMR (CDCl₃) δ (ppm) 1.06 (s, 9H) 1.13-1.23 (m, 2H) 1.41-1.51 (m, 2H) 1.72-2.19 (m, 15H) 2.57-2.68 (m, 2H) 3.23 (t, J = 6.9 Hz, 4H) 3.61 (s, 3H) 4.00-4.07 (m, 1H) 4.87 (s, 2H) 7.22 (s, 1H) 7.36-7.47 (m, 7H) 7.63-7.68 (m, 4H). |
| 30(30h) | | 1H NMR (CDCl₃) δ (ppm) 1.09-1.20 (m, 2H) 1.40-1.51 (m, 2H) 1.70-2.18 (m, 15H) 2.54-2.69 (m, 2H) 3.21 (t, J = 6.9 Hz, 4H) 3.62-3.70 (m, 1H) 3.68 (s, 3H) 3.98-4.06 (m, 1H) 4.76 (s, 2H) 7.21 (s, 1H) 7.36 (s, 1H). |
| 30(30i) | | 1H NMR (CDCl₃) δ (ppm) 1.12-1.22 (m, 2H) 1.42-1.52 (m, 2H) 1.71-2.19 (m, 15H) 2.58-2.72 (m, 2H) 3.21 (t, J = 6.9 Hz, 4H) 3.67 (s, 3H) 3.92 (s, 3H) 3.99-4.07 (m, 1H) 5.29 (s, 2H) 7.22 (s, 1H) 7.24-7.26 (m, 1H) 7.36-7.40 (m, 2H) 7.67-7.70 (m, 2H). MS (APCI) m/z: 533 [M + H]⁺. |
| 31(31a) | | 1H NMR (CDCl₃) δ (ppm) 1.06 (s, 9H) 1.11-1.23 (m, 2H) 1.40-1.51 (m, 2H) 1.69-1.82 (m, 2H) 1.85-2.01 (m, 6H) 2.02-2.10 (m, 1H) 2.11-2.20 (m, 4H) 2.55-2.70 (m, 2H) 3.37 (s, 4H) 3.61 (s, 3H) 3.97-4.06 (m, 1H) 4.75 (s, 4H) 4.87 (s, 2H) 7.21 (s, 1H) 7.36-7.48 (m, 7H) 7.63-7.69 (m, 4H). |
| 31(31b) | | 1H NMR (CDCl₃) δ (ppm) 1.11-1.23 (m, 2H) 1.41-1.52 (m, 2H) 1.65-2.08 (m, 10H) 2.09-2.20 (m, 4H) 2.55-2.70 (m, 2H) 3.37 (s, 4H) 3.67 (s, 3H) 3.96-4.05 (m, 1H) 4.75 (s, 4H) 4.78 (s, 2H) 7.21 (s, 1H) 7.36 (s, 1H). |
| 31(31c) | | 1H NMR (CDCl₃) δ (ppm) 1.11-1.24 (m, 2H) 1.40-1.52 (m, 2H) 1.70-1.82 (m, 2H) 1.85-2.02 (m, 5H) 2.03-2.11 (m, 2H) 2.11-2.20 (m, 4H) 2.56-2.72 (m, 2H) 3.37 (s, 4H) 3.67 (s, 3H) 3.92 (s, 3H) 3.97-4.06 (m, 1H) 4.75 (s, 4H) 5.29 (s, 2H) 7.21 (s, 1H) 7.23-7.28 (m, 1H) 7.34-7.42 (m, 2H) 7.65-7.72 (m, 2H). MS (APCI) m/z: 575 [M + H]⁺. |
| 32(32a) | | 1H NMR (CDCl₃) δ (ppm) 1.06 (s, 9H) 1.16-1.27 (m, 2H) 1.41-1.51 (m, 2H) 1.71-2.19 (m, 15H) 2.57-2.68 (m, 2H) 3.20-3.27 (m, 4H) 3.61 (s, 3H), 3.79 (t, J = 6.1 Hz, 2H) 3.83 (s, 2H) 3.99-4.08 (m, 1H) 4.87 (s, 2H) 7.22 (s, 1H) 7.37-7.47 (m, 7H) 7.64-7.68 (m, 4H). |

TABLE 31

| Example No. | Structural formula | Physicochemical data |
|---|---|---|
| 32(32b) |  | 1H NMR (CDCl₃) δ (ppm) 1.14-1.25 (m, 2H) 1.40-1.51 (m, 2H) 1.70-2.19 (m, 15H) 2.55-2.69 (m, 2H) 3.19-3.28 (m, 4H) 3.61-3.69 (m, 1H) 3.67 (s, 3H) 3.79 (t, J = 6.9 Hz, 2H) 3.82 (s, 2H) 3.98-4.06 (m, 1H) 4.76 (s, 2H) 7.21 (s, 1H) 7.36 (s, 1H). |

TABLE 31-continued

| Example No. | Structural formula | Physicochemical data |
|---|---|---|
| 32(32c) | | 1H NMR (CDCl₃) δ (ppm) 1.09-2.44 (m, 28H) 2.56-2.72 (m, 2H) 3.19-3.42 (m, 5H) 3.59-3.69 (m, 3H) 3.76-3.87 (m, 4H) 3.98-4.09 (m, 1H) 4.63-4.76 (m, 2H) 7.22 (s, 1H) 7.38 (s, 1H). MS (ESI) m/z: 605 [M + H]⁺. |
| 33(33a) | | 1H NMR (CDCl₃) δ (ppm) 1.16-1.26 (m, 2H) 1.44-1.54 (m, 2H) 1.72-1.82 (m, 2H) 1.88-2.21 (m, 13H) 2.60-2.67 (m, 1H) 2.71-2.78 (m, 1H) 3.21-3.26 (m, 4H) 3.79 (t, J = 6.9 Hz, 2H) 3.83 (s, 2H) 3.91 (s, 3H) 3.99-4.07 (m, 1H) 7.22 (s, 1H) 7.38 (s, 1H) 10.08 (s, 1H). |
| 33(33b) | | 1H NMR (CDCl₃) δ (ppm) 1.16-1.26 (m, 2H) 1.41-1.52 (m, 2H) 1.71-1.81 (m, 2H) 1.88-1.97 (m, 4H) 2.02-2.20 (m, 7H) 2.10 (t, J = 6.9 Hz, 2H) 2.58-2.70 (m, 2H) 3.21-3.26 (m, 4H) 3.57 (s, 3H) 3.79 (t, J = 6.9 Hz, 2H) 3.83 (s, 2H) 3.99-4.07 (m, 1H) 5.63 (dd, J = 11.5, 1.5 Hz, 1H) 6.28 (dd, J = 17.6, 1.5 Hz, 1H) 6.58 (dd, J = 17.6, 11.5 Hz, 1H) 7.22 (s, 1H) 7.37 (s, 1H). |
| 33(33c) | | 1H NMR (CDCl₃) δ (ppm) 1.15-1.26 (m, 2H) 1.40-1.50 (m, 2H) 1.70-1.95 (m, 6H) 1.99-2.19 (m, 9H) 2.55-2.65 (m, 2H) 3.20-3.27 (m, 6H) 3.49 (s, 3H) 3.79 (t, J = 6.9 Hz, 2H) 3.83 (s, 2H) 3.99-4.07 (m, 1H) 4.47 (t, J = 6.5 Hz, 2H) 6.21 (t, J = 6.9 Hz, 1H) 7.21 (s, 1H) 7.36 (s, 1H) 7.75 (d, J = 6.9 Hz, 1H) 7.88 (dd, J = 6.9, 1.9 Hz, 1H). MS (APCI) m/z: 614 [M + H]⁺. |
| 34(34a) | | 1H NMR (CDCl₃) δ (ppm) 1.48 (s, 9H) 1.84-1.95 (m, 2H) 2.09-2.17 (m, 2H) 2.94-3.04 (m, 2H) 3.12-3.22 (m, 1H) 3.97 (s, 3H) 4.11-4.21 (m, 2H) 8.11 (d, J = 8.5 Hz, 2H) 8.18 (d, J = 8.5 Hz, 2H). |
| 34(34b) | | 1H NMR (DMSO-d₆) δ (ppm) 1.42 (s, 9H) 1.62-1.73 (m, 2H) 2.03-2.10 (m, 2H) 2.93-3.07 (m, 2H) 3.26-3.33 (m, 1H) 3.90-3.97 (m, 2H) 8.10-8.15 (m, 4H) 13.38 (s, 1H). |
| 34(34c) | | 1H NMR (CDCl₃) δ (ppm) 1.48 (s, 9H) 1.84-1.95 (m, 2H) 2.09-2.16 (m, 2H) 2.94-3.03 (m, 2H) 3.06 (d, J = 4.9 Hz, 3H) 3.14-3.21 (m, 1H) 4.11-4.19 (m, 2H) 6.19 (d, J = 4.9 Hz, 1H) 7.90 (d, J = 8.5 Hz, 2H) 8.11 (d, J = 8.5 Hz, 2H). |

TABLE 32

| Example No. | Structural formula | Physicochemical data |
|---|---|---|
| 34(34d) | | 1H NMR (CDCl₃) δ (ppm) 1.48 (s, 9H) 1.83-1.95 (m, 2H) 2.09-2.18 (m, 2H) 2.93-3.04 (m, 2H) 3.13-3.21 (m, 1H) 3.40 (d, J = 4.9 Hz, 3H) 4.10-4.21 (m, 2H) 7.74-7.80 (m, 1H) 7.88 (d, J = 8.5 Hz, 2H) 8.05 (d, J = 8.5 Hz, 2H). |

TABLE 32-continued

| Example No. | Structural formula | Physicochemical data |
|---|---|---|
| 34(34e) | (structure) | 1H NMR (CDCl₃) δ (ppm) 1.49 (s, 9H) 1.84-1.96 (m, 2H) 2.11-2.19 (m, 2H) 2.95-3.05 (m, 2H) 3.15-3.24 (m, 1H) 3.86 (s, 3H) 4.12-4.21 (m, 2H) 5.41 (s, 2H) 7.27-7.34 (m, 3H) 7.46 (t, J = 7.9 Hz, 1H) 7.85 (d, J = 8.5 Hz, 2H) 8.20 (d, J = 8.5 Hz, 2H). |
| 34(34f) | (structure) | 1H NMR (CDCl₃) δ (ppm) 1.86-2.00 (m, 3H) 2.11-2.18 (m, 2H) 2.76-2.85 (m, 2H) 3.12-3.27 (m, 3H) 3.85 (s, 3H) 5.41 (s, 2H) 7.28-7.33 (m, 3H) 7.46 (t, J = 7.9 Hz, 1H) 7.85 (d, J = 8.5 Hz, 2H) 8.20 (d, J = 8.5 Hz, 2H). |
| 34(34g) | (structure) | 1H NMR (CDCl₃) δ (ppm) 2.00-2.21 (m, 6H) 2.34 (s, 3H) 2.91-3.06 (m, 3H) 3.85 (s, 3H) 5.41 (s, 2H) 7.28-7.33 (m, 3H) 7.46 (t, J = 7.9 Hz, 1H) 7.85 (d, J = 8.5 Hz, 2H) 8.20 (d, J = 8.5 Hz, 2H). MS (APCI) m/z: 499 [M + H]⁺. |
| 35(35a) | (structure) | 1H NMR (CDCl₃) δ (ppm) 1.55-1.65 (m, 2H) 1.80-1.90 (m, 2H) 2.06-2.11 (m, 2H) 2.16-2.22 (m 2H) 2.42-2.50 (m, 1H) 2.62-2.70 (m, 1H) 3.67 (s, 3H) 3.72 (s, 3H) 5.28 (s, 2H) 6.96-7.05 (m, 3H) 7.23-7.26 (m, 1H). |
| 35(35b) | (structure) | 1H NMR (CDCl₃) δ (ppm) 1.15-2.16 (m, 10H) 2.60-2.68 (m, 1H) 3.56 (t, J = 5.7 Hz, 2H) 3.67 (s, 3H) 5.26 (s, 2H) 6.97-7.05 (m, 3H) 7.23-7.26 (m, 1H). |
| 35(35c) | (structure) | 1H NMR (CDCl₃) δ (ppm) 1.40-2.28 (m, 8H) 2.35-2.45 (m, 1H) 2.62-2.70 (m, 1H) 3.68 (s, 3H) 5.27 (s, 2H) 6.96-7.05 (m, 3H) 7.24-7.33 (m, 1H) 8.64-8.66 (m, 1H). |
| 35(35d) | (structure) | 1H NMR (CDCl₃) δ (ppm) 1.38-2.08 (m, 9H) 2.30-2.41 (m, 1H) 2.60-2.68 (m, 1H) 3.67 (s, 3H) 5.27 (s, 2H) 6.96-7.06 (m, 3H) 7.23-7.26 (m, 1H) 7.41 (d, J = 5.3 Hz, 1H). |
| 35(35e) | (structure) | 1H NMR (CDCl₃) δ (ppm) 1.48 (s, 9H) 1.50-2.25 (m, 13H) 2.70-2.76 (m, 1H) 2.85-2.91 (m, 1H) 3.23 (t, J = 10.3 Hz, 1H) 3.69 (s, 3H) 4.19-4.23 (m, 1H) 4.39 (br s, 1H) 4.49-4.51 (m, 1H) 5.27 (s, 2H) 6.14 (s, 1H) 6.97-7.06 (m, 3H) 7.23-7.26 (m, 1H). |

TABLE 33

| Example No. | Structural formula | Physicochemical data |
|---|---|---|
| 35(35f) | 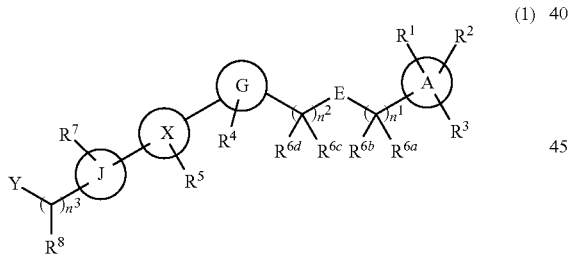 | Cl 1H NMR (CDCl$_3$) δ (ppm) 1.35-2.20 (m, 14H) 2.63-2.72 (m, 1H) 2.80-2.97 (m, 2H) 3.17 (t, J = 10.7 Hz, 1H) 3.66 (s, 3H) 4.04-4.08 (m, 1H) 4.43-4.47 (m, 1H) 5.24 (s, 2H) 6.09 (s, 1H) 6.95-7.03 (m, 3H) 7.20-7.24 (m, 1H). |
| 35(35g) | | Cl 1H NMR (CDCl$_3$) δ (ppm) 1.43-2.38 (m, 14H) 2.67-2.72 (m, 1H) 2.82-2.87 (m, 1H) 3.20-3.27 (m, 5H) 2.84-2.89 (m, 1H) 3.66 (s, 3H) 3.98-4.01 (m, 1H) 4.42-4.45 (m, 1H) 5.24 (s, 2H) 6.09 (s, 1H) 6.94-7.03 (m, 3H) 7.21-7.30 (m, 1H). MS (APCI) m/z: 512 [M + H]$^+$. |
| 36(36a) | | 1H NMR (CDCl$_3$) δ (ppm) 1.33-1.49 (m, 21H) 1.51-1.65 (m, 2H) 1.93-2.04 (m, 2H) 2.78 (d, J = 6.4 Hz, 3H) 3.13-3.22 (m, 1H) 3.29-3.38 (m, 1H) 3.63-3.76 (m, 2H) 5.68-5.69 (m, 1H). |
| 36(36b) | | i-Pr 1H NMR (DMSO-d$_6$) δ (ppm) 1.14 (d, J = 4.4 Hz, 6H) 1.38-1.48 (m, 2H) 1.53-1.69 (m, 9H) 1.90-1.97 (m, 4H) 2.15 (s, 3H) 2.25-2.49 (m, 5H) 2.71-2.86 (m, 4H) 3.54 (s, 3H) 5.75 (t, J = 6.4 Hz, 1H) 6.82-6.85 (m, 3H) 7.19 (q, J = 8.0 Hz, 1H). MS (ESI) m/z: 480 [M + H]$^+$. |

The invention claimed is:

1. A method for increasing IL10 in a subject, comprising administering an effective amount of a compound of general formula (1)

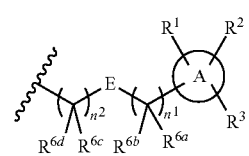

or a pharmacologically acceptable salt thereof,
wherein the symbols in the formula are defined below:

A: a 5- to 6-membered aromatic heterocycle, a 4- to 7-membered saturated heterocycle, benzene, cyclohexane or a ring having the following structure, wherein each of the rings has at least one bond;

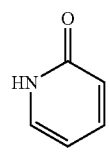

E: —CH$_2$—, —O—, or a single bond;

G: a 5-membered aromatic heterocycle; if the ring has a nitrogen atom(s), then at least one of the nitrogen atom(s) is next to an atom that is attached to a right-hand portion, wherein the right-hand portion refers to the following portion in the compound of general formula (1):

wherein the symbols indicating the respective substituents are the same as defined above;

X: any ring selected from the following rings, wherein the any ring includes a ring condensed with additional atoms to form a bicyclic ring:

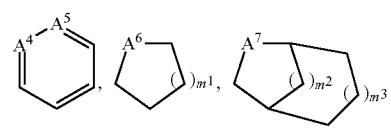

wherein
A$^4$, A$^5$: each independently, —CH= or —N=,
A$^6$, A$^7$: each independently, —CH$_2$—, —O—, or —NH—,
m$^1$, m$^2$, m$^3$: each independently, 0, 1, 2, or 3;

J: a 5-membered aromatic heterocycle wherein J is optionally condensed with X to have a bicyclic structure, or a 5-membered unsaturated heterocycle;

Y:
an amino group optionally substituted with 1-2 groups independently selected from Substituent group $Y^1$,
a phenyl group optionally substituted with 1-3 groups independently selected from Substituent group $Y^1$,
a C3-C8 cycloalkyl group optionally substituted with 1-3 groups independently selected from Substituent group $Y^1$, wherein the C3-C8 cycloalkyl group optionally has the following bridged structures:

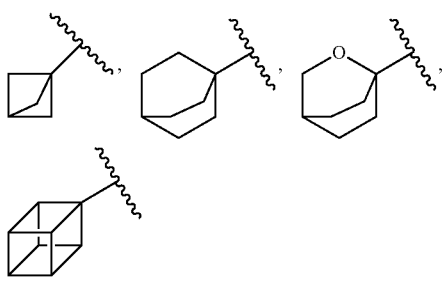

a C3-C8 cycloalkenyl group optionally substituted with 1-3 groups independently selected from Substituent group $Y^1$,
a 4- to 7-membered saturated heterocyclic group optionally substituted with 1-3 groups independently selected from Substituent group $Y^1$,
a 4- to 7-membered unsaturated heterocyclic group optionally substituted with 1-3 groups independently selected from Substituent group $Y^1$, or
a group formed by attachment to $R^7$, optionally substituted with 1-3 groups independently selected from Substituent group $Y^1$, selected from the following:

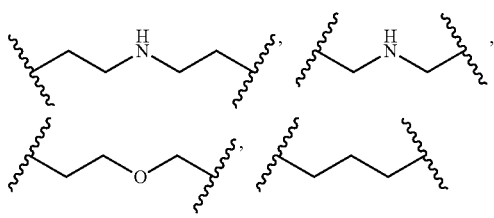

Substituent group $Y^1$:
a hydroxyl group,
an amino group optionally substituted with 1-2 groups independently selected from Substituent group $Y^2$,
a cyano group,
a halogen atom,
a C1-C6 alkyl group optionally substituted with 1-3 groups independently selected from Substituent group $Y^2$,
a C1-C6 alkoxy group optionally substituted with 1-3 groups independently selected from Substituent group $Y^2$,
a 4- to 7-membered saturated heterocyclic group optionally substituted with 1-3 groups independently selected from Substituent group $Y^2$, and
any group optionally substituted with 1-3 groups independently selected from Substituent group $Y^2$, selected from the following:

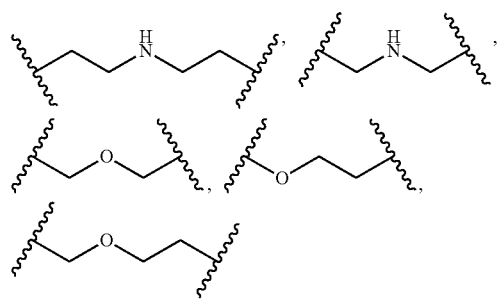

Substituent group $Y^2$:
a hydroxyl group,
a halogen atom,
a C1-C6 alkyl group optionally substituted with 1-3 groups independently selected from Substituent group $Y^3$,
a C1-C6 alkoxy group optionally substituted with 1-3 groups independently selected from Substituent group $Y^3$,
an amino group optionally substituted with 1-2 groups independently selected from Substituent group $Y^3$,
a 4- to 7-membered saturated heterocyclic group optionally substituted with 1-3 groups independently selected from Substituent group $Y^3$, and
any group optionally substituted with 1-3 groups independently selected from Substituent group $Y^3$, selected from the following:

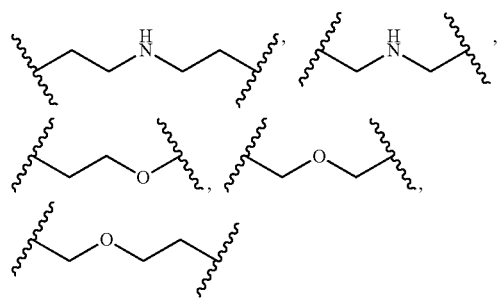

Substituent group $Y^3$:
a hydroxyl group,
a halogen atom,
a cyano group,
a C1-C6 alkyl group optionally substituted with 1-3 groups independently selected from Substituent group $Y^4$,
a C1-C6 alkoxy group optionally substituted with 1-3 groups independently selected from Substituent group $Y^4$, and
any group optionally substituted with 1-3 groups independently selected from Substituent group $Y^4$, selected from the following:

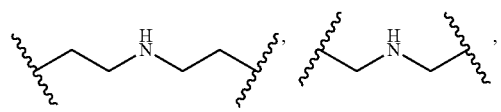

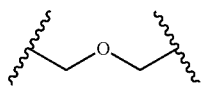

Substituent group Y⁴:
a fluorine atom;
R¹, R², R³: each independently, a hydrogen atom, a carboxyl group, a cyano group, a halogen atom, a C1-C6 alkyl group, a C1-C6 alkoxy group, a C3-C8 cycloalkyl group, a C3-C8 cycloalkoxy group, a hydroxy C1-C6 alkyl group, a halo C1-C6 alkyl group, a halo C1-C6 alkoxy group, a C1-C6 alkoxycarbonyl group, a C1-C6 alkyl C3-C8 cycloalkyl group, a C3-C8 cycloalkyl C1-C6 alkoxy group, a 4- to 7-membered unsaturated heterocyclic group, a C1-C6 alkyl 4- to 7-membered unsaturated heterocyclic group, a di (C1-C6 alkyl) amino 4- to 7-membered unsaturated heterocyclic group, a 4- to 7-membered unsaturated heterocyclic carbonyl group, or a C3-C8 cycloalkylcarbonyl group;
R⁴: a hydrogen atom, a C1-C6 alkyl group, a halo C1-C6 alkyl group, or a group formed by attachment to $R^{6c}$ or $R^{6d}$, selected from the following:

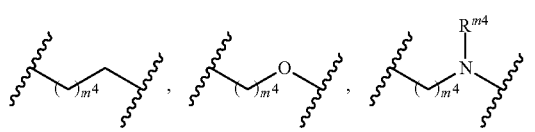

wherein $m^4$ is 0, 1, or 2, and $R^{m4}$ is a hydrogen atom or a methyl group,
R⁵: a hydrogen atom, a halogen atom, or a C1-C6 alkyl group;
$R^{6a}$, $R^{6b}$, $R^{6c}$, $R^{6d}$: each independently, a hydrogen atom or a C1-C6 alkyl group;
R⁷: a single bond, a hydrogen atom, or a methyl group;
R⁸: a hydrogen atom or a methyl group; and
n¹, n², n³: each independently, 0, 1, or 2.

2. A method of treating celiac disease in a subject, comprising administering an effective amount of a compound of general formula (1)

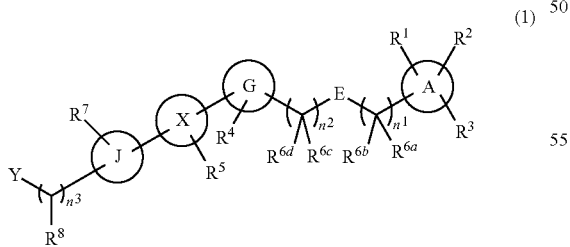

(1)

or a pharmacologically acceptable salt thereof,
wherein the symbols in the formula are defined below:
A: a 5- to 6-membered aromatic heterocycle, a 4- to 7-membered saturated heterocycle, benzene, cyclohexane or a ring having the following structure, wherein each of the rings has at least one bond;

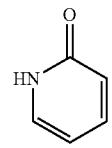

E: —CH₂—, —O—, or a single bond;
G: a 5-membered aromatic heterocycle; if the ring has a nitrogen atom(s), then at least one of the nitrogen atom(s) is next to an atom that is attached to a right-hand portion, wherein the right-hand portion refers to the following portion in the compound of general formula (1):

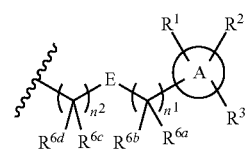

wherein the symbols indicating the respective substituents are the same as defined above;
X: any ring selected from the following rings, wherein the any ring includes a ring condensed with additional atoms to form a bicyclic ring:

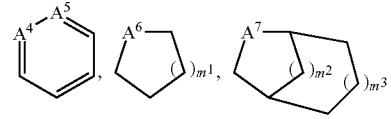

wherein
A⁴, A⁵: each independently, —CH= or —N=,
A⁶, A⁷: each independently, —CH₂—, —O—, or —NH—,
$m^1$, $m^2$, $m^3$: each independently, 0, 1, 2, or 3;
J: a 5-membered aromatic heterocycle wherein J is optionally condensed with X to have a bicyclic structure, or a 5-membered unsaturated heterocycle;
Y:
an amino group optionally substituted with 1-2 groups independently selected from Substituent group Y¹,
a phenyl group optionally substituted with 1-3 groups independently selected from Substituent group Y¹,
a C3-C8 cycloalkyl group optionally substituted with 1-3 groups independently selected from Substituent group Y¹, wherein the C3-C8 cycloalkyl group optionally has the following bridged structures:

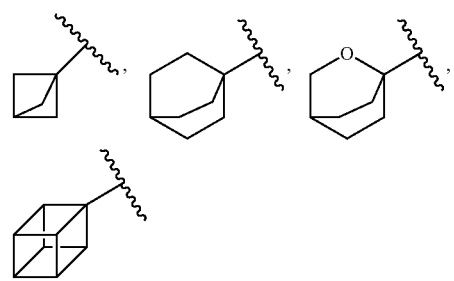

a C3-C8 cycloalkenyl group optionally substituted with 1-3 groups independently selected from Substituent group Y¹, a 4- to 7-membered saturated heterocyclic group optionally substituted with 1-3 groups independently selected from Substituent group Y¹, a 4- to 7-membered unsaturated heterocyclic group optionally substituted with 1-3 groups independently selected from Substituent group Y¹, or a group formed by attachment to R⁷, optionally substituted with 1-3 groups independently selected from Substituent group Y¹, selected from the following:

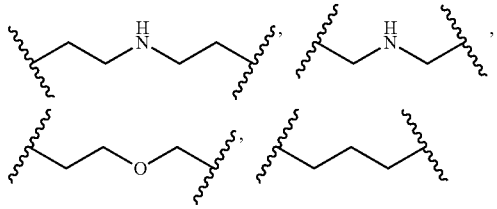

Substituent group Y¹:
a hydroxyl group,
an amino group optionally substituted with 1-2 groups independently selected from Substituent group Y²,
a cyano group,
a halogen atom,
a C1-C6 alkyl group optionally substituted with 1-3 groups independently selected from Substituent group Y²,
a C1-C6 alkoxy group optionally substituted with 1-3 groups independently selected from Substituent group Y²,
a 4- to 7-membered saturated heterocyclic group optionally substituted with 1-3 groups independently selected from Substituent group Y², and
any group optionally substituted with 1-3 groups independently selected from Substituent group Y², selected from the following:

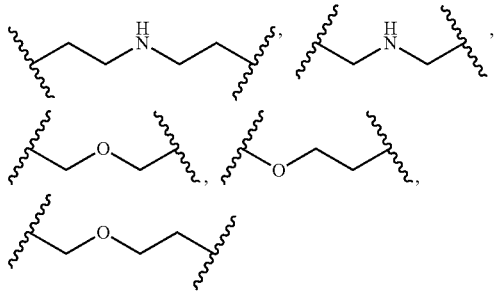

Substituent group Y²:
a hydroxyl group,
a halogen atom,
a C1-C6 alkyl group optionally substituted with 1-3 groups independently selected from Substituent group Y³,
a C1-C6 alkoxy group optionally substituted with 1-3 groups independently selected from Substituent group Y³,
an amino group optionally substituted with 1-2 groups independently selected from Substituent group Y³, a 4- to 7-membered saturated heterocyclic group optionally substituted with 1-3 groups independently selected from Substituent group Y³, and any group optionally substituted with 1-3 groups independently selected from Substituent group Y³, selected from the following:

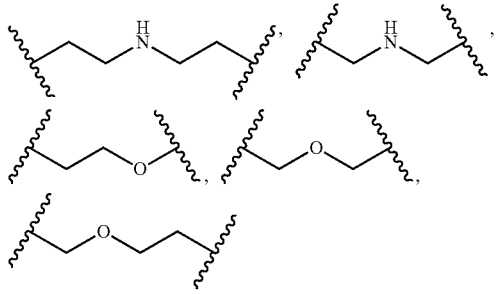

Substituent group Y³:
a hydroxyl group,
a halogen atom,
a cyano group,
a C1-C6 alkyl group optionally substituted with 1-3 groups independently selected from Substituent group Y⁴,
a C1-C6 alkoxy group optionally substituted with 1-3 groups independently selected from Substituent group Y⁴, and
any group optionally substituted with 1-3 groups independently selected from Substituent group Y⁴, selected from the following:

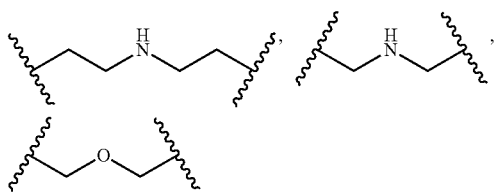

Substituent group Y⁴:
a fluorine atom;
$R^1$, $R^2$, $R^3$: each independently, a hydrogen atom, a carboxyl group, a cyano group, a halogen atom, a C1-C6 alkyl group, a C1-C6 alkoxy group, a C3-C8 cycloalkyl group, a C3-C8 cycloalkoxy group, a hydroxy C1-C6 alkyl group, a halo C1-C6 alkyl group, a halo C1-C6 alkoxy group, a C1-C6 alkoxycarbonyl group, a C1-C6 alkyl C3-C8 cycloalkyl group, a C3-C8 cycloalkyl C1-C6 alkoxy group, a 4- to 7-membered unsaturated heterocyclic group, a C1-C6 alkyl 4- to 7-membered unsaturated heterocyclic group, a di (C1-C6 alkyl) amino 4- to 7-membered unsaturated heterocyclic group, a 4- to 7-membered unsaturated heterocyclic carbonyl group, or a C3-C8 cycloalkylcarbonyl group;
$R^4$: a hydrogen atom, a C1-C6 alkyl group, a halo C1-C6 alkyl group, or a group formed by attachment to $R^{6c}$ or $R^{6d}$, selected from the following:

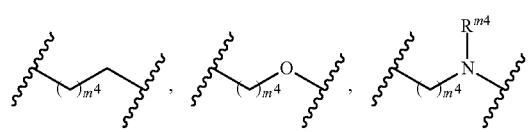

wherein $m^4$ is 0, 1, or 2, and $R^{m4}$ is a hydrogen atom or a methyl group, $R^5$: a hydrogen atom, a halogen atom, or a C1-C6 alkyl group;

$R^{6a}$, $R^{6b}$, $R^{6c}$, $R^{6d}$: each independently, a hydrogen atom or a C1-C6 alkyl group;

$R^7$: a single bond, a hydrogen atom, or a methyl group;

$R^8$: a hydrogen atom or a methyl group; and $n^1$, $n^2$, $n^3$: each independently, 0, 1, or 2.

3. A method according to claim 2, wherein each of $R^{6a}$, $R^{6b}$, $R^{6c}$ is a hydrogen atom, $R^{6d}$ is a hydrogen atom or a methyl group, $n^1$ is 0, $n^2$ is 1, and E is —O—.

4. A method according to claim 2, wherein G-$R^4$ is

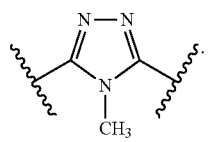

5. A method according to claim 2, wherein X is benzene, pyridine or cyclohexane.

6. A method according to claim 2, wherein a compound of general formula (1) is a compound of general formula (1')

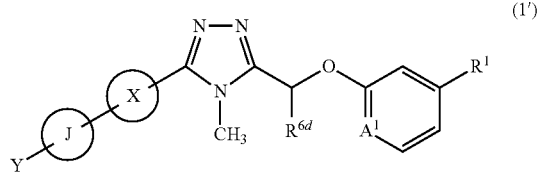

(1')

or a pharmacologically acceptable salt thereof, wherein the symbols in the formula are defined below:

$R^1$: a hydrogen atom, a carboxyl group, a cyano group, a fluorine atom, a chlorine atom, a methyl group, an isopropyl group, a t-butyl group, a trifluoromethyl group, a trifluoromethoxy group, a cyclopropylmethoxy group, a 1,1-difluoro-2-methylpropyl group, a 1,1-difluoro-2,2-dimethylpropyl group, a 1-methyl-1-cyclobutyl group, a methoxycarbonyl group, an ethoxycarbonyl group, an isopropoxycarbonyl group, a 1-hydroxy-1-methylethyl group, an azetidine-1-carbonyl group, a 3-methyloxetan-3-yl group, a 4,5-dihydrooxazol-2-yl group, or a cyclopropylcarbonyl group;

$R^{6d}$: a hydrogen atom or a methyl group;

$A^1$: =N—, or =CH—;

X: benzene, pyridine or cyclohexane;

J: any ring selected from the following ring group:

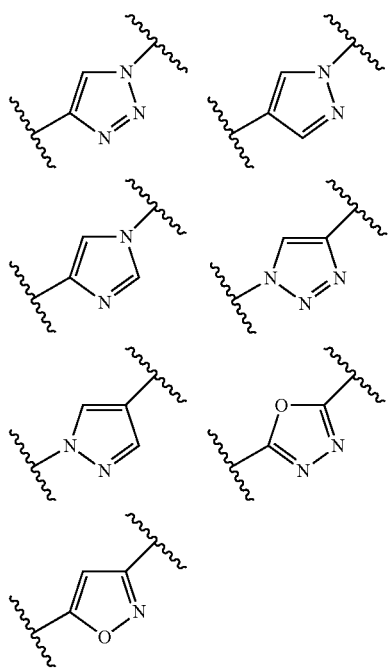

Y:
an amino group optionally substituted with 1-2 groups independently selected from Substituent group $Y^1$,
a phenyl group optionally substituted with 1-3 groups independently selected from Substituent group $Y^1$,
any group optionally substituted with 1-3 groups independently selected from Substituent group $Y^1$, selected from the following:
a cyclobutyl group, a cyclopentyl group, a cyclohexyl group,

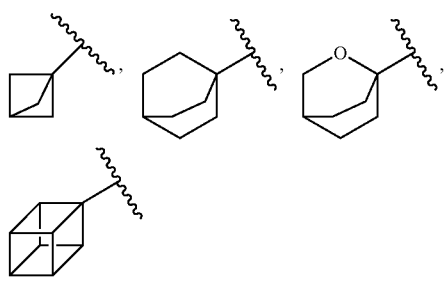

a cyclohexenyl group optionally substituted with 1-3 groups independently selected from Substituent group $Y^1$,
any group optionally substituted with 1-3 groups independently selected from Substituent group $Y^1$, selected from the following:
a piperidinyl group, an azetidinyl group, a tetrahydropyranyl group, a morpholinyl group, or
a tetrahydropyridinyl group optionally substituted with 1-3 groups independently selected from Substituent group $Y^1$;

Substituent group $Y^1$:
a hydroxyl group,
an amino group optionally substituted with 1-2 groups independently selected from Substituent group $Y^2$, a cyano group,
a fluorine atom,
a methyl group, an ethyl group or an isopropyl group optionally substituted with 1-3 groups independently selected from Substituent group $Y^2$,
a methoxy group optionally substituted with 1-3 groups independently selected from Substituent group $Y^2$,
an azetidinyl group, a pyrrolidinyl group or a morpholinyl group optionally substituted with 1-3 groups independently selected from Substituent group $Y^2$, and
any group optionally substituted with 1-3 groups independently selected from Substituent group $Y^2$, selected from the following:

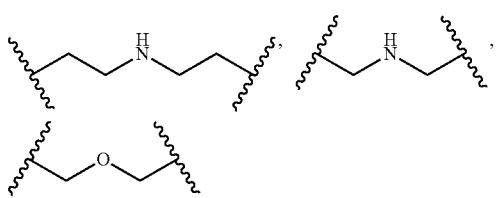

Substituent group $Y^2$:
a hydroxyl group,
a fluorine atom,
a methyl group optionally substituted with 1-3 groups independently selected from Substituent group $Y^3$,
a methoxy group optionally substituted with 1-3 groups independently selected from Substituent group $Y^3$,
an amino group optionally substituted with 1-2 groups independently selected from Substituent group $Y^3$,
an azetidinyl group, a pyrrolidinyl group or a morpholinyl group optionally substituted with 1-3 groups independently selected from Substituent group $Y^3$, and
any group optionally substituted with 1-3 groups independently selected from Substituent group $Y^3$, selected from the following:

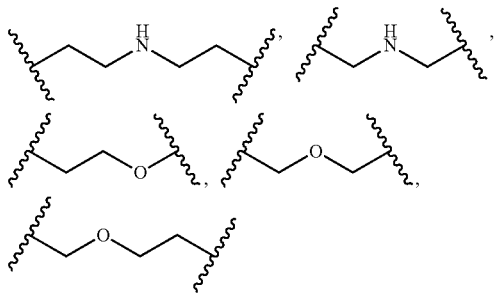

Substituent group $Y^3$:
a hydroxyl group,
a fluorine atom,
a cyano group,
a methyl group optionally substituted with 1-3 groups independently selected from Substituent group $Y^4$, and
a methoxy group optionally substituted with 1-3 groups independently selected from Substituent group $Y^4$;
Substituent group $Y^4$:
a fluorine atom.

7. A method according to claim 2, wherein a compound of general formula (1) is selected from the group consisting of
4-Fluoro-1-methyl-4-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}piperidine,
4-{4-[(1R)-1-(Azetidin-1-yl)ethyl]phenyl}-1-[trans-4-(4-methyl-5-{[3-(propan-2-yl)phenoxy]methyl}-4H-1,2,4-triazol-3-yl)cyclohexyl]-1H-1,2,3-triazole,
(3R,6S)-N,N-Dimethyl-6-{1-[trans-4-(4-methyl-5-{(1R)-1-[3-(propan-2-yl)phenoxy]ethyl}-4H-1,2,4-triazol-3-yl)cyclohexyl]-1H-1,2,3-triazol-4-yl}tetrahydro-2H-pyran-3-amine,
4-Fluoro-1-methyl-4-{1-[(3R,6S)-6-(4-methyl-5-{[3-(propan-2-yl)phenoxy]methyl}-4H-1,2,4-triazol-3-yl)tetrahydro-2H-pyran-3-yl]-1H-1,2,3-triazol-4-yl}piperidine,
3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro [1,2,4]triazolo [4,3-a]pyridine,
1,5-Anhydro-6-azetidin-1-yl-2,3,4,6-tetradeoxy-2-{4-[trans-4-(4-methyl-5-{[3-(trifluoromethyl)phenoxy]methyl}-4H-1,2,4-triazol-3-yl)cyclohexyl]-1H-1,2,3-triazol-1-yl}-Derythro-hexitol,
2-({5-[trans-4-(1-{trans-4-[3-(Fluoromethyl)azetidin-1-yl]cyclohexyl}-1H-1,2,3-triazol-4-yl)cyclohexyl]-4-methyl-4H-1,2,4-triazol-3-yl}methoxy)-4-(trifluoromethyl)pyridine,
3-(trans-4-{1-[trans-4-(Azetidin-1-yl)cyclohexyl]-1H-pyrazol-4-yl}cyclohexyl)-4-methyl-5-{[3-(trifluoromethyl)phenoxy]methyl}-4H-1,2,4-triazole,
4-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]morpholine,
6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane,
6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane,
2-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-6-oxa-2-azaspiro[3.4]octane,
{1-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-1H-pyrazol-1-yl)cyclohexyl]azetidine-3,3-diyl}dimethanol,
Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate,
8-Methyl-3-[trans-4-(4-methyl-5-{(1R)-1-[3-(propan-2-yl)phenoxy]ethyl}-4H-1,2,4-triazol-3-yl)cyclohexyl]-1-oxa-2,8-diazaspiro[4.5]dec-2-ene, and
pharmacologically acceptable salts thereof.

8. A method according to claim 2, wherein a compound of general formula (1) is 6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-2-oxa-6-azaspiro[3.3]heptane, or a pharmacologically acceptable salt thereof.

9. A method of treating celiac disease in a subject, comprising administering an effective amount of 6-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-1-oxa-6-azaspiro[3.3]heptane, or a pharmacologically acceptable salt thereof, and the inflammatory disease is celiac disease.

10. A method according to claim 2, wherein a compound of general formula (1) is 2-[trans-4-(4-{trans-4-[4-Methyl-5-({[4-(trifluoromethyl)pyridin-2-yl]oxy}methyl)-4H-1,2,4-triazol-3-yl]cyclohexyl}-1H-pyrazol-1-yl)cyclohexyl]-6-oxa-2-azaspiro[3.4]octane, or a pharmacologically acceptable salt thereof.

\* \* \* \* \*

UNITED STATES PATENT AND TRADEMARK OFFICE
CERTIFICATE OF CORRECTION

PATENT NO. : 12,297,187 B2
APPLICATION NO. : 18/057511
DATED : May 13, 2025
INVENTOR(S) : Toru Taniguchi et al.

It is certified that error appears in the above-identified patent and that said Letters Patent is hereby corrected as shown below:

In the Claims

Claim 7, Column 200, Lines 12-15, "3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro [1,2,4]triazolo [4,3-a]pyridine," should read as --3-{trans-4-[4-(4-Fluoro-1-methylpiperidin-4-yl)-1H-1,2,3-triazol-1-yl]cyclohexyl}-8-[3-(trifluoromethyl)phenoxy]-5,6,7,8-tetrahydro[1,2,4]triazolo[4,3-a]pyridine,--.

Claim 7, Column 200, Lines 47-50, "Methyl 3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate," should read as --Methyl-3-{[4-methyl-5-(trans-4-{1-[trans-4-(2-oxa-6-azaspiro[3.3]hept-6-yl)cyclohexyl]-1H-pyrazol-4-yl}cyclohexyl)-4H-1,2,4-triazol-3-yl]methoxy}benzoate,--.

Signed and Sealed this
Twenty-eighth Day of October, 2025

John A. Squires
*Director of the United States Patent and Trademark Office*